US007521222B2

(12) United States Patent
Zazopoulos et al.

(10) Patent No.: US 7,521,222 B2
(45) Date of Patent: Apr. 21, 2009

(54) FARNESYL DIBENZODIAZEPINONE AND PROCESSES FOR ITS PRODUCTION

(75) Inventors: Emmanuel Zazopoulos, Montreal (CA); Chris M. Farnet, Outremont (CA)

(73) Assignee: Thallion Pharmaceuticals, Inc., Montreal (CA)

( * ) Notice: Subject to any disclaimer, the term of this patent is extended or adjusted under 35 U.S.C. 154(b) by 46 days.

(21) Appl. No.: 11/511,586

(22) Filed: Aug. 28, 2006

(65) Prior Publication Data
US 2008/0199940 A1 Aug. 21, 2008

Related U.S. Application Data

(62) Division of application No. 10/762,107, filed on Jan. 21, 2004, now Pat. No. 7,101,872.

(60) Provisional application No. 60/441,126, filed on Jan. 21, 2003, provisional application No. 60/492,997, filed on Aug. 7, 2003, provisional application No. 60/518,286, filed on Nov. 10, 2003.

(51) Int. Cl.
*C12N 1/20* (2006.01)
*C12N 15/70* (2006.01)
*C07H 21/02* (2006.01)

(52) U.S. Cl. .............................. 435/252.3; 435/252.33; 435/252.31; 435/252.32; 435/252.35; 435/320.1; 536/23.1; 536/23.2

(58) Field of Classification Search ................. 435/252, 435/320.13; 536/23.1
See application file for complete search history.

(56) References Cited

U.S. PATENT DOCUMENTS

| | | | |
|---|---|---|---|
| 3,854,480 | A | 12/1974 | Zaffaroni |
| 4,452,775 | A | 6/1984 | Kent |
| 5,039,660 | A | 8/1991 | Leonard et al. |
| 5,393,665 | A | 2/1995 | Fayerman et al. |
| 5,466,590 | A | 11/1995 | Sariaslani et al. |
| 5,523,288 | A | 6/1996 | Cohen et al. |
| 5,541,181 | A | 7/1996 | Ohkuma et al. |
| 5,556,772 | A | 9/1996 | Sorge et al. |
| 5,783,561 | A | 7/1998 | Horwitz et al. |
| 5,830,695 | A | 11/1998 | Serizawa et al. |
| 6,140,306 | A | 10/2000 | Lambert, Jr. et al. |
| 6,683,300 | B2 | 1/2004 | Doroshenko et al. |
| 7,257,562 | B2 | 8/2007 | Farnet et al. |

OTHER PUBLICATIONS

Berge et al, "Pharmaceutical Salts," Journal of Pharmaceutical Sciences (1977), V. 66, No. 1, pp. 1-19.
Goodfellow, "Suprageneric Classification of Actinomycetes," Bergey's Manual of Systematic Bacteriology (1989), V. 4, pp. 2333-2339.
Embley and Stackebrandt, "The Molecular Phylogeny and Systematics of the Actinomycetes," Annu. Rev. Microbiol. (1994), V. 48, pp. 257-289.
Zazopoulos et al, "A Genomics-Guided Approach for Discovering and Expressing Cryptic Metabolic Pathways," Nature Biotechnology (2003), V. 21, pp. 187-190.
Stryer, :Biochemistry 3$^{rd}$ Edition (1998), W.H. Freeman and Co., New York, pp. 752-754.
Altschul et al, "Basic Local Alignment Search Tool," Journal of Molecular Biology (1990), V. 215, No. 3, pp. 403-410.
Takagi et al, "A Gene Cluster for the Mevalonate Pathway from *Streptomyces* sp. Strain CL190," Journal of Bacteriology (2000), V. 182, No. 15, pp. 4153-4157.
Carrillo et al, "The Multiple Sequence Alignment Problem in Biology," Applied Math (1998), V. 48, No. 5, pp. 1073-1082.
Murakami et al, "Thiostrepton-Induced Gene Expression in *Streptomyces lividans*," Journal of Bacteriology (1989), V. 171, No. 3, pp. 1459-1466.
Thompson et al, "Cloning of Antibiotic Resistance and Nutritional Genes in *Streptomycetes*," Journal of Bacteriology (1982), V. 151, No. 2, pp. 668-677.
Hopwood et al, "Plasmid and Phage Vectors for Gene Cloning and Analysis in *Streptomyces*," Methods in Enzymology (1987), V. 153, pp. 116-166.
Neilson et al, "Taq Extender PCR Additive for Improved Length, Yield, and Reliability of PCR Products," Strategies (1994), V. 7, p. 27.
Matteucci et al, "Synthesis of Deoxyoligonucleotides on a Polymer Support," American Chemical Society (1981), V. 103, No. 11, pp. 3185-3191.
Gluzman et al, "SV40-Transformed Simian Cells Support the Replication of Early SV40 Mutants," Cell (1981), V. 23, No. 1, pp. 175-182.
Vaara, "Agents that Increase the Permeability of the Outer Membrane," Microbiological Reviews (1992), V. 56, No. 3, pp. 395-411.
Tsubery et al., "Structure-Function Studies of Polymyxin B Nonapeptide: Implications to Sensitization of Gram-Negative Bacteria," Journal of Medical Chemistry (2000), V. 43, No. 16, pp. 3085-3092.

(Continued)

*Primary Examiner*—Nashaat T Nashed
*Assistant Examiner*—Iqbal H Chowdhury

(57) ABSTRACT

This invention relates to a novel farnesylated dibenzodiazepinone, named ECO-04601, its pharmaceutically acceptable salts and derivatives, and to methods for obtaining such compounds. One method of obtaining the ECO-04601 compound is by cultivation of a novel strain of *Micromonospora* sp., 046-ECO11; another method involves expression of biosynthetic pathway genes in transformed host cells. The present invention further relates to *Micromonospora* sp. strain 046-ECO11, to the use of ECO-04601 and its pharmaceutically acceptable salts and derivatives as pharmaceuticals, in particular to their use as inhibitors of cancer cell growth, bacterial cell growth, mammalian lipoxygenase, and to pharmaceutical compositions comprising ECO-04601 or a pharmaceutically acceptable salt or derivative thereof. Finally, the invention relates to novel polynucleotide sequences and their encoded proteins, which are involved in the biosynthesis of ECO-04601.

4 Claims, 21 Drawing Sheets

OTHER PUBLICATIONS

Carter et al, "5-Lipoxygenase Inhibitory Activity of Zileuton," Journal of Pharmacology and Experimental Therapeutics (1991), V. 256, No. 3, pp. 929-937.

Safayhi et al, "Concentration-Dependent Potentiating and Inhibitory Effects of Boswellia Extracts on 5-Lipoxygenase Product Formation in Stimulated PMNL," Planta Medica (2000), V. 66, No. 2, pp. 110-113.

Workman, P., "UKCCR Guidelines for the Walfare of Animals in Experimental Neoplasia," United Kingdom Coordinated Committee on Cancer Research, British Journal of Cancer 2nd Edition (1997), V. 77, pp. 1-10.

Premont et al, "[$^3$H] Norepinephrine Binding by Rat Glial Cells in Culture. Lack of Correlation between Binding and Adenylate Cyclase Activation," Biochimica et Biophysica Acta (1975), V. 381, No. 2, pp. 368-376.

Dimitradou et al, "Identification and Characterization of a New Cytotoxic Agent from Actinomycetes," Poster Presentation Presented at the AACR Annual Meeting, Orlando, FL, Mar. 27 to 31, 2004.

Charan et al, Diazepinomicin, a new antimicrobial alkaloid from a marine *Micromonospora sp.* J. Nat Prod. Aug. 2004;67(8):1431-3.

Igarashi et al, "Revision of the Structure Assigned to the Antibiotic BU-4664L from *Micromonopora*," Journal of Antibiotics (2005), V. 58, No. 7, pp. 350-352.

Correction to p. 352. Igarashi et al, "Revision of the Structure Assigned to the Antibiotic BU-4664L from *Micromonopora*," Journal of Antibiotics (2005), V. 58, No. 7, pp. 350-352.

Charan et al, "A New Antimicrobial Alkaloid from a *Micromonospora* sp.," Abstract and Figures from Poster Presentation #p. 157 at the 44th Annual Meeting of the American Society of Pharmacognosy, Chapel Hill, N.C., Jul. 12-16, 2003.

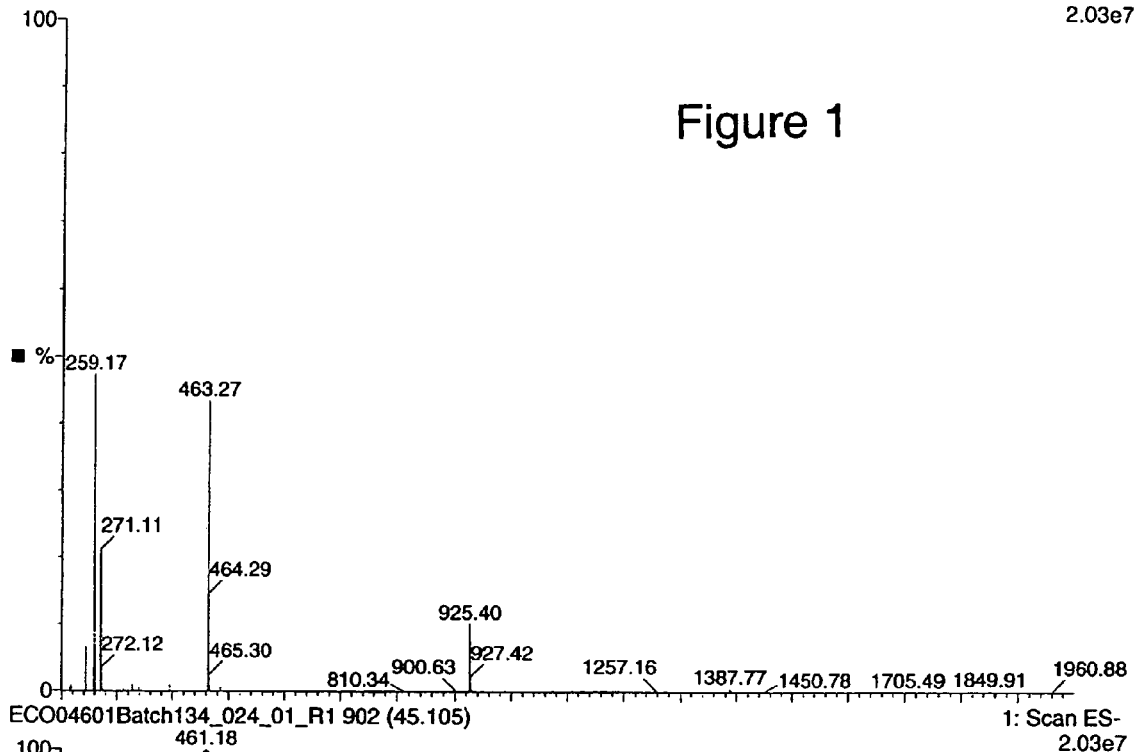
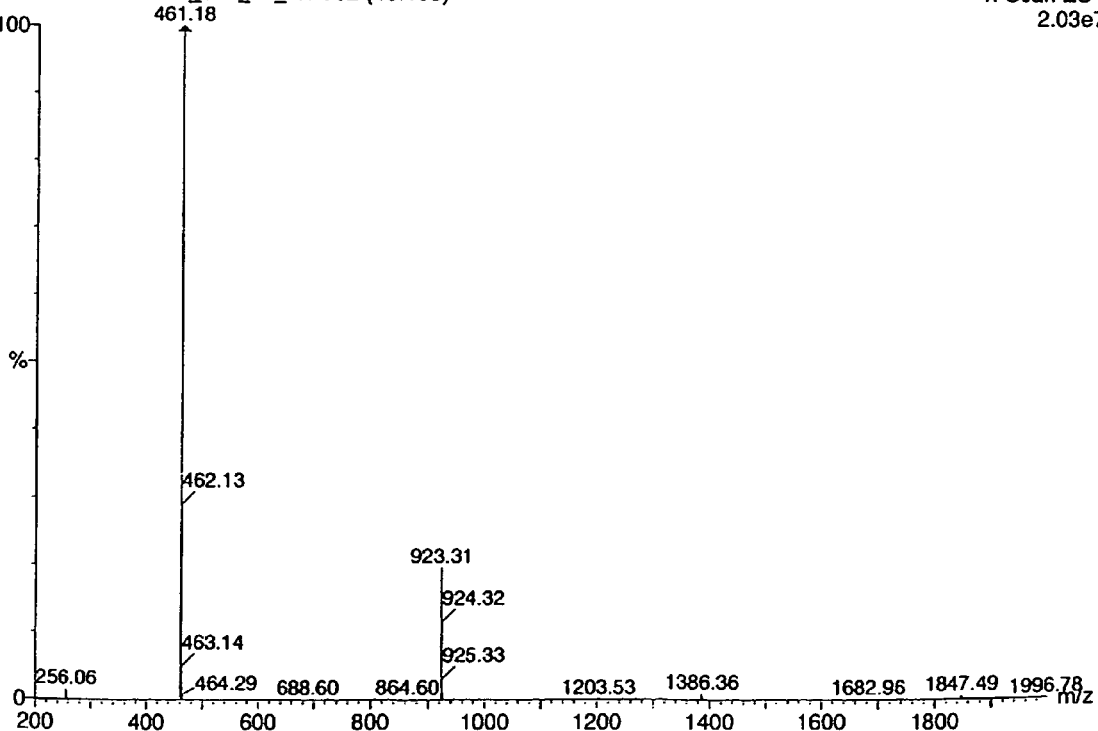
Figure 1

Figure 16

SEQUENCE LISTING TABLE

| SEQ ID NO. | AMINO ACID (AA) or NUCLEIC ACID (NA) | FUNCTION | ORF NO. |
|---|---|---|---|
| 1. | NA | CONTIG 1 | |
| 2. | AA | ABCC | 1 |
| 3. | NA | ABCC | |
| 4. | AA | RECH | 2 |
| 5. | NA | RECH | |
| 6. | AA | REGD | 3 |
| 7. | NA | REGD | |
| 8. | AA | IDSA | 4 |
| 9. | NA | IDSA | |
| 10. | AA | MVKA | 5 |
| 11. | NA | MVKA | |
| 12. | AA | DMDA | 6 |
| 13. | NA | DMDA | |
| 14. | AA | MVKP | 7 |
| 15. | NA | MVKP | |
| 16. | AA | IPPI | 8 |
| 17. | NA | IPPI | |
| 18. | AA | HMGA | 9 |
| 19. | NA | HMGA | |
| 20. | AA | KASH | 10 |
| 21. | NA | KASH | |
| 22. | AA | IPTN | 11 |
| 23. | NA | IPTN | |
| 24. | AA | SPKG | 12 |
| 25. | NA | SPKG | |
| 26. | AA | RREB | 13 |

Figure 16 con't.

| | | | |
|---|---|---|---|
| 27. | NA | RREB | |
| 28. | AA | UNES | 14 |
| 29. | NA | UNES | |
| 30. | AA | UNEZ | 15 |
| 31. | NA | UNEZ | |
| 32. | AA | OXDS | 16 |
| 33. | NA | OXDS | |
| 34. | AA | UNFD | 17 |
| 35. | NA | UNFD | |
| 36. | AA | UNFA | 18 |
| 37. | NA | UNFA | |
| 38. | AA | CSMB | 19 |
| 39. | NA | CSMB | |
| 40. | AA | AAKD | 20 |
| 41. | NA | AAKD | |
| 42. | AA | ALDB | 21 |
| 43. | NA | ALDB | |
| 44. | AA | UNFC | 22 |
| 45. | NA | UNFC | |
| 46. | AA | HYDK | 23 |
| 47. | NA | HYDK | |
| 48. | AA | ADSA | 24 |
| 49. | NA | ADSA | |
| 50. | AA | HOXV | 25 |
| 51. | NA | HOXV | |
| 52. | AA | SDRA | 26 |
| 53. | NA | SDRA | |
| 54. | AA | DHBS | 27 |
| 55. | NA | DHBS | |
| 56. | AA | SDRA | 28 |
| 57. | NA | SDRA | |
| 58. | AA | UNIQ | 29 |
| 59. | NA | UNIQ | |
| 60. | AA | UNFE | 30 |

2

Figure 16 con't.

| | | | |
|---|---|---|---|
| 61. | NA | UNFE | |
| 62. | AA | EFFT | 31 |
| 63. | NA | EFFT | |
| 64. | NA | CONTIG 2 | |
| 65. | AA | HOYH | 32 |
| 66. | NA | HOYH | |
| 67. | AA | DAHP | 33 |
| 68. | NA | DAHP | |
| 69. | AA | REGG | 34 |
| 70. | NA | REGG | |
| 71. | AA | UNFJ | 35 |
| 72. | NA | UNFJ | |
| 73. | NA | CONTIG 3 | |
| 74. | AA | RECI | 36 |
| 75. | NA | RECI | |
| 76. | AA | UNIQ | 37 |
| 77. | NA | UNIQ | |
| 78. | AA | OXAH | 38 |
| 79. | NA | OXAH | |
| 80. | AA | ABCA | 39 |
| 81. | NA | ABCA | |
| 82. | AA | UNIQ | 40 |
| 83. | NA | UNIQ | |
| 84. | AA | | 41 |
| 85. | NA | | |
| 86. | AA | | 42 |
| 87. | NA | | |
| 88. | AA | | 43 |
| 89. | NA | | |

| RT | Response | Ar/Ht | RFact | ECL | Peak Name | Percent | Comment 1 | Comment 2 |
|---|---|---|---|---|---|---|---|---|
| 1.630 | 4.486E+8 | 0.026 | ----- | 7.012 | Solvent Peak | ----- | < min rt | |
| 1.874 | 754 | 0.024 | ----- | 7.505 | | ----- | < min rt | |
| 2.521 | 1314 | 0.026 | ----- | 8.810 | | ----- | < min rt | |
| 8.150 | 16710 | 0.041 | 0.980 | 14.621 | 15:0 ISO | 26.83 | ECL deviates 0.000 | Reference 0.000 |
| 8.288 | 3943 | 0.042 | 0.977 | 14.711 | 15:0 ANTEISO | 6.32 | ECL deviates 0.000 | Reference 0.001 |
| 9.767 | 2378 | 0.042 | 0.956 | 15.627 | 16:ISO | 3.73 | ECL deviates 0.001 | Reference -0.001 |
| 10.086 | 1692 | 0.047 | 0.953 | 15.819 | 16:1 CIS 9 | 2.64 | ECL deviates 0.002 | Reference |
| 10.385 | 2413 | 0.045 | 0.949 | 15.999 | 16:0 | 3.75 | ECL deviates -0.001 | Reference -0.003 |
| 11.106 | 11222 | 0.044 | 0.941 | 16.417 | 16:0 9? METHYL | 17.31 | ECL deviates 0.001 | Reference |
| 11.475 | 8905 | 0.046 | 0.937 | 16.630 | 17:0 ISO | 13.68 | ECL deviates 0.000 | Reference 0.000 |
| 11.634 | 11190 | 0.046 | 0.936 | 16.722 | 17:0 ANTEISO | 17.17 | ECL deviates 0.001 | Reference -0.001 |
| 11.757 | 2741 | 0.046 | 0.935 | 16.793 | 17:1 CIS 9 | 4.20 | ECL deviates 0.001 | Reference |
| 13.468 | 2898 | 0.049 | 0.920 | 17.771 | 18:1 CIS 9 | 4.37 | ECL deviates 0.002 | Reference |

ECL Deviation: 0.001    Reference ECL Shift: 0.001    Number Reference peaks: 6
Total Response: 64093    Total Named: 64093
Percent Named: 100.00%    Total Amount: 61014

Matches:

| Library | Sim Index | Entry Name |
|---|---|---|
| ACTIN3 1.07 | 0.293 | *Micromonospora chalcea* |

Alignment:

| | | |
|---|---|---|
| 0.00 | % | 499 | Micromonospora chalcea |
| 1.00 | % | 499 | Micromonospora aurantiaca |
| 1.50 | % | 499 | Micromonospora nigra |
| 1.60 | % | 499 | Micromonospora halophytica nigra |
| 1.60 | % | 499 | Micromonospora fusca |
| 1.60 | % | 499 | Micromonospora brunnea |
| 1.80 | % | 499 | Micromonospora halophytica halophytica |
| 1.80 | % | 499 | Micromonospora sagamiensis flava |
| 2.00 | % | 499 | Micromonospora pallida |
| 2.00 | % | 499 | Micromonospora sagamiensis nonreductans |

Figure 19
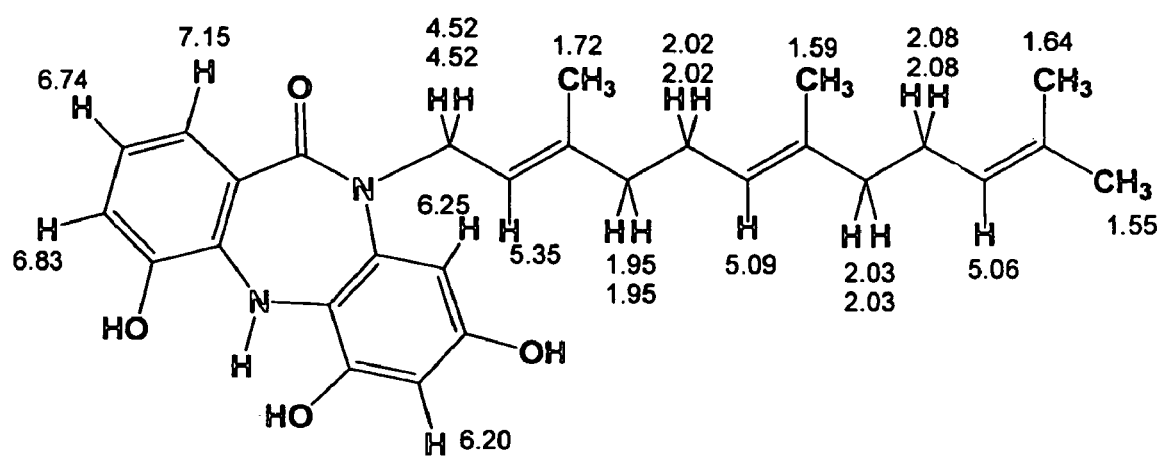
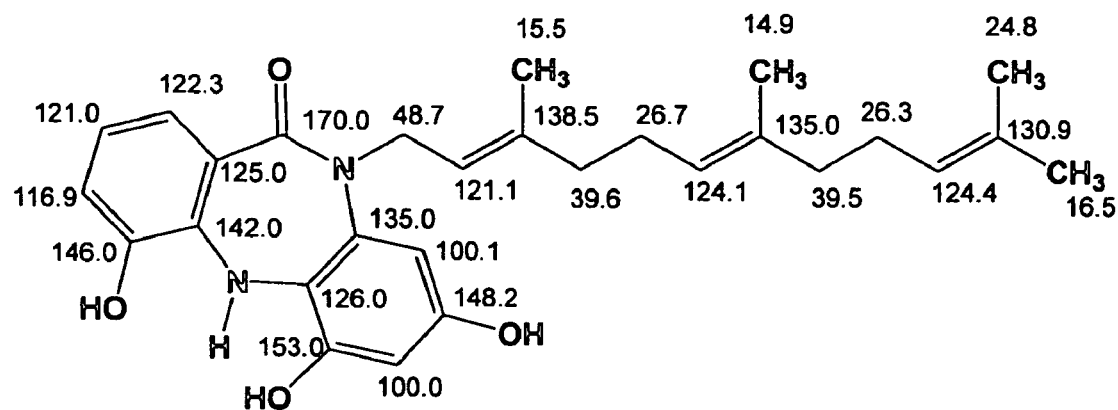

SEQUENCE LISTING

<160> NUMBER OF SEQ ID NOS: 89

<210> SEQ ID NO 1
<211> LENGTH: 36602
<212> TYPE: DNA
<213> ORGANISM: Micromonospora sp. strain 046-ECO11

<400> SEQUENCE: 1

```
ccggtgcacc gggttctcca ggatcgccgt cgcgcccacc ggccccgaca ggtagacgac    60
gttcagggac ttgccgcgcc cttcgtagtt ggcccgcacc acctgcgcgt cgccgatccg   120
gcccctggtc tccagcgtgc ggttctccca cacctgccat ccgacgaagg tcaggaacag   180
cgcggtgaac agggacgtga cgagcagcca gaggccagct gtcagcacgg tcgcccctc    240 gccccgtagc aggccgagga cgacctcctc gtagcgcgag gggcggccga cggggccggt   300
gcccgctccg tcgacagcca tcccgccgct ccttcgccga ctgcccggga catccacggt   360
agccagcgag tccagtccgg tgaggaaggg gtggcgagaa gtcgatatga ctgagaggca   420
tatttatgac tcccagtcat atcgctcgga agtgaccgaa cgacctgacg ccgccggggc   480
tgtgagcggc agcgtgggcc aggccgcgag gtcctggagc atctgccggt cgtgggtggc   540
```

-continued

```
gacgaccacc gccgcccggg tcgtcagcag ggcggcggtg aggtcgtcga ccagcggcgc    600
cgacaggtgg ttcgtcggtt cgtcgaggat cagcaggtcg ggacgttcgg ccaggcgcag    660
cgccaggttc agccgccgtt gctgtccgtg cgacatccgg ccgacggggg tacgccgggc    720
ctcggcgtcg agcaggttcg tcgcgctcag cggcagggcc gtgccggagc cgacgcgccc    780
gctggagcgg agccggccca cgtgctgctc gtacaggtcg tgcgcgagca cgcgccggcgg   840 ccagtcgggc acctcctgac cgaggtacgc gacgcgcgcg ccggacaggt gccggacctc    900
cccggtcgac ggcgtgaggt cgccggccag cacggagagc agcgtcgact tgcccgcgcc    960
gttgggtccg gtcaccagca ggcggtcccc gccgtcgagc gtgagcgtga cccgggtacg   1020
caggcgcccg gccaccgtga cgtcgtggca tcgcaggatg ggcagtccgg cacgggtgtc   1080
cagcggcggc cagcgcagcg gctgcggtgg ctccggcacg gtgacgcggt gcgcgtcgag   1140
cgcctcctgc cggcggcgca cgcgcctgac cagtccgggc gcgcgggact ggcgctggtg   1200
cttgccgtgc cccttctccg gccgccagcc ggtgctgagc cggtcccgcg cctcccgtac   1260
cccgtcggcc agccgctggt gctcggcctg ctgcgcctcg tggtcgcgta cccagtgcgc   1320
gaagtcgcgg cggcgcccgt cctgccaggc gacgtagtcc ccggcgtagc ggcgcgggcg   1380
cccgtccgcg ctggggtcga ggtccaggaa ctccgtggcg acgtcccgca gcagggcgcg   1440
gtcgtgggtc accagcacga cgccgcccgg gtggtcgcgt agccgggcgg tgaggaaggc   1500
caggctgtcg gcgtcgaggt ggttcgtcgg ctcgtccagc atcagcaggt cgaccctcgc   1560
tcccagcagg cacgccagcc gtacccggta gcgctggccg acgacaacg tggccagctg    1620 ccggtcccgg tccggcacg cgtcgaggcc ggccagcgcc acgtcgacgc gccgctgcgc    1680
gtcccaggcg tccagccggg tcgccgcgtc gagcgcggcc gcgtacgcgt cgtccgcgcc   1740
cgcccggccc tcggtgagcg cgatcgtcgc ctcgtcgagc gcccgcagcg cgcgttcgga   1800
ctcccggatc gcctcccgga cgagcgtgcc cactgtctcg ccgtggcgcg actccaggtt   1860
ctgccgggcg acgccgatcg tgcccagccg ttccaccacg ccctggtcgg gcgcgatgag   1920 gccgccagc acgtgcagca gggtggtctt gccgcgcccg ttctcgccga cgactgcgag    1980
gcgggaagcg gcggagacgg tcacgctgac gtcggacagc acgacccggc cgccgcgtac   2040
gacgcggacg ccgtcggccc gcacgtgcgc ccggtgcccg gcgggcagcg aaccgcccga   2100
ggtggatggg gaggaaggaa tgttgtcgag gttgtgcaca gtccgctctt cggctcgtcg   2160
tggagccggc cagcgcgagg acaccgcccg gcgggaacgc cgggacggcg gagcagagct   2220
ggtacgtcag aagaagccgg tcaccctgcc gccgtcagcg gagggaccag ggcttcatga   2280
cagcggcgta gaacctcatg cggtcaacac tacccggggc cgggccggag atcgccgcag   2340
ttatcggcgg cggcgggcgt cggcctcggc gtcgagcagg tcgttcaccg ccagcgccga   2400
gttgatcaga gcgaggtggc tgaacgcctg cggatccacg gttgcggtac tccatttgca   2460
gtacacctgt cggtatccgg tcagcgccgt atcctgcgct ttctctgtcg gcagagcggc   2520
gcggtcgccc gccgcccgcc gacgtggctg cgggccggt cgggctcgga ccgctcggtg    2580
cggcgtcgcg gcccggccgt agcatgtttc acctgttcag agcggcttcc gggcgctcgg   2640
gccgtcggcc gcggtggtta ccggcgaggg ctatttcggt catgcgagag ggttctgcca   2700
atcgtggcat tgtttagtta agtccgatat cagcgggatg ctgcctgata tatgacggct   2760
gcgcccgggc ctgccggata gctatgatga gcgacgacgg tgatcgatgg caaatgttgt   2820
tgctgtgggg tagcgtcacc gccgagtcca ggcttttctt gagctgtgtg cgcatattcc   2880
```

```
gggggggatta tgacaacggg acggccgggg gagaaccggg cgacagacgc ggcacgaaat   2940
ccggggtggg ccgccggggg gccggcgtcc cagccatggg gcgggggaa cgacgagcag    3000
gtcctgcgcg agatcctcgg ggtcgacgtg caccgcgagc tgattgactt cgcgggtggt   3060
gccggcggaa atccgcacct ggtcgccgaa ctcgcgcgcg ggctcgccga agagggattg   3120
attcgggaga caaacggtcg ggcggaattg gtgtcccggc gaattccccg gcgcgtgctg   3180
agttttgtca tgcgtcgatt gaatgatgtc agcgccggct gccagcagtt cttgaaggtt   3240
gccgcggcat tgggcagatc cttcatgctg gaggacgttt cgagaatgct gggccgatcg   3300
tcggcggccc tgctcccgcc ggtggacgag gcgatcgcat cgggcttcgt cgtcgccgcc   3360
gagcatcaac tcgcctttca gagcgacttc ctgctgcgcg gcatcatcga gtccattccc   3420
gggcccgccc gcgacgcctt acgacgtgag gcgatgagcc tttccgggcg acggcgcccg   3480
gcggccgacc agaatcgccg gttggacgcg gcgcctaccg cgccggtgag cgcgaccggg   3540
gaggacgcca ccgatcctg ttcccgggcg caccgcctga taatgaacgg gaacgcgaag   3600
gccggcattc gcgtcgccga ggcggttctc gccggcccgg ccgcgtcgct cgctgcccgg   3660
cgtgacgcgg aggcgtgtct ggtgctggcc gatctgctgc tcggcgggga gggcggcggc   3720
ccgatgaccg aggcgatcct gcgcgaacgc gacgccgagt ccggtgacgc cgcactggcg   3780
atggcgctga ccgcccggtc caccgggctg tggtcggcgg gaaagctggc ggagggcctg   3840
aagctgggac gggcggcggt gcgggcgggc gcggaggccg aaccggtgtg gcgtctgcac   3900
gcccagctcg cgctcgccgg gaaactcgcg aacctccgcg agttcgacga ggccgaggcg   3960
ttgatcaacg aggcggaagc gggcctgcgc ggactgcccg cgccgatctg gacggccgcg   4020
acggcggtga tgcggtcccg gttgctgctc caggcggggc ggatcgggga ggcgcgtcgg   4080
gaggcggcgc tggccaccac cgccgtggag ggggacgcgg tgccgatgct gcggcctctc   4140
gcctacgcgg tgctcagcac cgcctccttc tacatgggg acctgcccgc cgcgatcgag   4200
tacctcaggc gggggcagcg ggacgcggac cgccacgtgg tcctcgactc ggtgcagtac   4260
tcgtgggcg aagtgctgat cacggtcaag caggaaggcc cgcgggccgc cgcccagctg   4320
ctcgcgggca agcaccaccg cctgcccacg cagcgccgcc tctacgtcga ggtgccgagc   4380
gccgccgcct tcctggtcct gctcgcccgc gacgtggacg accgtgacct cgaacgccgc   4440
gtcctcgaca cggtcaacgg gctcgccgcg gacaacccca ggatccaggt cgtcagcctc   4500
accgccatgc acgcccacgc gctggcgaac agcgctccgg ccgccctggc gctcatcatc   4560
gtgcagtcac gggacccgat ctcggtggcg ctggccaccg aggaactcgc caagctctac   4620
gccgcgcagg cccaggcggg gggacggccg gcgacgccgg cccgcgccga ggaggccgcc   4680
accccgccgg cgagctgctg gtcgaccctg tccgacatgg agcagcggat cgcctacctg   4740
gtgagcgtgg gtctgacgaa ccggcagatc gccaagcagg tccacctgtc cgcgcacacc   4800
gtcaactacc acctgcggaa gatctaccgg aaactgggtt tcaacacccg ggccgagctg   4860
gcgcacgccg cggccacgta ctccggccgg gcggcgatct actccatgag cggcgaccag   4920
gactggggcg ccgatccat gaccggcaag gccagctgaa ccgcattccc ggcgtccgcc    4980
ggctgaaccg cgcccggcg tacgccggcc ggttcagccg gcggacgccg gctggcgtgt    5040
ggtggccagc gccggccgga ccgcctcgtg cgcgatgaag cagcgggtca gttccacccg    5100
gctgttgatg tcgagcttgg agaagacgcg ccgcaggtga ctgtcgacgg tgtgcgggga   5160
caggaacagc gaactcgccg cctcgcggtt ggtcatcccg tccacgatgg cccgcacgac    5220
ccgcagctcc gcgctggtca ggctctccca ccccgaccgg ggccggtcgg ggaccagcgg   5280
```

```
gcggacgttg tgagccggca ggccacgcag ctcggcctcc acgcgctcca ggtcgcgtcg    5340
cgcgccgcac tcccggtagc cgtccgtcgc ggcctcgagc agacgggtgg cctcggcccg    5400
gtcccgggtg ctgcgggccg cgtcctccac cgcgccggcc gccgcgagcg tacggccggc    5460
gagccggtgc agatccgcgg cccgcagcag cgccgccgga tcgtcgcgca ggagacccgc    5520
ggcgtgttcc gccgccgccg ccagcgactg gacgaacggg ttgccgcggg cgacgcgccg    5580
ggcgacctcc acggcgcgct cggcctccgc gtcgagcccc gcccggcggg cctggcgtac    5640
gagcgtcgcc gcagcggccg gcgcctcggt gaacagcagc ggatcgggtg cgacctgtcc    5700
ggcgacgttg atcagcgtct gcaccatcat cgccggacgg ccgctggcag cgtggaaccg    5760
ggccagcgcc cagtccatcc gcgccgagtc gtcggcggag gccagccgct cggccgcccg    5820
caactggtcg ctggccgtgg cgaggtcacc gtggtgcacg ccgaggtggg ccaggaccag    5880
gcgcgccggc acgcagtcgc ccggccggga gtggtcggcg gctcgcagcg ccgcctccgc    5940
ctcggcgcgt gcctcgtcca gccgtccggc cgctgccagc agctcggccc ggtggccgcg    6000
ccagagcgac tccgagccgg tgtgactggg ctcctgcgcc agcggtcgta cggtgtccag    6060
caccgcctgc gcctcgtcga gctgatcggc gcgcccagc gcccggacca gccaggtcca    6120
cagcggccgc cggccgggcg cgcagcccgg ggactggtgc cggggctcca gctcggcgga    6180
ggaggcaccg cccaggtgct tcgtggtgtc cgcgagcgcc cggtccagct tggcgcggtc    6240
cagctcgcac acgtcgtggc gggcctgcgt ccggcgcagg aagccggccg ccaggcggtg    6300
gctgccggcg gcccgcatcc cgtgtcccag ttcgagcacg agctgcgcct cgacgtccgc    6360
cgcgaggtcg cggcggagca tcacctccgc gaggcggccg gcctcggcgg cccgccccgc    6420 cccgccagc aggcgcagcg cacggggccag tgctcgtggc gcctcggcgg atccgttctc    6480
caggtgggac acggcggctg ccgccacgtc gtcgcacccg caccggcccg agcgcggccc    6540
cgccgtcgcg gcgggcgtgg ccgcgtccgg cgcgagcgcg gtgacgcgta cgccggcggg    6600
ggagtggggc gtcccgggcc gcggatcggg ccgcccgcgc cggaccgggt cgcccgccgc    6660
cggtgccggc gcgatccgg gctcggcacg ctccggttcc gggtacgcgg cgtggcgaag    6720
cgcctctccg agcaccgggt gggcgaaggt cagctccgcg ccgtcgcgtc gtatcagccc    6780
gacccgcacc gcctcgtcga tcgcggcgga cacgtcggcg gccgagccgt ccagcaggcc    6840
cgtcacccgg tcgacgggaa acgtgtggcc gagccggccg ccgccgcga gcaggcgccg    6900 cagcgggggc ggcagctcct ccagcagccc gcgaacggcg gcgaggacac cgtcgggcag    6960
ctcgtcggac accaccgacg ccgccccgtc cacgatgatc atctggccgg ccttgatgaa    7020
cgcgctgaag acgatctcca tcaccttcgg gttgccgccg cagcgggccg cccagcgcag    7080
gacggaggcg tccggccggg cgccgaggat gccggcgcac aggtcggcca ccgcctcctc    7140
gcccggctcg cgcagccgta cccgtaccgc gacgtgctcg gccagccagt cgacggcgtg    7200
ctgagcgatc gaccccggcgg cgaccggccg gcgggccagc agccagagca ccggcgagga    7260
cgccaggcgc ggcacgagcc cgcgcagggc cagggcgctg acgtcgtcga tgcgctgggc    7320
gtcgtccagg gcgaccacga gcgggcgccg gcgcgccgcg acctcgacca gatcgccgac    7380
ccggtcgatc agccagaacg ggttggcgcc cggcagggcg agctgctcga ccgccgcttc    7440
gccgggcatc gcgtggcgca ggaagttgac gagcaggtgt acgggcaccg gctgatccgt    7500
gacgcttgcc cgcccggcca ccactgtcag cccgcgggcc gccgcctcca ggccggtgac    7560
cttcagcagg tgggtcttgc cgatgccgaa cggcccgtcg acgacgacgc agcccccgga    7620
```

-continued

```
tccccgcatg gtggcgtcga gcagttcccc caatgaggac aattcctgcc cgcgccccgc    7680
catgcgattc atgatgacca tcccgttttc ctctgctgaa tcgtccgacg tgcgccgcga    7740
gccgatgtcc caccgcgttc gaccgtccgt tctggacagt tgaacgccgg atcggggcgg    7800
gctactcagt tatacgggat ctgcggccgt tcgtcggcga cgtcgctggc agcgcgcact    7860
actcgcgtga gtagtgggca gggtgtcagg ccgcgattac tgtcaggcca tgccgggctc    7920
ggcgtgccgg cgcggacgaa atggcgacgc cgatggggag atcggcgtcg tttccgcgcc    7980
ggcgcaaaac gtccggaacg gaatcgacta atcgccgctc gacgcgactg gtccagcgaa    8040
tccaggggag tccgagatgc gtgagtgtaa tggtgaccgc cgtcttgatc gggagacgcg    8100
ggcatgaccg tcggatatct cgggacggtc accgactcgg cgcccgtcga cgccgcgctg    8160
cgcgacttct tcgccgagcg ccgcgccgag cacgcgagc tcggcgacga cttcgcggcc    8220
ctggtcgccg agctggagag ctacgtcctg cggggcggca agcgcatccg gcccgccttc    8280
gcctggctgg gctggatcgg cgccggcggc gaccccgagg accccgtggc gaccgcggtg    8340
ctgaacgcct gcgccgggtt cgagctgctg cacgcgtccg gcctcatcca cgacgacatc    8400
atcgacgcgt cgcagacccg ccgcggccat cccgccgcgc acgtcgcgta cgccgaacgg    8460
catcgggcgc ggcgcttctc cggtgacccg ggaacgttcg gcaccggcac cgccatcctg    8520
atcggagacc tcgtcctgat ctgggccgac gtcctggtcc cgcgcctccgg cctgccggcc    8580 gacgcgcacg tgcgggtctc gccggtgtgg tcggcggtgc gctccgaggt catgtacggc    8640
cagctgctcg atctgatcag ccaggtgagc cggagcgagg acgtcgacgc ggcgctgcgc    8700
atcaaccagt acaagaccgc gtcgtacacg gtggagcggc cactgcagtt cggcgcggcg    8760
atcgccggcg cggacgacga cctcttcgcg gcctaccgcg ccttcggcgc cgacgtgggt    8820
attgccttcc agctgcgcga cgacctgctc ggcgtgttcg gcgacccggt ggtgacgggc    8880
aagccgtccg gcgacgacct gcgggagggc aagcggacgg tcctgctcgc cacggcgctc    8940
aagcgcgccg acgaacggga cccggacgcg gcggcctacc tgcgggcgaa ggtcggcacg    9000
gacctcgcgg acgaggagat cgcccgcatc cgcgccatct tccgcgacgt cggcgcggtc    9060
gaggagatcg agcggcagat ctcgcagcgc accgaccggg cgctggccgc gctggaggcg    9120
agcagcgcca ccgcccccgc gaagcatcag ctcgccgaca tggcgatcaa ggccacccag    9180
cgggcccagt gatgtccacg gaaccggtga ccgtcgtcgc ccgcggcgtt ctcgacggcc    9240
ggggtgacgg gccgggccgc ctcggcaccg gccgcgccca cggcaaggcc atcctgctgg    9300
gcgaacacgc cgtcgtgtac ggcgctccgg cgctcgccgt cccggtgccg caactgaccg    9360
ccgtggccaa ggcgcggcgg gccggcgcg acggcggcga cgaggtctcc ttcgccatcg    9420
ccgggctgga gagcccggag gtgacgtcgc ttccgaccga cggcctgcaa catctggtga    9480
cggagttccg gcagcgggcc gccgtcaccg agccgatgcg cgtcgacgtg ctcgtggact    9540
gcgccatccc gcagggccgg gggctcgggt cgagcgccgc ctgcgcccgc gccgcggtgc    9600
tggccctcgc ggacgcgttc gaccgccgcc tcgacgccgc cacggtgttc gatctggtgc    9660
agacctcgga gaacgtggcg cacggccggg ccagcggcat cgacgccctg ccaccggtg    9720 cgaccgcgcc gctgatcttc cgcaacggcg tgggccggga actgccggtc gccatggcgg    9780
gcgccgcgcg tgccgcgcga gggtcggcc cggccggctt cgacgcggtg ctcgtcatcg    9840
ccgacagcgg cgtcagcggc agcacccggg acgcggtgga gctgctgcgg ggtgccttcg    9900
agcgctcccc gcgcacgcgc gacgagttcg tcagccgggt gaccagcctg accgaggcgg    9960
cggcgcacga cctgctccag ggccgggtcg ccgacttcgg cgcgcggctg accgagaacc    10020
```

```
accggctgtt gcgcgaggtc ggcatcagca ccgaacggat cgaccggatg gtcgacgccg   10080
cgctcgcggc gggcagcccg ggcgccaaga tcagcggcgg tggcctgggc ggctgcatga   10140
tcgcactggc ccgggaccgc caggaatccg cggcggtggt gcggagcgtc cagcaggccg   10200
gcgccgtccg cacctggacc gtcccgatgg ggaggttcac cggccatgac gactgaccac   10260
cggggcggagc cgtccgagcc ggcgctcgac cggcccgcga ccgccgtggc ccatccgaac   10320
atcgcgctga tcaagtactg gggcaagcgc gacgagcagc tgatgatccc gtacgccgac   10380
agcctgtcga tgacgctcga cgtcttcccg accaccacca ccgtccggat cgacagcggc   10440
gcggcggccg acgaggtcgt cctcgacggc tcgcccgccg acggcgaacg gcgacagcgc   10500
gtcgtcacct tcctggacct ggtacgcaag ctggccgggc gcacggaacg ggcctgcgtc   10560
gacacccgca actccgtgcc caccggcgcc ggcctggcgt cctcggcgag cggattcgcc   10620
gccctcgccc tcgccggcgc cgccgcgtac ggcctcgacc tggacaccac cgcgctgtcc   10680
cgcctggccc ggcggggatc cgtgtcggcc tcccggtcgg tcttcggcgg cttcgcgatg   10740
tgccacgcag gccccggcgc cgggaccgcc gcggacctcg gctcctacgc cgagccggtg   10800
cccgtcgcgc ccctcgacgt cgcgctggtg atcgcgatcg tcgacgccgg gccgaaggcg   10860
gtgtcgagcc gcgaggggat gcggcgaacc gtccggacct ccccgctcta tcagtcgtgg   10920
gtcgcctccg gccgcgccga cctggccgag atgcgggccg cgctgctcca gggagacctg   10980
gacgcggtcg gcgagatcgc cgaacgcaac gccctcggca tgcacgccac catgctggcc   11040
gcccggccgg cggtgcgcta cctggcgccg gtcactgtcg ccgtgctcga cagcgtgctg   11100
cgcctgcgcg ccgacggcgt ctccgcctac gccacgatgg acgcgggacc gaacgtcaag   11160
gtgctctgcc gccgcgcgga cgccgaccgg gtcgccgaca ccctgcgcga cgccgcgccg   11220
agctgcgccg tggtcgtcgc cggaccgggg ccggcggccc ggccggaccc gggcagccgg   11280
ccgtgaccgg cccgggcgcc gtgcgccgcc acgcgccggg caagctgttc gtcgccggtg   11340
agtacgcggt gctggagccg ggccacccgg cgctgctggt ggcggtcgac aggggagtgg   11400
acgtcaccgt ctccggcgcc gacgccacct tcgttgtcga ctccgacctc tgcccggagc   11460
aggcgtgcct gcggtggcag gacggccggc tcgtcggcgc gggcgacggg cagccggcgc   11520
ccgacgcccct cggcgccgtg gtctcggcga tcgaggtggt cggcgaactc ctgaccggac   11580
gagggctgcg cccgctgccc atgcgggtgg cgatcaccag ccggctgcac cgcgacggca   11640
cgaagttcgg cctcgggtcg agcggggcgg tgacagtcgc cacggtgacc gcagtggccg   11700
cgtaccacgg ggtggagctg tcgctcgaat cgcggttccg gctggcgatg ctggcgacgg   11760
tgcgtgacgg cgccgacgcc tccggcgcgtg atctggccgc gagcgtctgg ggcggctgga   11820
tcgcctacca ggcgcccgac cgcgcggccg tgcgcgagat ggcgcggcgg cgcggcgtcg   11880
aggagacgat gcgcgcgccc tggccgggcc tgcgggtccg gcggctgcca ccaccgcgtg   11940
gcctcgcgct ggaggtgggc tggaccggcg agccggcgag cagcagctcg ttgaccgggc   12000
ggctggccgc ctcccggtgg cggggcagcc cggcgcggtg gagcttcacc agccgtagcc   12060
aggagtgtgt gcgtaccgcc atcgacgcgc tggagcgggg cgacgaccag gaactgctgc   12120
accaggtccg gcgggcccgg cacgtgcttg ccgagctgga cgacgaggtc cggctcggga   12180
tcttcacccc ccggctgacg gcgctgtgcg acgccgccga ccgtcggc ggcgcggcca   12240
aaccgtccgg cgccggtggc ggggactgcg gcatcgcgtt gctggacgcc accgccgcga   12300
cgcggaccgc gcggctgcgc gagcagtggg ccgccgccgg ggtgctcccc atgccgatcc   12360
```

```
aggtccatca gacgaacggg agcgcgcgat gatcgccaac cgcaaggacg accacgtccg   12420
gctcgccgcc gagcagcagg gccggctcgg cggtcaccac gagttcgacg acgtgtcctt   12480
cgtgcaccac gccctggccg gcatcgaccg gtccgacgtc tcgctggcca cgtcgttcgg   12540
cggcatcgac tggccggtgc cgctgtgcat caacgcgatg accggcggca gcaccaagac   12600
cggcctgatc aaccgggacc tggcgatcgc ggcccgggag accggcgtac cgatcgccac   12660
cgggtcgatg agcgcctact cgccgacga gtcggtggcc gagagtttca gcgtgatgcg   12720
ccgggagaac cccgacgggt tcatcatggc caacgtcaac gccaccgcct ccgtcgaacg   12780
ggcccggcgg gctgtcgacc tgatgcgggc cgacgcgctg cagatccacc tgaacaccat   12840
ccaggagacg gtgatgccgg aggggaccg gtcgttcgcc gcctgggggc gcggatcga   12900 acagatcgtc gccggcgtcg gtgtgccggt gatcgtcaag gaggtcggct tcgggctcag   12960
ccgcgaaacg ctgctgcggc tgcgggacat gggcgtccgg gtggccgacg tcgccggccg   13020
cggcggcacg aacttcgcgc gcatcgagaa cgaccggcgg gacgccgccg actactcctt   13080
cctcgacggg tggggacagt cgacacccgc ctgcctgctg gacgcccagg gcgtggacct   13140
gcccgtgctg gcctccggcg gcatccgcaa cccgctcgac gtggtccgcg ggctggcgct   13200
cggcgccggc gcggccgggg tgtccggact gttcctgcgc acgctcctgg acggcggcgt   13260
gccggcgctg ctgtcgctgc tgtccacctg gctcgaccag atcgaagccc tgatgaccgc   13320
cctgggcgcg cggaccccgg ccgacctgac ccgctgcgac ctgctgatcc agggtcggct   13380
gagcgcgttc tgcgcggccc ggggcatcga caccaccgc ctcgccaccc gttccggcgc   13440
cacccacgag atgatcggag gcattcgatg aacgacgcga tcgccggtgt gcccatgaaa   13500
tgggtaggtc ccgtgcggat ctcgggaaac gtggcgcaga tcgagacgga ggttccgctc   13560
gccacgtacg agtcgccgct ctggccgtcc gtcggccggg gcgcgaagat ctcccggatg   13620
gtcgaggcgg gcatcgtcgc cacgctcgtc gacgagcgca tgacccgctc ggtgttcgtg   13680
cgcgccaagg acgcgcagac cgcctacctg gcctcgcttg aggtcgacgc gcggttcgac   13740
gaactgcgtg acatcgtgcg cacctgcggc aggttcgtcg agctgatcgg gttccaccac   13800
gagatcaccg cgaacctgct gttcctgcgg ttcagtttca ccaccggcga cgcgtccggg   13860
cacaacatgg cgacgctggc cgccgacgcg ctgctgaagc acatcctgga caccattccg   13920
ggcatctcgt acggctcgat ctcgggcaac tactgcaccg acaagaaggc caccgcgata   13980
aacggcattc tcggccgggg caagaacgtg gtcaccgagc tggtcgtgcc gcgggagatc   14040
gtccacgaca gcctgcacac gacggcggcg gcgatcgccc agctgaacgt gcacaagaac   14100
atgatcggca cgttgctcgc cggcggtatc cgctcggcca acgcccacta cgcgaacatg   14160
ctgctcgggt tctacctggc cacgggtcag gacgccgcga acatcgtcga gggctcccag   14220
ggcgtgacgg tcgccgagga ccgcgacggc gacctctact tctcctgcac gctgcccaac   14280
ctgatcgtgg gcaccgtcgg caacggcaag gggctcggct tcgtcgagga gaacctggag   14340
cggctcggct gccgcgcctc gcgtgatccg ggcgagaacg cccggcggct cgcggtcatc   14400
gcggccgcga cggtgctctg cggcgagctg tccctgctcg ccgcgcagac caacccgggc   14460
gagctgatgc gggcgcacgt ccggctcgaa cgcccgaccg agaccacgaa gatcggagcc   14520
tgacgatggc cgagagaccc gccgtcggca tccacgacct gtccgccgcg acggcgcatc   14580
acgtgctgac acacgagacc ctggccgcga gcaacggcgc cgacgtggcc aagtaccacc   14640
gtggcatcgg gctgcgggcg atgagcgtgc ccgccccgga cgaggacatc gtgacgatgg   14700
ctgctgccgc cgccgcgccg gtggtcgccc gccacggcac cgaccggatc cggaccgtcg   14760
```

```
tgttcgccac ggagtcgtcg gtcgaccagg cgaaggcggc cgggatacac gtccactccc   14820
tgctcggcct cccctcggcc acccgggtgg tcgagctgaa gcaggcctgc tacggcggta   14880
cggcgggact gcagttcgcc atcggcctgg tgcaccgtga cccgtcgcag caggtcctgg   14940
tgatcgccag cgacgtgtcg aagtacgcgc tgggtgagcc cggcgaggcg acccagggcg   15000
ccgcggcggt cgccatgctc gtcggcgcgg acccggcgct ggtacgcgtc gaggacccgt   15060
cgggcatgtt caccgccgac gtcatggact tctggcggcc gaactaccgc accaccgccc   15120
tggtcgacgg gcacgagtcc atctccgcct acctgcaggc gctggagggc tcgtggaagg   15180
actacaccga gcgcggcggt cgcaccctgg acgagttcgg cgcgttctgc taccaccagc   15240
cgttcccgag gatggccgac aaggcgcacc ggcacctgct caactactgc gggcgcgacg   15300
tcgacgacgc gctggtggcc ggggccatcg gcacaccac cgcgtacaac gccgagatcg   15360
gcaacagcta cacggcgtcg atgtatctcg ggctcgcggc actgctcgac accgccgacg   15420
acctgaccgg ccggaccgtc ggcttcctca gctacgggtc cggcagcgtc gccgagttct   15480
tcgccggcac tgtcgtgccc gggtaccgcg cgcacacgcg acccgaccag caccgcgcgg   15540
cgatcgaccg gcggcaggag atcgactacg cgacgtaccg ggagttgcac gagcacgcct   15600
tcccggtcga cggcggcgac tatccggcgc cggaggtgac caccgggccg taccggctgg   15660
ccgggctctc cggtcacaag cgcgtctacg agccgcgata ggaccggcca cgccggccgc   15720
cctgaccgaa cgaaccatgc ttggaggatc gatgtccgga actcccgagg tggccgagct   15780
ctactcgacc atcgaggaat cggcccggca actggacgtg ccgtgttcgc gcgaccgggt   15840
ctggcccatc ctgtccgcgt acggcgacgc gttcgcccat cccgaggcgg tggtcgcctt   15900
ccgggtggcg accgcgctgc gtcacgcggg cgagctggac tgccggttcc ggacgcatcc   15960
ggacgaccgg gacccgtacg cctcggcgct cgcccggggc ctcaccccgc gcacggacca   16020
ccccgtcggc gcgctgctct ccgaggtcca ccggcgctgc ccggtggaga gccacggcat   16080
cgacttcggg gtggtcggcg gcttcaagaa gatctacgcg gccttcgccc cggacgagct   16140
gcaggtggcc acgtcgctcg ccggcattcc ggcgatgccc cgcagcctcg ccgcgaacgc   16200
cgacttcttc acccggcacg gcctcgacga ccgggtcggc gtgctgggat tcgactaccc   16260
ggcccggacc gtgaacgtct acttcaacga cgtgccgcgt gagtgcttcg agccggagac   16320
catccggtcg acgctgcgcc ggaccgggat ggccgagccg agcgagcaga tgctccggct   16380
cggcaccggg gcgttcgggc tctacgtcac gctgggctgg gactcccgg agatcgagcg   16440 gatctgctac gccgcggcga ccacggacct gaccacgctt ccggtacccg tggaaccgga   16500
gatcgagaag ttcgtgaaaa gcgttccgta cggcggcggg gaccggaagt tcgtctacgg   16560
cgtggcgctg acccccaagg gggagtacta caaactcgag tcgcactaca aatggaagcc   16620
gggcgcggtg aacttcattt gaacagcggc cggttccgcc gcccgggcgg cggaaccggg   16680
atcaatgcct gttcgctcgg gttcaacact ggcgcgctcc gctaaagtgc gaacatgacg   16740
actggactgt ccagtgtgtg ggcccgggtg aagaactggg tcgtcgcgtt ggctgtggcg   16800
gcggtgctga tgatcagcgc gctggccggt gaccatcctg cccccgaggg cctcggtctg   16860
ctcggcttcg cgctggtggc ggcgagcggc ctggcgctgg ccgccagtcg tcgggccccg   16920
atcgccgtgc tggtcgccac cgggctgtgc gtggtgggct acaacgcgat cggcttcggg   16980
gtgcccgcca tcgcgtacct gttcgcggtc tacgcggcgg tccgggcgg gcaccggctc   17040 gtcacgctcg gggcgagcgc cgccctgctc gtcgtcctgc cgctggcgat catggtctcg   17100
```

```
cccgcggacg gcgccctcaa ggaggcgctc gcgcagtcgc ggggcgtgct ggaactggcc    17160
tggctgatcg ccgcggcggc ggccggtgag gcgctgcggc aggccgaacg gcgagcggac    17220
gaggcggaac ggacccgcga ggagaccgcc cggctgcgcg ccacccagga gcggctgcac    17280
atcgcacggg agctgcacga ctcgctcacc caccagatct cgatcatcaa ggtgcaggcg    17340
gaggtggcgg tccacctggc ccgcaagcgg ggcgagcagg tgccggagtc gctgctggcg    17400
atccaggagg ccggccgggc ggcgactcgc gagctgcgcg cgaccctgga gacgctgcgt    17460
gacctgacca gtccccgtc gcacgggctc gaccacctcc cggagctgct ggccggggcc    17520
gagaagatcg gcctggccac cacgctgacc atcgagggcg accagcggga cgtgccggag    17580
gcggtgggcc gcaccgcgta ccggatcgtg caggagtcgc tcaccaacac cgcccggcac    17640
gcctccgccg cggccgccgc ggtccggatc gactaccgcc cggacgcgct gagcatccgg    17700
atcgacgacg acgggacggc ccggccgggc gccgccccgg tgcccggcgt cgggctgctg    17760
gggatgcacg agcgcgtcct cgcgctgggc ggccggctgc gggcggaacc ccgcaccggc    17820
ggaggcttca ccgtccaggc cgaactcccg gtggtgcgcg tcccatgatc aggatcatgc    17880
tgctcgacga ccagccgctg ctgcgcagcg ggttccgcgc gctcctcgac gccgaggacg    17940
acatcgaggt ggtggccgag ggcgggaacg gccgggaggg cctggcgctg gcccggcagc    18000
acctgcccga tctcgccctg atcgacatcc agatgccggt catggacggc gtcgagacga    18060
cccggcagat cgtcgcggat ccggcgctgg ccggggtacg cgtcgtcatc ctcaccaact    18120
acggcctcga cgagtacgtc ttccacgcgc tgcgcgccgg cgccaccggc ttcctggtca    18180
aggacatcga gccggacgac ctgctgcacg ccgtgcgggt cgccgcgcgc ggtgacgcgc    18240
tgctcgcgcc gtcgatcacc cggatgctga tcaacaggta cgtgtcggag ccgctctgcg    18300
cggacgtcac gcccggcatg gaggagctga ccaaccggga acgcgaggcg gtcgccctgg    18360
ccgcccgggg cctgtccaac gacgagatcc ccgatcgcat ggtgatcagc ccgctgaccg    18420
cgaagaccca cgtcaaccgc gccatgacca agctgcaggc ccgcgaccgc gcccagctgg    18480
tggtgttcgc ctacgagtcc ggcctggtgt cacccggcaa tcgctgaccg gcagccccgc    18540
ccggtctgtc gcctcggcag tgctgcggct gcggtatgcg gctgctcccg gcgcagacgc    18600
cggagcccgt ggataccgtc accgcagtag atcgatcgat tgtctccttc ggcatgacga    18660
cccgtagcgg ggtcgttacc tacgctggcg cagatgcctg ttcccgcagc cgaagggct    18720 tccatgttca tccgtcgttt gctcaccgcc gccgcagccg gcgtcctcgg tgggctcgca    18780
ctcgtcgcac cggcggccgc gcaggtgacg gccgccgacg gtgacggtgg ttccggccgc    18840
gccggatccg tgctggcgct cgcgctcgcg ttgctcggcc tcgtcctggg cgggtgggcg    18900
ttgcgctccg cggggcgcgg cggcggtcgt ggcaacgcga tcgccgcgct ggtgctcgcg    18960
gtggccggcc tgatcgccgg cgtggtcgcc ctggccggct ccgacggtgg tgtcggcagc    19020
ggcaacggcc gtggtggcgc catcgtggcc gtcgtgctgg cgctgatcgg gatcgccgtc    19080
ggcggcctgg cattcacccg ctcccggcgc gccgcctgac cggcgctgcc gaccgaacac    19140
cccggtgacc caaccgaacc cgaagggag tccatgcgc aaagtgttcg ccggactggc    19200
agcgttcctg ctgctcgtgc tcgtggtgca gttcttcctg gccgccagcg gcgcgttcag    19260
caacgaggcc aacgaggagg cgttccgccc tcaccggatc ctgggcctgg ggagcatcct    19320
cgtcgccgtg gtgctgacgg tggccgccgc ggtgatgcgg atgcccggcc ggatcatcgg    19380
cctgtccggg ctggtcgccg ggctgggcat cctgcaggcc ctgatcgcgg tcatcgccaa    19440
ggcgttcggc gactcggccg gtgactcggc cgtcggccgg tacgtgttcg gcctgcacgc    19500
```

```
ggtcaacgga ctggtgatgg tggccgtcgc ccgcgtcatc ctgcgcagcg tccgggcggc  19560
gccggacacg accaccacgc ccggcgtgga cacgacggtc accggtccgg cggccgactc  19620
ggcgcgaacg gcgtcatgag cacgctccaa tggatcctcg tggaccacgt cgtggcgctg  19680
ctcggtgtcg cgacgtggtt cgcaacgggt gtcacggcag ctctcggccg ccaccggatc  19740
gcgttggcgc tcctcggcgc cgcggtgctg gtgacagtcg cccgcctggg caccgtggcg  19800
ctgctggccg accgcggctg gtggttcgtc caggagaagg ttctgctggg gctgccgatg  19860
ctcggcgccg cggggctcgt cgcggtgctc ctggccggcc cgcgcctgct cgcggcccgg  19920
cagtcaccgg cggcggacct gccggccggc gcgctggtcg cggtgctgac cgccggcttc  19980
gccgcgctgg ccgcctggt ggtgacgttc accgccgggt accgctgac gtggagcacc   20040
gcgctgatcg ccgtcgccct cgtctgcgcc gccgcgctgc tcaccgcgcg ggtggtcgga  20100
cgacccgccg ccccggccgc ggaggccggc tccccgagc acacgccggc ggcggccggg   20160
cccacggcgc tgtcccgccg ccggttcctc ggcgtggccg ggggagtggt cgcggcgggc  20220
gccggcgcca ccggcgtcgg cctgctcttc cgcgacccgg aggcgatggt caccggaggc  20280
ggccccggac acgccggtgg cgcccgcccc aaggtctccg tggcggacct gcgcggcccc  20340
ggcgctccgg cggcgggcgg cacggcgcga cgccacgtgc tcaccgcccg gacgggcacc  20400
gtcacgattc cgtccggacg tccgatcgac gcctggagct acgagggccg cctgcccggg  20460
ccggccatca ccgcgaccga gggcgacctg atcgaggtga cgctccgcaa cgccgacatc  20520
gaggacggcg tcaccgtgca ctggcacggg tacgacgtgc cgtgcggcga ggacggcgcg  20580
ccgggcgcca cgcagcacgc ggtgcagccc ggcggcgagt tcgtctaccg gttccaggcg  20640
gaccaggtgg ggacgtactg gtaccacacc caccaggcgt cgcaccccgc cgtgcgcaaa  20700
gggctgtacg ggacgctcgt cgtgacgccg cgcgaggacc ggccggaagc ggagcgcggg  20760
ctggacctga cgctgccggt gcacacgttc gacgacgtca cgatcctcgg cgaccaggag  20820
ggacgcgccg tccacgacgt ccgccccggc cagccggtgc gactgcgtct gatcaacacc  20880
gactccaacc cgcactggtt cgccgtcgtc ggctcgccct tccgcgtggt ggccgtcgac  20940
ggccgcgacc tcaaccagcc gggcgaggta cgcgaggtcg ggctccgcct gcccgccgga  21000
ggccggtacg acctgaccct ggccatgccg gacgccaagg tcacgctgct gctcgacaac  21060
gactccgacc agggcgtcct gctgcgcccg ccgggcgtcg gcggtggtga ccgcccgctg  21120
ccggacaccg ccgactggcc cgagttcgac ctgctgggct acggcgagcc ggcgcccgtg  21180
ccgttcgacg ccgacgacgc cgaccgccac ttcaccatcg tcctcgaccg ggccctggcc  21240
atggtcgacg gcaagcccgc gtacgcccag accgtcgacg tcgcgcacac tccctccgtc  21300
cccgaccagc tcgtccggga ggggacgtc gtgcgcttca cggtggtcaa ccggagcctc   21360
gaaacccacc cgtggcacct gcacggccat ccggtgctga tcctgtcccg cgacggccgg  21420
ccgtactccg gcagcccgct gtggatggac accttcgacg tgcggccggg agaggtgtgg  21480
gaggtggcgt tccgggcgga caatccgggt gtctggatga accactgcca caacctgccg  21540
caccaggagc agggcatgat gctgcggctc gtctacgacg gtgtcaccac gcccttcgcc  21600
agcacgagcc acgcacactg aggggactcg catgaccgca gacctgcacg gcctggccag  21660
cgtccgctac atcgtcgacg acgtgtcggc ggcgatcgag ttctacacca cccacctggg  21720
tttcacggtg tcgaccgcgt tcccgccggc cttcgccgac gtggtgcgcg gccgctgcg   21780
gctcctgctg tccgggccga ccagctcggg cgcccgggtc accccggcgg acgcggccgg  21840
```

```
gtgcgggcgc aaccgcatcc acctgatcgt cgacgatctc gacgccgaac gggagcggct   21900
ggagcgcgcc ggggtgacgt tgcgcagcga cgtcgtggcc gggccgggcg gccgtcagtt   21960
cctgatcgcc gacccggcgg gcaacctggt cgaggtgttc gagccggcag cccgcggctg   22020
aaccgccgac ggacgccctc ccacctcgcg acgcccgaag cccgacacct ggccgcgtcg   22080
cggccacgat caccgtggcc gcgacgcggt gacggggtgc cttaccgggg cggggtgggc   22140
gcggcgagcc gcgcggccag gatggagatg atcacgcgc  cggcgatcac gtgggtgccg   22200
gcgaggacga gctgcgtcga caccggggtg tcccgggcga aggcgggcgc ggcgagggac   22260
agcacggtga acgcgacggt gccggccacg aaggcacgca cgggccgccg ggcccgccgc   22320
gccacgacca ccgccaggac gattccgccg atcgaccaga gcacgacgct gcgggcgatg   22380
gcccccaccg ggatcgcctg cgcctgctcc tcccagacgc cggccgcctc catcggtacg   22440
ccgaagcccc gggcggcgag cgtgaacgcc tccgcggcca cggccccggc gagggtggcc   22500
agcacgccga ccagccacac cggagcgtg  gccggcgacc aggtgggccg tgccgcgacg   22560
ggagttcggg gagtggcctc atccacggcg tcgcctccgg tcgggtgcct cgatgtgttc   22620
tcgggagaat gcgggacgc  cacgacggca gtcaacatgg acagttgaac gccctggcgt   22680
cacgggcggt tcccgcgccg gcccgccgcc tcggccgcgg cggcggccgt gccgtcggcg   22740
agcagggaga ccagcaggtc gcccaggatc cgtgggccgt gctgggtgag gacggactcc   22800
aggtggaact ggacggaacg gaatcccggg ccgcgcagcg cgtgcacgtc cccgctgtcc   22860
gggctgcggc tgatctcgat cgggcccgc  cggccaccgg ccaccacgtc gtgcgcggag   22920
cgggcggtgt aggtgttgta gaaccccacg agttccggcc ggccgaacag gtcgatccgc   22980
ttctgcacac cctggtgg  caccgcgcgc cgggcgaggg ggaacccag   ttcggcggcg   23040 agcacctggt ggcccaggca gatggacagg aacggcaccg ttccggcgag caggtcgcgg   23100
gtgagcccgc gcagggtccg catacgcggg tcggtcaggt cgcccgggtc gccggggccg   23160
ggaccgacga cgacgaggtc gtgtccgtcc ggccgcagcc ggctgtcgaa ccgggcgatg   23220
ctcgaccgca gcccgagggc ccgcaactgg tggtcgagca tggccatgaa cgtgtcctcg   23280
ttgtcgacga cgagcacgcg gcgtccggtc agcgccgggt tcggggtgcg ccgctccgcg   23340
ccgtcgagcc agaacctcga cagtgtggtg ttgcgctcgc gcaacgcccg ccgtacccgg   23400
gggtcggtgg ccagggacga acgagcccgc gcggccgtgg tccgcccgcc gtccgggccg   23460
tccgggtcga cgccgaggcc gagcgccgcg cgcatggcgc ccgccttggc ccgcgtctcg   23520
gccacctccg actccggctt ggagtccgc  acgagggtgg cgccgacgcc caggcgcagc   23580
gtgcccgcgt cgtcgatctc ggcggtgcgg atcatgatgg ccgagtcgag cgtacggctg   23640
ccggccgagt cacggcccat caacgcgagc acgccgccgt agtagccgcg gccggtcgtc   23700
tcgtggcggg tgatgacccg gaacgcgttc tcgatcgggc tgccggtgac cgtcggcgcg   23760
agcagggtct cccgcagcac gtcgcgcacg tccaggtcgc tgcggccggt caggatgtac   23820
tcggagtgcg tcacccgcgc catttccttg aggaacgggc cgtgcacctg ccgccggag   23880 gcgcacatcc gcgccatcat tttcagttcc tcgtcgacga ccatgtagag ttcgttagcc   23940
tctttcgggt cgttcaggaa ttccagcaga ccggaaacgg ccgggccgtt cgggggtgc   24000 cggtaggtcc cgctgatggg attcatcgag acggttccgt cgatcatgct gacgtgtcgt   24060
tccggtgacg cgccgatgaa cgtgccggcg ccggagtgga acagaaacgt ccagtaggaa   24120
cccagttcgc cggtcagcaa ccggcggaag agcgccagtt ccgtggcgat cgagtagtcg   24180
gccagccgcg cggtgaaggt gcgccggatg acgaagttgg atccggcgcc cagcccgatc   24240
```

```
tcgtcaccca ccacccgctt gacgatcgcg gcgtagtcct cgtcgctgag gtcgaagtcg    24300
gcgtcggtca ccggcacacc gcgttcgggc aggcccgcca gcgcctgtcc gcggtcgagc    24360
ccgaactgct cgtggacgcg catcgcgagc agcggcgcgc cgtcgtcgtg gcagtcgaac    24420
ccccgttcgg tgacctgccg gtacggcacc gccacgagca ggtcgtgccg cgcgccggtc    24480
gccggctcgg tgggcagggg cagctcgccg agagtgtcca cgtcgcacac ctcgccggtc    24540
agaacctcca cgtacgcgca cccggccgcg ccgggccggt gcagcagggc gaaggcgcgc    24600
ccgtcgccgc cgagaccgga cagcagatcg gggaatccgg tcacgttcga ttccgtcccg    24660
tccatgtcgc tcccttttgcc tgagagatcg cctgtcgata ctgcgtccgg caaaaggcgt    24720
cgcacatgac gtgaagtcgc cgacggcatc acgtgtttcc ggtaacgcgc cgacgttatg    24780
gcgtgaacga ctgaatcggc gggctactac tcgggcgagt agtgcccacg cagatcgacc    24840
gcgattactg tcgaccgcaa tgccgatacg acgagggcgg tgaagacgac tgtggacgtg    24900
ctggtccaga aatacggggg cacctcgctg cagaccctcg accgcgttcg gcacgccgcg    24960
ctgcggatcg ccgaggcgcg gcggcacggc tccgccgtga cagtggtcgt gtcggcgcgc    25020
ggcagccgga ccgacgacct gctgcggctg gcggccgacg tcggcgccgc gggtccgtcc    25080
cgggaactcg accagttgct cgcagtcgg gagtccgagt cggcggcgct gatgcgctg      25140 gcgttgaccg ggctgggagt gccggccgtc tcgctgaccg ggcaccaggc ggagatccac    25200
accaccgacc ggcacggcga cgcgctgatc tcgcggatcg gggcggcgcg ggtggaagcg    25260
gcgctgggcc gtggcgaggt cgccgtggtc accggattcc agggcatcga ccgggccggt    25320
gacgtcgcca cgctggggcg cggcggctcc gacacgacag cggtggcgct cgcggcccgg    25380
ctccgcgcgt cggcgtgcga gatctacacc gacgtggacg cgtcttcag cgccgacccc     25440 cgcatccttc cggcggcgcg ttgcctgccg tgggtggagc ccggcgtcat ggcggagatg    25500
gcgttcgccg gcgcgcgggt cctgcacacc cgatgcatcg agctggccgc catgaagggg    25560
gtcgaagtgc gcgtgcgcaa cgcgtcgtcg caggcgcccg gaacgatagt cgtggaccgg    25620
cccgacgacc ggccgctgga gaccggcgg gccgtggtgg cggtcaccca cgacaccgat    25680
gtcgtccgcg tgctggtgca ctgccgcgac ggccgccggg acatggcacc cgacgtgttc    25740
gaggtgctgg ccgcccatgg ggcggtggcg gacctggtgg cccggtccgg gccctacgag    25800
agcgagttcc ggatggggtt caccatccgc cgcagccagg ccgaagcggt gcggaccgcg    25860
ctgcacgacc tcaccgcgtc cttcgacggc ggggtccact tcgacgagaa cgtcggcaag    25920
gtgtccgtgg tcggcatggg cctgctcagc cgccccgagc acacggcccg gctgatggcg    25980
gcgctggccg cggcggggat ctcgacgagc tggatctcca cctcccagat gcggctgtcg    26040
gtgatcgtgt cgcgggaccg caccgtcgac gccgtcgaag ccctgcaccg cgcgttccgc    26100
ctggaccggt ccgagccggc ggacgccacg tccctgacct cccgccgttc cgccaccgcc    26160
tgagagaggt aggaaaccgt ggccgtactc aacgcttcgt tcgctcgtgg cctgcgtctg    26220
cgccgactgt tccgacgcgg cgacggacgc ctgctcgtcg tcccgctcga ccactccgtc    26280
accgacgggc cgctgcgccg cggcgacctg aactcgctgc tcggtgagct cgccggcacc    26340
ggcgtggacg ccgtggtgct gcacaagggc agcctgcggc acgtcgacca cggctggttc    26400
ggcgacatgt cgctgatcgt gcatctgagc gtgagcaccc ggcacgcccc ggacccggac    26460
gcgaagtacc tggtcgcgca cgtggaggag gcgctgcggc tgggcgccga cgcggtcagc    26520
gtgcacgtca acctcggctc accgcaggag gcgcggcaga tcgccgacct ggcggcggtg    26580
```

```
gcgggggagt gcgaccgctg gaacgtcccg ctgctggcca tggtgtacgc ccgcgggccg    26640
cagatcaccg actcccgggc accggagctg gtggcgcacg ccgcgacgct cgccgcggac    26700
ctcggcgccg acatcgtcaa gaccgactac gtgggcacgc ccgagcagat ggccgaggtg    26760
gtgcgcggct gcccgatccc gctgatcgtg gccggcggcc cgcgctcggc cgacactccg    26820
acggtgctcg cctacgtctc ggacgcgctg cgcggcggcg tggccgggat ggccatgggc    26880
cgcaacgtgt tccaggccga gcagcccggc ctgatggccg ccgccgtggc acggctggtg    26940
cacgagccac ggcacgtgcc ggaccggtac gacgtcgacg accggctcgc ccttacgtcc    27000
tgagactccc tgaccgtcca ccgaggagaa acccgtgaag ctgtgctggc tggacatccg    27060
taacgtcaac ggcgccaagg aggcaatcgt cgaggaggcg gtccaccagc gggtggacgc    27120
cgtcgtggcg gccgatccgg ccgacctgga gacgcttccc ccgacggtga agaaggtgct    27180
gttcccgcag ggcgggccgc tgccggagaa gctggaaccg gccgacctgg tgatcgtcga    27240
gccgccccgg cacggcgagc ccgccgagct ggcggcccgg tacccggagg tggagttcgg    27300
ccggttcgtc gagatcgtcg acgcggacag cctggaggac gcctgccggt ccgcgcgcca    27360
cgaccggtgg agcctgctgt acttccgcga ccccaccaag atcccgctgg agatcgtgct    27420
ggcggccgcg gcgggcgcgg agggcagcat catcacccag gtcgccgacg tcgaggaggc    27480
ggagatcgtc ttcggcgtcc tggagcacgg ctcggacgga gtgatgctgg cgccccgcgc    27540
cgtgggggag gccaccgagc tgcggaccgc cgcggtgagc acggcggcgg acctgtcgct    27600
cgtggagctg gaggtcaccg gcatccggcg ggtgggcatg ggcgagcgcg cctgcgtcga    27660
cacgtgcacg aacttccgtc tggacgaggg catcctggtc ggctcgcact ccaccggcat    27720
gatcctgtgc tgcagcgaga cgcatccgct gccgtacatg ccgacccggc cgttccgggt    27780
caacgccggc gcgctgcact cgtacacgct ctccgccggc gggcggacca actacctcag    27840
cgagctggtc tccggcggcc gggtgctcgc cgtggactcg caggggaagt cccgcgtcgt    27900
cacagtggga cgggtcaaga tcgagacgcg tccgctgctg gcgatcgacg cggtctcccc    27960
ctccgggaca cgcgtcaacc tcatcgtcca ggacgactgg cacgtgcgcg tgctcgggcc    28020
gggcggcacc gtgctcaacg tgaccgagct gaccgccggc acgaaggtgc tcggttacct    28080
gccggtggag aagcggcacg tcggctaccc gatcgacgag ttctgcatcg agaagtgaca    28140
ggcggcggga aggggagcgg gcgatgaccg cgcagccggt gctggacttc cacgtacgcc    28200
tggcgccccg gccggggcg cgggagcggc tgctcgccgc gctgcgcgag tgcgggctgg    28260 cgcggcggt ggtgtgcgcg ggcggcacca tcgacctgga ccggctgtcc cgccagctcg    28320
tcaccggcgg ccacgtcgag accgacgccg acaacgacgc ggtggcggcg gcctgcgccg    28380
gcaccgacgg ccggctggtg ccgttcttct tcgccaaccc gcaccggccg gccgaggcgt    28440
accgggcccg cgccgccgag ttccgcggcc tggagatctc accgccgtc cacggcgtcg    28500 ccctgaccga cccgcgggtc gccgacctcg tggccgtggc ggcggagttc gaccatccgg    28560
tgtacgtggt ctgcctggac cgacccggcg cgggcgtggc cgacctggtc ggcctgagcc    28620
gccggttccc gcaggtgagc ttcgtgctcg ggcacagcgg cgtcggcaac atcgacctct    28680
acgccctgac cctgatccag gacgagccga acatctcgct ggagacctcc ggcggctaca    28740
cctgcgtggc cgaggcggcg ctacgccgcc tcggcgacga ccgggtggtg ttcggctccg    28800
agtacccgct gcagcacccg gccgtggaac tggccaagtt ccaggcgttg cgactgccgc    28860
cggagcggtg gcggcggatc gcctgggaca acgcgcatcg actgctagga gaggagaagc    28920
ggtgagcgag ccaagttcga gcctgccccg gctcggccag tggcacggcc tcgaggacct    28980
```

```
gcggcgcctc caggagaagc aactggcgga gacgttcacc tgggcggccc ggtcgccgtt   29040
ctaccgggcg cggctggcct ccggcgcgcc gccggtgacg cccgccgacc tggccgacct   29100
gccgctgacc accaagcagg acctgcggga caactacccc ttcggcatgc tcgccgtgcc   29160
ccgcgaacgg ctggcgacct accacgagtc gagcgggacc gccgggaagc ccaccccctc   29220
ctactacacc gcggaggact ggaccgacct ggcggagcgc ttcgcccgca agtggatcgg   29280
catgtccgcc gacgacgtct tcctggtccg cacgccgtac gcgctgctgc tgaccgggca   29340
tctcgcccac gccgcagccc ggctgcgtgg ggccacggtg gtacctggcg acaaccggtc   29400
gctggcgatg ccgtacgccc gggtggtccg ggtgatgcac gacctggacg tcacgctcac   29460
ctggtcggtg ccgacggagt gcctgatctg ggccgccgcg gcgatcgcgg ccgggcaccg   29520
gcccgacatc gacttcccgg cgctgcgcgc gctgttcgtc ggcggcgagc cgatgaccga   29580
cgcccgccgg cggcggatca gccgcctgtg ggggtgccg gtcatcgagg agtacggctc   29640
gacggagacc ggcagcctgg ccggggagtg ccccgaggga cgcctgcacc tgtgggccga   29700
ccgggcgctg ttcgaggtgt acgacccgga caccggcgcc gtccgcgcgg acggcgacgg   29760
ccagctcgtg gtcacgccgc tgttccggga ggcgatgccg ctgctgcggt acaacctgga   29820
ggacaacgtg tcggtctcct acgacgactg cggatgcggc tggaagctgc ccaccgtgcg   29880
ggtgctcggc cggtcggcgt tcggctaccg ggtcggcggc accaccatca cccagcacca   29940
gctggaggaa ctggtcttct ccctgccgga ggcgcaccgg gtgatgttct ggcgggccaa   30000
ggcggagccg gcgctgttgc gggtcgagat cgaggtggcc gccgcgcacc gggtcgccgc   30060
cgaggcggag ctgaccgccg cgatccgggc cgccttcggc gtggacagcg aggtcaccgg   30120
cctggccgcc ggaaccctga tcccgctcga cgcgctgacc agcatgccgg acgtggtgaa   30180
gccacgcagc ctgttcggtc cggacgagga ctggagcaaa gcgctcctct actactgagg   30240
gaaccgacat gccgcagatg agggtcgccg tggccggcgc cggcatcgcc gggctcgcct   30300
tcgccgccgc cctgcgccgg accgggatcg actgccacgt gtacgaacag gccgaccagc   30360
tcatggaggt gggcgcgggc gtgcaggtcg cgccgaacgc cacccggctg ctgcaccggc   30420
tgggcctgcg tgaccgcctg cgtacggtgg ctgtcgcgcc gcaggcgatc gagatgcgcc   30480
gctgggacga cggcacgctg ctgcaacgca cccagctggg cagcgtgtgc ggacgccgct   30540
tcggcgcgcc gtactacgtg gtgcaccgcg cggacctgca cagcagcctg ctgtcgctgg   30600
tgccgccgga ccgggtgcac ctgggcgccc gcctcaccgc cgtgacgcag accgccgacg   30660
aggcgtacct gcacctgtcc aacggcacca cggtcgcggc ggatctcgtc gtgggcgccg   30720
acggcatcca ctcggtcgcg cgggagcaga tcgtggcgga ccggccgcgc ttctccggac   30780
agtccatcta ccgcgggctg gtgccggccg agcgggtgcc gttcctgctc accgaacccc   30840
gggtgcagtt gtggttcggg ccggaccagc actgcgtctg ctaccggtg tccgccggcc   30900 ggcaggtgag cttcggcgcg acggtgcccg ccaccgactg gcggcaggag tcgtggtcgg   30960
gccggggcga cgtgacgcaa ctcgcggccg cgtacgcggg ctggcacccg gacgtcaccc   31020
ggctgatcgc cgcggccgac cgggtcggca ggtgggcgct gcacgaccgg acagcatcg   31080 accggctcag cgcgggacgg gtgaccctga tcgcgacgc cgcgcacccg atgctgccgt   31140
tccaggcgca gggcgcgaac caggccgtcg aggacgcggt ggtgctcgcg gtctgcctgg   31200
ccggcgtgga accggcgggc ctgggcgccg cgctgcgccg ctacgaacgg atccgcctgc   31260
cccggaccac ccggatccag cggcagtccc gggccaacgc cgagatgttc cacctggccg   31320
```

-continued

```
acggcgccga ccagcgccgc cgggacgtcg ccgcacaatc ctcgtccggc ctggaccgcc    31380
acgaatggct cttcgggtac gacgccgaga aagccaccac gaccagcggg agcgcctgat    31440
ggaactgacc ggaatcgagt cgaaggtcgc cctggtcacg ggcgcggggc agggcatcgg    31500
cgccgccgtg gccggtgtcc tggcgagggc gggcgcgcag gtggcggcgg tggaccgcaa    31560
cgccgaggcg ctgaccaccg tcgtgacgaa gctcgccgcc gagggcgact cggcgcgcgc    31620
ctactgcgtc gacgtgtgcg acagcgaggc ggtggacgcg ctggtgcgcc gggtcgagga    31680
cgagatgggg ccggtcgcca tcctggtcaa cgccgccggc gtgctgcaca ccggacgggt    31740
cgtcgagctg tcggaccggc agtggcgccg gaccttctcg gtgaacgccg acggcgtgtt    31800
ccacgtgtcc cgggcggtgg cgcggcggat ggtgggccgc cgtcgtggcg cgatcgtcac    31860
cgtggcgtcg aacgccgccg gggtgccgcg taccgagatg gccgcgtacg ccgcctccaa    31920
ggccgcgtcc gcgcagttca cccgctgcct ggggcttgag ctgtccggct acggcatccg    31980
gtgcaacgtg gtctcgcccg gctccaccga cacccccatg ctgcgggcca tgctcggcga    32040
gggcgccgac ccgagcgcgg tgatcgaggg cacgccgggc gcgtaccgcg tcggcatccc    32100
gctgcgcaag ctggcccagc cgcgcgacgt ggccgaggcg gtcgcctatc tggtgtccga    32160
ccaggcgggc cacgtgacca tgcacgacct gtacgtcgac ggcggcgcgg ccctgcacgt    32220
gtgacgccct cgcacggaaa ccggaggcga gaaccgatgg ccatgacccc gatcgcgccg    32280
taccgcatgc ccggcgacgg cgacctgccc ggcaccgcgc tgccctggcg tccgcacccg    32340
gaccgggccg ccgtgctggt gcacgacctg caacgctact tcctgcgccc gttcgaggcc    32400
ggggagtccc cgatggccga actgctcccc aacgtcgcga agctgctcgc cacggcgcgg    32460
gcggccggcg tgccggtgct gtacaccgcg cagcccggcg gcatgagccg gcaggaccgc    32520
gggttgctgc acgacctgtg gggccccggc atgagcagcg ccgaggacga ccggggcatc    32580
gtcgacgacg tcgccccgca gccggcgac acggtgctga ccaagtggcg ctacagcgcg    32640
ttcttccgca gcgacctgga ggagcgactg cgcggtgcgg gacgggacca gctcgtggtc    32700
tgcggcgtgt acgcgcacat ggggtgcctg atcaccgcct gcgacgcgtt cagccgcgac    32760
atcgaggcgt tcctggtggc ggacgcgctg gccgacctat cgcgcgagga ccacctgatg    32820
gcgctgcgct acgccgcgga ccgctgcgcg gtgccgttgt ggacggcgga tgtgctggac    32880
gggctggcgg acgccgccgg gcgtccggat cagagcagca cccaacgatg aggagaacat    32940
cgatgtcgga tcggacccgg gtcgtggtcg tcggcggaac ctcggggatc gggcggcact    33000
tcgcccgatt ctgcgccgaa cgcggagacg acgtggtgat caccggccgt tcggcggccc    33060
ggaccaagac cgtggcggac gagatcggcg ggcggacccg tgggctcgct ctcgacctgg    33120
ccgagccgga gacgatcgcg gacgcgctcg ccgacgtgcc gcacgtcgac cggctcgtgg    33180
tcgcggcgct ggaccgcgac tacaacaccg tccgcgcgta ccggccgggc gacgcggcgc    33240
ggctgctgac cgtcaagctg gtcggctaca cggcggtcct gcacgccctc gccccgcgga    33300
tgaccgacga gagcgcagtc gtgctgctcg gcggcctggc cagccaccgg ccgtatcccg    33360
gctccacctc cgtcacgacc gccaacgcgg ggatcagcgc gctggtgcgg accctggctg    33420
tggaactctc gccggtccgg gtcaacgccc tgcacccgag catcgtctcc gacacgccgt    33480
tctgagcgca caagcccgcc gcgcgggagg ccgccgcgac ccgcgcgctc agccgacggc    33540
cggtcaccat gcaggactgc gccgaggcga tcgacttcct gctgacgaac cgctcgataa    33600
acggggtcaa cctgaacatc gacgcggggg acgtgctcat ctgacgccgg aggcgatccg    33660
ccacggcccc caccacccgg tcgcgccctg cccgtgctcc cgctgctcgc gggggtaccg    33720
```

```
ggccaggtcg cgggcggaga agagcgccat gccggcgtgg aatccggtca ccggcaccgg   33780
gacccgcgcc cagtaggcga gccggccgtc gacgtggaac tccacctccg acgtcggcgc   33840
ccggtaggtg atggcgtatc cgtgcgcccg gcccggctcc gtcggcacgt ccaggaccac   33900
ccggtggatg tagtgctcgt gcggctgggt cacgccgggc agcaccaggc gctcgaccgt   33960
cgcgtacacg gtgtcgttcg tggcggcggc gttgaacacg acgccggtct ccaggtcgaa   34020
caggttcacc gtgccgaacg cgtccagcag gtcgtgcggg atctgccggt acgtccgcac   34080
gcccatctcc acctcgacgg tcagcgagcc ctccgccggc acggcgaagc gccgcaccga   34140
ccggtacatc tgcttggcgt tgttctgccg gggatcggtg tcgtggaagc gggtgaacgg   34200
gtcgacggtc agctccagcc gcccgtcgcc ggtgcggacc tgggcgttgc ggtcctggta   34260
cctgtgggtc tgcccgtccg cgccggcgat cgacatgatc gcccagcggg cggggtccag   34320
ctcgcggctg gtgaagtcgt cgtacgtcca cgcgctggtt ctcagtgccg acgtcatgca   34380
gtcaccatcg gacgccggcc gggcgcgggc atcacccgtt cacgcggttc ggccggaccc   34440
ggcacgccaa tgcgccggcc acgccccgga aatcccgtga ttaagccatg ccggagcgtg   34500
aacggtcgcc gagactgacg ccgcacccat ctccgcatcg tctgcgacgt tctcaccagg   34560
gggagagagc aatggacacg gcagctccgg caacggacgg cggtcgctac ctcgccgtcc   34620
atcacagcgc agagttcagg gaactacggc gacgatcgag cacgttcacg ctctgggcca   34680
gcgtcgcctt cttcggctgg tggttcctcg gcagcctgct cgccacctac gcgccggact   34740
tcttccggga gaaggtggcc ggcccggtca acgtgggtct gctcttcgtc ttcctgtcgt   34800
tcgccttcgt ggtgacgctc gccgccttct acctgcgtta cgcccgcacg catctcgatc   34860
cgctcagcga gaagatccgt gccgacctgg aaggagcgtc ccgatgagcg tcatcctcgc   34920
cgacccgcca cccccggtcg acaacacgtg ggcgacgccc gcgatcgccg tgccggtcac   34980
catcgtcctc gcgctcgcgg tgctctacct ggtccggtcg gcgcgcgcca gcaccaccac   35040
cgcggacggc ttcctgctgg ccgaccggcg gatcgggccg gtgcagaacg cgctggcggt   35100
ggcctccgcg ccgctgatgt actcgacgat gtacatcatc accggccaca tcgcgctcag   35160
cggctacgac gccatcctgc tgatgaccgc cttcaccatg ggcaccatgc tcgcgctgtt   35220
cctcttcgcc gggccggtgc gcaacgtggg cggctacacg ctcggtgacc tgctcgcggt   35280
ccgtacccgg gagcggccgg cgcggatcgc gtcggcggtg ctcacgctgc tgacgtacgt   35340
catgctgacg gtgatcatga tggccgccat cgcgttcatc ttcaaccgct ggttcggcgt   35400
cgacgccctc gtcggcctgg tcctcccggt gttcgtcgtc ggtctgatca cggtggggta   35460
cgtgtacctc ggcgggatgc tcggggtcac ccgcatcctg gtgttcaagc tggtgctgtc   35520
ggtggtcgtc gtgggcgtgc tgaccgcctg ggtgctggcc cgcttcgacc tgaacctctt   35580
cagcctgctg gagcgggccg aggcgaacgc ggcgccggtg cccagcggca gcgacctgct   35640
gggcccgggc cggctgttcg gcgagggcgc gaccacgctc gtgcacctgt cgaagctgtt   35700
cgccatcgcc gtcggagtgg cggccattcc gttcctgttc atgcgcaact cgcggtgac    35760
cagcgggcgg gacgcgcgcc ggtcgaccgg gtgggcgtcg atgatcatcg tcgggttcta   35820
cctgtgcctg tccgtcgtcg ggctcggtgc cgtcgcgatc ctcggccggg acaacatcgg   35880
cgtcatcaag gcccaccgcg acatcagctt ccccaagctc gccgacgagc tcggcggtcc   35940
ggtgatggtc ggctccctgg ccggcgtcgc ggtcctgacg atcgtcggcg tcttcgcgcc   36000
gctgctgcac agcgccgtga cgacggtgac caaggacctg aacgtgatcc gcggccggcg   36060
```

-continued

```
gctggatccg gccgccgagc tgcgggacat caagcgcaac accctgatca tcggcgtcgg    36120
ctccgtgctg ctggcggtcg tgatgctgcc ggtacggacc cacatcttca tcccgacctc    36180
gatcgacatt gccggcgcgg tggtcctgcc gatcgtcgtc tacgcgttgt tctggcggcg    36240
tttcaacacc cgcggactgc agtggacggt ctacggcggc ctcgcgctca ccgcgttcct    36300
ggtgctgttc tccaacggtg tctcgggcga gccggacgcc atcttcccgg accgcaactt    36360
caagttcgtg gacgtcgagc cgcgctgat cacggtgccg gtcggcttcc tgctcggcta    36420
cctcggctcg atcaccagcc gggagcgcga cgacgccgcg ttcgccgaga tgcaggtccg    36480
gtccctcacc ggagctgtcg tcacgggacc gccgcggccg gccgccgtgg acgacgagga    36540
ccgcgacggc cgccaggacc gggcgcccag cccggtgagc tgaacatccg caacggtgtg    36600
gg                                                                    36602
```

<210> SEQ ID NO 2
<211> LENGTH: 571
<212> TYPE: PRT
<213> ORGANISM: Micromonospora sp. strain 046-ECO11

<400> SEQUENCE: 2

```
Val His Asn Leu Asp Asn Ile Pro Ser Ser Pro Ser Thr Ser Gly Gly
 1               5                  10                  15

Ser Leu Pro Ala Gly His Arg Ala His Val Arg Ala Asp Gly Val Arg
            20                  25                  30

Val Val Arg Gly Gly Arg Val Val Leu Ser Asp Val Ser Val Thr Val
        35                  40                  45

Ser Ala Ala Ser Arg Leu Ala Val Val Gly Glu Asn Gly Arg Gly Lys
    50                  55                  60

Thr Thr Leu Leu His Val Leu Ala Gly Leu Ile Ala Pro Asp Gln Gly
65                  70                  75                  80

Val Val Glu Arg Leu Gly Thr Ile Gly Val Ala Arg Gln Asn Leu Glu
                85                  90                  95

Ser Arg His Gly Glu Thr Val Gly Thr Leu Val Arg Glu Ala Ile Arg
            100                 105                 110

Glu Ser Glu Arg Ala Leu Arg Ala Leu Asp Glu Ala Thr Ile Ala Leu
        115                 120                 125

Thr Glu Gly Arg Ala Gly Ala Asp Asp Ala Tyr Ala Ala Ala Leu Asp
    130                 135                 140

Ala Ala Thr Arg Leu Asp Ala Trp Asp Ala Gln Arg Arg Val Asp Val
145                 150                 155                 160

Ala Leu Ala Gly Leu Asp Ala Cys Pro Asp Arg Asp Arg Gln Leu Ala
                165                 170                 175

Thr Leu Ser Val Gly Gln Arg Tyr Arg Val Arg Leu Ala Cys Leu Leu
            180                 185                 190

Gly Ala Arg Val Asp Leu Leu Met Leu Asp Glu Pro Thr Asn His Leu
        195                 200                 205

Asp Ala Asp Ser Leu Ala Phe Leu Thr Ala Arg Leu Arg Asp His Pro
    210                 215                 220

Gly Gly Val Val Leu Val Thr His Asp Arg Ala Leu Leu Arg Asp Val
225                 230                 235                 240

Ala Thr Glu Phe Leu Asp Leu Asp Pro Ser Ala Asp Gly Arg Pro Arg
                245                 250                 255

Arg Tyr Ala Gly Asp Tyr Val Ala Trp Gln Asp Gly Arg Arg Arg Asp
            260                 265                 270
```

```
Phe Ala His Trp Val Arg Asp His Glu Ala Gln Gln Ala Glu His Gln
        275                 280                 285

Arg Leu Ala Asp Gly Val Arg Glu Ala Arg Asp Arg Leu Ser Thr Gly
        290                 295                 300

Trp Arg Pro Glu Lys Gly His Gly Lys His Gln Arg Gln Ser Arg Ala
305                 310                 315                 320

Pro Gly Leu Val Gln Ala Leu Arg Arg Gln Glu Ala Leu Asp Ala
                325                 330                 335

His Arg Val Thr Val Pro Glu Pro Pro Gln Pro Leu Arg Trp Pro Pro
                340                 345                 350

Leu Asp Thr Arg Ala Gly Leu Pro Ile Leu Arg Cys His Asp Val Thr
                355                 360                 365

Val Ala Gly Arg Leu Arg Thr Arg Val Thr Leu Thr Leu Asp Gly Gly
        370                 375                 380

Asp Arg Leu Leu Val Thr Gly Pro Asn Gly Ala Gly Lys Ser Thr Leu
385                 390                 395                 400

Leu Ser Val Leu Ala Gly Asp Leu Thr Pro Ser Thr Gly Glu Val Arg
                405                 410                 415

His Leu Ser Gly Ala Arg Val Ala Tyr Leu Gly Gln Glu Val Pro Asp
                420                 425                 430

Trp Pro Pro Ala Leu Leu Ala His Asp Leu Tyr Glu Gln His Val Gly
                435                 440                 445

Arg Leu Arg Ser Ser Gly Arg Val Gly Ser Gly Thr Ala Leu Pro Leu
        450                 455                 460

Ser Ala Thr Asn Leu Leu Asp Ala Glu Ala Arg Arg Thr Pro Val Gly
465                 470                 475                 480

Arg Met Ser His Gly Gln Gln Arg Arg Leu Asn Leu Ala Leu Arg Leu
                485                 490                 495

Ala Glu Arg Pro Asp Leu Leu Ile Leu Asp Glu Pro Thr Asn His Leu
                500                 505                 510

Ser Ala Pro Leu Val Asp Asp Leu Thr Ala Ala Leu Leu Thr Thr Arg
                515                 520                 525

Ala Ala Val Val Val Ala Thr His Asp Arg Gln Met Leu Gln Asp Leu
                530                 535                 540

Ala Ala Trp Pro Thr Leu Pro Leu Thr Ala Pro Ala Ala Ser Gly Arg
545                 550                 555                 560

Ser Val Thr Ser Glu Arg Tyr Asp Trp Glu Ser
                565                 570

<210> SEQ ID NO 3
<211> LENGTH: 1716
<212> TYPE: DNA
<213> ORGANISM: Micromonospora sp. strain 046-ECO11

<400> SEQUENCE: 3
gtgcacaacc tcgacaacat tccttcctcc ccatccacct cgggcggttc gctgccgcc      60 gggcaccggg cgcacgtgcg ggccgacggc gtccgcgtcg tacgcggcgg ccgggtcgtg    120
ctgtccgacg tcagcgtgac cgtctccgcc gcttcccgcc tcgcagtcgt cggcgagaac    180
ggccgcggca agaccaccct gctgcacgtg ctggccggcc tcatcgcgcc cgaccagggc    240
gtggtggaac ggctgggcac gatcggcgtc gcccggcaga acctggagtc cgccacggc     300 gagacagtgg gcacgctcgt ccgggaggcg atccgggagt ccgaacgcgc gctgcgggcg    360
ctcgacgagg cgacgatcgc gctcaccgag ggccgggcgg gcgcggacga cgcgtacgcg    420
```

```
gccgcgctcg acgcggcgac ccggctggac gcctgggacg cgcagcggcg cgtcgacgtg    480
gcgctggccg gcctcgacgc gtgcccggac cgggaccggc agctggccac gttgtccgtc    540
ggccagcgct accgggtacg gctggcgtgc ctgctgggag cgagggtcga cctgctgatg    600
ctggacgagc cgacgaacca cctcgacgcc gacagcctgg ccttcctcac cgcccggcta    660
cgcgaccacc cgggcggcgt cgtgctggtg acccacgacc gcgccctgct gcgggacgtc    720
gccacggagt tcctggacct cgaccccagc gcggacgggc cccgcgccg ctacgccggg     780
gactacgtcg cctggcagga cgggcgccgc cgcgacttcg cgcactgggt acgcgaccac    840
gaggcgcagc aggccgagca ccagcggctg gccgacgggg tacgggaggc gcgggaccgg    900
ctcagcaccg gctggcggcc ggagaagggg cacggcaagc accagcgcca gtcccgcgcg    960
cccggactgg tccaggcgct gcgccgccgg caggaggcgc tcgacgcgca ccgcgtcacc   1020
gtgccggagc accgcagcc gctgcgctgg ccgccgctgg acacccgtgc cggactgccc    1080
atcctgcgat gccacgacgt cacggtggcc gggcgcctgc gtaccgggt cacgctcacg     1140
ctcgacggcg gggaccgcct gctggtgacc ggacccaacg gcgcgggcaa gtcgacgctg   1200
ctctccgtgc tggccggcga cctcacgccg tcgaccgggg aggtccggca cctgtccggc   1260
gcgcgcgtcg cgtacctcgg tcaggaggtg cccgactggc cgccggcgct gctcgcgcac   1320
gacctgtacg agcagcacgt gggccggctc cgctccagcg ggcgcgtcgg ctccggcacg   1380
gccctgccgc tgagcgcgac gaacctgctc gacgccgagg cccggcgtac ccccgtcggc   1440
cggatgtcgc acggacagca acggcggctg aacctggcgc tgcgcctggc cgaacgtccc   1500
gacctgctga tcctcgacga accgacgaac cacctgtcgg cgccgctggt cgacgacctc   1560
accgccgccc tgctgacgac ccgggcggcg gtggtcgtcg ccacccacga ccggcagatg   1620
ctccaggacc tcgcggcctg gcccacgctg ccgctcacag ccccggcggc gtcaggtcgt   1680
tcggtcactt ccgagcgata tgactgggag tcataa                              1716
```

<210> SEQ ID NO 4  
<211> LENGTH: 689  
<212> TYPE: PRT  
<213> ORGANISM: Micromonospora sp. strain 046-ECO11

<400> SEQUENCE: 4

```
Met Thr Thr Gly Arg Pro Gly Glu Asn Arg Ala Thr Asp Ala Ala Arg
1               5                   10                  15

Asn Pro Gly Trp Ala Ala Gly Gly Pro Ala Ser Gln Pro Trp Gly Gly
            20                  25                  30

Gly Asn Asp Glu Gln Val Leu Arg Glu Ile Leu Gly Val Asp Val His
        35                  40                  45

Arg Glu Leu Ile Asp Phe Ala Gly Ala Gly Gly Asn Pro His Leu
    50                  55                  60

Val Ala Glu Leu Ala Arg Gly Leu Ala Glu Gly Leu Ile Arg Glu
65                  70                  75                  80

Thr Asn Gly Arg Ala Glu Leu Val Ser Arg Arg Ile Pro Arg Arg Val
                85                  90                  95

Leu Ser Phe Val Met Arg Arg Leu Asn Asp Val Ser Ala Gly Cys Gln
            100                 105                 110

Gln Phe Leu Lys Val Ala Ala Leu Gly Arg Ser Phe Met Leu Glu
        115                 120                 125

Asp Val Ser Arg Met Leu Gly Arg Ser Ser Ala Ala Leu Leu Pro Pro
    130                 135                 140
```

-continued

Val Asp Glu Ala Ile Ala Ser Gly Phe Val Ala Ala Glu His Gln
145                 150                 155                 160

Leu Ala Phe Gln Ser Asp Phe Leu Leu Arg Gly Ile Ile Glu Ser Ile
                165                 170                 175

Pro Gly Pro Ala Arg Asp Ala Leu Arg Arg Glu Ala Met Ser Leu Ser
            180                 185                 190

Gly Arg Arg Arg Pro Ala Ala Asp Gln Asn Arg Arg Leu Asp Ala Ala
        195                 200                 205

Pro Thr Ala Pro Val Ser Ala Thr Gly Glu Asp Ala Thr Gly Ser Cys
    210                 215                 220

Ser Arg Ala His Arg Leu Ile Met Asn Gly Asn Ala Lys Ala Gly Ile
225                 230                 235                 240

Arg Val Ala Glu Ala Val Leu Ala Gly Pro Ala Ala Ser Leu Ala Ala
                245                 250                 255

Arg Arg Asp Ala Glu Ala Cys Leu Val Leu Ala Asp Leu Leu Leu Gly
            260                 265                 270

Gly Glu Gly Gly Gly Pro Met Thr Glu Ala Ile Leu Arg Glu Arg Asp
        275                 280                 285

Ala Glu Ser Gly Asp Ala Ala Leu Ala Met Ala Leu Thr Ala Arg Ser
    290                 295                 300

Thr Gly Leu Trp Ser Ala Gly Lys Leu Ala Glu Gly Leu Lys Leu Gly
305                 310                 315                 320

Arg Ala Ala Val Arg Ala Gly Ala Glu Ala Glu Pro Val Trp Arg Leu
                325                 330                 335

His Ala Gln Leu Ala Leu Ala Gly Lys Leu Ala Asn Leu Arg Glu Phe
            340                 345                 350

Asp Glu Ala Glu Ala Leu Ile Asn Glu Ala Glu Ala Gly Leu Arg Gly
        355                 360                 365

Leu Pro Ala Pro Ile Trp Thr Ala Ala Thr Ala Val Met Arg Ser Arg
    370                 375                 380

Leu Leu Leu Gln Ala Gly Arg Ile Gly Glu Ala Arg Arg Glu Ala Ala
385                 390                 395                 400

Leu Ala Thr Thr Ala Val Glu Gly Asp Ala Val Pro Met Leu Arg Pro
                405                 410                 415

Leu Ala Tyr Ala Val Leu Ser Thr Ala Ser Phe Tyr Met Gly Asp Leu
            420                 425                 430

Pro Ala Ala Ile Glu Tyr Leu Arg Arg Gly Gln Arg Asp Ala Asp Arg
        435                 440                 445

His Val Val Leu Asp Ser Val Gln Tyr Ser Trp Ala Glu Val Leu Ile
    450                 455                 460

Thr Val Lys Gln Glu Gly Pro Arg Ala Ala Ala Gln Leu Leu Ala Gly
465                 470                 475                 480

Lys His His Arg Leu Pro Thr Gln Arg Arg Leu Tyr Val Glu Val Pro
                485                 490                 495

Ser Ala Ala Ala Phe Leu Val Leu Leu Ala Arg Asp Val Asp Asp Arg
            500                 505                 510

Asp Leu Glu Arg Arg Val Leu Asp Thr Val Asn Gly Leu Ala Ala Asp
        515                 520                 525

Asn Pro Arg Ile Gln Val Ser Leu Thr Ala Met His Ala His Ala
    530                 535                 540

Leu Ala Asn Ser Ala Pro Ala Ala Leu Ala Leu Ile Ile Val Gln Ser
545                 550                 555                 560

Arg Asp Pro Ile Ser Val Ala Leu Ala Thr Glu Glu Leu Ala Lys Leu

```
                        565                 570                 575
Tyr Ala Ala Gln Ala Gln Ala Gly Gly Arg Pro Ala Thr Pro Ala Arg
            580                 585                 590

Ala Glu Glu Ala Ala Thr Pro Pro Ala Ser Cys Trp Ser Thr Leu Ser
        595                 600                 605

Asp Met Glu Gln Arg Ile Ala Tyr Leu Val Ser Val Gly Leu Thr Asn
        610                 615                 620

Arg Gln Ile Ala Lys Gln Val His Leu Ser Ala His Thr Val Asn Tyr
625                 630                 635                 640

His Leu Arg Lys Ile Tyr Arg Lys Leu Gly Phe Asn Thr Arg Ala Glu
            645                 650                 655

Leu Ala His Ala Ala Ala Thr Tyr Ser Gly Arg Ala Ala Ile Tyr Ser
            660                 665                 670

Met Ser Gly Asp Gln Asp Trp Gly Ala Gly Ser Met Thr Gly Lys Ala
            675                 680                 685

Ser

<210> SEQ ID NO 5
<211> LENGTH: 2070
<212> TYPE: DNA
<213> ORGANISM: Micromonospora sp. strain 046-ECO11

<400> SEQUENCE: 5
atgacaacgg gacggccggg ggagaaccgg gcgacagacg cggcacgaaa tccggggtgg     60
gccgccgggg ggccggcgtc ccagccatgg ggcggggga acgacgagca ggtcctgcgc    120
gagatcctcg gggtcgacgt gcaccgcgag ctgattgact cgcgggtgg tgccggcgga    180 aatccgcacc tggtcgccga actcgcgcgc gggctcgccg aagagggatt gattcgggag    240
acaaacggtc gggcggaatt ggtgtcccgg cgaattcccc ggcgcgtgct gagttttgtc    300
atgcgtcgat tgaatgatgt cagcgccggc tgccagcagt tcttgaaggt tgccgcggca    360
ttgggcagat ccttcatgct ggaggacgtt tcgagaatgc tgggccgatc gtcggcggcc    420
ctgctcccgc cggtgacga ggcgatcgca tcgggcttcg tcgtcgccgc cgagcatcaa    480
ctcgcctttc agagcgactt cctgctgcgc ggcatcatcg agtccattcc cgggcccgcc    540
cgcgacgcct tacgacgtga ggcgatgagc ctttccgggc gacggcgccc ggcggccgac    600
cagaatcgcc ggttggacgc ggcgcctacc cgccggtga gcgcgaccgg ggaggacgcc    660
accggatcct gttcccgggc gcaccgcctg ataatgaacg gaacgcgaa ggccggcatt    720 cgcgtcgccg aggcggttct cgccggcccg gccgcgtcgc tcgctgcccg gcgtgacgcg    780
gaggcgtgtc tggtgctggc cgatctgctg ctcggcgggg agggcggcgg cccgatgacc    840
gaggcgatcc tgcgcgaacg cgacgccgag tccggtgacg ccgcactggc gatggcgctg    900 accgccggt ccaccgggct gtggtcggcg ggaaagctgg cggagggcct gaagctggga    960
cgggcggcgg tgcgggcggg cgcggaggcc gaaccggtgt ggcgtctgca cgcccagctc   1020
gcgctcgccg ggaaactcgc gaacctccgc gagttcgacg aggccgaggc gttgatcaac   1080
gaggcggaag cgggcctgcg cggactgccc cgccgatct ggacggccgc gacggcggtg   1140
atgcggtccc ggttgctgct ccaggcgggg cggatcgggg aggcgcgtcg ggaggcggcg   1200
ctggccacca ccgccgtgga gggggacgcg gtgccgatgc tgcggcctct cgcctacgcg   1260
gtgctcagca ccgcctcctt ctacatgggg gacctgcccg ccgcgatcga gtacctcagg   1320
cgggggcagc gggacgcgga ccgccacgtg gtcctcgact cggtgcagta ctcgtgggcg   1380
```

```
gaagtgctga tcacggtcaa gcaggaaggc ccgcgggccg ccgcccagct gctcgcgggc    1440
aagcaccacc gcctgccac gcagcgccgc ctctacgtcg aggtgccgag cgccgccgcc    1500
ttcctggtcc tgctcgcccg cgacgtggac gaccgtgacc tcgaacgccg cgtcctcgac    1560
acggtcaacg gctcgccgc ggacaaccc aggatccagg tcgtcagcct caccgccatg    1620
cacgcccacg cgctggcgaa cagcgctccg gccgccctgg cgctcatcat cgtgcagtca    1680
cgggacccga tctcggtggc gctggccacc gaggaactcg ccaagctcta cgccgcgcag    1740
gcccaggcgg ggggacggcc ggcgacgccg gcccgcgccg aggaggccgc caccccgccg    1800
gcgagctgct ggtcgaccct gtccgacatg gagcagcgga tcgcctacct ggtgagcgtg    1860
ggtctgacga accggcagat cgccaagcag gtccacctgt ccgcgcacac cgtcaactac    1920
cacctgcgga agatctaccg gaaactgggt ttcaacaccc gggccgagct ggcgcacgcc    1980
gcggccacgt actccggccg ggcggcgatc tactccatga gcggcgacca ggactggggc    2040
gccggatcca tgaccggcaa ggccagctga                                    2070

<210> SEQ ID NO 6
<211> LENGTH: 895
<212> TYPE: PRT
<213> ORGANISM: Micromonospora sp. strain 046-ECO11

<400> SEQUENCE: 6

Met Val Ile Met Asn Arg Met Ala Gly Arg Gly Gln Glu Leu Ser Ser
1               5                   10                  15

Leu Gly Glu Leu Leu Asp Ala Thr Met Arg Gly Ser Gly Gly Cys Val
                20                  25                  30

Val Val Asp Gly Pro Phe Gly Ile Gly Lys Thr His Leu Leu Lys Val
            35                  40                  45

Thr Gly Leu Glu Ala Ala Arg Gly Leu Thr Val Ala Gly Arg
        50                  55                  60

Ala Ser Val Thr Asp Gln Pro Val Pro Val His Leu Leu Val Asn Phe
65                  70                  75                  80

Leu Arg His Ala Met Pro Gly Glu Ala Ala Val Glu Gln Leu Ala Leu
                85                  90                  95

Pro Gly Ala Asn Pro Phe Trp Leu Ile Asp Arg Val Gly Asp Leu Val
            100                 105                 110

Glu Val Ala Ala Arg Arg Pro Leu Val Val Ala Leu Asp Asp Ala
        115                 120                 125

Gln Arg Ile Asp Asp Val Ser Ala Leu Ala Leu Arg Gly Leu Val Pro
    130                 135                 140

Arg Leu Ala Ser Ser Pro Val Leu Trp Leu Leu Ala Arg Arg Pro Val
145                 150                 155                 160

Ala Ala Gly Ser Ile Ala Gln His Ala Val Asp Trp Leu Ala Glu His
                165                 170                 175

Val Ala Val Arg Val Arg Leu Arg Glu Pro Gly Glu Glu Ala Val Ala
            180                 185                 190

Asp Leu Cys Ala Gly Ile Leu Gly Ala Arg Pro Asp Ala Ser Val Leu
        195                 200                 205

Arg Trp Ala Ala Arg Cys Gly Gly Asn Pro Lys Val Met Glu Ile Val
    210                 215                 220

Phe Ser Ala Phe Ile Lys Ala Gly Gln Met Ile Ile Val Asp Gly Ala
225                 230                 235                 240

Ala Ser Val Val Ser Asp Glu Leu Pro Asp Gly Val Leu Ala Ala Val
                245                 250                 255
```

```
Arg Gly Leu Leu Glu Glu Leu Pro Pro Leu Arg Arg Leu Leu Ala
        260                 265                 270

Ala Gly Gly Arg Leu Gly His Thr Phe Pro Val Asp Arg Val Thr Gly
        275                 280                 285

Leu Leu Asp Gly Ser Ala Ala Asp Val Ser Ala Ala Ile Asp Glu Ala
        290                 295                 300

Val Arg Val Gly Leu Ile Arg Arg Asp Gly Ala Glu Leu Thr Phe Ala
305                 310                 315                 320

His Pro Val Leu Gly Glu Ala Leu Arg His Ala Ala Tyr Pro Glu Pro
                    325                 330                 335

Glu Arg Ala Glu Pro Gly Ser Ala Pro Ala Pro Ala Ala Gly Asp Pro
                340                 345                 350

Val Arg Arg Gly Arg Pro Asp Pro Arg Pro Gly Thr Pro His Ser Pro
            355                 360                 365

Ala Gly Val Arg Val Thr Arg Ser Ala Pro Asp Ala Ala Thr Pro Ala
        370                 375                 380

Ala Thr Ala Gly Pro Arg Ser Gly Arg Cys Gly Cys Asp Asp Val Ala
385                 390                 395                 400

Ala Ala Ala Val Ser His Leu Glu Asn Gly Ser Ala Glu Ala Pro Arg
                    405                 410                 415

Ala Leu Ala Arg Ala Leu Arg Leu Leu Ala Gly Ala Gly Arg Ala Ala
                420                 425                 430

Glu Ala Gly Arg Leu Ala Glu Val Met Leu Arg Arg Asp Leu Ala Ala
            435                 440                 445

Asp Val Glu Ala Gln Leu Val Leu Glu Leu Gly His Gly Met Arg Ala
        450                 455                 460

Ala Gly Ser His Arg Leu Ala Ala Gly Phe Leu Arg Arg Thr Gln Ala
465                 470                 475                 480

Arg His Asp Val Cys Glu Leu Asp Arg Ala Lys Leu Asp Arg Ala Leu
                    485                 490                 495

Ala Asp Thr Thr Lys His Leu Gly Gly Ala Ser Ser Ala Glu Leu Glu
                500                 505                 510

Pro Arg His Gln Ser Pro Gly Cys Ala Pro Gly Arg Arg Pro Leu Trp
            515                 520                 525

Thr Trp Leu Val Arg Ala Leu Gly Ala Ala Asp Gln Leu Asp Glu Ala
        530                 535                 540

Gln Ala Val Leu Asp Thr Val Arg Pro Leu Ala Gln Glu Pro Ser His
545                 550                 555                 560

Thr Gly Ser Glu Ser Leu Trp Arg Gly His Arg Ala Glu Leu Leu Ala
                    565                 570                 575

Ala Ala Gly Arg Leu Asp Glu Ala Arg Ala Glu Ala Glu Ala Ala Leu
                580                 585                 590

Arg Ala Ala Asp His Ser Arg Pro Gly Asp Cys Val Pro Ala Arg Leu
            595                 600                 605

Val Leu Ala His Leu Gly Val His His Gly Asp Leu Ala Thr Ala Ser
        610                 615                 620

Asp Gln Leu Arg Ala Ala Glu Arg Leu Ala Ser Ala Asp Asp Ser Ala
625                 630                 635                 640

Arg Met Asp Trp Ala Leu Ala Arg Phe His Ala Ala Ser Gly Arg Pro
                    645                 650                 655

Ala Met Met Val Gln Thr Leu Ile Asn Val Ala Gly Gln Val Ala Pro
                660                 665                 670
```

-continued

```
Asp Pro Leu Leu Phe Thr Glu Ala Pro Ala Ala Ala Thr Leu Val
            675                 680                 685

Arg Gln Ala Arg Arg Ala Gly Leu Asp Ala Glu Ala Glu Arg Ala Val
        690                 695                 700

Glu Val Ala Arg Arg Val Ala Arg Gly Asn Pro Phe Val Gln Ser Leu
705                 710                 715                 720

Ala Ala Ala Ala Glu His Ala Ala Gly Leu Leu Arg Asp Asp Pro Ala
                725                 730                 735

Ala Leu Leu Arg Ala Ala Asp Leu His Arg Leu Ala Gly Arg Thr Leu
            740                 745                 750

Ala Ala Ala Gly Ala Val Glu Asp Ala Ala Arg Ser Thr Arg Asp Arg
        755                 760                 765

Ala Glu Ala Thr Arg Leu Leu Glu Ala Ala Thr Asp Gly Tyr Arg Glu
    770                 775                 780

Cys Gly Ala Arg Arg Asp Leu Glu Arg Val Glu Ala Glu Leu Arg Gly
785                 790                 795                 800

Leu Pro Ala His Asn Val Arg Pro Leu Val Pro Asp Arg Pro Arg Ser
                805                 810                 815

Gly Trp Glu Ser Leu Thr Ser Ala Glu Leu Arg Val Val Arg Ala Ile
            820                 825                 830

Val Asp Gly Met Thr Asn Arg Glu Ala Ala Ser Ser Leu Phe Leu Ser
        835                 840                 845

Pro His Thr Val Asp Ser His Leu Arg Arg Val Phe Ser Lys Leu Asp
    850                 855                 860

Ile Asn Ser Arg Val Glu Leu Thr Arg Cys Phe Ile Ala His Glu Ala
865                 870                 875                 880

Val Arg Pro Ala Leu Ala Thr Thr Arg Gln Pro Ala Ser Ala Gly
                885                 890                 895

<210> SEQ ID NO 7
<211> LENGTH: 2688
<212> TYPE: DNA
<213> ORGANISM: Micromonospora sp. strain 046-ECO11

<400> SEQUENCE: 7
atggtcatca tgaatcgcat ggcggggcgc gggcaggaat tgtcctcatt gggggaactg      60
ctcgacgcca ccatgcgggg atccggggc tgcgtcgtcg tcgacgggcc gttcggcatc      120
ggcaagaccc acctgctgaa ggtcaccggc ctggaggcgg cggcccgcgg gctgacagtg      180
gtggccgggc gggcaagcgt cacggatcag ccggtgcccg tacacctgct cgtcaacttc      240
ctgcgccacg cgatgcccgg cgaagcggcg gtcgagcagc tcgccctgcc gggcgccaac      300
ccgttctggc tgatcgaccg ggtcggcgat ctggtcgagg tcgcggcgcg ccggcgcccg      360
ctcgtggtcg ccctggacga cgcccagcgc atcgacgacg tcagcgcct ggccctgcgc      420 gggctcgtgc gcgcgctggc gtcctcgccg gtgctctggc tgctggcccg ccggccggtc      480
gccgccgggt cgatcgctca gcacgccgtc gactggctgg ccgagcacgt cgcggtacgg      540
gtacggctgc gcgagccggg cgaggaggcg gtggccgacc tgtgcgccgg catcctcggc      600
gcccggccgg acgcctccgt cctgcgctgg gcggcccgct gcggcggcaa cccgaaggtg      660
atggagatct cttcagcgc gttcatcaag gccggccaga tgatcatcgt ggacggggcg      720
gcgtcggtgg tgtccgacga gctgcccgac ggtgtcctcg ccgccgttcg cgggctgctg      780
gaggagctgc cgccccgct gcggcgcctg ctcgcggccg gcggccggct cggccacacg      840
tttcccgtcg accgggtgac gggcctgctg acgggctcgg ccgccgacgt gtccgccgcg      900
```

```
atcgacgagg cggtgcgggt cgggctgata cgacgcgacg gcgcggagct gaccttcgcc    960
cacccggtgc tcggagaggc gcttcgccac gccgcgtacc cggaaccgga gcgtgccgag   1020
cccggatccg cgccgcacc ggcggcgggc gacccggtcc ggcgcgggcg gcccgatccg   1080
cggcccggga cgccccactc ccccgccggc gtacgcgtca cgcgctccgc gccggacgcg   1140
gccacgcccg ccgcgacggc ggggccgcgc tcgggccggt gcgggtgcga cgacgtggcg   1200
gcagccgccg tgtcccacct ggagaacgga tccgccgagg cgccacgagc actggcccgt   1260
gcgctgcgcc tgctggccgg ggcggggcgg ccgccgaggc cggccgcct cgcggaggtg   1320
atgctccgcc gcgacctcgc ggcggacgtc gaggcgcagc tcgtgctcga actgggacac   1380
gggatgcggg ccgccggcag ccaccgcctg gcggccggct tcctgcgccg gacgcaggcc   1440
cgccacgacg tgtgcgagct ggaccgcgcc aagctggacc gggcgctcgc ggacaccacg   1500
aagcacctgg gcggtgcctc ctccgccgag ctggagcccc ggcaccagtc cccgggctgc   1560
gcgcccggcc ggcggccgct gtggacctgg ctggtccggg cgctgggcgc ggccgatcag   1620
ctcgacgagg cgcaggcggt gctggacacc gtacgaccgc tggcgcagga gcccagtcac   1680
accggctcgg agtcgctctg gcgcggccac cgggccgagc tgctggcagc ggccggacgg   1740
ctggacgagg cacgcgccga ggcggaggcg gcgctgcgag ccgccgacca ctcccggccg   1800
ggcgactgcg tgccggcgcg cctggtcctg gcccacctcg gcgtgcacca cggtgacctc   1860
gccacggcca gcgaccagtt gcgggcggcc gagcggctgg cctccgccga cgactcggcg   1920
cggatggact gggcgctggc ccggttccac gctgccagcg gccgtccggc gatgatggtg   1980
cagacgctga tcaacgtcgc cggacaggtc gcacccgatc cgctgctgtt caccgaggcg   2040
ccggccgctg cggcgacgct cgtacgccag gcccgccggg cggggctcga cgcggaggcc   2100
gagcgcgccg tggaggtcgc ccggcgcgtc gcccgcggca acccgttcgt ccagtcgctg   2160
gcggcggcg cggaacacgc cgcgggtctc ctgcgcgacg atccggcggc gctgctgcgg   2220
gccgcggatc tgcaccggct cgccggccgt acgctcgcgg cggccggcgc ggtggaggac   2280
gcggcccgca gcacccggga ccgggccgag gccaccccgtc tgctcgaggc cgcgacggac   2340
ggctaccggg agtgcggcgc gcgacgcgac ctggagcgcg tggaggccga gctgcgtggc   2400
ctgccggctc acaacgtccg cccgctggtc cccgaccggc cccggtcggg gtgggagagc   2460
ctgaccagcg cggagctgcg ggtcgtgcgg gccatcgtgg acgggatgac caaccgcgag   2520
gcggcgagtt cgctgttcct gtccccgcac accgtcgaca gtcacctgcg gcgcgtcttc   2580
tccaagctcg acatcaacag ccgggtggaa ctgacccgct gcttcatcgc gcacgaggcg   2640
gtccggccgg cgctggccac cacacgccag ccggcgtccg ccggctga             2688
```

<210> SEQ ID NO 8
<211> LENGTH: 362
<212> TYPE: PRT
<213> ORGANISM: Micromonospora sp. strain 046-ECO11

<400> SEQUENCE: 8

Met Thr Val Gly Tyr Leu Gly Thr Val Thr Asp Ser Ala Pro Val Asp
1               5                   10                  15

Ala Ala Leu Arg Asp Phe Phe Ala Glu Arg Ala Glu Ala Arg Glu
            20                  25                  30

Leu Gly Asp Asp Phe Ala Ala Leu Val Ala Glu Leu Glu Ser Tyr Val
        35                  40                  45

Leu Arg Gly Gly Lys Arg Ile Arg Pro Ala Phe Ala Trp Leu Gly Trp

```
                 50                  55                  60
Ile Gly Ala Gly Gly Asp Pro Glu Asp Pro Val Ala Thr Ala Val Leu
 65                  70                  75                  80

Asn Ala Cys Ala Gly Phe Glu Leu Leu His Ala Ser Gly Leu Ile His
                 85                  90                  95

Asp Asp Ile Ile Asp Ala Ser Gln Thr Arg Arg Gly His Pro Ala Ala
                100                 105                 110

His Val Ala Tyr Ala Glu Arg His Arg Ala Arg Arg Phe Ser Gly Asp
                115                 120                 125

Pro Gly Thr Phe Gly Thr Gly Thr Ala Ile Leu Ile Gly Asp Leu Val
130                 135                 140

Leu Ile Trp Ala Asp Val Leu Val Arg Ala Ser Gly Leu Pro Ala Asp
145                 150                 155                 160

Ala His Val Arg Val Ser Pro Val Trp Ser Ala Val Arg Ser Glu Val
                165                 170                 175

Met Tyr Gly Gln Leu Leu Asp Leu Ile Ser Gln Val Ser Arg Ser Glu
                180                 185                 190

Asp Val Asp Ala Ala Leu Arg Ile Asn Gln Tyr Lys Thr Ala Ser Tyr
                195                 200                 205

Thr Val Glu Arg Pro Leu Gln Phe Gly Ala Ala Ile Ala Gly Ala Asp
                210                 215                 220

Asp Asp Leu Phe Ala Ala Tyr Arg Ala Phe Gly Ala Asp Val Gly Ile
225                 230                 235                 240

Ala Phe Gln Leu Arg Asp Asp Leu Leu Gly Val Phe Gly Asp Pro Val
                245                 250                 255

Val Thr Gly Lys Pro Ser Gly Asp Asp Leu Arg Glu Gly Lys Arg Thr
                260                 265                 270

Val Leu Leu Ala Thr Ala Leu Lys Arg Ala Asp Glu Arg Asp Pro Asp
                275                 280                 285

Ala Ala Ala Tyr Leu Arg Ala Lys Val Gly Thr Asp Leu Ala Asp Glu
                290                 295                 300

Glu Ile Ala Arg Ile Arg Ala Ile Phe Arg Asp Val Gly Ala Val Glu
305                 310                 315                 320

Glu Ile Glu Arg Gln Ile Ser Gln Arg Thr Asp Arg Ala Leu Ala Ala
                325                 330                 335

Leu Glu Ala Ser Ser Ala Thr Ala Pro Ala Lys His Gln Leu Ala Asp
                340                 345                 350

Met Ala Ile Lys Ala Thr Gln Arg Ala Gln
                355                 360

<210> SEQ ID NO 9
<211> LENGTH: 1089
<212> TYPE: DNA
<213> ORGANISM: Micromonospora sp. strain 046-ECO11

<400> SEQUENCE: 9
atgaccgtcg gatatctcgg gacggtcacc gactcggcgc cgtcgacgc  cgcgctgcgc      60 gacttcttcg ccgagcgccg cgccgaggca cgcgagctcg gcgacgactt cgcggccctg     120
gtcgccgagc tggagagcta cgtcctgcgg ggcggcaagc gcatccggcc cgccttcgcc     180
tggctgggct ggatcggcgc cggcggcgac ccggaggacc cggtggcgac cgcggtgctg     240
aacgcctgcg ccgggttcga gctgctgcac gcgtccggcc tcatccacga cgacatcatc     300
gacgcgtcgc agaccgcccg cggccatccc gccgcgcacg tcgcgtacgc cgaacggcat     360
```

-continued

```
cgggcgcggc gcttctccgg tgacccggga acgttcggca ccggcaccgc catcctgatc    420
ggagacctcg tcctgatctg ggccgacgtc ctggtccgcg cctccggcct gccggccgac    480
gcgcacgtgc gggtctcgcc ggtgtggtcg gcggtgcgct ccgaggtcat gtacggccag    540
ctgctcgatc tgatcagcca ggtgagccgg agcgaggacg tcgacgcggc gctgcgcatc    600
aaccagtaca agaccgcgtc gtacacggtg gagcggccac tgcagttcgg cgcggcgatc    660
gccggcgcgg acgacgacct cttcgcgccc taccgcgcct tcggcgccga cgtgggtatt    720
gccttccagc tgcgcgacga cctgctcggc gtgttcggcg acccggtggt gacgggcaag    780
ccgtccggcg acgacctgcg ggagggcaag cggacggtcc tgctcgccac ggcgctcaag    840
cgcgccgacg aacgggaccc ggacgcggcg gcctacctgc gggcgaaggt cggcacggac    900
ctcgcggacg aggagatcgc ccgcatccgc gccatcttcc gcgacgtcgg cgcggtcgag    960
gagatcgagc ggcagatctc gcagcgcacc gaccgggcgc tggccgcgct ggaggcgagc   1020
agcgccaccg cccccgcgaa gcatcagctc gccgacatgg cgatcaaggc cacccagcgg   1080
gcccagtga                                                           1089
```

<210> SEQ ID NO 10
<211> LENGTH: 354
<212> TYPE: PRT
<213> ORGANISM: Micromonospora sp. strain 046-ECO11

<400> SEQUENCE: 10

```
Met Ser Thr Glu Pro Val Thr Val Ala Arg Gly Val Leu Asp Gly
1               5                   10                  15

Arg Gly Asp Gly Pro Gly Arg Leu Gly Thr Gly Arg Ala His Gly Lys
            20                  25                  30

Ala Ile Leu Leu Gly Glu His Ala Val Val Tyr Gly Ala Pro Ala Leu
        35                  40                  45

Ala Val Pro Val Pro Gln Leu Thr Ala Val Ala Lys Ala Arg Arg Ala
    50                  55                  60

Gly Gly Asp Gly Gly Asp Glu Val Ser Phe Ala Ile Ala Gly Leu Glu
65                  70                  75                  80

Ser Pro Glu Val Thr Ser Leu Pro Thr Asp Gly Leu Gln His Leu Val
                85                  90                  95

Thr Glu Phe Arg Gln Arg Ala Ala Val Thr Glu Pro Met Arg Val Asp
            100                 105                 110

Val Leu Val Asp Cys Ala Ile Pro Gln Gly Arg Gly Leu Gly Ser Ser
        115                 120                 125

Ala Ala Cys Ala Arg Ala Ala Val Leu Ala Leu Ala Asp Ala Phe Asp
    130                 135                 140

Arg Arg Leu Asp Ala Ala Thr Val Phe Asp Leu Val Gln Thr Ser Glu
145                 150                 155                 160

Asn Val Ala His Gly Arg Ala Ser Gly Ile Asp Ala Leu Ala Thr Gly
                165                 170                 175

Ala Thr Ala Pro Leu Ile Phe Arg Asn Gly Val Gly Arg Glu Leu Pro
            180                 185                 190

Val Ala Met Ala Gly Ala Ala Arg Ala Arg Gly Ser Gly Pro Ala
        195                 200                 205

Gly Phe Asp Ala Val Leu Val Ile Ala Asp Ser Gly Val Ser Gly Ser
    210                 215                 220

Thr Arg Asp Ala Val Glu Leu Leu Arg Gly Ala Phe Glu Arg Ser Pro
225                 230                 235                 240
```

```
Arg Thr Arg Asp Glu Phe Val Ser Arg Val Thr Ser Leu Thr Glu Ala
            245                 250                 255

Ala Ala His Asp Leu Leu Gln Gly Arg Val Ala Asp Phe Gly Ala Arg
            260                 265                 270

Leu Thr Glu Asn His Arg Leu Leu Arg Glu Val Gly Ile Ser Thr Glu
            275                 280                 285

Arg Ile Asp Arg Met Val Asp Ala Ala Leu Ala Ala Gly Ser Pro Gly
            290                 295                 300

Ala Lys Ile Ser Gly Gly Leu Gly Gly Cys Met Ile Ala Leu Ala
305             310                 315                 320

Arg Asp Arg Gln Glu Ser Ala Ala Val Val Arg Ser Val Gln Gln Ala
            325                 330                 335

Gly Ala Val Arg Thr Trp Thr Val Pro Met Gly Arg Phe Thr Gly His
            340                 345                 350

Asp Asp
```

<210> SEQ ID NO 11
<211> LENGTH: 1065
<212> TYPE: DNA
<213> ORGANISM: Micromonospora sp. strain 046-ECO11

<400> SEQUENCE: 11

```
atgtccacgg aaccggtgac cgtcgtcgcc cgcggcgttc tcgacggccg gggtgacggg      60
ccgggccgcc tcggcaccgg ccgcgcccac ggcaaggcca tcctgctggg cgaacacgcc     120
gtcgtgtacg cgctccggc gctcgccgtc ccggtgccgc aactgaccgc cgtggccaag     180
gcgcggcggg ccggcggcga cggcggcgac gaggtctcct tcgccatcgc cgggctggag     240
agcccggagg tgacgtcgct tccgaccgac ggcctgcaac atctggtgac ggagttccgg     300
cagcgggccg ccgtcaccga gccgatgcgc gtcgacgtgc tcgtggactg cgccatcccg     360
cagggccggg ggctcgggtc gagcgccgcc tgcgccgcg ccgcggtgct ggccctcgcg     420
gacgcgttcg accgccgcct cgacgccgcc acggtgttcg atctggtgca gacctcggag     480
aacgtggcgc acgccgggc cagcggcatc gacgccctgg ccaccggtgc gaccgcgccg     540
ctgatcttcc gcaacggcgt gggccgggaa ctgccggtcg ccatggcggg cgccgcgcgt     600
gccgcgcgag gtcgggccc ggccggcttc gacgcggtgc tcgtcatcgc cgacagcggc     660
gtcagcggca gcacccggga cgcggtggag ctgctgcggg gtgccttcga cgctccccg     720
cgcacgcgcg acgagttcgt cagccgggtg accagcctga ccgaggcggc ggcgcacgac     780
ctgctccagg gccgggtcgc cgacttcggc gcgcggctga ccgagaacca ccggctgttg     840
cgcgaggtcg gcatcagcac cgaacggatc gaccggatgg tcgacgccgc gctcgcggcg     900
ggcagcccgg gcgccaagat cagcggcggt ggcctgggcg gctgcatgat cgcactggcc     960
cgggaccgcc aggaatccgc ggcggtggtg cggagcgtcc agcaggccgg cgccgtccgc    1020
acctggaccg tcccgatggg gaggttcacc ggccatgacg actga                   1065
```

<210> SEQ ID NO 12
<211> LENGTH: 346
<212> TYPE: PRT
<213> ORGANISM: Micromonospora sp. strain 046-ECO11

<400> SEQUENCE: 12

```
Met Thr Thr Asp His Arg Ala Glu Pro Ser Glu Pro Ala Leu Asp Arg
1               5                   10                  15

Pro Ala Thr Ala Val Ala His Pro Asn Ile Ala Leu Ile Lys Tyr Trp
```

```
                    20                  25                  30
Gly Lys Arg Asp Glu Gln Leu Met Ile Pro Tyr Ala Asp Ser Leu Ser
         35                  40                  45
Met Thr Leu Asp Val Phe Pro Thr Thr Thr Val Arg Ile Asp Ser
 50                  55                  60
Gly Ala Ala Asp Glu Val Val Leu Asp Gly Ser Pro Ala Asp Gly
 65                  70                  75                  80
Glu Arg Arg Gln Arg Val Val Thr Phe Leu Asp Leu Val Arg Lys Leu
                 85                  90                  95
Ala Gly Arg Thr Glu Arg Ala Cys Val Asp Thr Arg Asn Ser Val Pro
            100                 105                 110
Thr Gly Ala Gly Leu Ala Ser Ser Ala Ser Gly Phe Ala Ala Leu Ala
            115                 120                 125
Leu Ala Gly Ala Ala Ala Tyr Gly Leu Asp Leu Asp Thr Thr Ala Leu
            130                 135                 140
Ser Arg Leu Ala Arg Arg Gly Ser Val Ser Ala Ser Arg Ser Val Phe
145                 150                 155                 160
Gly Gly Phe Ala Met Cys His Ala Gly Pro Gly Ala Gly Thr Ala Ala
                165                 170                 175
Asp Leu Gly Ser Tyr Ala Glu Pro Val Pro Val Ala Pro Leu Asp Val
            180                 185                 190
Ala Leu Val Ile Ala Ile Val Asp Ala Gly Pro Lys Ala Val Ser Ser
            195                 200                 205
Arg Glu Gly Met Arg Arg Thr Val Arg Thr Ser Pro Leu Tyr Gln Ser
            210                 215                 220
Trp Val Ala Ser Gly Arg Ala Asp Leu Ala Glu Met Arg Ala Ala Leu
225                 230                 235                 240
Leu Gln Gly Asp Leu Asp Ala Val Gly Glu Ile Ala Glu Arg Asn Ala
                245                 250                 255
Leu Gly Met His Ala Thr Met Leu Ala Ala Arg Pro Ala Val Arg Tyr
            260                 265                 270
Leu Ala Pro Val Thr Val Ala Val Leu Asp Ser Val Leu Arg Leu Arg
            275                 280                 285
Ala Asp Gly Val Ser Ala Tyr Ala Thr Met Asp Ala Gly Pro Asn Val
            290                 295                 300
Lys Val Leu Cys Arg Arg Ala Asp Ala Asp Arg Val Ala Asp Thr Leu
305                 310                 315                 320
Arg Asp Ala Ala Pro Ser Cys Ala Val Val Ala Gly Pro Gly Pro
                325                 330                 335
Ala Ala Arg Pro Asp Pro Gly Ser Arg Pro
            340                 345
```

<210> SEQ ID NO 13
<211> LENGTH: 1041
<212> TYPE: DNA
<213> ORGANISM: Micromonospora sp. strain 046-ECO11

<400> SEQUENCE: 13

```
atgacgactg accaccgggc ggagccgtcc gagccggcgc tcgaccggcc cgcgaccgcc    60
gtggcccatc cgaacatcgc gctgatcaag tactggggca agcgcgacga gcagctgatg   120
atcccgtacg ccgacagcct gtcgatgacg ctcgacgtct tcccgaccac caccaccgtc   180
cggatcgaca gcggcgcggc ggccgacgag gtcgtcctcg acggctcgcc cgccgacggc   240
gaacggcgac agcgcgtcgt caccttcctg gacctggtac gcaagctggc cgggcgcacg   300
```

```
gaacgggcct gcgtcgacac ccgcaactcc gtgcccaccg gcgccggcct ggcgtcctcg      360
gcgagcggat tcgccgccct cgccctcgcc ggcgccgccg cgtacggcct cgacctggac      420
accaccgcgc tgtcccgcct ggccggcgg ggatccgtgt cggcctcccg gtcggtcttc       480
ggcggcttcg cgatgtgcca cgcaggcccc ggcgccggga ccgccgcgga cctcggctcc      540
tacgccgagc cggtgcccgt cgcgcccctc gacgtcgcgc tggtgatcgc gatcgtcgac      600
gccgggccga aggcggtgtc gagccgcgag gggatgcggc gaaccgtccg gacctccccg      660
ctctatcagt cgtgggtcgc ctccggccgc gccgacctgg ccgagatgcg ggccgcgctg      720
ctccagggag acctggacgc ggtcggcgag atcgccgaac gcaacgccct cggcatgcac      780
gccaccatgc tggccgcccg gccggcggtg cgctacctgg cgccggtcac tgtcgccgtg      840
ctcgacagcg tgctgcgcct gcgcgccgac ggcgtctccg cctacgccac gatggacgcg      900
ggaccgaacg tcaaggtgct ctgccgccgc gcggacgccg accgggtcgc cgacaccctg      960
cgcgacgccg cgccgagctg cgccgtggtc gtcgccggac cggggccggc ggcccggccg     1020
gacccgggca gccggccgtg a                                               1041

<210> SEQ ID NO 14
<211> LENGTH: 369
<212> TYPE: PRT
<213> ORGANISM: Micromonospora sp. strain 046-ECO11

<400> SEQUENCE: 14

Val Thr Gly Pro Gly Ala Val Arg Arg His Ala Pro Gly Lys Leu Phe
1               5                   10                  15

Val Ala Gly Glu Tyr Ala Val Leu Glu Pro Gly His Pro Ala Leu Leu
            20                  25                  30

Val Ala Val Asp Arg Gly Val Asp Val Thr Val Ser Gly Ala Asp Ala
        35                  40                  45

His Leu Val Val Asp Ser Asp Leu Cys Pro Glu Gln Ala Cys Leu Arg
    50                  55                  60

Trp Gln Asp Gly Arg Leu Val Gly Ala Gly Asp Gly Gln Pro Ala Pro
65                  70                  75                  80

Asp Ala Leu Gly Ala Val Val Ser Ala Ile Glu Val Val Gly Glu Leu
                85                  90                  95

Leu Thr Gly Arg Gly Leu Arg Pro Leu Pro Met Arg Val Ala Ile Thr
            100                 105                 110

Ser Arg Leu His Arg Asp Gly Thr Lys Phe Gly Leu Gly Ser Ser Gly
        115                 120                 125

Ala Val Thr Val Ala Thr Val Thr Ala Val Ala Tyr His Gly Val
    130                 135                 140

Glu Leu Ser Leu Glu Ser Arg Phe Arg Leu Ala Met Leu Ala Thr Val
145                 150                 155                 160

Arg Asp Gly Ala Asp Ala Ser Gly Gly Asp Leu Ala Ala Ser Val Trp
                165                 170                 175

Gly Gly Trp Ile Ala Tyr Gln Ala Pro Asp Arg Ala Ala Val Arg Glu
            180                 185                 190

Met Ala Arg Arg Arg Gly Val Glu Glu Thr Met Arg Ala Pro Trp Pro
        195                 200                 205

Gly Leu Arg Val Arg Arg Leu Pro Pro Arg Gly Leu Ala Leu Glu
    210                 215                 220

Val Gly Trp Thr Gly Glu Pro Ala Ser Ser Ser Ser Leu Thr Gly Arg
225                 230                 235                 240
```

Leu Ala Ala Ser Arg Trp Arg Gly Ser Pro Ala Arg Trp Ser Phe Thr
            245                 250                 255

Ser Arg Ser Gln Glu Cys Val Arg Thr Ala Ile Asp Ala Leu Glu Arg
            260                 265                 270

Gly Asp Gln Glu Leu Leu His Gln Val Arg Ala Arg His Val
            275                 280                 285

Leu Ala Glu Leu Asp Asp Glu Val Arg Leu Gly Ile Phe Thr Pro Arg
        290                 295                 300

Leu Thr Ala Leu Cys Asp Ala Ala Glu Thr Val Gly Gly Ala Ala Lys
305                 310                 315                 320

Pro Ser Gly Ala Gly Gly Asp Cys Gly Ile Ala Leu Leu Asp Ala
                325                 330                 335

Thr Ala Ala Thr Arg Thr Ala Arg Leu Arg Glu Gln Trp Ala Ala Ala
            340                 345                 350

Gly Val Leu Pro Met Pro Ile Gln Val His Gln Thr Asn Gly Ser Ala
            355                 360                 365

Arg

<210> SEQ ID NO 15
<211> LENGTH: 1110
<212> TYPE: DNA
<213> ORGANISM: Micromonospora sp. strain 046-ECO11

<400> SEQUENCE: 15
gtgaccggcc cgggcgccgt gcgccgccac gcgccgggca agctgttcgt cgccggtgag      60
tacgcggtgc tggagccggg ccacccggcg ctgctggtgg cggtcgacag gggagtggac     120
gtcaccgtct ccggcgccga cgcccacctc gttgtcgact ccgacctctg cccggagcag     180
gcgtgcctgc ggtggcagga cggccggctc gtcggcgcgg cgacgggca gccggcgccc      240 gacgccctcg cgccgtggt ctcggcgatc gaggtggtcg cgaactcct gaccggacga       300 gggctgcgcc cgctgcccat gcgggtggcg atcaccagcc ggctgcaccg cgacggcacg     360
aagttcggcc tcgggtcgag cggggcgtg acagtcgcca cggtgaccgc agtggccgcg      420
taccacgggg tggagctgtc gctcgaatcg cggttccggc tggcgatgct ggcgacggtg     480
cgtgacggcg ccgacgcctc cggcggtgat ctggccgcga cgtctgggg cggctggatc      540 gcctaccagg cgcccgaccg cgcggccgtg cgcgagatgg cgcggcggcg cggcgtcgag     600
gagacgatgc gcgcgccctg gccgggcctg cgggtccggc ggctgccacc accgcgtggc    660
ctcgcgctgg aggtgggctg gaccggcgag ccggcgagca gcagctcgtt gaccgggcgg    720
ctggccgcct cccggtggcg gggcagcccg gcgcggtgga gcttcaccag ccgtagccag    780
gagtgtgtgc gtaccgccat cgacgcgctg gagcggggcg acgaccagga actgctgcac    840
caggtccggc gggcccggca cgtgcttgcc gagctggacg acgaggtccg gctcgggatc    900 ttcaccccc ggctgacggc gctgtgcgac gccgccgaga ccgtcggcgg cgcggccaaa    960
ccgtccggcg ccggtggcgg ggactgcggc atcgcgttgc tggacgccac cgccgcgacg   1020
cggaccgcgc ggctgcgcga gcagtgggcc gccgccgggg tgctccccat gccgatccag   1080
gtccatcaga cgaacgggag cgcgcgatga                                    1110

<210> SEQ ID NO 16
<211> LENGTH: 360
<212> TYPE: PRT
<213> ORGANISM: Micromonospora sp. strain 046-ECO11

```
<400> SEQUENCE: 16

Met Ile Ala Asn Arg Lys Asp Asp His Val Arg Leu Ala Ala Glu Gln
1               5                   10                  15

Gln Gly Arg Leu Gly Gly His His Glu Phe Asp Asp Val Ser Phe Val
            20                  25                  30

His His Ala Leu Ala Gly Ile Asp Arg Ser Asp Val Ser Leu Ala Thr
        35                  40                  45

Ser Phe Gly Gly Ile Asp Trp Pro Val Pro Leu Cys Ile Asn Ala Met
    50                  55                  60

Thr Gly Gly Ser Thr Lys Thr Gly Leu Ile Asn Arg Asp Leu Ala Ile
65                  70                  75                  80

Ala Ala Arg Glu Thr Gly Val Pro Ile Ala Thr Gly Ser Met Ser Ala
                85                  90                  95

Tyr Phe Ala Asp Glu Ser Val Ala Glu Ser Phe Ser Val Met Arg Arg
            100                 105                 110

Glu Asn Pro Asp Gly Phe Ile Met Ala Asn Val Asn Ala Thr Ala Ser
        115                 120                 125

Val Glu Arg Ala Arg Arg Ala Val Asp Leu Met Arg Ala Asp Ala Leu
130                 135                 140

Gln Ile His Leu Asn Thr Ile Gln Glu Thr Val Met Pro Glu Gly Asp
145                 150                 155                 160

Arg Ser Phe Ala Ala Trp Gly Pro Arg Ile Glu Gln Ile Val Ala Gly
                165                 170                 175

Val Gly Val Pro Val Ile Val Lys Glu Val Gly Phe Gly Leu Ser Arg
            180                 185                 190

Glu Thr Leu Leu Arg Leu Arg Asp Met Gly Val Arg Val Ala Asp Val
        195                 200                 205

Ala Gly Arg Gly Gly Thr Asn Phe Ala Arg Ile Glu Asn Asp Arg Arg
210                 215                 220

Asp Ala Ala Asp Tyr Ser Phe Leu Asp Gly Trp Gly Gln Ser Thr Pro
225                 230                 235                 240

Ala Cys Leu Leu Asp Ala Gln Gly Val Asp Leu Pro Val Leu Ala Ser
                245                 250                 255

Gly Gly Ile Arg Asn Pro Leu Asp Val Val Arg Gly Leu Ala Leu Gly
            260                 265                 270

Ala Gly Ala Ala Gly Val Ser Gly Leu Phe Leu Arg Thr Leu Leu Asp
        275                 280                 285

Gly Gly Val Pro Ala Leu Leu Ser Leu Ser Thr Trp Leu Asp Gln
290                 295                 300

Ile Glu Ala Leu Met Thr Ala Leu Gly Ala Arg Thr Pro Ala Asp Leu
305                 310                 315                 320

Thr Arg Cys Asp Leu Leu Ile Gln Gly Arg Leu Ser Ala Phe Cys Ala
                325                 330                 335

Ala Arg Gly Ile Asp Thr His Arg Leu Ala Thr Arg Ser Gly Ala Thr
            340                 345                 350

His Glu Met Ile Gly Gly Ile Arg
        355                 360

<210> SEQ ID NO 17
<211> LENGTH: 1083
<212> TYPE: DNA
<213> ORGANISM: Micromonospora sp. strain 046-ECO11

<400> SEQUENCE: 17
```

```
atgatcgcca accgcaagga cgaccacgtc cggctcgccg ccgagcagca gggccggctc    60
ggcggtcacc acgagttcga cgacgtgtcc ttcgtgcacc acgccctggc cggcatcgac   120
cggtccgacg tctcgctggc cacgtcgttc ggcggcatcg actggccggt gccgctgtgc   180
atcaacgcga tgaccggcgg cagcaccaag accggcctga tcaaccggga cctggcgatc   240
gcggcccggg agaccggcgt accgatcgcc accgggtcga tgagcgccta cttcgccgac   300
gagtcggtgg ccgagagttt cagcgtgatg cgccgggaga accccgacgg gttcatcatg   360
gccaacgtca acgccaccgc ctccgtcgaa cgggcccggc gggctgtcga cctgatgcgg   420
gccgacgcgc tgcagatcca cctgaacacc atccaggaga cggtgatgcc ggaggggac    480
cggtcgttcg ccgcctgggg gccgcggatc gaacagatcg tcgccggcgt cggtgtgccg   540
gtgatcgtca aggaggtcgg cttcgggctc agccgcgaaa cgctgctgcg gctgcgggac   600
atgggcgtcc gggtggccga cgtcgccggc gcggcggca cgaacttcgc gcgcatcgag    660
aacgaccggc gggacgccgc cgactactcc ttcctcgacg ggtggggaca gtcgacaccc   720
gcctgcctgc tggacgccca gggcgtggac ctgcccgtgc tggcctccgg cggcatccgc   780
aacccgctcg acgtggtccg cgggctggcg ctcggcgccg gcgcggccgg ggtgtccgga   840
ctgttcctgc gcacgctcct ggacggcggc gtgccggcgc tgctgtcgct gctgtccacc   900
tggctcgacc agatcgaagc cctgatgacc gccctgggcg cgcggacccc ggccgacctg   960
acccgctgcg acctgctgat ccagggtcgg ctgagcgcgt tctgcgcggc ccggggcatc  1020
gacacccacc gcctcgccac ccgttccggc gccacccacg agatgatcgg aggcattcga  1080
tga                                                                1083
```

<210> SEQ ID NO 18
<211> LENGTH: 351
<212> TYPE: PRT
<213> ORGANISM: Micromonospora sp. strain 046-ECO11

<400> SEQUENCE: 18

```
Met Asn Asp Ala Ile Ala Gly Val Pro Met Lys Trp Val Gly Pro Val
1               5                   10                  15

Arg Ile Ser Gly Asn Val Ala Gln Ile Glu Thr Glu Val Pro Leu Ala
            20                  25                  30

Thr Tyr Glu Ser Pro Leu Trp Pro Ser Val Gly Arg Gly Ala Lys Ile
        35                  40                  45

Ser Arg Met Val Glu Ala Gly Ile Val Ala Thr Leu Val Asp Glu Arg
    50                  55                  60

Met Thr Arg Ser Val Phe Val Arg Ala Lys Asp Ala Gln Thr Ala Tyr
65                  70                  75                  80

Leu Ala Ser Leu Glu Val Asp Ala Arg Phe Asp Glu Leu Arg Asp Ile
                85                  90                  95

Val Arg Thr Cys Gly Arg Phe Val Glu Leu Ile Gly Phe His His Glu
            100                 105                 110

Ile Thr Ala Asn Leu Leu Phe Leu Arg Phe Ser Phe Thr Thr Gly Asp
        115                 120                 125

Ala Ser Gly His Asn Met Ala Thr Leu Ala Ala Asp Ala Leu Leu Lys
    130                 135                 140

His Ile Leu Asp Thr Ile Pro Gly Ile Ser Tyr Gly Ser Ile Ser Gly
145                 150                 155                 160

Asn Tyr Cys Thr Asp Lys Lys Ala Thr Ala Ile Asn Gly Ile Leu Gly
                165                 170                 175
```

```
Arg Gly Lys Asn Val Val Thr Glu Leu Val Val Pro Arg Glu Ile Val
                180                 185                 190

His Asp Ser Leu His Thr Thr Ala Ala Ile Ala Gln Leu Asn Val
            195                 200                 205

His Lys Asn Met Ile Gly Thr Leu Leu Ala Gly Gly Ile Arg Ser Ala
        210                 215                 220

Asn Ala His Tyr Ala Asn Met Leu Leu Gly Phe Tyr Leu Ala Thr Gly
225                 230                 235                 240

Gln Asp Ala Ala Asn Ile Val Glu Gly Ser Gln Gly Val Thr Val Ala
                245                 250                 255

Glu Asp Arg Asp Gly Asp Leu Tyr Phe Ser Cys Thr Leu Pro Asn Leu
            260                 265                 270

Ile Val Gly Thr Val Gly Asn Gly Lys Gly Leu Gly Phe Val Glu Glu
        275                 280                 285

Asn Leu Glu Arg Leu Gly Cys Arg Ala Ser Arg Asp Pro Gly Glu Asn
    290                 295                 300

Ala Arg Arg Leu Ala Val Ile Ala Ala Thr Val Leu Cys Gly Glu
305                 310                 315                 320

Leu Ser Leu Leu Ala Ala Gln Thr Asn Pro Gly Glu Leu Met Arg Ala
                325                 330                 335

His Val Arg Leu Glu Arg Pro Thr Glu Thr Thr Lys Ile Gly Ala
            340                 345                 350

<210> SEQ ID NO 19
<211> LENGTH: 1056
<212> TYPE: DNA
<213> ORGANISM: Micromonospora sp. strain 046-ECO11

<400> SEQUENCE: 19
atgaacgacg cgatcgccgg tgtgcccatg aaatgggtag gtcccgtgcg atctcggga      60
aacgtggcgc agatcgagac ggaggttccg ctcgccacgt acgagtcgcc gctctggccg    120
tccgtcggcc ggggcgcgaa gatctcccgg atggtcgagg cgggcatcgt cgccacgctc    180
gtcgacgagc gcatgacccg ctcggtgttc gtgcgcgcca aggacgcgca gaccgcctac    240
ctggcctcgc ttgaggtcga cgcgcggttc gacgaactgc gtgacatcgt gcgcacctgc    300
ggcaggttcg tcgagctgat cgggttccac cacgagatca ccgcgaacct gctgttcctg    360
cggttcagtt tcaccaccgg cgacgcgtcc gggcacaaca tggcgacgct ggccgccgac    420
gcgctgctga agcacatcct ggacaccatt ccgggcatct cgtacggctc gatctcgggc    480
aactactgca ccgacaagaa ggccaccgcg ataaacggca ttctcggccg gggcaagaac    540
gtggtcaccg agctggtcgt gccgcgggag atcgtccacg acagcctgca cacgacggcg    600
gcggcgatcg cccagctgaa cgtgcacaag aacatgatcg gcacgttgct cgccggcggt    660
atccgctcgg ccaacgccca ctacgcgaac atgctgctcg gttctacct ggccacgggt     720
caggacgccg cgaacatcgt cgagggctcc cagggcgtga cggtcgccga ggaccgcgac    780
ggcgacctct acttctcctg cacgctgccc aacctgatcg tgggcaccgt cggcaacggc    840
aaggggctcg gcttcgtcga ggagaacctg gagcggctcg gctgccgcgc ctcgcgtgat    900
ccgggcgaga cgccggcg ctcgcggtc atcgcggccg cgacggtgct ctgcggcgag      960
ctgtccctgc tcgccgcgca gaccaacccg ggcgagctga tgcgggcgca cgtccggctc   1020
gaacgcccga ccgagaccac gaagatcgga gcctga                              1056

<210> SEQ ID NO 20
```

```
<211> LENGTH: 391
<212> TYPE: PRT
<213> ORGANISM: Micromonospora sp. strain 046-ECO11

<400> SEQUENCE: 20
```

| | | | | | | | | | | | | | | |
|---|---|---|---|---|---|---|---|---|---|---|---|---|---|---|
| Met | Ala | Glu | Arg | Pro | Ala | Val | Gly | Ile | His | Asp | Leu | Ser | Ala | Ala | Thr |
| 1 | | | | 5 | | | | | 10 | | | | | 15 |

| Ala | His | His | Val | Leu | Thr | His | Glu | Thr | Leu | Ala | Ala | Ser | Asn | Gly | Ala |
| | | | 20 | | | | | 25 | | | | | 30 | | |

| Asp | Val | Ala | Lys | Tyr | His | Arg | Gly | Ile | Gly | Leu | Arg | Ala | Met | Ser | Val |
| | | | 35 | | | | | 40 | | | | | 45 | | |

| Pro | Ala | Pro | Asp | Glu | Asp | Ile | Val | Thr | Met | Ala | Ala | Ala | Ala | Ala | Ala |
| 50 | | | | | 55 | | | | | 60 | | | | | |

| Pro | Val | Val | Ala | Arg | His | Gly | Thr | Asp | Arg | Ile | Arg | Thr | Val | Val | Phe |
| 65 | | | | | 70 | | | | | 75 | | | | | 80 |

| Ala | Thr | Glu | Ser | Ser | Val | Asp | Gln | Ala | Lys | Ala | Ala | Gly | Ile | His | Val |
| | | | | 85 | | | | | 90 | | | | | 95 | |

| His | Ser | Leu | Leu | Gly | Leu | Pro | Ser | Ala | Thr | Arg | Val | Val | Glu | Leu | Lys |
| | | | | 100 | | | | | 105 | | | | | 110 | |

| Gln | Ala | Cys | Tyr | Gly | Gly | Thr | Ala | Gly | Leu | Gln | Phe | Ala | Ile | Gly | Leu |
| | | | | 115 | | | | | 120 | | | | | 125 | |

| Val | His | Arg | Asp | Pro | Ser | Gln | Gln | Val | Leu | Val | Ile | Ala | Ser | Asp | Val |
| | 130 | | | | | 135 | | | | | 140 | | | | |

| Ser | Lys | Tyr | Ala | Leu | Gly | Glu | Pro | Gly | Glu | Ala | Thr | Gln | Gly | Ala | Ala |
| 145 | | | | | 150 | | | | | 155 | | | | | 160 |

| Ala | Val | Ala | Met | Leu | Val | Gly | Ala | Asp | Pro | Ala | Leu | Val | Arg | Val | Glu |
| | | | | 165 | | | | | 170 | | | | | 175 | |

| Asp | Pro | Ser | Gly | Met | Phe | Thr | Ala | Asp | Val | Met | Asp | Phe | Trp | Arg | Pro |
| | | | 180 | | | | | 185 | | | | | 190 | | |

| Asn | Tyr | Arg | Thr | Thr | Ala | Leu | Val | Asp | Gly | His | Glu | Ser | Ile | Ser | Ala |
| | | | 195 | | | | | 200 | | | | | 205 | | |

| Tyr | Leu | Gln | Ala | Leu | Glu | Gly | Ser | Trp | Lys | Asp | Tyr | Thr | Glu | Arg | Gly |
| | 210 | | | | | 215 | | | | | 220 | | | | |

| Gly | Arg | Thr | Leu | Asp | Glu | Phe | Gly | Ala | Phe | Cys | Tyr | His | Gln | Pro | Phe |
| 225 | | | | | 230 | | | | | 235 | | | | | 240 |

| Pro | Arg | Met | Ala | Asp | Lys | Ala | His | Arg | His | Leu | Leu | Asn | Tyr | Cys | Gly |
| | | | | 245 | | | | | 250 | | | | | 255 | |

| Arg | Asp | Val | Asp | Asp | Ala | Leu | Val | Ala | Gly | Ala | Ile | Gly | His | Thr | Thr |
| | | | 260 | | | | | 265 | | | | | 270 | | |

| Ala | Tyr | Asn | Ala | Glu | Ile | Gly | Asn | Ser | Tyr | Thr | Ala | Ser | Met | Tyr | Leu |
| | | | 275 | | | | | 280 | | | | | 285 | | |

| Gly | Leu | Ala | Ala | Leu | Leu | Asp | Thr | Ala | Asp | Leu | Thr | Gly | Arg | Thr |
| | 290 | | | | | 295 | | | | | 300 | | | | |

| Val | Gly | Phe | Leu | Ser | Tyr | Gly | Ser | Gly | Ser | Val | Ala | Glu | Phe | Phe | Ala |
| 305 | | | | | 310 | | | | | 315 | | | | | 320 |

| Gly | Thr | Val | Val | Pro | Gly | Tyr | Arg | Ala | His | Thr | Arg | Pro | Asp | Gln | His |
| | | | | 325 | | | | | 330 | | | | | 335 | |

| Arg | Ala | Ala | Ile | Asp | Arg | Arg | Gln | Glu | Ile | Asp | Tyr | Ala | Thr | Tyr | Arg |
| | | | 340 | | | | | 345 | | | | | 350 | | |

| Glu | Leu | His | Glu | His | Ala | Phe | Pro | Val | Asp | Gly | Gly | Asp | Tyr | Pro | Ala |
| | | | 355 | | | | | 360 | | | | | 365 | | |

| Pro | Glu | Val | Thr | Thr | Gly | Pro | Tyr | Arg | Leu | Ala | Gly | Leu | Ser | Gly | His |
| | 370 | | | | | 375 | | | | | 380 | | | | |

| Lys | Arg | Val | Tyr | Glu | Pro | Arg |

-continued

```
385             390
```

<210> SEQ ID NO 21
<211> LENGTH: 1176
<212> TYPE: DNA
<213> ORGANISM: Micromonospora sp. strain 046-ECO11

<400> SEQUENCE: 21

```
atggccgaga gacccgccgt cggcatccac gacctgtccg ccgcgacggc gcatcacgtg    60
ctgacacacg agaccctggc cgcgagcaac ggcgccgacg tggccaagta ccaccgtggc   120
atcgggctgc gggcgatgag cgtgcccgcc ccggacgagg acatcgtgac gatggctgct   180
gccgccgccg cgccggtggt cgcccgccac ggcaccgacc ggatccggac cgtcgtgttc   240
gccacggagt cgtcggtcga ccaggcgaag gcggccggga tacacgtcca ctccctgctc   300
ggcctcccct cggccacccg ggtggtcgag ctgaagcagg cctgctacgg cggtacggcg   360
ggactgcagt tcgccatcgg cctggtgcac cgtgaccccgt cgcagcaggt cctggtgatc   420
gccagcgacg tgtcgaagta cgcgctgggt gagcccggcg aggcgaccca gggcgccgcg   480
gcggtcgcca tgctcgtcgg cgcggacccc gcgctggtac gcgtcgagga cccgtcgggc   540
atgttcaccg ccgacgtcat ggacttctgg cggccgaact accgcaccac cgccctggtc   600
gacgggcacg agtccatctc cgcctacctg caggcgctgg agggctcgtg aaggactac   660
accgagcgcg gcggtcgcac cctggacgag ttcggcgcgt tctgctacca ccagccgttc   720
ccgaggatgg ccgacaaggc gcaccggcac ctgctcaact actgcgggcg cgacgtcgac   780
gacgcgctgg tggccggggc catcgggcac accaccgcgt acaacgccga gatcggcaac   840
agctacacgg cgtcgatgta tctcgggctc gcggcactgc tcgacaccgc cgacgacctg   900
accggccgga ccgtcggctt cctcagctac gggtccggca gcgtcgccga gttcttcgcc   960
ggcactgtcg tgcccgggta ccgcgcgcac acgcgacccg accagcaccg cgcggcgatc  1020
gaccggcggc aggagatcga ctacgcgacg taccgggagt gcacgagca cgccttcccg  1080
gtcgacggcg cgactatcc ggcgccggag gtgaccaccg gccgtaccg gctggccggg  1140
ctctccggtc acaagcgcgt ctacgagccg cgatag                              1176
```

<210> SEQ ID NO 22
<211> LENGTH: 290
<212> TYPE: PRT
<213> ORGANISM: Micromonospora sp. strain 046-ECO11

<400> SEQUENCE: 22

```
Val Ala Glu Leu Tyr Ser Thr Ile Glu Glu Ser Ala Arg Gln Leu Asp
 1               5                  10                  15

Val Pro Cys Ser Arg Asp Arg Val Trp Pro Ile Leu Ser Ala Tyr Gly
            20                  25                  30

Asp Ala Phe Ala His Pro Glu Ala Val Val Ala Phe Arg Val Ala Thr
        35                  40                  45

Ala Leu Arg His Ala Gly Glu Leu Asp Cys Arg Phe Arg Thr His Pro
    50                  55                  60

Asp Asp Arg Asp Pro Tyr Ala Ser Ala Leu Ala Arg Gly Leu Thr Pro
65                  70                  75                  80

Arg Thr Asp His Pro Val Gly Ala Leu Leu Ser Glu Val His Arg Arg
                85                  90                  95

Cys Pro Val Glu Ser His Gly Ile Asp Phe Gly Val Val Gly Gly Phe
            100                 105                 110
```

```
Lys Lys Ile Tyr Ala Ala Phe Ala Pro Asp Glu Leu Gln Val Ala Thr
            115                 120                 125

Ser Leu Ala Gly Ile Pro Ala Met Pro Arg Ser Leu Ala Ala Asn Ala
    130                 135                 140

Asp Phe Phe Thr Arg His Gly Leu Asp Asp Arg Val Gly Val Leu Gly
145                 150                 155                 160

Phe Asp Tyr Pro Ala Arg Thr Val Asn Val Tyr Phe Asn Asp Val Pro
                165                 170                 175

Arg Glu Cys Phe Glu Pro Glu Thr Ile Arg Ser Thr Leu Arg Arg Thr
            180                 185                 190

Gly Met Ala Glu Pro Ser Glu Gln Met Leu Arg Leu Gly Thr Gly Ala
        195                 200                 205

Phe Gly Leu Tyr Val Thr Leu Gly Trp Asp Ser Pro Glu Ile Glu Arg
    210                 215                 220

Ile Cys Tyr Ala Ala Thr Thr Asp Leu Thr Thr Leu Pro Val Pro
225                 230                 235                 240

Val Glu Pro Glu Ile Glu Lys Phe Val Lys Ser Val Pro Tyr Gly Gly
                245                 250                 255

Gly Asp Arg Lys Phe Val Tyr Gly Val Ala Leu Thr Pro Lys Gly Glu
            260                 265                 270

Tyr Tyr Lys Leu Glu Ser His Tyr Lys Trp Lys Pro Gly Ala Val Asn
    275                 280                 285

Phe Ile
    290

<210> SEQ ID NO 23
<211> LENGTH: 873
<212> TYPE: DNA
<213> ORGANISM: Micromonospora sp. strain 046-ECO11

<400> SEQUENCE: 23
gtggccgagc tctactcgac catcgaggaa tcggcccggc aactggacgt gccgtgttcg      60
cgcgaccggg tctggcccat cctgtccgcg tacggcgacg cgttcgccca tcccgaggcg     120
gtggtcgcct tccgggtggc gaccgcgctg cgtcacgcgg gcgagctgga ctgccggttc     180
cggacgcatc cggacgaccg ggacccgtac gcctcggcgc tcgcccgggg cctcaccccg     240
cgcacggacc accccgtcgg cgcgctgctc tccgaggtcc accggcgctg cccggtggag     300
agccacggca tcgacttcgg ggtggtcggc ggcttcaaga agatctacgc ggccttcgcc     360
ccggacgagc tgcaggtggc cacgtcgctc gccggcattc cggcgatgcc ccgcagcctc     420
gccgcgaacg ccgacttctt cacccggcac ggcctcgacg accgggtcgg cgtgctggga     480
ttcgactacc cggcccggac cgtgaacgtc tacttcaacg acgtgccgcg tgagtgcttc     540
gagccggaga ccatccggtc gacgctgcgc cggaccggga tggccgagcc gagcgagcag     600
atgctccggc tcggcaccgg ggcgttcggg ctctacgtca cgctgggctg ggactccccg     660
gagatcgagc ggatctgcta cgccgcggcg accacggacc tgaccacgct tccggtaccc     720
gtggaaccgg agatcgagaa gttcgtgaaa agcgttccgt acggcggcgg ggaccggaag     780
ttcgtctacg gcgtggcgct gaccccccaag ggggagtact acaaactcga gtcgcactac     840
aaatggaagc cgggcgcggt gaacttcatt tga                                  873

<210> SEQ ID NO 24
<211> LENGTH: 370
<212> TYPE: PRT
<213> ORGANISM: Micromonospora sp. strain 046-ECO11
```

<400> SEQUENCE: 24

```
Val Trp Ala Arg Val Lys Asn Trp Val Val Ala Leu Ala Val Ala Ala
1               5                   10                  15
Val Leu Met Ile Ser Ala Leu Ala Gly Asp His Pro Ala Pro Glu Gly
            20                  25                  30
Leu Gly Leu Leu Gly Phe Ala Leu Val Ala Ala Ser Gly Leu Ala Leu
        35                  40                  45
Ala Ala Ser Arg Arg Ala Pro Ile Ala Val Leu Val Ala Thr Gly Leu
    50                  55                  60
Cys Val Val Gly Tyr Asn Ala Ile Gly Phe Gly Val Pro Ala Ile Ala
65                  70                  75                  80
Tyr Leu Phe Ala Val Tyr Ala Ala Val Arg Ala Gly His Arg Leu Val
                85                  90                  95
Thr Leu Gly Ala Ser Ala Ala Leu Leu Val Val Leu Pro Leu Ala Ile
            100                 105                 110
Met Val Ser Pro Ala Asp Gly Ala Leu Lys Glu Ala Leu Ala Gln Ser
        115                 120                 125
Arg Gly Val Leu Glu Leu Ala Trp Leu Ile Ala Ala Ala Ala Ala Gly
    130                 135                 140
Glu Ala Leu Arg Gln Ala Glu Arg Arg Ala Asp Glu Ala Glu Arg Thr
145                 150                 155                 160
Arg Glu Glu Thr Ala Arg Leu Arg Ala Thr Gln Glu Arg Leu His Ile
                165                 170                 175
Ala Arg Glu Leu His Asp Ser Leu Thr His Gln Ile Ser Ile Ile Lys
            180                 185                 190
Val Gln Ala Glu Val Ala Val His Leu Ala Arg Lys Arg Gly Glu Gln
        195                 200                 205
Val Pro Glu Ser Leu Leu Ala Ile Gln Glu Ala Gly Arg Ala Ala Thr
    210                 215                 220
Arg Glu Leu Arg Ala Thr Leu Glu Thr Leu Arg Asp Leu Thr Lys Ser
225                 230                 235                 240
Pro Ser His Gly Leu Asp His Leu Pro Glu Leu Leu Ala Gly Ala Glu
                245                 250                 255
Lys Ile Gly Leu Ala Thr Thr Leu Thr Ile Glu Gly Asp Gln Arg Asp
            260                 265                 270
Val Pro Glu Ala Val Gly Arg Thr Ala Tyr Arg Ile Val Gln Glu Ser
        275                 280                 285
Leu Thr Asn Thr Ala Arg His Ala Ser Ala Ala Ala Ala Val Arg
    290                 295                 300
Ile Asp Tyr Arg Pro Asp Ala Leu Ser Ile Arg Ile Asp Asp Gly
305                 310                 315                 320
Thr Ala Arg Pro Gly Ala Ala Pro Val Pro Gly Val Gly Leu Leu Gly
                325                 330                 335
Met His Glu Arg Val Leu Ala Leu Gly Gly Arg Leu Arg Ala Glu Pro
            340                 345                 350
Arg Thr Gly Gly Gly Phe Thr Val Gln Ala Glu Leu Pro Val Val Arg
        355                 360                 365
Val Pro
    370
```

<210> SEQ ID NO 25
<211> LENGTH: 1113
<212> TYPE: DNA

<213> ORGANISM: Micromonospora sp. strain 046-ECO11

<400> SEQUENCE: 25

```
gtgtgggccc gggtgaagaa ctgggtcgtc gcgttggctg tggcggcggt gctgatgatc    60
agcgcgctgg ccggtgacca tcctgccccc gagggcctcg gtctgctcgg cttcgcgctg   120
gtggcggcga gcggcctggc gctggccgcc agtcgtcggg ccccgatcgc cgtgctggtc   180
gccaccgggc tgtgcgtggt gggctacaac gcgatcggct tcggggtgcc cgccatcgcg   240
tacctgttcg cggtctacgc ggcggtccgg gccgggcacc ggctcgtcac gctcggggcg   300
agcgccgccc tgctcgtcgt cctgccgctg gcgatcatgg tctcgcccgc ggacggcgcc   360
ctcaaggagg cgctcgcgca gtcgcgggc gtgctggaac tggcctggct gatcgccgcg   420
gcggcggccg tgaggcgct gcggcaggcc gaacggcgag cggacgaggc ggaacggacc   480
cgcgaggaga ccgcccggct gcgcgccacc caggagcggc tgcacatcgc acgggagctg   540
cacgactcgc tcacccacca gatctcgatc atcaaggtgc aggcggaggt ggcggtccac   600
ctggcccgca agcggggcga gcaggtgccg gagtcgctgc tggcgatcca ggaggccggc   660
cggcggcgga ctcgcgagct gcgcgcgacc ctggagacgc tgcgtgacct gaccaagtcc   720
ccgtcgcacg ggctcgacca cctcccggag ctgctggccg gggccgagaa gatcggcctg   780
gccaccacgc tgaccatcga gggcgaccag cgggacgtgc cggaggcggt gggccgcacc   840
gcgtaccgga tcgtgcagga gtcgctcacc aacaccgccc ggcacgcctc cgccgcggcc   900
gccgcggtcc ggatcgacta ccgcccggac gcgctgagca tccggatcga cgacgacggg   960
acggcccggc cgggcgccgc cccggtgccc ggcgtcgggc tgctggggat gcacgagcgc  1020
gtcctcgcgc tgggcggccg gctgcgggcg gaaccccgca ccggcggagg cttcaccgtc  1080
caggccgaac tcccggtggt gcgcgtccca tga                               1113
```

<210> SEQ ID NO 26
<211> LENGTH: 220
<212> TYPE: PRT
<213> ORGANISM: Micromonospora sp. strain 046-ECO11

<400> SEQUENCE: 26

```
Met Ile Arg Ile Met Leu Leu Asp Asp Gln Pro Leu Leu Arg Ser Gly
1               5                   10                  15

Phe Arg Ala Leu Leu Asp Ala Glu Asp Asp Ile Glu Val Val Ala Glu
            20                  25                  30

Gly Gly Asn Gly Arg Glu Gly Leu Ala Leu Ala Arg Gln His Leu Pro
        35                  40                  45

Asp Leu Ala Leu Ile Asp Ile Gln Met Pro Val Met Asp Gly Val Glu
    50                  55                  60

Thr Thr Arg Gln Ile Val Ala Asp Pro Ala Leu Ala Gly Val Arg Val
65                  70                  75                  80

Val Ile Leu Thr Asn Tyr Gly Leu Asp Glu Tyr Val Phe His Ala Leu
                85                  90                  95

Arg Ala Gly Ala Thr Gly Phe Leu Val Lys Asp Ile Glu Pro Asp Asp
            100                 105                 110

Leu Leu His Ala Val Arg Val Ala Ala Arg Gly Asp Ala Leu Leu Ala
        115                 120                 125

Pro Ser Ile Thr Arg Met Leu Ile Asn Arg Tyr Val Ser Glu Pro Leu
    130                 135                 140

Cys Ala Asp Val Thr Pro Gly Met Glu Glu Leu Thr Asn Arg Glu Arg
145                 150                 155                 160
```

```
Glu Ala Val Ala Leu Ala Ala Arg Gly Leu Ser Asn Asp Glu Ile Ala
            165                 170                 175

Asp Arg Met Val Ile Ser Pro Leu Thr Ala Lys Thr His Val Asn Arg
            180                 185                 190

Ala Met Thr Lys Leu Gln Ala Arg Asp Arg Ala Gln Leu Val Val Phe
            195                 200                 205

Ala Tyr Glu Ser Gly Leu Val Ser Pro Gly Asn Arg
            210                 215                 220

<210> SEQ ID NO 27
<211> LENGTH: 663
<212> TYPE: DNA
<213> ORGANISM: Micromonospora sp. strain 046-ECO11

<400> SEQUENCE: 27
atgatcagga tcatgctgct cgacgaccag ccgctgctgc gcagcgggtt ccgcgcgctc      60
ctcgacgccg aggacgacat cgaggtggtg gccgagggcg ggaacggccg ggagggcctg     120
gcgctggccc ggcagcacct gcccgatctc gccctgatcg acatccagat gccggtcatg     180
gacggcgtcg agacgacccg gcagatcgtc gcggatccgg cgctggccgg ggtacgcgtc     240
gtcatcctca ccaactacgg cctcgacgag tacgtcttcc acgcgctgcg cgccggcgcc     300
accggcttcc tggtcaagga catcgagccg acgacctgc tgcacgccgt gcgggtcgcc      360
gcgcgcggtg acgcgctgct cgcgccgtcg atcaccccgga tgctgatcaa caggtacgtg    420
tcggagccgc tctgcgcgga cgtcacgccc ggcatggagg agctgaccaa ccgggaacgc     480
gaggcggtcg ccctggccgc ccggggcctg tccaacgacg agatcgccga tcgcatggtg     540
atcagcccgc tgaccgcgaa gacccacgtc aaccgcgcca tgaccaagct gcaggcccgc     600
gaccgcgccc agctggtggt gttcgcctac gagtccggcc tggtgtcacc cggcaatcgc     660
tga                                                                    663

<210> SEQ ID NO 28
<211> LENGTH: 131
<212> TYPE: PRT
<213> ORGANISM: Micromonospora sp. strain 046-ECO11

<400> SEQUENCE: 28

Met Phe Ile Arg Arg Leu Leu Thr Ala Ala Ala Ala Gly Val Leu Gly
1               5                   10                  15

Gly Leu Ala Leu Val Ala Pro Ala Ala Ala Gln Val Thr Ala Ala Asp
            20                  25                  30

Gly Asp Gly Gly Ser Gly Arg Ala Gly Ser Val Leu Ala Leu Ala Leu
        35                  40                  45

Ala Leu Leu Gly Leu Val Leu Gly Gly Trp Ala Leu Arg Ser Ala Gly
    50                  55                  60

Arg Gly Gly Gly Arg Gly Asn Ala Ile Ala Ala Leu Val Leu Ala Val
65                  70                  75                  80

Ala Gly Leu Ile Ala Gly Val Val Ala Leu Ala Gly Ser Asp Gly Gly
                85                  90                  95

Val Gly Ser Gly Asn Gly Arg Gly Gly Ala Ile Val Ala Val Val Leu
            100                 105                 110

Ala Leu Ile Gly Ile Ala Val Gly Gly Leu Ala Phe Thr Arg Ser Arg
        115                 120                 125

Arg Ala Ala
        130
```

<210> SEQ ID NO 29
<211> LENGTH: 396
<212> TYPE: DNA
<213> ORGANISM: Micromonospora sp. strain 046-ECO11

<400> SEQUENCE: 29

```
atgttcatcc gtcgtttgct caccgccgcc gcagccggcg tcctcggtgg gctcgcactc      60
gtcgcaccgg cggccgcgca ggtgacggcc gccgacggtg acggtggttc cggccgcgcc     120
ggatccgtgc tggcgctcgc gctcgcgttg ctcggcctcg tcctgggcgg gtgggcgttg     180
cgctccgcgg ggcgcggcgg cggtcgtggc aacgcgatcg ccgcgctggt gctcgcggtg     240
gccggcctga tcgccggcgt ggtcgccctg gccggctccg acggtggtgt cggcagcggc     300
aacggccgtg gtggcgccat cgtggccgtc gtgctggcgc tgatcgggat cgccgtcggc     360
ggcctggcat tcacccgctc ccggcgcgcc gcctga                               396
```

<210> SEQ ID NO 30
<211> LENGTH: 154
<212> TYPE: PRT
<213> ORGANISM: Micromonospora sp. strain 046-ECO11

<400> SEQUENCE: 30

```
Met Arg Lys Val Phe Ala Gly Leu Ala Ala Phe Leu Leu Leu Val Leu
1               5                   10                  15

Val Val Gln Phe Phe Leu Ala Ala Ser Gly Ala Phe Ser Asn Glu Ala
            20                  25                  30

Asn Glu Glu Ala Phe Arg Pro His Arg Ile Leu Gly Leu Gly Ser Ile
        35                  40                  45

Leu Val Ala Val Val Leu Thr Val Ala Ala Ala Val Met Arg Met Pro
    50                  55                  60

Gly Arg Ile Ile Gly Leu Ser Gly Leu Val Ala Gly Leu Gly Ile Leu
65                  70                  75                  80

Gln Ala Leu Ile Ala Val Ile Ala Lys Ala Phe Gly Asp Ser Ala Gly
                85                  90                  95

Asp Ser Ala Val Gly Arg Tyr Val Phe Gly Leu His Ala Val Asn Gly
            100                 105                 110

Leu Val Met Val Ala Val Ala Arg Val Ile Leu Arg Ser Val Arg Ala
        115                 120                 125

Ala Pro Asp Thr Thr Thr Thr Pro Gly Val Asp Thr Thr Val Thr Gly
    130                 135                 140

Pro Ala Ala Asp Ser Ala Arg Thr Ala Ser
145                 150
```

<210> SEQ ID NO 31
<211> LENGTH: 465
<212> TYPE: DNA
<213> ORGANISM: Micromonospora sp. strain 046-ECO11

<400> SEQUENCE: 31

```
atgcgcaaag tgttcgccgg actggcagcg ttcctgctgc tcgtgctcgt ggtgcagttc      60
ttcctggccg ccagcggcgc gttcagcaac gaggccaacg aggaggcgtt ccgccctcac     120
cggatcctgg gcctggggag catcctcgtc gccgtggtgc tgacggtggc cgccgcggtg     180
atgcggatgc ccggccggat catcggcctg tccggcctgg tcgccgggct gggcatcctg     240
caggccctga tcgcggtcat cgccaaggcg ttcggcgact cggccggtga ctcggccgtc     300
```

```
ggccggtacg tgttcggcct gcacgcggtc aacggactgg tgatggtggc cgtcgcccgc    360
gtcatcctgc gcagcgtccg ggcggcgccg gacacgacca ccacgcccgg cgtggacacg    420
acggtcaccg gtccggcggc cgactcggcg cgaacggcgt catga                    465
```

```
<210> SEQ ID NO 32
<211> LENGTH: 661
<212> TYPE: PRT
<213> ORGANISM: Micromonospora sp. strain 046-ECO11

<400> SEQUENCE: 32

Met Ser Thr Leu Gln Trp Ile Leu Val Asp His Val Ala Leu Leu
 1               5                  10                  15

Gly Val Ala Thr Trp Phe Ala Thr Gly Val Thr Ala Ala Leu Gly Arg
                20                  25                  30

His Arg Ile Ala Leu Ala Leu Leu Gly Ala Ala Val Leu Val Thr Val
                35                  40                  45

Ala Arg Leu Gly Thr Val Ala Leu Leu Ala Asp Arg Gly Trp Trp Phe
 50                  55                  60

Val Gln Glu Lys Val Leu Leu Gly Leu Pro Met Leu Gly Ala Ala Gly
 65                  70                  75                  80

Leu Val Ala Val Leu Leu Ala Gly Pro Arg Leu Leu Ala Ala Arg Gln
                85                  90                  95

Ser Pro Ala Ala Asp Leu Pro Ala Gly Ala Leu Val Ala Val Leu Thr
                100                 105                 110

Ala Gly Phe Ala Ala Leu Ala Gly Leu Val Val Thr Phe Thr Ala Gly
                115                 120                 125

Tyr Pro Leu Thr Trp Ser Thr Ala Leu Ile Ala Val Ala Leu Val Cys
                130                 135                 140

Ala Ala Ala Leu Leu Thr Ala Arg Val Val Gly Arg Pro Ala Ala Pro
145                 150                 155                 160

Ala Ala Glu Ala Gly Ser Pro Glu His Thr Pro Ala Ala Ala Gly Pro
                165                 170                 175

Thr Ala Leu Ser Arg Arg Arg Phe Leu Gly Val Ala Gly Gly Val Val
                180                 185                 190

Ala Ala Gly Ala Gly Ala Thr Gly Val Gly Leu Leu Phe Arg Asp Pro
                195                 200                 205

Glu Ala Met Val Thr Gly Gly Gly Pro Gly His Ala Gly Gly Ala Arg
                210                 215                 220

Pro Lys Val Ser Val Ala Asp Leu Arg Gly Pro Gly Ala Pro Ala Ala
225                 230                 235                 240

Gly Gly Thr Ala Arg Arg His Val Leu Thr Ala Arg Thr Gly Thr Val
                245                 250                 255

Thr Ile Pro Ser Gly Arg Pro Ile Asp Ala Trp Ser Tyr Glu Gly Arg
                260                 265                 270

Leu Pro Gly Pro Ala Ile Thr Ala Thr Glu Gly Asp Leu Ile Glu Val
                275                 280                 285

Thr Leu Arg Asn Ala Asp Ile Glu Asp Gly Val Thr Val His Trp His
                290                 295                 300

Gly Tyr Asp Val Pro Cys Gly Glu Asp Gly Ala Pro Gly Ala Thr Gln
305                 310                 315                 320

His Ala Val Gln Pro Gly Gly Glu Phe Val Tyr Arg Phe Gln Ala Asp
                325                 330                 335

Gln Val Gly Thr Tyr Trp Tyr His Thr His Gln Ala Ser His Pro Ala
                340                 345                 350
```

```
Val Arg Lys Gly Leu Tyr Gly Thr Leu Val Val Thr Pro Arg Glu Asp
            355                 360                 365

Arg Pro Glu Ala Glu Arg Gly Leu Asp Leu Thr Leu Pro Val His Thr
        370                 375                 380

Phe Asp Asp Val Thr Ile Leu Gly Asp Gln Glu Gly Arg Ala Val His
385                 390                 395                 400

Asp Val Arg Pro Gly Gln Pro Val Arg Leu Arg Leu Ile Asn Thr Asp
                405                 410                 415

Ser Asn Pro His Trp Phe Ala Val Val Gly Ser Pro Phe Arg Val Val
            420                 425                 430

Ala Val Asp Gly Arg Asp Leu Asn Gln Pro Gly Glu Val Arg Glu Val
            435                 440                 445

Gly Leu Arg Leu Pro Ala Gly Gly Arg Tyr Asp Leu Thr Leu Ala Met
        450                 455                 460

Pro Asp Ala Lys Val Thr Leu Leu Asp Asn Asp Ser Asp Gln Gly
465                 470                 475                 480

Val Leu Arg Pro Pro Gly Val Gly Gly Asp Arg Pro Leu Pro
                485                 490                 495

Asp Thr Ala Asp Trp Pro Glu Phe Asp Leu Leu Gly Tyr Gly Glu Pro
            500                 505                 510

Ala Pro Val Pro Phe Asp Ala Asp Ala Asp Arg His Phe Thr Ile
            515                 520                 525

Val Leu Asp Arg Ala Leu Ala Met Val Asp Gly Lys Pro Ala Tyr Ala
            530                 535                 540

Gln Thr Val Asp Gly Arg Ala His Pro Ser Val Pro Asp Gln Leu Val
545                 550                 555                 560

Arg Glu Gly Asp Val Val Arg Phe Thr Val Val Asn Arg Ser Leu Glu
                565                 570                 575

Thr His Pro Trp His Leu His Gly His Pro Val Leu Ile Leu Ser Arg
            580                 585                 590

Asp Gly Arg Pro Tyr Ser Gly Ser Pro Leu Trp Met Asp Thr Phe Asp
            595                 600                 605

Val Arg Pro Gly Glu Val Trp Glu Val Ala Phe Arg Ala Asp Asn Pro
        610                 615                 620

Gly Val Trp Met Asn His Cys His Asn Leu Pro His Gln Glu Gln Gly
625                 630                 635                 640

Met Met Leu Arg Leu Val Tyr Asp Gly Val Thr Thr Pro Phe Ala Ser
                645                 650                 655

Thr Ser His Ala His
            660

<210> SEQ ID NO 33
<211> LENGTH: 1986
<212> TYPE: DNA
<213> ORGANISM: Micromonospora sp. strain 046-ECO11

<400> SEQUENCE: 33
atgagcacgc tccaatggat cctcgtggac cacgtcgtgg cgctgctcgg tgtcgcgacg      60
tggttcgcaa cgggtgtcac ggcagctctc ggccgccacc ggatcgcgtt ggcgctcctc     120
ggcgccgcgg tgctggtgac agtcgcccgc ctgggcaccg tggcgctgct ggccgaccgc     180
ggctggtggt cgtccagga gaaggttctg ctggggctgc cgatgctcgg cgccgcgggg     240
ctcgtcgcgg tgctcctggc cggcccgcgc ctgctcgcgg cccggcagtc accggcggcg     300
```

-continued

```
gacctgccgg ccggcgcgct ggtcgcggtg ctgaccgccg gcttcgccgc gctggccggc       360
ctggtggtga cgttcaccgc cgggtacccg ctgacgtgga gcaccgcgct gatcgccgtc       420
gccctcgtct cgccgccgc gctgctcacc gcgcgggtgg tcggacgacc cgccgccccg        480
gccgcggagg ccggctcccc ggagcacacg ccggcggcg ccgggcccac ggcgctgtcc        540
cgccgccggt tcctcggcgt ggccggggga gtggtcgcgg cgggcgccgg cgccaccggc       600
gtcggcctgc tcttccgcga cccggaggcg atggtcaccg gaggcggccc cggacacgcc       660
ggtggcgccc gccccaaggt ctccgtggcg gacctgcgcg ccccggcgc tccggcggcg        720
ggcggcacgg cgcgacgcca cgtgctcacc gcccggacgg gcaccgtcac gattccgtcc       780
ggacgtccga tcgacgcctg gagctacgag ggccgcctgc ccgggccggc catcaccgcg       840
accgagggcg acctgatcga ggtgacgctc cgcaacgccg acatcgagga cggcgtcacc       900
gtgcactggc acgggtacga cgtgccgtgc ggcgaggacg cgcgccgggg cgccacgcag       960
cacgcggtga gcccggcgg cgagttcgtc taccggttcc aggcggacca ggtggggacg       1020
tactggtacc acacccacca ggcgtcgcac cccgccgtgc gcaaagggct gtacgggacg       1080
ctcgtcgtga cgccgcgcga ggaccggccg aagcggagc gcgggctgga cctgacgctg       1140
ccggtgcaca cgttcgacga cgtcacgatc ctcggcgacc aggagggacg cgccgtccac       1200
gacgtccgcc ccgccagcc ggtgcgactg cgtctgatca caccgactc caacccgcac        1260
tggttcgccg tcgtcggctc gcccttccgc gtggtggccg tcgacggccg cgacctcaac       1320
cagccgggcg aggtacgcga ggtcgggctc cgcctgcccg ccggaggccg gtacgacctg       1380
accctggcca tgccggacgc caaggtcacg ctgctgctcg acaacgactc cgaccagggc       1440
gtcctgctgc gccgccggg cgtcggcggt ggtgaccgcc cgctgccgga caccgccgac       1500
tggcccgagt tcgacctgct gggctacggc gagccggcgc ccgtgccgtt cgacgccgac       1560
gacgccgacc gccacttcac catcgtcctc gaccgggccc tggccatggt cgacggcaag       1620
cccgcgtacg cccagaccgt cgacggtcgc gcacatccct ccgtccccga ccagctcgtc       1680
cgggaggggg acgtcgtgcg cttcacggtg gtcaaccgga gcctcgaaac ccacccgtgg       1740
cacctgcacg gccatccggt gctgatcctg tcccgcgacg gccggccgta ctccggcagc       1800
ccgctgtgga tggacacctt cgacgtgcgg ccgggagagg tgtgggaggt ggcgttccgg       1860
gcggacaatc cgggtgtctg gatgaaccac tgccacaacc tgccgcacca ggagcagggc       1920
atgatgctgc ggctcgtcta cgacggtgtc accacgccct cgccagcac gagccacgca        1980
cactga                                                                  1986
```

<210> SEQ ID NO 34
<211> LENGTH: 129
<212> TYPE: PRT
<213> ORGANISM: Micromonospora sp. strain 046-ECO11

<400> SEQUENCE: 34

Met Thr Ala Asp Leu His Gly Leu Ala Ser Val Arg Tyr Ile Val Asp
1               5                   10                  15

Asp Val Ser Ala Ala Ile Glu Phe Tyr Thr Thr His Leu Gly Phe Thr
            20                  25                  30

Val Ser Thr Ala Phe Pro Pro Ala Phe Ala Asp Val Val Arg Gly Pro
        35                  40                  45

Leu Arg Leu Leu Leu Ser Gly Pro Thr Ser Ser Gly Ala Arg Val Thr
    50                  55                  60

Pro Ala Asp Ala Ala Gly Cys Gly Arg Asn Arg Ile His Leu Ile Val

```
                65                  70                  75                  80
Asp Asp Leu Asp Ala Glu Arg Glu Arg Leu Glu Arg Ala Gly Val Thr
                    85                  90                  95

Leu Arg Ser Asp Val Val Ala Gly Pro Gly Gly Arg Gln Phe Leu Ile
                100                 105                 110

Ala Asp Pro Ala Gly Asn Leu Val Glu Val Phe Glu Pro Ala Ala Arg
            115                 120                 125

Gly
```

<210> SEQ ID NO 35
<211> LENGTH: 390
<212> TYPE: DNA
<213> ORGANISM: Micromonospora sp. strain 046-ECO11

<400> SEQUENCE: 35

```
atgaccgcag acctgcacgg cctggccagc gtccgctaca tcgtcgacga cgtgtcggcg      60
gcgatcgagt tctacaccac ccacctgggt tcacggtgt cgaccgcgtt cccgccggcc     120
ttcgccgacg tggtgcgcgg gccgctgcgc ctcctgctgt ccgggccgac cagctcgggc     180
gcccgggtca ccccggcgga cgcggccggg tgcgggcgca accgcatcca cctgatcgtc     240
gacgatctcg acgccgaacg ggagcggctg gagcgcgccg gggtgacgtt gcgcagcgac     300
gtcgtggccg ggccgggcgg ccgtcagttc ctgatcgccg acccggcggg caacctggtc     360
gaggtgttcg agccggcagc ccgcggctga                                       390
```

<210> SEQ ID NO 36
<211> LENGTH: 178
<212> TYPE: PRT
<213> ORGANISM: Micromonospora sp. strain 046-ECO11

<400> SEQUENCE: 36

```
Met Leu Thr Ala Val Val Ala Ser Pro His Ser Pro Glu Asn Thr Ser
1               5                   10                  15

Arg His Pro Thr Gly Gly Asp Ala Val Asp Glu Ala Thr Pro Arg Thr
                20                  25                  30

Pro Val Ala Ala Arg Pro Thr Trp Ser Pro Ala Thr Ala Pro Val Trp
            35                  40                  45

Leu Val Gly Val Leu Ala Thr Leu Ala Gly Ala Val Ala Ala Glu Ala
        50                  55                  60

Phe Thr Leu Ala Ala Arg Gly Phe Gly Val Pro Met Glu Ala Ala Gly
65                  70                  75                  80

Val Trp Glu Glu Gln Ala Gln Ala Ile Pro Val Gly Ala Ile Ala Arg
                85                  90                  95

Ser Val Val Leu Trp Ser Ile Gly Gly Ile Val Leu Ala Val Val Val
                100                 105                 110

Ala Arg Arg Ala Arg Arg Pro Val Arg Ala Phe Val Ala Gly Thr Val
            115                 120                 125

Ala Phe Thr Val Leu Ser Leu Ala Ala Pro Ala Phe Ala Arg Asp Thr
        130                 135                 140

Pro Val Ser Thr Gln Leu Val Leu Ala Gly Thr His Val Ile Ala Gly
145                 150                 155                 160

Ala Val Ile Ile Ser Ile Leu Ala Ala Arg Leu Ala Ala Pro Thr Pro
                165                 170                 175

Pro Arg
```

<210> SEQ ID NO 37
<211> LENGTH: 537
<212> TYPE: DNA
<213> ORGANISM: Micromonospora sp. strain 046-ECO11

<400> SEQUENCE: 37

```
atgttgactg ccgtcgtggc gtccccgcat tctcccgaga acacatcgag gcacccgacc      60
ggaggcgacg ccgtggatga ggccactccc cgaactcccg tcgcggcacg gcccacctgg     120
tcgccggcca ccgctccggt gtggctggtc ggcgtgctgg ccaccctcgc cggggccgtg     180
gccgcggagg cgttcacgct cgccgcccgg ggcttcggcg taccgatgga ggcggccggc     240
gtctgggagg agcaggcgca ggcgatcccg gtggggcca  tcgcccgcag cgtcgtgctc     300
tggtcgatcg gcggaatcgt cctggcggtg gtcgtggcgc ggcgggcccg gcggcccgtg     360
cgtgccttcg tggccggcac cgtcgcgttc accgtgctgt ccctcgccgc gcccgccttc     420
gcccgggaca ccccggtgtc gacgcagctc gtcctcgccg gcacccacgt gatcgccggc     480
gccgtgatca tctccatcct ggccgcgcgg ctcgccgcgc ccaccccgcc ccggtaa        537
```

<210> SEQ ID NO 38
<211> LENGTH: 661
<212> TYPE: PRT
<213> ORGANISM: Micromonospora sp. strain 046-ECO11

<400> SEQUENCE: 38

```
Met Asp Gly Thr Glu Ser Asn Val Thr Gly Phe Pro Asp Leu Leu Ser
  1               5                  10                  15

Gly Leu Gly Gly Asp Gly Arg Ala Phe Ala Leu Leu His Arg Pro Gly
             20                  25                  30

Ala Ala Gly Cys Ala Tyr Val Glu Val Leu Thr Gly Glu Val Cys Asp
         35                  40                  45

Val Asp Thr Leu Gly Glu Leu Pro Leu Pro Thr Glu Pro Ala Thr Gly
     50                  55                  60

Ala Arg His Asp Leu Leu Val Ala Val Pro Tyr Arg Gln Val Thr Glu
 65                  70                  75                  80

Arg Gly Phe Asp Cys His Asp Asp Gly Ala Pro Leu Leu Ala Met Arg
                 85                  90                  95

Val His Glu Gln Phe Gly Leu Asp Arg Gly Gln Ala Leu Ala Gly Leu
            100                 105                 110

Pro Glu Arg Gly Val Pro Val Thr Asp Ala Asp Phe Asp Leu Ser Asp
        115                 120                 125

Glu Asp Tyr Ala Ala Ile Val Lys Arg Val Val Gly Asp Glu Ile Gly
    130                 135                 140

Leu Gly Ala Gly Ser Asn Phe Val Ile Arg Arg Thr Phe Thr Ala Arg
145                 150                 155                 160

Leu Ala Asp Tyr Ser Ile Ala Thr Glu Leu Ala Leu Phe Arg Arg Leu
                165                 170                 175

Leu Thr Gly Glu Leu Gly Ser Tyr Trp Thr Phe Leu Phe His Ser Gly
            180                 185                 190

Ala Gly Thr Phe Ile Gly Ala Ser Pro Glu Arg His Val Ser Met Ile
        195                 200                 205

Asp Gly Thr Val Ser Met Asn Pro Ile Ser Gly Thr Tyr Arg His Pro
    210                 215                 220

Pro Asn Gly Pro Ala Val Ser Gly Leu Leu Glu Phe Leu Asn Asp Pro
225                 230                 235                 240

Lys Glu Ala Asn Glu Leu Tyr Met Val Val Asp Glu Glu Leu Lys Met
```

```
                      245                 250                 255
Met Ala Arg Met Cys Ala Ser Gly Gly Gln Val His Gly Pro Phe Leu
                260                 265                 270

Lys Glu Met Ala Arg Val Thr His Ser Glu Tyr Ile Leu Thr Gly Arg
            275                 280                 285

Ser Asp Leu Asp Val Arg Asp Val Leu Arg Glu Thr Leu Leu Ala Pro
        290                 295                 300

Thr Val Thr Gly Ser Pro Ile Glu Asn Ala Phe Arg Val Ile Thr Arg
305                 310                 315                 320

His Glu Thr Thr Gly Arg Gly Tyr Tyr Gly Gly Val Leu Ala Leu Met
                325                 330                 335

Gly Arg Asp Ser Ala Gly Ser Arg Thr Leu Asp Ser Ala Ile Met Ile
            340                 345                 350

Arg Thr Ala Glu Ile Asp Asp Ala Gly Thr Leu Arg Leu Gly Val Gly
        355                 360                 365

Ala Thr Leu Val Arg Asp Ser Lys Pro Glu Ser Glu Val Ala Glu Thr
    370                 375                 380

Arg Ala Lys Ala Gly Ala Met Arg Ala Ala Leu Gly Leu Gly Val Asp
385                 390                 395                 400

Pro Asp Gly Pro Asp Gly Gly Arg Thr Thr Ala Ala Arg Ala Arg Ser
                405                 410                 415

Ser Leu Ala Thr Asp Pro Arg Val Arg Arg Ala Leu Arg Glu Arg Asn
            420                 425                 430

Thr Thr Leu Ser Arg Phe Trp Leu Asp Gly Ala Glu Arg Arg Thr Pro
        435                 440                 445

Asn Pro Ala Leu Thr Gly Arg Arg Val Leu Val Asp Asn Glu Asp
    450                 455                 460

Thr Phe Met Ala Met Leu Asp His Gln Leu Arg Ala Leu Gly Leu Arg
465                 470                 475                 480

Ser Ser Ile Ala Arg Phe Asp Ser Arg Leu Arg Pro Asp Gly His Asp
                485                 490                 495

Leu Val Val Val Gly Pro Gly Pro Gly Asp Pro Gly Asp Leu Thr Asp
            500                 505                 510

Pro Arg Met Arg Thr Leu Arg Gly Leu Thr Arg Asp Leu Leu Ala Gly
        515                 520                 525

Thr Val Pro Phe Leu Ser Ile Cys Leu Gly His Gln Val Leu Ala Ala
    530                 535                 540

Glu Leu Gly Phe Pro Leu Ala Arg Arg Ala Val Pro Asn Gln Gly Val
545                 550                 555                 560

Gln Lys Arg Ile Asp Leu Phe Gly Arg Pro Glu Leu Val Gly Phe Tyr
                565                 570                 575

Asn Thr Tyr Thr Ala Arg Ser Ala His Asp Val Val Ala Gly Gly Arg
            580                 585                 590

Arg Gly Pro Ile Glu Ile Ser Arg Ser Pro Asp Ser Gly Asp Val His
        595                 600                 605

Ala Leu Arg Gly Pro Gly Phe Arg Ser Val Gln Phe His Leu Glu Ser
    610                 615                 620

Val Leu Thr Gln His Gly Pro Arg Ile Leu Gly Asp Leu Leu Val Ser
625                 630                 635                 640

Leu Leu Ala Asp Gly Thr Ala Ala Ala Ala Glu Ala Ala Gly Arg
                645                 650                 655

Arg Gly Asn Arg Pro
            660
```

<210> SEQ ID NO 39
<211> LENGTH: 1986
<212> TYPE: DNA
<213> ORGANISM: Micromonospora sp. strain 046-ECO11

<400> SEQUENCE: 39

```
atggacggga cggaatcgaa cgtgaccgga ttccccgatc tgctgtccgg tctcggcggc      60
gacgggcgcg ccttcgccct gctgcaccgg cccggcgcgg ccgggtgcgc gtacgtggag     120
gttctgaccg cgcaggtgtg cgacgtggac actctcggcg agctgccccct gcccaccgag    180
ccggcgaccg gcgcgcggca cgacctgctc gtggcggtgc cgtaccggca ggtcaccgaa     240
cgggggttcg actgccacga cgacggcgcg ccgctgctcg cgatgcgcgt ccacgagcag     300
ttcgggctcg accgcggaca ggcgctggcg ggcctgcccg aacgcggtgt gccggtgacc     360
gacgccgact tcgacctcag cgacgaggac tacgccgcga tcgtcaagcg ggtggtgggt     420
gacgagatcg ggctgggcgc cggatccaac ttcgtcatcc ggcgcacctt caccgcgcgg     480
ctggccgact actcgatcgc cacggaactg gcgctcttcc gccggttgct gaccggcgaa     540
ctgggttcct actggacgtt tctgttccac tccggcgccg gcacgttcat cggcgcgtca     600
ccggaacgac acgtcagcat gatcgacgga accgtctcga tgaatcccat cagcgggacc     660
taccggcacc ccccgaacgg cccggccgtt tccggtctgc tggaattcct gaacgacccg     720
aaagaggcta cgaactcta catggtcgtc gacgaggaac tgaaaatgat ggcgcggatg     780
tgcgcctccg gcgccaggt gcacggcccg ttcctcaagg aaatggcgcg ggtgacgcac     840
tccgagtaca tcctgaccgg ccgcagcgac ctggacgtgc gcgacgtgct gcgggagacc     900
ctgctcgcgc gacggtcac cggcagcccg atcgagaacg cgttccgggt catcacccgc     960
cacgagacga ccggccgcgg ctactacggc ggcgtgctcg cgttgatggg ccgtgactcg    1020
gccggcagcc gtacgctcga ctcggccatc atgatccgca ccgccgagat cgacgacgcg    1080
ggcacgctgc gcctgggcgt cggcgccacc ctcgtgcggg actccaagcc ggagtcggag    1140
gtggccgaga cgcggggccaa ggcgggcgcc atgcgcgcgg cgctcggcct cggcgtcgac    1200
ccggacggcc cggacggcgg gcggaccacg gccgcgcggg ctcgttcgtc cctggccacc    1260
gaccccccgg tacggcgggc gttgcgcgag cgcaacacca cactgtcgag ttctggctc    1320
gacggcgcgg agcggcgcac cccgaacccg cgcctgaccg gacgccgcgt gctcgtcgtc    1380
gacaacgagg acacgttcat ggccatgctc gaccaccagt gcgggccct cgggctgcgg    1440
tcgagcatcg cccggttcga cagccggctg cggccggacg acacgacct cgtcgtcgtc    1500
ggtcccggcc ccggcgaccc gggcgacctg accacccgc gtatgcggac cctgcgcggg    1560
ctcacccgcg acctgctcgc cggaacggtg ccgttcctgt ccatctgcct gggccaccag    1620
gtgctcgccg ccgaactggg gttccccctc gccggcgcg cggtgcccaa ccagggtgtg    1680
cagaagcgga tcgacctgtt cggccggccg gaactcgtgg ggttctacaa cacctacacc    1740
gcccgctccg cgcacgacgt ggtggccggt ggcggcgggg gcccgatcga gatcagccgc    1800
agcccggaca gcggggacgt gcacgcgctg cgcggccccgg gattccgttc cgtccagttc    1860
cacctggagt ccgtcctcac ccagcacggc ccacggatcc tgggcgacct gctggtctcc    1920
ctgctcgccg acgcacgcg cgccgccgcg gccgaggcgg cgggccggcg cgggaaccgc    1980
ccgtga                                                               1986
```

<210> SEQ ID NO 40

```
<211> LENGTH: 427
<212> TYPE: PRT
<213> ORGANISM: Micromonospora sp. strain 046-ECO11

<400> SEQUENCE: 40

Val Lys Thr Thr Val Asp Val Leu Val Gln Lys Tyr Gly Gly Thr Ser
1               5                   10                  15

Leu Gln Thr Leu Asp Arg Val Arg His Ala Ala Leu Arg Ile Ala Glu
            20                  25                  30

Ala Arg Arg His Gly Ser Ala Val Thr Val Val Ser Ala Arg Gly
        35                  40                  45

Ser Arg Thr Asp Asp Leu Leu Arg Leu Ala Ala Asp Val Gly Ala Ala
    50                  55                  60

Gly Pro Ser Arg Glu Leu Asp Gln Leu Leu Ala Val Gly Glu Ser Glu
65                  70                  75                  80

Ser Ala Ala Leu Met Ala Leu Ala Leu Thr Gly Leu Gly Val Pro Ala
                85                  90                  95

Val Ser Leu Thr Gly His Gln Ala Glu Ile His Thr Thr Asp Arg His
            100                 105                 110

Gly Asp Ala Leu Ile Ser Arg Ile Gly Ala Ala Arg Val Glu Ala Ala
        115                 120                 125

Leu Gly Arg Gly Glu Val Ala Val Val Thr Gly Phe Gln Gly Ile Asp
    130                 135                 140

Arg Ala Gly Asp Val Ala Thr Leu Gly Arg Gly Gly Ser Asp Thr Thr
145                 150                 155                 160

Ala Val Ala Leu Ala Ala Arg Leu Arg Ala Ser Ala Cys Glu Ile Tyr
                165                 170                 175

Thr Asp Val Asp Gly Val Phe Ser Ala Asp Pro Arg Ile Leu Pro Ala
            180                 185                 190

Ala Arg Cys Leu Pro Trp Val Glu Pro Gly Val Met Ala Glu Met Ala
        195                 200                 205

Phe Ala Gly Ala Arg Val Leu His Thr Arg Cys Ile Glu Leu Ala Ala
    210                 215                 220

Met Glu Gly Val Glu Val Arg Val Arg Asn Ala Ser Ser Gln Ala Pro
225                 230                 235                 240

Gly Thr Ile Val Val Asp Arg Pro Asp Arg Pro Leu Glu Thr Arg
                245                 250                 255

Arg Ala Val Val Ala Val Thr His Asp Thr Asp Val Val Arg Val Leu
            260                 265                 270

Val His Cys Arg Asp Gly Arg Asp Met Ala Pro Asp Val Phe Glu
        275                 280                 285

Val Leu Ala Ala His Gly Ala Val Ala Asp Leu Val Ala Arg Ser Gly
    290                 295                 300

Pro Tyr Glu Ser Glu Phe Arg Met Gly Phe Thr Ile Arg Arg Ser Gln
305                 310                 315                 320

Ala Glu Ala Val Arg Thr Ala Leu His Asp Leu Thr Ala Ser Phe Asp
                325                 330                 335

Gly Gly Val His Phe Asp Glu Asn Val Gly Lys Val Ser Val Val Gly
            340                 345                 350

Met Gly Leu Leu Ser Arg Pro Glu His Thr Ala Arg Leu Met Ala Ala
        355                 360                 365

Leu Ala Ala Ala Gly Ile Ser Thr Ser Trp Ile Ser Thr Ser Gln Met
    370                 375                 380

Arg Leu Ser Val Ile Val Ser Arg Asp Arg Thr Val Asp Ala Val Glu
```

```
                385                 390                 395                 400
Ala Leu His Arg Ala Phe Arg Leu Asp Arg Ser Glu Pro Ala Asp Ala
                    405                 410                 415

Thr Ser Leu Thr Ser Arg Arg Ser Ala Thr Ala
            420                 425
```

<210> SEQ ID NO 41
<211> LENGTH: 1284
<212> TYPE: DNA
<213> ORGANISM: Micromonospora sp. strain 046-ECO11

<400> SEQUENCE: 41

```
gtgaagacga ctgtggacgt gctggtccag aaatacgggg gcacctcgct gcagaccctc    60
gaccgcgttc ggcacgccgc gctgcggatc gccgaggcgc ggcggcacgg ctccgccgtg   120
acagtggtcg tgtcggcgcg cggcagccgg accgacgacc tgctgcggct ggcggccgac   180
gtcggcgccg cgggtccgtc ccgggaactc gaccagttgc tcgcagtcgg cgagtccgag   240
tcggcggcgc tgatggcgct ggcgttgacc gggctgggag tgccggccgt ctcgctgacc   300
gggcaccagg cggagatcca caccaccgac cggcacggcg acgcgctgat ctcgcggatc   360
ggggcggcgc gggtggaagc ggcgctgggc cgtggcgagg tcgccgtggt caccggattc   420
cagggcatcg accgggccgg tgacgtcgcc acgctgggc gcggcggctc cgacacgaca   480
gcggtggcgc tcgcggcccg gctccgcgcg tcggcgtgcg agatctacac cgacgtggac   540
ggcgtcttca gcgccgaccc ccgcatcctt ccggcgcgcg gttgcctgcc gtgggtggag   600
cccggcgtca tggcggagat ggcgttcgcc ggcgcgcggg tcctgcacac ccgatgcatc   660
gagctggccg ccatggaagg ggtcgaagtg cgcgtgcgca acgcgtcgtc gcaggcgccc   720
ggaacgatag tcgtggaccg gcccgacgac cggccgctgg agacccggcg ggccgtggtg   780
gcggtcaccc acgacaccga tgtcgtccgc gtgctggtgc actgccgcga cggccgccgg   840
gacatggcac ccgacgtgtt cgaggtgctg ccgcccatg gggcggtggc ggacctggtg   900
gcccggtccg ggccctacga gagcgagttc cggatggggt tcaccatccg ccgcagccag   960
gccgaagcgg tgcggaccgc gctgcacgac ctcaccgcgt ccttcgacgg cggggtccac  1020
ttcgacgaga acgtcggcaa ggtgtccgtg gtcggcatgg gcctgctcag ccgccccgag  1080
cacacggccc ggctgatggc ggcgctggcc cggcggggga tctcgacgag ctggatctcc  1140
acctcccaga tgcggctgtc ggtgatcgtg tcgcgggacc gcaccgtcga cgccgtcgaa  1200
gccctgcacc gcgcgttccg cctggaccgg tccagccgg cggacgccac gtccctgacc  1260
tcccgccgtt ccgccaccgc ctga                                        1284
```

<210> SEQ ID NO 42
<211> LENGTH: 274
<212> TYPE: PRT
<213> ORGANISM: Micromonospora sp. strain 046-ECO11

<400> SEQUENCE: 42

```
Val Ala Val Leu Asn Ala Ser Phe Ala Arg Gly Leu Arg Leu Arg Arg
1               5                   10                  15

Leu Phe Arg Arg Gly Asp Gly Arg Leu Leu Val Val Pro Leu Asp His
                20                  25                  30

Ser Val Thr Asp Gly Pro Leu Arg Arg Gly Asp Leu Asn Ser Leu Leu
            35                  40                  45

Gly Glu Leu Ala Gly Thr Gly Val Asp Ala Val Val Leu His Lys Gly
        50                  55                  60
```

```
Ser Leu Arg His Val Asp His Gly Trp Phe Gly Asp Met Ser Leu Ile
 65                  70                  75                  80

Val His Leu Ser Val Ser Thr Arg His Ala Pro Asp Pro Asp Ala Lys
                 85                  90                  95

Tyr Leu Val Ala His Val Glu Glu Ala Leu Arg Leu Gly Ala Asp Ala
            100                 105                 110

Val Ser Val His Val Asn Leu Gly Ser Pro Gln Glu Ala Arg Gln Ile
        115                 120                 125

Ala Asp Leu Ala Ala Val Ala Gly Glu Cys Asp Arg Trp Asn Val Pro
    130                 135                 140

Leu Leu Ala Met Val Tyr Ala Arg Gly Pro Gln Ile Thr Asp Ser Arg
145                 150                 155                 160

Ala Pro Glu Leu Val Ala His Ala Ala Thr Leu Ala Ala Asp Leu Gly
                165                 170                 175

Ala Asp Ile Val Lys Thr Asp Tyr Val Gly Thr Pro Glu Gln Met Ala
            180                 185                 190

Glu Val Val Arg Gly Cys Pro Ile Pro Leu Ile Val Ala Gly Gly Pro
        195                 200                 205

Arg Ser Ala Asp Thr Pro Thr Val Leu Ala Tyr Val Ser Asp Ala Leu
    210                 215                 220

Arg Gly Gly Val Ala Gly Met Ala Met Gly Arg Asn Val Phe Gln Ala
225                 230                 235                 240

Glu Gln Pro Gly Leu Met Ala Ala Val Ala Arg Leu Val His Glu
                245                 250                 255

Pro Arg His Val Pro Asp Arg Tyr Asp Val Asp Arg Leu Ala Leu
            260                 265                 270

Thr Ser

<210> SEQ ID NO 43
<211> LENGTH: 825
<212> TYPE: DNA
<213> ORGANISM: Micromonospora sp. strain 046-ECO11

<400> SEQUENCE: 43
gtggccgtac tcaacgcttc gttcgctcgt ggcctgcgtc tgcgccgact gttccgacgc    60
ggcgacggac gcctgctcgt cgtcccgctc gaccactccg tcaccgacgg gccgctgcgc   120
cgcggcgacc tgaactcgct gctcggtgag ctcgccggca ccggcgtgga cgccgtggtg   180
ctgcacaagg gcagcctgcg gcacgtcgac cacggctggt tcggcgacat gtcgctgatc   240
gtgcatctga gcgtgagcac ccggcacgcc ccggacccgg acgcgaagta cctggtcgcg   300
cacgtggagg aggcgctgcg gctgggcgcc gacgcggtca gcgtgcacgt caacctcggc   360
tcaccgcagg aggcgcggca gatcgccgac ctggcggcgg tggcggggga gtgcgaccgc   420
tggaacgtcc cgctgctggc catggtgtac gcccgcgggc cgcagatcac cgactcccgg   480
gcaccggagc tggtggcgca cgccgcgacg ctcgccgcgg acctcggcgc cgacatcgtc   540
aagaccgact acgtgggcac gcccgagcag atggccgagg tggtgcgcgg ctgccccgatc  600
ccgctgatcg tggccggcgg cccgcgctcg gccgacactc cgacggtgct cgcctacgtc   660
tcggacgcgc tgcgcggcgg cgtggccggg atggccatgg gccgcaacgt gttccaggcc   720
gagcagcccg gcctgatggc cgccgccgtg gcacggctgg tgcacgagcc acggcacgtg   780
ccggaccggt acgacgtcga cgaccggctc gcccttacgt cctga                   825
```

<210> SEQ ID NO 44
<211> LENGTH: 367
<212> TYPE: PRT
<213> ORGANISM: Micromonospora sp. strain 046-ECO11

<400> SEQUENCE: 44

```
Val Lys Leu Cys Trp Leu Asp Ile Arg Asn Val Asn Gly Ala Lys Glu
1               5                   10                  15
Ala Ile Val Glu Glu Ala Val His Gln Arg Val Asp Ala Val Val Ala
            20                  25                  30
Ala Asp Pro Ala Asp Leu Glu Thr Leu Pro Pro Thr Val Lys Lys Val
        35                  40                  45
Leu Phe Pro Gln Gly Gly Pro Leu Pro Glu Lys Leu Glu Pro Ala Asp
    50                  55                  60
Leu Val Ile Val Glu Pro Ala Arg His Gly Glu Pro Ala Glu Leu Ala
65                  70                  75                  80
Ala Arg Tyr Pro Glu Val Glu Phe Gly Arg Phe Val Glu Ile Val Asp
                85                  90                  95
Ala Asp Ser Leu Glu Asp Ala Cys Arg Ser Ala Arg His Asp Arg Trp
            100                 105                 110
Ser Leu Leu Tyr Phe Arg Asp Pro Thr Lys Ile Pro Leu Glu Ile Val
        115                 120                 125
Leu Ala Ala Ala Gly Ala Glu Gly Ser Ile Ile Thr Gln Val Ala
    130                 135                 140
Asp Val Glu Glu Ala Glu Ile Val Phe Gly Val Leu Glu His Gly Ser
145                 150                 155                 160
Asp Gly Val Met Leu Ala Pro Arg Ala Val Gly Glu Ala Thr Glu Leu
                165                 170                 175
Arg Thr Ala Ala Val Ser Thr Ala Ala Asp Leu Ser Leu Val Glu Leu
            180                 185                 190
Glu Val Thr Gly Ile Arg Arg Val Gly Met Gly Glu Arg Ala Cys Val
        195                 200                 205
Asp Thr Cys Thr Asn Phe Arg Leu Asp Glu Gly Ile Leu Val Gly Ser
    210                 215                 220
His Ser Thr Gly Met Ile Leu Cys Cys Ser Glu Thr His Pro Leu Pro
225                 230                 235                 240
Tyr Met Pro Thr Arg Pro Phe Arg Val Asn Ala Gly Ala Leu His Ser
                245                 250                 255
Tyr Thr Leu Ser Ala Gly Gly Arg Thr Asn Tyr Leu Ser Glu Leu Val
            260                 265                 270
Ser Gly Gly Arg Val Leu Ala Val Asp Ser Gln Gly Lys Ser Arg Val
        275                 280                 285
Val Thr Val Gly Arg Val Lys Ile Glu Thr Arg Pro Leu Leu Ala Ile
    290                 295                 300
Asp Ala Val Ser Pro Ser Gly Thr Arg Val Asn Leu Ile Val Gln Asp
305                 310                 315                 320
Asp Trp His Val Arg Val Leu Gly Pro Gly Gly Thr Val Leu Asn Val
                325                 330                 335
Thr Glu Leu Thr Ala Gly Thr Lys Val Leu Gly Tyr Leu Pro Val Glu
            340                 345                 350
Lys Arg His Val Gly Tyr Pro Ile Asp Glu Phe Cys Ile Glu Lys
        355                 360                 365
```

<210> SEQ ID NO 45
<211> LENGTH: 1104

-continued

```
<212> TYPE: DNA
<213> ORGANISM: Micromonospora sp. strain 046-ECO11

<400> SEQUENCE: 45
gtgaagctgt gctggctgga catccgtaac gtcaacggcg ccaaggaggc aatcgtcgag      60
gaggcggtcc accagcgggt ggacgccgtc gtggcggccg atccggccga cctggagacg     120
cttcccccga cggtgaagaa ggtgctgttc ccgcagggcg ggccgctgcc ggagaagctg     180
gaaccggccg acctggtgat cgtcgagccg gcccggcacg gcgagcccgc cgagctggcg     240
gcccggtacc cggaggtgga gttcggccgg ttcgtcgaga tcgtcgacgc ggacagcctg     300
gaggacgcct gccggtccgc gcgccacgac cggtggagcc tgctgtactt ccgcgacccc     360
accaagatcc cgctggagat cgtgctggcg gccgcgcgg gcgcggaggg cagcatcatc     420
acccaggtcg ccgacgtcga ggaggcggag atcgtcttcg gcgtcctgga gcacggctcg     480
gacggagtga tgctggcgcc ccgcgccgtg ggggaggcca ccgagctgcg gaccgccgcg     540
gtgagcacgg cggcggacct gtcgctcgtg gagctggagg tcaccggcat ccggcgggtg     600
ggcatgggcg agcgcgcctg cgtcgacacg tgcacgaact tccgtctgga cgagggcatc     660
ctggtcggct cgcactccac cggcatgatc ctgtgctgca gcgagacgca tccgctgccg     720
tacatgccga cccggccgtt ccgggtcaac gccggcgcgc tgcactcgta cacgctctcc     780
gccggcgggc ggaccaacta cctcagcgag ctggtctccg gcggcgggt gctcgccgtg     840
gactcgcagg ggaagtcccg cgtcgtcaca gtgggacggg tcaagatcga cgcgtccg      900
ctgctggcga tcgacgcggt ctccccctcc gggacacgcg tcaacctcat cgtccaggac     960
gactggcacg tgcgcgtgct cgggccgggc ggcaccgtgc tcaacgtgac cgagctgacc    1020
gccggcacga aggtgctcgg ttacctgccg gtggagaagc ggcacgtcgg ctacccgatc    1080
gacgagttct gcatcgagaa gtga                                          1104

<210> SEQ ID NO 46
<211> LENGTH: 253
<212> TYPE: PRT
<213> ORGANISM: Micromonospora sp. strain 046-ECO11

<400> SEQUENCE: 46

Met Thr Ala Gln Pro Val Leu Asp Phe His Val Arg Leu Ala Pro Arg
  1               5                  10                  15

Pro Gly Ala Arg Glu Arg Leu Leu Ala Ala Leu Arg Glu Cys Gly Leu
             20                  25                  30

Ala Arg Ala Val Val Cys Ala Gly Gly Thr Ile Asp Leu Asp Arg Leu
         35                  40                  45

Ser Arg Gln Leu Val Thr Gly Gly His Val Glu Thr Asp Ala Asp Asn
     50                  55                  60

Asp Ala Val Ala Ala Ala Cys Ala Gly Thr Asp Gly Arg Leu Val Pro
 65                  70                  75                  80

Phe Phe Phe Ala Asn Pro His Arg Pro Ala Glu Ala Tyr Arg Ala Arg
                 85                  90                  95

Ala Ala Glu Phe Arg Gly Leu Glu Ile Ser Pro Ala Val His Gly Val
            100                 105                 110

Ala Leu Thr Asp Pro Arg Val Ala Asp Leu Val Ala Val Ala Ala Glu
        115                 120                 125

Phe Asp His Pro Val Tyr Val Val Cys Leu Asp Arg Pro Gly Ala Gly
    130                 135                 140

Val Ala Asp Leu Val Gly Leu Ser Arg Arg Phe Pro Gln Val Ser Phe
```

-continued

```
            145                 150                 155                 160
Val Leu Gly His Ser Gly Val Gly Asn Ile Asp Leu Tyr Ala Leu Thr
                165                 170                 175
Leu Ile Gln Asp Glu Pro Asn Ile Ser Leu Glu Thr Ser Gly Gly Tyr
            180                 185                 190
Thr Cys Val Ala Glu Ala Ala Leu Arg Arg Leu Gly Asp Asp Arg Val
        195                 200                 205
Val Phe Gly Ser Glu Tyr Pro Leu Gln His Pro Ala Val Glu Leu Ala
    210                 215                 220
Lys Phe Gln Ala Leu Arg Leu Pro Pro Glu Arg Trp Arg Ile Ala
225                 230                 235                 240
Trp Asp Asn Ala His Arg Leu Leu Gly Glu Glu Lys Arg
                245                 250

<210> SEQ ID NO 47
<211> LENGTH: 762
<212> TYPE: DNA
<213> ORGANISM: Micromonospora sp. strain 046-ECO11

<400> SEQUENCE: 47
atgaccgcgc agccggtgct ggacttccac gtacgcctgg cgccccggcc cggggcgcgg      60
gagcggctgc tcgccgcgct cgcgagtgc gggctggcgc gggcggtggt gtgcgcgggc     120
ggcaccatcg acctggaccg gctgtcccgc cagctcgtca ccggcggcca cgtcgagacc     180
gacgccgaca cgacgcggt ggcggcggcc tgcgccggca ccgacggccg gctggtgccg     240
ttcttcttcg ccaacccgca ccggccggcc gaggcgtacc gggcccgcgc cgccgagttc     300
cgcggcctgg agatctcacc cgccgtccac ggcgtcgccc tgaccgaccc gcgggtcgcc     360
gacctcgtgg ccgtggcggc ggagttcgac catccggtgt acgtggtctg cctggaccga     420
cccggcgcgg cgtggccga cctggtcggc ctgagccgcc ggttcccgca ggtgagcttc     480
gtgctcgggc acagcggcgt cggcaacatc gacctctacg ccctgaccct gatccaggac     540
gagccgaaca tctcgctgga gacctccggc ggctacacct gcgtggccga ggcggcgcta     600
cgccgcctcg gcgacgaccg ggtggtgttc ggctccgagt acccgctgca gcaccccggcc    660 gtggaactgg ccaagttcca ggcgttgcga ctgccgccgg agcggtggcg gcggatcgcc     720
tgggacaacg cgcatcgact gctaggagag gagaagcggt ga                        762

<210> SEQ ID NO 48
<211> LENGTH: 438
<212> TYPE: PRT
<213> ORGANISM: Micromonospora sp. strain 046-ECO11

<400> SEQUENCE: 48

Val Ser Glu Pro Ser Ser Leu Pro Arg Leu Gly Gln Trp His Gly
1               5                   10                  15

Leu Glu Asp Leu Arg Arg Leu Gln Glu Lys Gln Leu Ala Glu Thr Phe
                20                  25                  30

Thr Trp Ala Ala Arg Ser Pro Phe Tyr Arg Ala Arg Leu Ala Ser Gly
            35                  40                  45

Ala Pro Pro Val Thr Pro Ala Asp Leu Ala Asp Leu Pro Leu Thr Thr
        50                  55                  60

Lys Gln Asp Leu Arg Asp Asn Tyr Pro Phe Gly Met Leu Ala Val Pro
65                  70                  75                  80

Arg Glu Arg Leu Ala Thr Tyr His Glu Ser Ser Gly Thr Ala Gly Lys
                85                  90                  95
```

Pro Thr Pro Ser Tyr Tyr Thr Ala Glu Asp Trp Thr Asp Leu Ala Glu
            100                 105                 110

Arg Phe Ala Arg Lys Trp Ile Gly Met Ser Ala Asp Val Phe Leu
        115                 120                 125

Val Arg Thr Pro Tyr Ala Leu Leu Leu Thr Gly His Leu Ala His Ala
    130                 135                 140

Ala Ala Arg Leu Arg Gly Ala Thr Val Val Pro Gly Asp Asn Arg Ser
145                 150                 155                 160

Leu Ala Met Pro Tyr Ala Arg Val Val Arg Val Met His Asp Leu Asp
                165                 170                 175

Val Thr Leu Thr Trp Ser Val Pro Thr Glu Cys Leu Ile Trp Ala Ala
            180                 185                 190

Ala Ala Ile Ala Ala Gly His Arg Pro Asp Ile Asp Phe Pro Ala Leu
        195                 200                 205

Arg Ala Leu Phe Val Gly Gly Glu Pro Met Thr Asp Ala Arg Arg Arg
    210                 215                 220

Arg Ile Ser Arg Leu Trp Gly Val Pro Val Ile Glu Glu Tyr Gly Ser
225                 230                 235                 240

Thr Glu Thr Gly Ser Leu Ala Gly Glu Cys Pro Gly Arg Leu His
                245                 250                 255

Leu Trp Ala Asp Arg Ala Leu Phe Glu Val Tyr Asp Pro Asp Thr Gly
            260                 265                 270

Ala Val Arg Ala Asp Gly Asp Gly Gln Leu Val Val Thr Pro Leu Phe
        275                 280                 285

Arg Glu Ala Met Pro Leu Leu Arg Tyr Asn Leu Glu Asp Asn Val Ser
    290                 295                 300

Val Ser Tyr Asp Asp Cys Gly Cys Gly Trp Lys Leu Pro Thr Val Arg
305                 310                 315                 320

Val Leu Gly Arg Ser Ala Phe Gly Tyr Arg Val Gly Gly Thr Thr Ile
                325                 330                 335

Thr Gln His Gln Leu Glu Glu Leu Val Phe Ser Leu Pro Glu Ala His
            340                 345                 350

Arg Val Met Phe Trp Arg Ala Lys Ala Glu Pro Ala Leu Leu Arg Val
        355                 360                 365

Glu Ile Glu Val Ala Ala His Arg Val Ala Ala Glu Ala Glu Leu
    370                 375                 380

Thr Ala Ala Ile Arg Ala Ala Phe Gly Val Asp Ser Glu Val Thr Gly
385                 390                 395                 400

Leu Ala Pro Gly Thr Leu Ile Pro Leu Asp Ala Leu Thr Ser Met Pro
                405                 410                 415

Asp Val Val Lys Pro Arg Ser Leu Phe Gly Pro Asp Glu Asp Trp Ser
            420                 425                 430

Lys Ala Leu Leu Tyr Tyr
        435

<210> SEQ ID NO 49
<211> LENGTH: 1317
<212> TYPE: DNA
<213> ORGANISM: Micromonospora sp. strain 046-ECO11

<400> SEQUENCE: 49
gtgagcgagc caagttcgag cctgccccgg ctcggccagt ggcacggcct cgaggacctg     60
cggcgcctcc aggagaagca actggcggag acgttcacct gggcggcccg gtcgccgttc    120

```
taccgggcgc ggctggcctc cggcgcgccg ccggtgacgc ccgccgacct ggccgacctg    180
ccgctgacca ccaagcagga cctgcgggac aactacccct tcggcatgct cgccgtgccc    240
cgcgaacggc tggcgaccta ccacgagtcg agcgggaccg ccgggaagcc cacccctcc    300
tactacaccg cggaggactg gaccgacctg gcggagcgct tcgcccgcaa gtggatcggc    360
atgtccgccg acgacgtctt cctggtccgc acgccgtacg cgctgctgct gaccgggcat    420
ctcgcccacg ccgcagcccg gctgcgtggg gccacggtgg tacctggcga caaccggtcg    480
ctggcgatgc cgtacgcccg ggtggtccgg gtgatgcacg acctggacgt cacgctcacc    540
tggtcggtgc cgacggagtg cctgatctgg gccgccgcgg cgatcgcggc cgggcaccgg    600
cccgacatcg acttcccggc gctgcgcgcg ctgttcgtcg gcggcgagcc gatgaccgac    660
gcccgccggc ggcggatcag ccgcctgtgg ggggtgccgg tcatcgagga gtacggctcg    720
acggagaccg gcagcctggc cggggagtgc cccgagggac gcctgcacct gtgggccgac    780
cgggcgctgt tcgaggtgta cgacccggac accggcgccg tccgcgcgga cggcgacggc    840
cagctcgtgg tcacgccgct gttccgggag gcgatgccgc tgctgcggta caacctggag    900
gacaacgtgt cggtctccta cgacgactgc ggatgcggct ggaagctgcc caccgtgcgg    960
gtgctcggcc ggtcggcgtt cggctaccgg gtcggcggca ccaccatcac ccagcaccag   1020
ctggaggaac tggtcttctc cctgccggag gcgcaccggg tgatgttctg cggggccaag   1080
gcggagccgg cgctgttgcg ggtcgagatc gaggtggccg ccgcgcaccg ggtcgccgcc   1140
gaggcggagc tgaccgccgc gatccgggcc gccttcggcg tggacagcga ggtcaccggc   1200
ctggcgccgg aaccctgat cccgctcgac gcgctgacca gcatgccgga cgtggtgaag   1260
ccacgcagcc tgttcggtcc ggacgaggac tggagcaaag cgctcctcta ctactga      1317

<210> SEQ ID NO 50
<211> LENGTH: 396
<212> TYPE: PRT
<213> ORGANISM: Micromonospora sp. strain 046-ECO11

<400> SEQUENCE: 50

Met Pro Gln Met Arg Val Ala Val Ala Gly Ala Gly Ile Ala Gly Leu
1               5                  10                  15

Ala Phe Ala Ala Ala Leu Arg Arg Thr Gly Ile Asp Cys His Val Tyr
            20                  25                  30

Glu Gln Ala Asp Gln Leu Met Glu Val Gly Ala Gly Val Gln Val Ala
        35                  40                  45

Pro Asn Ala Thr Arg Leu Leu His Arg Leu Gly Leu Arg Asp Arg Leu
    50                  55                  60

Arg Thr Val Ala Val Ala Pro Gln Ala Ile Glu Met Arg Arg Trp Asp
65                  70                  75                  80

Asp Gly Thr Leu Leu Gln Arg Thr Gln Leu Gly Ser Val Cys Gly Arg
                85                  90                  95

Arg Phe Gly Ala Pro Tyr Tyr Val Val His Arg Ala Asp Leu His Ser
            100                 105                 110

Ser Leu Leu Ser Leu Val Pro Pro Asp Arg Val His Leu Gly Ala Arg
        115                 120                 125

Leu Thr Ala Val Thr Gln Thr Ala Asp Glu Ala Tyr Leu His Leu Ser
    130                 135                 140

Asn Gly Thr Thr Val Ala Ala Asp Leu Val Val Gly Ala Asp Gly Ile
145                 150                 155                 160

His Ser Val Ala Arg Glu Gln Ile Val Ala Asp Arg Pro Arg Phe Ser
```

```
                  165                 170                 175
Gly Gln Ser Ile Tyr Arg Gly Leu Val Pro Ala Glu Arg Val Pro Phe
             180                 185                 190
Leu Leu Thr Glu Pro Arg Val Gln Leu Trp Phe Gly Pro Asp Gln His
         195                 200                 205
Cys Val Cys Tyr Pro Val Ser Ala Gly Arg Gln Val Ser Phe Gly Ala
     210                 215                 220
Thr Val Pro Ala Thr Asp Trp Arg Gln Glu Ser Trp Ser Gly Arg Gly
225                 230                 235                 240
Asp Val Thr Gln Leu Ala Ala Tyr Ala Gly Trp His Pro Asp Val
                 245                 250                 255
Thr Arg Leu Ile Ala Ala Asp Arg Val Gly Arg Trp Ala Leu His
             260                 265                 270
Asp Arg Asp Ser Ile Asp Arg Leu Ser Ala Gly Arg Val Thr Leu Ile
         275                 280                 285
Gly Asp Ala Ala His Pro Met Leu Pro Phe Gln Ala Gln Gly Ala Asn
     290                 295                 300
Gln Ala Val Glu Asp Ala Val Val Leu Ala Val Cys Leu Ala Gly Val
305                 310                 315                 320
Glu Pro Ala Gly Leu Gly Ala Ala Leu Arg Arg Tyr Glu Arg Ile Arg
                 325                 330                 335
Leu Pro Arg Thr Thr Arg Ile Gln Arg Gln Ser Arg Ala Asn Ala Glu
             340                 345                 350
Met Phe His Leu Ala Asp Gly Ala Asp Gln Arg Arg Asp Val Ala
         355                 360                 365
Ala Gln Ser Ser Ser Gly Leu Asp Arg His Glu Trp Leu Phe Gly Tyr
     370                 375                 380
Asp Ala Glu Lys Ala Thr Thr Thr Ser Gly Ser Ala
385                 390                 395

<210> SEQ ID NO 51
<211> LENGTH: 1191
<212> TYPE: DNA
<213> ORGANISM: Micromonospora sp. strain 046-ECO11

<400> SEQUENCE: 51
atgccgcaga tgagggtcgc cgtggccggc gccggcatcg ccgggctcgc cttcgccgcc        60
gccctgcgcc ggaccgggat cgactgccac gtgtacgaac aggccgacca gctcatggag       120
gtgggcgcgg gcgtgcaggt cgcgccgaac gccacccggc tgctgcaccg gctgggcctg       180
cgtgaccgcc tgcgtacggt ggctgtcgcg ccgcaggcga tcgagatgcg ccgctgggac       240
gacggcacgc tgctgcaacg cacccagctg ggcagcgtgt gcgacgccgc cttcggcgcg       300
ccgtactacg tggtgcaccg cgcggacctg cacagcagcc tgctgtcgct ggtgccgccg       360
gaccgggtgc acctgggcgc cgcctcacc gccgtgacga agaccgccga cgaggcgtac        420
ctgcacctgt ccaacggcac cacggtcgcg gcggatctcg tcgtgggcgc cgacggcatc       480
cactcggtcg cgcgggagca gatcgtggcg gaccggccgc gcttctccgg acagtccatc       540
taccgcgggc tggtgccggc cgagcgggtg ccgttcctgc tcaccgaacc ccgggtgcag       600
ttgtggttcg gccggacca gcactgcgtc tgctacccgg tgtccgccgg ccggcaggtg       660
agcttcggcg cgacggtgcc cgccaccgac tggcggcagg agtcgtggtc gggccggggc       720
gacgtgacgc aactcgcggc cgcgtacgcg ggctggcacc cggacgtcac ccggctgatc       780
gccgcggccg accgggtcgg caggtgggcg ctgcacgacc gggacagcat cgaccggctc       840
```

```
agcgcgggac gggtgaccct gatcggcgac gccgcgcacc cgatgctgcc gttccaggcg    900
cagggcgcga accaggccgt cgaggacgcg gtggtgctcg cggtctgcct ggccggcgtg    960
gaaccggcgg gcctgggcgc cgcgctgcgc cgctacgaac ggatccgcct gccccggacc   1020
acccggatcc agcggcagtc ccgggccaac gccgagatgt ccacctggcc gacggcgcc    1080 gaccagcgcc gccgggacgt cgccgcacaa tcctcgtccg gcctggaccg ccacgaatgg   1140
ctcttcgggt acgacgccga gaaagccacc acgaccagcg ggagcgcctg a            1191
```

<210> SEQ ID NO 52
<211> LENGTH: 261
<212> TYPE: PRT
<213> ORGANISM: Micromonospora sp. strain 046-ECO11

<400> SEQUENCE: 52

```
Met Glu Leu Thr Gly Ile Glu Ser Lys Val Ala Leu Val Thr Gly Ala
1               5                   10                  15

Gly Gln Gly Ile Gly Ala Ala Val Ala Gly Val Leu Ala Arg Ala Gly
            20                  25                  30

Ala Gln Val Ala Ala Val Asp Arg Asn Ala Glu Ala Leu Thr Thr Val
        35                  40                  45

Val Thr Lys Leu Ala Ala Glu Gly Asp Ser Ala Arg Ala Tyr Cys Val
50                  55                  60

Asp Val Cys Asp Ser Glu Ala Val Asp Ala Leu Val Arg Arg Val Glu
65                  70                  75                  80

Asp Glu Met Gly Pro Val Ala Ile Leu Val Asn Ala Ala Gly Val Leu
                85                  90                  95

His Thr Gly Arg Val Val Glu Leu Ser Asp Arg Gln Trp Arg Arg Thr
            100                 105                 110

Phe Ser Val Asn Ala Asp Gly Val Phe His Val Ser Arg Ala Val Ala
        115                 120                 125

Arg Arg Met Val Gly Arg Arg Gly Ala Ile Val Thr Val Ala Ser
130                 135                 140

Asn Ala Ala Gly Val Pro Arg Thr Glu Met Ala Ala Tyr Ala Ala Ser
145                 150                 155                 160

Lys Ala Ala Ser Ala Gln Phe Thr Arg Cys Leu Gly Leu Glu Leu Ser
                165                 170                 175

Gly Tyr Gly Ile Arg Cys Asn Val Val Ser Pro Gly Ser Thr Asp Thr
            180                 185                 190

Pro Met Leu Arg Ala Met Leu Gly Glu Gly Ala Asp Pro Ser Ala Val
        195                 200                 205

Ile Glu Gly Thr Pro Gly Ala Tyr Arg Val Gly Ile Pro Leu Arg Lys
    210                 215                 220

Leu Ala Gln Pro Arg Asp Val Ala Glu Ala Val Ala Tyr Leu Val Ser
225                 230                 235                 240

Asp Gln Ala Gly His Val Thr Met His Asp Leu Tyr Val Asp Gly Gly
                245                 250                 255

Ala Ala Leu His Val
            260
```

<210> SEQ ID NO 53
<211> LENGTH: 786
<212> TYPE: DNA
<213> ORGANISM: Micromonospora sp. strain 046-ECO11

<400> SEQUENCE: 53

-continued

```
atggaactga ccggaatcga gtcgaaggtc gccctggtca cgggcgcggg gcagggcatc      60
ggcgccgccg tggccggtgt cctggcgagg gcgggcgcgc aggtggcggc ggtggaccgc     120
aacgccgagg cgctgaccac cgtcgtgacg aagctcgccg ccgagggcga ctcggcgcgc     180
gcctactgcg tcgacgtgtg cgacagcgag gcggtggacg cgctggtgcg ccgggtcgag     240
gacgagatgg ggccggtcgc catcctggtc aacgccgccg gcgtgctgca caccggacgg     300
gtcgtcgagc tgtcggaccg gcagtggcgc cggaccttct cggtgaacgc cgacggcgtg     360
ttccacgtgt cccgggcggt ggcgcggcgg atggtgggcc gccgtcgtgg cgcgatcgtc     420
accgtggcgt cgaacgccgc cggggtgccg cgtaccgaga tggccgcgta cgccgcctcc     480
aaggccgcgt ccgcgcagtt caccgctgc ctggggcttg agctgtccgg ctacggcatc      540
cggtgcaacg tggtctcgcc cggctccacc gacaccccca tgctgcgggc catgctcggc     600
gagggcgccg accgagcgc ggtgatcgag ggcacgccgg gcgcgtaccg cgtcggcatc      660
ccgctgcgca agctggccca gccgcgcgac gtggccgagg cggtcgccta tctggtgtcc     720
gaccaggcgg gccacgtgac catgcacgac ctgtacgtcg acggcggcgc ggccctgcac     780
gtgtga                                                                786
```

<210> SEQ ID NO 54
<211> LENGTH: 224
<212> TYPE: PRT
<213> ORGANISM: Micromonospora sp. strain 046-ECO11

<400> SEQUENCE: 54

```
Met Ala Met Thr Pro Ile Ala Pro Tyr Arg Met Pro Gly Asp Gly Asp
 1               5                  10                  15

Leu Pro Gly Thr Ala Leu Pro Trp Arg Pro His Pro Asp Arg Ala Ala
            20                  25                  30

Val Leu Val His Asp Leu Gln Arg Tyr Phe Leu Arg Pro Phe Glu Ala
        35                  40                  45

Gly Glu Ser Pro Met Ala Glu Leu Leu Pro Asn Val Ala Lys Leu Leu
    50                  55                  60

Ala Thr Ala Arg Ala Ala Gly Val Pro Val Leu Tyr Thr Ala Gln Pro
65                  70                  75                  80

Gly Gly Met Ser Arg Gln Asp Arg Gly Leu Leu His Asp Leu Trp Gly
                85                  90                  95

Pro Gly Met Ser Ser Ala Glu Asp Asp Arg Gly Ile Val Asp Asp Val
            100                 105                 110

Ala Pro Gln Pro Gly Asp Thr Val Leu Thr Lys Trp Arg Tyr Ser Ala
        115                 120                 125

Phe Phe Arg Ser Asp Leu Glu Glu Arg Leu Arg Gly Ala Gly Arg Asp
    130                 135                 140

Gln Leu Val Val Cys Gly Val Tyr Ala His Met Gly Cys Leu Ile Thr
145                 150                 155                 160

Ala Cys Asp Ala Phe Ser Arg Asp Ile Glu Ala Phe Leu Val Ala Asp
                165                 170                 175

Ala Leu Ala Asp Leu Ser Arg Glu Asp His Leu Met Ala Leu Arg Tyr
            180                 185                 190

Ala Ala Asp Arg Cys Ala Val Pro Leu Trp Thr Ala Asp Val Leu Asp
        195                 200                 205

Gly Leu Ala Asp Ala Ala Gly Arg Pro Asp Gln Ser Ser Thr Gln Arg
    210                 215                 220
```

<210> SEQ ID NO 55
<211> LENGTH: 675
<212> TYPE: DNA
<213> ORGANISM: Micromonospora sp. strain 046-ECO11

<400> SEQUENCE: 55

```
atggccatga ccccgatcgc gccgtaccgc atgcccggcg acggcgacct gcccggcacc      60
gcgctgccct ggcgtccgca cccggaccgg gccgccgtgc tggtgcacga cctgcaacgc     120
tacttcctgc gcccgttcga ggccggggag tccccgatgg ccgaactgct ccccaacgtc     180
gcgaagctgc tcgccacggc gcgggcggcc ggcgtgccgg tgctgtacac cgcgcagccc     240
ggcggcatga ccggcaggac cgcgggttg ctgcacgacc tgtggggccc cggcatgagc      300
agcgccgagg acgaccgggg catcgtcgac gacgtcgccc gcagccgggc gacacggtg      360
ctgaccaagt ggcgctacag cgcgttcttc cgcagcgacc tggaggagcg actgcgcggt     420
gcgggacggg accagctcgt ggtctgcggc gtgtacgcgc acatggggtg cctgatcacc     480
gcctgcgacg cgttcagccg cgacatcgag gcgttcctgg tggcggacgc gctggccgac     540
ctatcgcgcg aggaccacct gatggcgctg cgctacgccg cggaccgctg cgcggtgccg     600
ttgtggacgg cggatgtgct ggacgggctg gcggacgccg ccgggcgtcc ggatcagagc     660
agcacccaac gatga                                                      675
```

<210> SEQ ID NO 56
<211> LENGTH: 233
<212> TYPE: PRT
<213> ORGANISM: Micromonospora sp. strain 046-ECO11

<400> SEQUENCE: 56

```
Met Ser Asp Arg Thr Arg Val Val Val Gly Gly Thr Ser Gly Ile
1               5                   10                  15

Gly Arg His Phe Ala Arg Phe Cys Ala Glu Arg Gly Asp Asp Val Val
            20                  25                  30

Ile Thr Gly Arg Ser Ala Ala Arg Thr Lys Thr Val Ala Asp Glu Ile
        35                  40                  45

Gly Gly Arg Thr Arg Gly Leu Ala Leu Asp Leu Ala Glu Pro Glu Thr
    50                  55                  60

Ile Ala Asp Ala Leu Ala Asp Val Pro His Val Asp Arg Leu Val Val
65                  70                  75                  80

Ala Ala Leu Asp Arg Asp Tyr Asn Thr Val Arg Ala Tyr Arg Pro Gly
                85                  90                  95

Asp Ala Ala Arg Leu Leu Thr Val Lys Leu Val Gly Tyr Thr Ala Val
            100                 105                 110

Leu His Ala Leu Ala Pro Arg Met Thr Asp Glu Ser Ala Val Val Leu
        115                 120                 125

Leu Gly Gly Leu Ala Ser His Arg Pro Tyr Pro Gly Ser Thr Ser Val
    130                 135                 140

Thr Thr Ala Asn Gly Gly Ile Ser Ala Leu Val Arg Thr Leu Ala Val
145                 150                 155                 160

Glu Leu Ser Pro Val Arg Val Asn Ala Leu His Pro Ser Ile Val Ser
                165                 170                 175

Asp Thr Pro Phe Trp Ser Asp Lys Pro Ala Ala Arg Glu Ala Ala Ala
            180                 185                 190

Thr Arg Ala Leu Ser Arg Arg Pro Val Thr Met Gln Asp Cys Ala Glu
        195                 200                 205
```

-continued

```
Ala Ile Asp Phe Leu Leu Thr Asn Arg Ser Ile Asn Gly Val Asn Leu
        210                 215                 220

Asn Ile Asp Gly Gly Asp Val Leu Ile
225                 230

<210> SEQ ID NO 57
<211> LENGTH: 702
<212> TYPE: DNA
<213> ORGANISM: Micromonospora sp. strain 046-ECO11

<400> SEQUENCE: 57
atgtcggatc ggacccgggt cgtggtcgtc ggcggaacct cggggatcgg gcggcacttc      60
gcccgattct gcgccgaacg cggagacgac gtggtgatca ccggccgttc ggcggcccgg     120
accaagaccg tggcgacga gatcggcggg cggacccgtg gctcgctct cgacctggcc     180 gagccggaga cgatcgcgga cgcgctcgcc gacgtgccgc acgtcgaccg gctcgtggtc     240
gcggcgctgg accgcgacta caacaccgtc cgcgcgtacc ggcgggcga cgcggcgcgg     300 ctgctgaccg tcaagctggt cggctacacg gcggtcctgc acgccctcgc ccgcggatg     360 accgacgaga gcgcagtcgt gctgctcggc ggcctggcca gccaccggcc gtatcccggc     420
tccacctccg tcacgaccgc caacggcggg atcagcgcgc tggtgcggac cctggctgtg     480
gaactctcgc cggtccgggt caacgccctg caccccgagca tcgtctccga cacgccgttc     540
tggagcgaca gcccgccgc gcgggaggcc gccgcgaccc gcgcgctcag ccgacggccg     600
gtcaccatgc aggactgcgc cgaggcgatc gacttcctgc tgacgaaccg ctcgataaac     660
ggggtcaacc tgaacatcga cggcggggac gtgctcatct ga                        702

<210> SEQ ID NO 58
<211> LENGTH: 246
<212> TYPE: PRT
<213> ORGANISM: Micromonospora sp. strain 046-ECO11

<400> SEQUENCE: 58

Met Thr Ser Ala Leu Arg Thr Ser Ala Trp Thr Tyr Asp Asp Phe Thr
1               5                   10                  15

Ser Arg Glu Leu Asp Pro Ala Arg Trp Ala Ile Met Ser Ile Ala Gly
            20                  25                  30

Ala Asp Gly Gln Thr His Arg Tyr Gln Asp Arg Asn Ala Gln Val Arg
        35                  40                  45

Thr Gly Asp Gly Arg Leu Glu Leu Thr Val Asp Pro Phe Thr Arg Phe
    50                  55                  60

His Asp Thr Asp Pro Arg Gln Asn Asn Ala Lys Gln Met Tyr Arg Ser
65                  70                  75                  80

Val Arg Arg Phe Ala Val Pro Ala Glu Gly Ser Leu Thr Val Glu Val
                85                  90                  95

Glu Met Gly Val Arg Thr Tyr Arg Gln Ile Pro His Asp Leu Leu Asp
            100                 105                 110

Ala Phe Gly Thr Val Asn Leu Phe Asp Leu Glu Thr Gly Val Val Phe
        115                 120                 125

Asn Ala Ala Ala Thr Asn Asp Thr Val Tyr Ala Thr Val Glu Arg Leu
    130                 135                 140

Val Leu Pro Gly Val Thr Gln Pro His Glu His Tyr Ile His Arg Val
145                 150                 155                 160

Val Leu Asp Val Pro Thr Glu Pro Gly Arg Ala His Gly Tyr Ala Ile
                165                 170                 175
```

```
Thr Tyr Arg Ala Pro Thr Ser Glu Val Glu Phe His Val Asp Gly Arg
            180                 185                 190

Leu Ala Tyr Trp Ala Arg Val Pro Val Pro Val Thr Gly Phe His Ala
            195                 200                 205

Gly Met Ala Leu Phe Ser Ala Arg Asp Leu Ala Arg Tyr Pro Arg Glu
            210                 215                 220

Gln Arg Glu His Gly Gln Gly Ala Thr Gly Trp Trp Gly Pro Trp Arg
225                 230                 235                 240

Ile Ala Ser Gly Val Arg
                245

<210> SEQ ID NO 59
<211> LENGTH: 741
<212> TYPE: DNA
<213> ORGANISM: Micromonospora sp. strain 046-ECO11

<400> SEQUENCE: 59
atgacgtcgg cactgagaac cagcgcgtgg acgtacgacg acttcaccag ccgcgagctg      60
gaccccgccc gctgggcgat catgtcgatc gccggcgcgg acgggcagac ccacaggtac     120
caggaccgca acgcccaggt ccgcaccggc gacggcggtg tggagctgac cgtcgacccg     180
ttcacccgct ccacgacac cgatccccgg cagaacaacg ccaagcagat gtaccggtcg     240
gtgcggcgct tcgccgtgcc ggcggagggc tcgctgaccg tcgaggtgga gatgggcgtg     300
cggacgtacc ggcagatccc gcacgacctg ctggacgcgt tcggcacggt gaacctgttc     360
gacctggaga ccggcgtcgt gttcaacgcc gccgccacga cgacaccgt gtacgcgacg     420 gtcgagcgcc tggtgctgcc cggcgtgacc cagccgcacg agcactacat ccaccgggtg     480
gtcctggacg tgccgacgga gccgggccgg cgcacggat acgccatcac ctaccgggcg     540
ccgacgtcgg aggtggagtt ccacgtcgac ggccggctcg cctactgggc gcgggtcccg     600
gtgccggtga ccggattcca cgccggcatg gcgctcttct ccgcccgcga cctgccccgg     660
tacccccgcg agcagcggga gcacgggcag ggcgcgaccg gtggtggggg gccgtggcgg     720
atcgcctccg gcgtcagatg a                                                741

<210> SEQ ID NO 60
<211> LENGTH: 111
<212> TYPE: PRT
<213> ORGANISM: Micromonospora sp. strain 046-ECO11

<400> SEQUENCE: 60

Met Asp Thr Ala Ala Pro Ala Thr Asp Gly Gly Arg Tyr Leu Ala Val
1               5                   10                  15

His His Ser Ala Glu Phe Arg Glu Leu Arg Arg Arg Ser Ser Thr Phe
            20                  25                  30

Thr Leu Trp Ala Ser Val Ala Phe Phe Gly Trp Trp Phe Leu Gly Ser
        35                  40                  45

Leu Leu Ala Thr Tyr Ala Pro Asp Phe Phe Arg Glu Lys Val Ala Gly
    50                  55                  60

Pro Val Asn Val Gly Leu Leu Phe Val Phe Leu Ser Phe Ala Phe Val
65                  70                  75                  80

Val Thr Leu Ala Ala Phe Tyr Leu Arg Tyr Ala Arg Thr His Leu Asp
            85                  90                  95

Pro Leu Ser Glu Lys Ile Arg Ala Asp Leu Glu Gly Ala Ser Arg
            100                 105                 110
```

<210> SEQ ID NO 61
<211> LENGTH: 336
<212> TYPE: DNA
<213> ORGANISM: Micromonospora sp. strain 046-ECO11

<400> SEQUENCE: 61

| | |
|---|---|
| atggacacgg cagctccggc aacggacggc ggtcgctacc tcgccgtcca tcacagcgca | 60 |
| gagttcaggg aactacggcg acgatcgagc acgttcacgc tctgggccag cgtcgccttc | 120 |
| ttcggctggt ggttcctcgg cagcctgctc gccacctacg cgccggactt cttccgggag | 180 |
| aaggtggccg ccccggtcaa cgtgggtctg ctcttcgtct tcctgtcgtt cgccttcgtg | 240 |
| gtgacgctcg ccgccttcta cctgcgttac gcccgcacgc atctcgatcc gctcagcgag | 300 |
| aagatccgtg ccgacctgga aggagcgtcc cgatga | 336 |

<210> SEQ ID NO 62
<211> LENGTH: 559
<212> TYPE: PRT
<213> ORGANISM: Micromonospora sp. strain 046-ECO11

<400> SEQUENCE: 62

Met Ser Val Ile Leu Ala Asp Pro Pro Pro Val Asp Asn Thr Trp
1               5                   10                  15

Ala Thr Pro Ala Ile Ala Val Pro Val Thr Ile Val Leu Ala Leu Ala
            20                  25                  30

Val Leu Tyr Leu Val Arg Ser Ala Arg Ala Ser Thr Thr Thr Ala Asp
            35                  40                  45

Gly Phe Leu Leu Ala Asp Arg Arg Ile Gly Pro Val Gln Asn Ala Leu
        50                  55                  60

Ala Val Ala Ser Ala Pro Leu Met Tyr Ser Thr Met Tyr Ile Ile Thr
65                  70                  75                  80

Gly His Ile Ala Leu Ser Gly Tyr Asp Ala Ile Leu Leu Met Thr Ala
                85                  90                  95

Phe Thr Met Gly Thr Met Leu Ala Leu Phe Leu Phe Ala Gly Pro Val
            100                 105                 110

Arg Asn Val Gly Gly Tyr Thr Leu Gly Asp Leu Leu Ala Val Arg Thr
            115                 120                 125

Arg Glu Arg Pro Ala Arg Ile Ala Ser Ala Val Leu Thr Leu Leu Thr
        130                 135                 140

Tyr Val Met Leu Thr Val Ile Met Met Ala Ala Ile Ala Phe Ile Phe
145                 150                 155                 160

Asn Arg Trp Phe Gly Val Asp Ala Leu Val Gly Leu Val Leu Pro Val
                165                 170                 175

Phe Val Val Gly Leu Ile Thr Val Gly Tyr Val Tyr Leu Gly Gly Met
            180                 185                 190

Leu Gly Val Thr Arg Ile Leu Val Phe Lys Leu Val Leu Ser Val Val
            195                 200                 205

Val Val Gly Val Leu Thr Ala Trp Val Leu Ala Arg Phe Asp Leu Asn
        210                 215                 220

Leu Phe Ser Leu Leu Glu Arg Ala Glu Ala Asn Ala Ala Pro Val Pro
225                 230                 235                 240

Ser Gly Ser Asp Leu Leu Gly Pro Gly Arg Leu Phe Gly Glu Gly Ala
                245                 250                 255

Thr Thr Leu Val His Leu Ser Lys Leu Phe Ala Ile Ala Val Gly Val
            260                 265                 270

Ala Ala Ile Pro Phe Leu Phe Met Arg Asn Phe Ala Val Thr Ser Gly

```
                275                 280                 285
Arg Asp Ala Arg Arg Ser Thr Gly Trp Ala Ser Met Ile Ile Val Gly
    290                 295                 300

Phe Tyr Leu Cys Leu Ser Val Val Gly Leu Gly Ala Val Ala Ile Leu
305                 310                 315                 320

Gly Arg Asp Asn Ile Gly Val Ile Lys Ala His Arg Asp Ile Ser Phe
                325                 330                 335

Pro Lys Leu Ala Asp Glu Leu Gly Gly Pro Val Met Val Gly Ser Leu
            340                 345                 350

Ala Gly Val Ala Val Leu Thr Ile Val Gly Val Phe Ala Pro Leu Leu
        355                 360                 365

His Ser Ala Val Thr Thr Val Thr Lys Asp Leu Asn Val Ile Arg Gly
    370                 375                 380

Arg Arg Leu Asp Pro Ala Ala Glu Leu Arg Asp Ile Lys Arg Asn Thr
385                 390                 395                 400

Leu Ile Ile Gly Val Gly Ser Val Leu Leu Ala Val Val Met Leu Pro
                405                 410                 415

Val Arg Thr His Ile Phe Ile Pro Thr Ser Ile Asp Ile Ala Gly Ala
            420                 425                 430

Val Val Leu Pro Ile Val Val Tyr Ala Leu Phe Trp Arg Arg Phe Asn
        435                 440                 445

Thr Arg Gly Leu Gln Trp Thr Val Tyr Gly Gly Leu Ala Leu Thr Ala
    450                 455                 460

Phe Leu Val Leu Phe Ser Asn Gly Val Ser Gly Glu Pro Asp Ala Ile
465                 470                 475                 480

Phe Pro Asp Arg Asn Phe Lys Phe Val Asp Val Glu Pro Ala Leu Ile
                485                 490                 495

Thr Val Pro Val Gly Phe Leu Leu Gly Tyr Leu Gly Ser Ile Thr Ser
            500                 505                 510

Arg Glu Arg Asp Asp Ala Ala Phe Ala Glu Met Gln Val Arg Ser Leu
        515                 520                 525

Thr Gly Ala Val Val Thr Gly Pro Pro Arg Pro Ala Ala Val Asp Asp
    530                 535                 540

Glu Asp Arg Asp Gly Arg Gln Asp Arg Ala Pro Ser Pro Val Ser
545                 550                 555
```

<210> SEQ ID NO 63
<211> LENGTH: 1680
<212> TYPE: DNA
<213> ORGANISM: Micromonospora sp. strain 046-ECO11

<400> SEQUENCE: 63

```
atgagcgtca tcctcgccga cccgccaccc ccggtcgaca cacgtgggc gacgcccgcg      60
atcgccgtgc cggtcaccat cgtcctcgcg ctcgcggtgc tctacctggt ccggtcggcg     120
cgcgccagca ccaccaccgc ggacggcttc ctgctggccg accggcggat cgggccggtg     180
cagaacgcgc tggcggtggc ctccgcgccg ctgatgtact cgacgatgta catcatcacc     240
ggccacatcg cgctcagcgg ctacgacgcc atcctgctga tgaccgcctt caccatgggc     300
accatgctcg cgctgttcct cttcgccggg ccggtgcgca acgtgggcgg ctacacgctc     360
ggtgacctgc tcgcggtccg tacccgggag cggccggcgc ggatcgcgtc ggcggtgctc     420
acgctgctga cgtacgtcat gctgacggtg atcatgatgg ccgccatcgc gttcatcttc     480
aaccgctggt tcggcgtcga cgccctcgtc ggcctggtcc tcccggtgtt cgtcgtcggt     540
```

-continued

```
ctgatcacgg tggggtacgt gtacctcggc gggatgctcg gggtcacccg catcctggtg    600
ttcaagctgg tgctgtcggt ggtcgtcgtg ggcgtgctga ccgcctgggt gctggcccgc    660
ttcgacctga acctcttcag cctgctggag cgggccgagg cgaacgcggc gccggtgccc    720
agcggcagcg acctgctggg cccgggccgg ctgttcggcg agggcgcgac cacgctcgtg    780
cacctgtcga agctgttcgc catcgccgtc ggagtggcgg ccattccgtt cctgttcatg    840
cgcaacttcg cggtgaccag cgggcgggac gcgcgccggt cgaccgggtg ggcgtcgatg    900
atcatcgtcg ggttctacct gtgcctgtcc gtcgtcgggc tcggtgccgt cgcgatcctc    960 ggcccgggaca acatcggcgt catcaaggcc caccgcgaca tcagcttccc caagctcgcc    1020
gacgagctcg gcggtccggt gatggtcggc tccctggccg gcgtcgcggt cctgacgatc    1080
gtcggcgtct tcgcgccgct gctgcacagc gccgtgacga cggtgaccaa ggacctgaac    1140
gtgatccgcg gccggcggct ggatccggcc gccgagctgc gggacatcaa gcgcaacacc    1200
ctgatcatcg gcgtcggctc cgtgctgctg gcggtcgtga tgctgccggt acggacccac    1260
atcttcatcc cgacctcgat cgacattgcc ggcgcggtgg tcctgccgat cgtcgtctac    1320
gcgttgttct ggcggcgttt caacacccgc ggactgcagt ggacggtcta cggcggcctc    1380
gcgctcaccg cgttcctggt gctgttctcc aacggtgtct cgggcgagcc ggacgccatc    1440
ttcccggacc gcaacttcaa gttcgtggac gtcgagcccg cgctgatcac ggtgccggtc    1500
ggcttcctgc tcggctacct cggctcgatc accagccggg agcgcgacga cgccgcgttc    1560
gccgagatgc aggtccggtc cctcaccgga gctgtcgtca cgggaccgcc gcggccggcc    1620
gccgtggacg acgaggaccg cgacggccgc caggaccggg cgcccagccc ggtgagctga    1680
```

<210> SEQ ID NO 64
<211> LENGTH: 5960
<212> TYPE: DNA
<213> ORGANISM: Micromonospora sp. strain 046-ECO11

<400> SEQUENCE: 64

```
ccacacccct cgggaggcaa ctgtggatcc ggtaccggtt ctggtcgtgg gcgcgggccc     60
ggtcggcatg gtcaccgcgc tggcgctcgc ccgtcacggc gtcgcctgcg tcctcgtcga    120
ccagggcttc gagacgtcgg tccatcccaa gctggactac gtcaacgccc gcagcatgga    180
gttcctccgc cagttcggcc tcgccgacga cgtccgtgcc gccggcgtcg cgcccgagca    240
ccgggccgac gtcatctggt cgaccggcct ggccggtgag ccgatcacca ggtgggggct    300
gccctcggtg acgcaggagt ggcgccgcat cgccgagcac aacgacggca cccagccggc    360
cgagcccggc cagcgatct cccagatcga cctggaaccg gtcctgcggg cccgctgccg    420
gcgggagccc cttgtcgacc tgcgcctcgg cgtacggttc gactcgctga cccaggacga    480 cgcggggtc accagcgtcc tcgccgacga caccggcggc gaggtccggg tgcggtcgga    540
gtacgtggtc gggtgcgacg gcgcgtcgag ccaggtccgc cgggccgtgg gcatcggtga    600 ggagggttc gacgtgcccg gcctgccggg cgccttcatg gtgcacttca ccagccggga    660
cctggacagc ctgcaccggc acggccggtt ctggcactac ttcgcgttcc ggtacgtgat    720
catcgcccag gacgaggtcg acacctggac cgcgcacgtc aacggcgtcg acccgaacga    780
gttcgacgag ccgccggccg acccggaggc gttcctgctc gacacgatcc gcaccgagct    840
gcggatcgac aaggtgctgc tcacctcgcg ctggcgtccc ggcttcatgc tcgccgacag    900
gtaccgcgcc ggccgggtgc tgctcgccgg tgactcggcc caccgatgt tccccaccgg    960 cgcgtacggc atgaacaccg gcatcggcga cgccgtcgac gtggcctgga agctggccgc    1020
```

```
tgtcgtccgg ggcttcggcg gccccgggct gctcgacagc tacgacgccg aacgccgccc   1080
ggtggggcgg cgcaacatgc gcacctcgca ccggcacctg ggcgtgcacc tgcgggcggg   1140
cgagctcctg cgcggcggcg ccccgctgcc gtccgtcgcg gccttcctcg acgccgagcg   1200
gggcgagaac gagtaccggg ggatcgagct cggctaccgc tactccggct cgccggtgct   1260
ctggccggag ggcccggggg agccctcgga cgacccgcgg gcgtacgccc cgacgacctg   1320
gcccggcgcc cgtccgccca gcctcctgct gagcgacggg cagcagatct tcgaccggtt   1380
cgacccggcc tcgttcaccc tcgtggactt caccggtgac ggcgccgccg gtccgctgct   1440
ggcggcggcg gccgcgcggg ggctcccggt cacccacacc gtggtgaccg accccgggc    1500 tcgtgagctg tgggaacgcg acctcgtcct gctgcggccg gaccaccacg tcgcctggcg   1560
gggaaacacc gtgccgccgg accccgacgc cgtggtccag cgcgtgcggg gtggcggata   1620
ggcgcgacgt gccgtcaccg gcggcccggg tcacgcgcac acgcgaccgg ccggtccggc   1680
tgactctcga ctggaggaca gatgcagcaa tccggttcaa cggcggaacg cagcccactc   1740
gggccgtggg agggcatgcc ggcggtccag caaccggact ggcaggacca cccgcgcgtac   1800 gcggagacct gtcaggcgtt ggcgtcggcc ccgccgctgg tcccacccgg ggaggtacgg   1860
gggttccggc agctgttgtc ggagctggcg tcgaccgacg ggctcctgct gcagttgggc   1920
gactgcgccg agagcctcta cgagtgcacc ccccggcaca cctcggacaa gatcgaggtc   1980
atcgaccggc tggggaccg gctcagcgag ctcaccgggc gcaacgtgct gcgggtgggc    2040
cggatggccg ggcagttcgc caagcccgg tcgcaggcga cggagtggca cgacgcgctg    2100
agcatcccct ccttccgcgg ccacatgatc aattccgagc tggccgcgcc cggtacgcgc   2160
aaggccgacc ctcgccgcat gtggtgggcg tacgaggcga cgaccgggt gcagcgggtc    2220 ctgcgcgccc accgggaggg caacggcgt gccgcgcgga ccgaggggcc gtggtcgagc    2280
cacgaggccc tggtcgtcga ctacgagtcc cgcctgatcc gccgggaccc ggacacgggc   2340
gagcactacc tggcgtcgac ccacctgccg tgggtggggg agcggacccg ccggtccgcc   2400
gaggcgcacg tggccatgct gtccacggtg gtgaacccgg tcggctgcaa gatcgggccg   2460
gacgccgacc cggacgacgt cctgcgggtg tgcgaggcgc tcgacccgcg gcgcgatccg   2520
ggccgtctcg tcctgatccc gcggatgggc cgggaccgga tccgggagtc cctgccgccg   2580
atcgtccgcg cggtggtgaa cgcggggcac cccgtgctct ggctgagcga tcccatgcac   2640
ggcaacaccg tcaaggcctc ggtcggcctg aagacgcgcc acctctccga cgtggtcacc   2700
gaggcgctgt ggttccgcga catcctcgac cagcagcggc agcacgccgc cgggctgcac   2760
atcgaggtcg ccgccaccga cgtgaccgag tgcgtcggcg gttcggtggc cggcgaggag   2820
gacctggcgc ggcactacac ctcgctgtgc gacccgcggc tcaacccggg tcaggccacc   2880
gagctgatcg aagcgtgggc caaggacacc gcgacggtcg gcccgggacc gcggcgctcc   2940
ggcccttcgg cgcggccgga ggtcgccgcc tgacgtcgcc ggtctttgcg ccggccgttt   3000
ccgaactgcg ggaaaattga cagaaggaga cctgccggag caaattcggc caggctagcc   3060
gcgccgtagt tcgtcgtcca ctacttgcgt gggtagtgtc aactacccgt gccgggaccg   3120
tcggtggtgt tgctcagcag gaatcccatc gcaatgatgt gtgagaaggc gtaatccttc   3180
gatcggtgac gcgcgtacct catcctatcc gcactgaatc ctgtctcagc tgaagcgagt   3240
gtttccaatg tggggcagct caaacacgct ggaagtgaag gcaacgacg agagattccc     3300 cctgcccgat gcagctacgg aggatcggtc tgtgcttggc gagacggttc cggtttccgc   3360
```

-continued

```
gctgctgccc ggtgactccc cgcggctggc gggcgagaac gtcgagcaca tccggctgct    3420
ggccgcgatg cacgacctcc cgccgatcct ggtgcaacgc ggcacgatgc gggtgatcga    3480
cggcatgcac cggctgcggg ccgccaagct gcgcggcgac gagaccgtgc gggtgacgtt    3540
cttcgacggg gacgacgccg cggcgttcct gctctcggtc gacgccaaca tcaaacacgg    3600
gctgccgttg tcccgcgccg accgggaggc cgccgccacc cgcatcctgc ggttgtatcc    3660
gcagtggtcg gaccgcgccg tcgccgcggc ggccgggctg tcaccgacca cggcgagcgg    3720
catccggcgc cgcctgctgc aaccggcggc gcgggagggc agccgggtgg gacgggacgg    3780
gcgggtgcgc ccgctggacg gctcggcggg ccgacggcgg ccagcgcggc tcatcgcgct    3840
ccggccggac gcgcccctgc gtgccatcgc gcaggaggcc ggggtgtcgg tgggcacggc    3900
gcgggacgtg cgcgcccggt tgcaggcggg ccggacccc gtcctgacct cgcagcgacc    3960
ggcggccgag cccgagccgg ccgccgacga cgggccggag gcgcgcagac gccggctcgg    4020
ccagccctcc gtgccgcctg tcgactggcc ggcggtacgg ggcaacctga tccgggaccc    4080
cgcggtgaag tacgccgagc tgggccgggc cttcgtccgc tgggccgacg ggcacgtggt    4140
ggatccggcg gcctggcgcg agttcgtcga cgccgtgccg ccgtactggc gcaaatcggt    4200
ggccgagctg gcccgttcgt gcgccagcgc ctggctggcg ttcgcccagg aactggagga    4260
ccgggcgtga aaatggcggc cggcatattt acggtggttg ccgacagcgc gtcgcattcc    4320
actgtcgcgg ccactacccg atcgagtagt ggaccggctt gaataacgcg cgttaatgtt    4380
ccttcgatcc gctgccctca ttttcggtg agcacatttt tgcggcggtc caatggagag    4440
gagaattccc ggtgaacatt ctgaggcggc cgcggaaacg gcatctcggg ggtgtcgcgg    4500
ccgtcgccgc ggcgatcgcc ctggtggcgt cgctgacaaa cggtgtggcg gctgccccgc    4560
aggcgccgac cttcgacctc gacaacggga acgccctgac cgacgtcatc tacccggccc    4620
tcaacaccga gccgcgggtc gagtacagcg gccggcccgg gtcctgggcc gcggaccgcg    4680
ccatgctcat cgaactgccg tggttcgacg ccctggcggc gtaccacccc accgcggtcg    4740
gcatcttctc caccatcggc cgccgtcccg ccgaggagca cacgacgcgc aacaagaaca    4800
tcgccgtcat ctactcggcc tacacctcgc tcagcaagct ctaccccag cacgaggcga    4860 cctggcagcg gatgatggcc accgcgggcc tggaccccgc cgtcaccgcg gaggaccgga    4920
ccaccgccag cggcatcggc atcctcgcct cgaagaacgc gatggcggcg cgccggaacg    4980
acggcacgaa ccgcgacggc gacgcgggcg gccgtcgcta caaccgtgag ccgtacgccg    5040
accacaccgg ctaccggccg gtcaacagcc cgtacgagct gcgcttcccg tcgcgctggc    5100
agccgaacac catctccaag cgcgaggtcg tcctgacgca ggagttcgcg acgcccagt    5160 tcggccgggt caagccgatc accttcgagc ggcccgagca gttccggctc accccgccgc    5220
cgaaccacca cctgttgaac ccgaagggct accggaagca ggccgacgag gtgctgcgcg    5280
cctcggcggg cctggacgac cgcaagaaga tgagcgcgga gatcttcagc gacaacatca    5340
cgccgtacgg cgccatcgcg cacacgctcc tgcggggccg gtacaacacc gaggactccg    5400
tccggttcat cgtgatgact gacgtcgccg ggttcgacgt ggcgatcgcg tcctggtact    5460
acatgcgcaa gtacgactcg gtgcagccgt tcagcgcgat ccgccacctg tacccgaaca    5520
agaagctgac cgcgtggggc ggcccgggcc gggcaccgt caacgacatc accggcaccc    5580
agtggcgcag ctacctcagc tcggtcgcca tcgcggctcc ggattacccg tcggtcaacg    5640
cggcggtctg cgtcgcctac gcccaggtcg cgcgccggtt caccggcacg gacaagctga    5700
ccgtcgtgat cccggtccgc aagggctcct cgatcgtgga accgggcgtg accccggccg    5760
```

-continued

```
ccgacatgat gctcacctgg aacagctact cggagtgggc cgccgagtgc gggcagagcc    5820
gggtctgggc cggcgagaac ttccccgcct cggtcgcggc cgccgaccag tacgcgccgc    5880
agatcggcga ccgtgccttc gacttcgtcc agagcaagct gaacgggcgc tgacgcccgc    5940
gtaccggtcc gtgctgccgg                                                5960
```

<210> SEQ ID NO 65
<211> LENGTH: 532
<212> TYPE: PRT
<213> ORGANISM: Micromonospora sp. strain 046-ECO11

<400> SEQUENCE: 65

```
Val Asp Pro Val Pro Val Leu Val Gly Ala Gly Pro Val Gly Met
1               5                   10                  15

Val Thr Ala Leu Ala Leu Ala Arg His Gly Val Ala Cys Val Leu Val
                20                  25                  30

Asp Gln Gly Phe Glu Thr Ser Val His Pro Lys Leu Asp Tyr Val Asn
            35                  40                  45

Ala Arg Ser Met Glu Phe Leu Arg Gln Phe Gly Leu Ala Asp Asp Val
        50                  55                  60

Arg Ala Ala Gly Val Ala Pro Glu His Arg Ala Asp Val Ile Trp Ser
65                  70                  75                  80

Thr Gly Leu Ala Gly Glu Pro Ile Thr Arg Trp Gly Leu Pro Ser Val
                85                  90                  95

Thr Gln Glu Trp Arg Arg Ile Ala Glu His Asn Asp Gly Thr Gln Pro
            100                 105                 110

Ala Glu Pro Gly Gln Arg Ile Ser Gln Ile Asp Leu Glu Pro Val Leu
        115                 120                 125

Arg Ala Arg Cys Arg Arg Glu Pro Leu Val Asp Leu Arg Leu Gly Val
    130                 135                 140

Arg Phe Asp Ser Leu Thr Gln Asp Asp Ala Gly Val Thr Ser Val Leu
145                 150                 155                 160

Ala Asp Asp Thr Gly Gly Glu Val Arg Val Arg Ser Glu Tyr Val Val
                165                 170                 175

Gly Cys Asp Gly Ala Ser Ser Gln Val Arg Arg Ala Val Gly Ile Gly
            180                 185                 190

Glu Glu Gly Phe Asp Val Pro Gly Leu Pro Gly Ala Phe Met Val His
        195                 200                 205

Phe Thr Ser Arg Asp Leu Asp Ser Leu His Arg His Gly Arg Phe Trp
    210                 215                 220

His Tyr Phe Ala Phe Arg Tyr Val Ile Ile Ala Gln Asp Glu Val Asp
225                 230                 235                 240

Thr Trp Thr Ala His Val Asn Gly Val Asp Pro Asn Glu Phe Asp Glu
                245                 250                 255

Pro Pro Ala Asp Pro Glu Ala Phe Leu Leu Asp Thr Ile Arg Thr Glu
            260                 265                 270

Leu Arg Ile Asp Lys Val Leu Leu Thr Ser Arg Trp Arg Pro Gly Phe
        275                 280                 285

Met Leu Ala Asp Arg Tyr Arg Ala Gly Arg Val Leu Leu Ala Gly Asp
    290                 295                 300

Ser Ala His Arg Met Phe Pro Thr Gly Ala Tyr Gly Met Asn Thr Gly
305                 310                 315                 320

Ile Gly Asp Ala Val Asp Val Ala Trp Lys Leu Ala Ala Val Val Arg
                325                 330                 335
```

Gly Phe Gly Gly Pro Gly Leu Leu Asp Ser Tyr Asp Ala Glu Arg Arg
            340                 345                 350

Pro Val Gly Arg Arg Asn Met Arg Thr Ser His Arg His Leu Gly Val
            355                 360                 365

His Leu Arg Ala Gly Glu Leu Leu Arg Gly Gly Ala Pro Leu Pro Ser
    370                 375                 380

Val Ala Ala Phe Leu Asp Ala Glu Arg Gly Glu Asn Glu Tyr Arg Gly
385                 390                 395                 400

Ile Glu Leu Gly Tyr Arg Tyr Ser Gly Ser Pro Val Leu Trp Pro Glu
                405                 410                 415

Gly Pro Gly Glu Pro Ser Asp Asp Pro Arg Ala Tyr Ala Pro Thr Thr
            420                 425                 430

Trp Pro Gly Ala Arg Pro Pro Ser Leu Leu Leu Ser Asp Gly Gln Gln
            435                 440                 445

Ile Phe Asp Arg Phe Asp Pro Ala Ser Phe Thr Leu Val Asp Phe Thr
    450                 455                 460

Gly Asp Gly Ala Ala Gly Pro Leu Leu Ala Ala Ala Ala Arg Gly
465                 470                 475                 480

Leu Pro Val Thr His Thr Val Val Thr Asp Pro Arg Ala Arg Glu Leu
                485                 490                 495

Trp Glu Arg Asp Leu Val Leu Leu Arg Pro Asp His His Val Ala Trp
            500                 505                 510

Arg Gly Asn Thr Val Pro Pro Asp Pro Asp Ala Val Val Gln Arg Val
            515                 520                 525

Arg Gly Gly Gly
    530

<210> SEQ ID NO 66
<211> LENGTH: 1599
<212> TYPE: DNA
<213> ORGANISM: Micromonospora sp. strain 046-ECO11

<400> SEQUENCE: 66
gtggatccgg taccggttct ggtcgtgggc gcgggcccgg tcggcatggt caccgcgctg      60
gcgctcgccc gtcacggcgt cgcctgcgtc ctcgtcgacc agggcttcga acgtcggtc     120 catcccaagc tggactacgt caacgcccgc agcatggagt cctccgcca gttcggcctc     180 gccgacgacg tccgtgccgc cggcgtcgcg cccgagcacc gggccgacgt catctggtcg     240
accggcctgg ccggtgagcc gatcaccagg tggggctgc cctcggtgac gcaggagtgg     300
cgccgcatcg ccgagcacaa cgacggcacc cagccggccg agcccggcca gcggatctcc     360
cagatcgacc tggaaccggt cctgcgggcc cgctgccggc gggagcccct tgtcgacctg     420
cgcctcggcg tacggttcga ctcgctgacc caggacgacg cggggtcac cagcgtcctc     480 gccgacgaca ccgcggcga ggtccgggtg cggtcggagt acgtggtcgg gtgcgacggc     540
gcgtcgagcc aggtccgccg ggccgtgggc atcggtgagg aggggttcga cgtgcccggc     600
ctgccgggcg ccttcatggt gcacttcacc agccggacc tggacagcct gcaccggcac     660
ggccggttct ggcactactt cgcgttccgg tacgtgatca tcgcccagga cgaggtcgac     720
acctggaccg cgcacgtcaa cggcgtcgac ccgaacgagt cgacgagcc gccgccgac     780 ccggaggcgt tcctgctcga cacgatccgc accgagctgc ggatcgacaa ggtgctgctc     840
acctcgcgct ggcgtcccgg cttcatgctc gccgacaggg accgcgcggg ccgggtgctg     900
ctcgccggtg actcggccca ccggatgttc cccaccggcg cgtacggcat gaacaccggc     960

-continued

```
atcggcgacg ccgtcgacgt ggcctggaag ctggccgctg tcgtccgggg cttcggcggc   1020
cccgggctgc tcgacagcta cgacgccgaa cgccgcccgg tggggcggcg caacatgcgc   1080
acctcgcacc ggcacctggg cgtgcacctg cgggcgggcg agctcctgcg cggcggcgcc   1140
ccgctgccgt ccgtcgcggc cttcctcgac gccgagcggg gcgagaacga gtaccggggg   1200
atcgagctcg gctaccgcta ctccggctcg ccggtgctct ggccggaggg cccggggggag   1260 ccctcggacg acccgcgggc gtacgccccg acgacctggc ccggcgcccg tccgcccagc   1320
ctcctgctga gcgacgggca gcagatcttc gaccggttcg acccggcctc gttcaccctc   1380
gtggacttca ccggtgacgg cgccgccggt ccgctgctgg cggcggcggc cgcgcggggg   1440
ctcccggtca cccacaccgt ggtgaccgac ccccgggctc gtgagctgtg ggaacgcgac   1500
ctcgtcctgc tgcggccgga ccaccacgtc gcctggcggg gaaacaccgt gccgccggac   1560
cccgacgccg tggtccagcg cgtgcggggt ggcggatag                          1599
```

```
<210> SEQ ID NO 67
<211> LENGTH: 423
<212> TYPE: PRT
<213> ORGANISM: Micromonospora sp. strain 046-ECO11

<400> SEQUENCE: 67

Met Gln Gln Ser Gly Ser Thr Ala Glu Arg Ser Pro Leu Gly Pro Trp
1               5                   10                  15

Glu Gly Met Pro Ala Val Gln Gln Pro Asp Trp Gln Asp His Pro Ala
            20                  25                  30

Tyr Ala Glu Thr Cys Gln Ala Leu Ala Ser Ala Pro Pro Leu Val Pro
        35                  40                  45

Pro Gly Glu Val Arg Gly Phe Arg Gln Leu Leu Ser Glu Leu Ala Ser
    50                  55                  60

Thr Asp Gly Leu Leu Leu Gln Leu Gly Asp Cys Ala Glu Ser Leu Tyr
65                  70                  75                  80

Glu Cys Thr Pro Arg His Thr Ser Asp Lys Ile Glu Val Ile Asp Arg
                85                  90                  95

Leu Gly Asp Arg Leu Ser Glu Leu Thr Gly Arg Asn Val Leu Arg Val
            100                 105                 110

Gly Arg Met Ala Gly Gln Phe Ala Lys Pro Arg Ser Gln Ala Thr Glu
        115                 120                 125

Trp His Asp Ala Leu Ser Ile Pro Ser Phe Arg Gly His Met Ile Asn
    130                 135                 140

Ser Glu Leu Ala Ala Pro Gly Thr Arg Lys Ala Asp Pro Arg Arg Met
145                 150                 155                 160

Trp Trp Ala Tyr Glu Ala Ser Asp Arg Val Gln Arg Val Leu Arg Ala
                165                 170                 175

His Arg Glu Gly Asn Arg Arg Ala Ala Arg Thr Glu Gly Pro Trp Ser
            180                 185                 190

Ser His Glu Ala Leu Val Val Asp Tyr Glu Ser Arg Leu Ile Arg Arg
        195                 200                 205

Asp Pro Asp Thr Gly Glu His Tyr Leu Ala Ser Thr His Leu Pro Trp
    210                 215                 220

Val Gly Glu Arg Thr Arg Arg Ser Ala Glu Ala His Val Ala Met Leu
225                 230                 235                 240

Ser Thr Val Val Asn Pro Val Gly Cys Lys Ile Gly Pro Asp Ala Asp
                245                 250                 255
```

```
Pro Asp Asp Val Leu Arg Val Cys Glu Ala Leu Asp Pro Arg Arg Asp
            260                 265                 270
Pro Gly Arg Leu Val Leu Ile Pro Arg Met Gly Arg Asp Arg Ile Arg
            275                 280                 285
Glu Ser Leu Pro Pro Ile Val Arg Ala Val Val Asn Ala Gly His Pro
            290                 295                 300
Val Leu Trp Leu Ser Asp Pro Met His Gly Asn Thr Val Lys Ala Ser
305                 310                 315                 320
Val Gly Leu Lys Thr Arg His Leu Ser Asp Val Val Thr Glu Ala Leu
                325                 330                 335
Trp Phe Arg Asp Ile Leu Asp Gln Gln Arg Gln His Ala Ala Gly Leu
                340                 345                 350
His Ile Glu Val Ala Ala Thr Asp Val Thr Glu Cys Val Gly Gly Ser
            355                 360                 365
Val Ala Gly Glu Glu Asp Leu Ala Arg His Tyr Thr Ser Leu Cys Asp
            370                 375                 380
Pro Arg Leu Asn Pro Gly Gln Ala Thr Glu Leu Ile Glu Ala Trp Ala
385                 390                 395                 400
Lys Asp Thr Ala Thr Val Gly Pro Gly Pro Arg Ser Gly Pro Ser
                405                 410                 415
Ala Arg Pro Glu Val Ala Ala
            420

<210> SEQ ID NO 68
<211> LENGTH: 1272
<212> TYPE: DNA
<213> ORGANISM: Micromonospora sp. strain 046-ECO11

<400> SEQUENCE: 68
atgcagcaat ccggttcaac ggcggaacgc agcccactcg gccgtgggga gggcatgccg      60
gcggtccagc aaccggactg gcaggaccac ccggcgtacg cggagacctg tcaggcgttg     120
gcgtcggccc cgccgctggt cccacccggg gaggtacggg ggttccggca gctgttgtcg     180
gagctggcgt cgaccgacgg gctcctgctg cagttgggcg actgcgccga gagcctctac     240
gagtgcaccc ccggcacac  tcggacaag  atcgaggtca tcgaccggct ggggaccgg      300
ctcagcgagc tcaccgggcg caacgtgctg cgggtgggcc ggatggccgg cagttcgcc      360
aagccccggt cgcaggcgac ggagtggcac gacgcgctga gcatcccctc cttccgcggc     420
cacatgatca attccgagct ggccgcgccc ggtacgcgca aggccgaccc tcgccgcatg     480
tggtgggcgt acgaggcgag cgaccgggtg cagcgggtcc tgcgcgccca ccgggagggc     540
aaccggcgtg ccgcgcggac cgaggggccg tggtcgagcc acgaggccct ggtcgtcgac     600
tacgagtccc gcctgatccg ccgggacccg gacacgggcg agcactacct ggcgtcgacc     660
cacctgccgt gggtggggga gcggaccgcc cggtccgccg aggcgcacgt ggccatgctg     720
tccacggtgg tgaacccggt cggctgcaag atcgggccgg acgccgaccc ggacgacgtc     780
ctgcggggtgt gcgaggcgct cgacccgcgc gcgatccgg  ccgtctcgt  cctgatcccg    840
cggatgggcc gggaccggat ccgggagtcc ctgccgccga tcgtccgcgc ggtggtgaac     900
gcggggcacc ccgtgctctg gctgagcgat cccatgcacg caacaccgt  caaggcctcg     960
gtcggcctga agacgcgcca cctctccgac gtggtcaccg aggcgctgtg gttccgcgac    1020
atcctcgacc agcagcggca gcacgccgcc gggctgcaca tcgaggtcgc cgccaccgac    1080
gtgaccgagt gcgtcggcgg ttcggtggcc ggcgaggagg acctggcgcg gcactacacc    1140
```

-continued

```
tcgctgtgcg acccgcggct caacccgggt caggccaccg agctgatcga agcgtgggcc    1200
aaggacaccg cgacggtcgg cccgggaccg cggcgctccg ccccttcggc gcggccgag    1260 gtcgccgcct ga                                                         1272
```

<210> SEQ ID NO 69
<211> LENGTH: 340
<212> TYPE: PRT
<213> ORGANISM: Micromonospora sp. strain 046-ECO11

<400> SEQUENCE: 69

```
Met Trp Gly Ser Ser Asn Thr Leu Glu Val Lys Gly Asn Asp Glu Arg
1               5                   10                  15

Phe Pro Leu Pro Asp Ala Ala Thr Glu Asp Arg Ser Val Leu Gly Glu
            20                  25                  30

Thr Val Pro Val Ser Ala Leu Leu Pro Gly Asp Ser Pro Arg Leu Ala
        35                  40                  45

Gly Glu Asn Val Glu His Ile Arg Leu Leu Ala Ala Met His Asp Leu
    50                  55                  60

Pro Pro Ile Leu Val Gln Arg Gly Thr Met Arg Val Ile Asp Gly Met
65                  70                  75                  80

His Arg Leu Arg Ala Ala Lys Leu Arg Gly Asp Glu Thr Val Arg Val
                85                  90                  95

Thr Phe Phe Asp Gly Asp Asp Ala Ala Phe Leu Leu Ser Val Asp
            100                 105                 110

Ala Asn Ile Lys His Gly Leu Pro Leu Ser Arg Ala Asp Arg Glu Ala
        115                 120                 125

Ala Ala Thr Arg Ile Leu Arg Leu Tyr Pro Gln Trp Ser Asp Arg Ala
    130                 135                 140

Val Ala Ala Ala Gly Leu Ser Pro Thr Thr Ala Ser Gly Ile Arg
145                 150                 155                 160

Arg Arg Leu Leu Gln Pro Ala Ala Arg Glu Gly Ser Arg Val Gly Arg
                165                 170                 175

Asp Gly Arg Val Arg Pro Leu Asp Gly Ser Ala Gly Arg Arg Ala
            180                 185                 190

Ser Ala Val Ile Ala Leu Arg Pro Asp Ala Pro Leu Arg Ala Ile Ala
        195                 200                 205

Gln Glu Ala Gly Val Ser Val Gly Thr Ala Arg Asp Val Arg Ala Arg
    210                 215                 220

Leu Gln Ala Gly Arg Asp Pro Val Leu Thr Ser Gln Arg Pro Ala Ala
225                 230                 235                 240

Glu Pro Glu Pro Ala Ala Asp Asp Gly Pro Glu Ala Arg Arg Arg
                245                 250                 255

Leu Gly Gln Pro Ser Val Pro Val Asp Trp Pro Ala Val Arg Gly
            260                 265                 270

Asn Leu Ile Arg Asp Pro Ala Val Lys Tyr Ala Glu Leu Gly Arg Ala
        275                 280                 285

Phe Val Arg Trp Ala Asp Gly His Val Val Asp Pro Ala Ala Trp Arg
    290                 295                 300

Glu Phe Val Asp Ala Val Pro Pro Tyr Trp Arg Lys Ser Val Ala Glu
305                 310                 315                 320

Leu Ala Arg Ser Cys Ala Ser Ala Trp Leu Ala Phe Ala Gln Glu Leu
                325                 330                 335

Glu Asp Arg Ala
            340
```

<210> SEQ ID NO 70
<211> LENGTH: 1023
<212> TYPE: DNA
<213> ORGANISM: Micromonospora sp. strain 046-ECO11

<400> SEQUENCE: 70

```
atgtggggca gctcaaacac gctggaagtg aagggcaacg acgagagatt ccccctgccc      60
gatgcagcta cggaggatcg gtctgtgctt ggcgagacgg ttccggtttc gcgcgctgctg    120
cccggtgact ccccgcggct ggcgggcgag aacgtcgagc acatccggct gctggccgcg    180
atgcacgacc tcccgccgat cctggtgcaa cgcggcacga tgcgggtgat cgacggcatg    240
caccggctgc gggccgccaa gctgcgcggc gacgagaccg tgcgggtgac gttcttcgac    300
ggggacgacg ccgcggcgtt cctgctctcg gtcgacgcca acatcaaaca cgggctgccg    360
ttgtcccgcg ccgaccggga ggccgccgcc acccgcatcc tgcggttgta tccgcagtgg    420
tcggaccgcg ccgtcgccgc ggcggccggg ctgtcaccga ccacggcgag cggcatccgg    480
cgccgcctgc tgcaaccggc ggcgcgggag ggcagccggg tgggacggga cgggcgggtg    540
cgcccgctgg acggctcggc gggccgacgg cgggccagcg cggtcatcgc gctccggccg    600
gacgcgcccc tgcgtgccat cgcgcaggag gccggggtgt cggtgggcac ggcgcgggac    660
gtgcgcgccc ggttgcaggc gggccgggac cccgtcctga cctcgcagcg accggcggcc    720
gagcccgagc cggccgccga cgacgggccg gaggcgcgca gacgccggct cggccagccc    780
tccgtgccgc ctgtcgactg gccggcggta cggggcaacc tgatccggga ccccgcggtg    840
aagtacgccg agctgggccg ggccttcgtc cgctgggccg acgggcacgt ggtggatccg    900
gcggcctggc gcgagttcgt cgacgccgtg ccgccgtact ggcgcaaatc ggtggccgag    960
ctggcccgtt cgtgcgccag cgcctggctg gcgttcgccc aggaactgga ggaccgggcg   1020
tga                                                                  1023
```

<210> SEQ ID NO 71
<211> LENGTH: 493
<212> TYPE: PRT
<213> ORGANISM: Micromonospora sp. strain 046-ECO11

<400> SEQUENCE: 71

```
Val Asn Ile Leu Arg Arg Pro Arg Lys Arg His Leu Gly Gly Val Ala
1               5                   10                  15

Ala Val Ala Ala Ala Ile Ala Leu Val Ala Ser Leu Thr Asn Gly Val
            20                  25                  30

Ala Ala Ala Pro Gln Ala Pro Thr Phe Asp Leu Asp Asn Gly Asn Ala
        35                  40                  45

Leu Thr Asp Val Ile Tyr Pro Ala Leu Asn Thr Glu Pro Arg Val Glu
    50                  55                  60

Tyr Ser Gly Arg Pro Gly Ser Trp Ala Ala Asp Arg Ala Met Leu Ile
65                  70                  75                  80

Glu Leu Pro Trp Phe Asp Ala Leu Ala Ala Tyr His Pro Thr Ala Val
                85                  90                  95

Gly Ile Phe Ser Thr Ile Gly Arg Arg Pro Ala Glu Glu His Thr Thr
            100                 105                 110

Arg Asn Lys Asn Ile Ala Val Ile Tyr Ser Ala Tyr Thr Ser Leu Ser
        115                 120                 125

Lys Leu Tyr Pro Gln His Glu Ala Thr Trp Gln Arg Met Met Ala Thr
    130                 135                 140
```

```
Ala Gly Leu Asp Pro Ala Val Thr Ala Glu Asp Arg Thr Thr Ala Ser
145                 150                 155                 160

Gly Ile Gly Ile Leu Ala Ser Lys Asn Ala Met Ala Ala Arg Arg Asn
            165                 170                 175

Asp Gly Thr Asn Arg Asp Gly Asp Ala Gly Arg Arg Tyr Asn Arg
            180                 185                 190

Glu Pro Tyr Ala Asp His Thr Gly Tyr Arg Pro Val Asn Ser Pro Tyr
            195                 200                 205

Glu Leu Arg Phe Pro Ser Arg Trp Gln Pro Asn Thr Ile Ser Lys Arg
210                 215                 220

Glu Val Val Leu Thr Gln Glu Phe Ala Thr Pro Gln Phe Gly Arg Val
225                 230                 235                 240

Lys Pro Ile Thr Phe Glu Arg Pro Glu Gln Phe Arg Leu Thr Pro Pro
                245                 250                 255

Pro Asn His His Leu Leu Asn Pro Lys Gly Tyr Arg Lys Gln Ala Asp
                260                 265                 270

Glu Val Leu Arg Ala Ser Ala Gly Leu Asp Asp Arg Lys Lys Met Ser
            275                 280                 285

Ala Glu Ile Phe Ser Asp Asn Ile Thr Pro Tyr Gly Ala Ile Ala His
            290                 295                 300

Thr Leu Leu Arg Gly Arg Tyr Asn Thr Glu Asp Ser Val Arg Phe Ile
305                 310                 315                 320

Val Met Thr Asp Val Ala Gly Phe Asp Val Ala Ile Ala Ser Trp Tyr
                325                 330                 335

Tyr Met Arg Lys Tyr Asp Ser Val Gln Pro Phe Ser Ala Ile Arg His
                340                 345                 350

Leu Tyr Pro Asn Lys Lys Leu Thr Ala Trp Gly Pro Gly Arg Gly
            355                 360                 365

Thr Val Asn Asp Ile Thr Gly Thr Gln Trp Arg Ser Tyr Leu Ser Ser
            370                 375                 380

Val Ala Ile Ala Ala Pro Asp Tyr Pro Ser Val Asn Ala Ala Val Cys
385                 390                 395                 400

Val Ala Tyr Ala Gln Val Ala Arg Arg Phe Thr Gly Thr Asp Lys Leu
                405                 410                 415

Thr Val Val Ile Pro Val Arg Lys Gly Ser Ser Ile Val Glu Pro Gly
                420                 425                 430

Val Thr Pro Ala Ala Asp Met Met Leu Thr Trp Asn Ser Tyr Ser Glu
                435                 440                 445

Trp Ala Ala Glu Cys Gly Gln Ser Arg Val Trp Ala Gly Glu Asn Phe
450                 455                 460

Pro Ala Ser Val Ala Ala Ala Asp Gln Tyr Ala Pro Gln Ile Gly Asp
465                 470                 475                 480

Arg Ala Phe Asp Phe Val Gln Ser Lys Leu Asn Gly Arg
                485                 490

<210> SEQ ID NO 72
<211> LENGTH: 1482
<212> TYPE: DNA
<213> ORGANISM: Micromonospora sp. strain 046-ECO11

<400> SEQUENCE: 72
gtgaacattc tgaggcggcc gcggaaacgg catctcgggg gtgtcgcggc cgtcgccgcg    60
gcgatcgccc tggtggcgtc gctgacaaac ggtgtggcgg ctgccccgca ggcgccgacc   120
```

-continued

| | |
|---|---|
| ttcgacctcg acaacgggaa cgccctgacc gacgtcatct acccggccct caacaccgag | 180 |
| ccgcgggtcg agtacagcgg ccggcccggg tcctgggccg cggaccgcgc catgctcatc | 240 |
| gaactgccgt ggttcgacgc cctggcggcg taccacccca ccgcggtcgg catcttctcc | 300 |
| accatcggcc gccgtcccgc cgaggagcac acgacgcgca acaagaacat cgccgtcatc | 360 |
| tactcggcct acacctcgct cagcaagctc taccccagc acgaggcgac ctggcagcgg | 420 |
| atgatggcca ccgcgggcct ggaccccgcc gtcaccgcgg aggaccggac caccgccagc | 480 |
| ggcatcggca tcctcgcctc gaagaacgcg atggcggcgc gccggaacga cggcacgaac | 540 |
| cgcgacggcc acgcgggcgg ccgtcgctac aaccgtgagc cgtacgccga ccacaccggc | 600 |
| taccggccgg tcaacagccc gtacgagctg cgcttcccgt cgcgctggca gccgaacacc | 660 |
| atctccaagc gcgaggtcgt cctgacgcag gagttcgcga cgcccagtt cggccgggtc | 720 |
| aagccgatca ccttcgagcg gcccgagcag ttccggctca cccgccgcc gaaccaccac | 780 |
| ctgttgaacc cgaagggcta ccggaagcag gccgacgagg tgctgcgcgc ctcggcgggc | 840 |
| ctggacgacc gcaagaagat gagcgcggag atcttcagcg acaacatcac gccgtacggc | 900 |
| gccatcgcgc acacgctcct gcggggccgg tacaacaccg aggactccgt ccggttcatc | 960 |
| gtgatgactg acgtcgccgg gttcgacgtg gcgatcgcgt cctggtacta catgcgcaag | 1020 |
| tacgactcgt gcagccgtt cagcgcgatc cgccacctgt acccgaacaa gaagctgacc | 1080 |
| gcgtggggcg gcccgggccg gggcaccgtc aacgacatca ccggcaccca gtggcgcagc | 1140 |
| tacctcagct cggtcgccat cgcggctccg gattacccgt cggtcaacgc ggcggtctgc | 1200 |
| gtcgcctacg cccaggtcgc gcgccggttc accggcacgg acaagctgac cgtcgtgatc | 1260 |
| ccggtccgca agggctcctc gatcgtggaa ccggggcgtga ccccggccgc cgacatgatg | 1320 |
| ctcacctgga acagctactc ggagtgggcc gccgagtgcg ggcagagccg ggtctgggcc | 1380 |
| ggcgagaact tccccgcctc ggtcgcggcc gccaccagt acgcgccgca gatcggcgac | 1440 |
| cgtgccttcg acttcgtcca gagcaagctg aacgggcgct ga | 1482 |

<210> SEQ ID NO 73
<211> LENGTH: 9762
<212> TYPE: DNA
<213> ORGANISM: Micromonospora sp. strain 046-ECO11

<400> SEQUENCE: 73

| | |
|---|---|
| cagccacggc gttccgaccc cccgcaagat ggcttgtata gcaaggtatc ttgcgatgca | 60 |
| tggacgggc acgtgagcgg atcactacga acatccgcaa gggcgtgctg gagtactgcg | 120 |
| tgctcgccct gctctcgcgg cgcgacatgt acggcctgga actggccgac tggctcgccg | 180 |
| tccgcggtct gaccgcgagc gagggcagcc tgtatccgct gctcgcccgc atgcggcagg | 240 |
| ccggctccgt gcagacccgg tgggtggccc ccgagcaggg gcacgcccgg cggtactacg | 300 |
| cgatcaccga ccaggggcgg gcgcacctgc gggtgttcgc ggcggtgtgg caggagatcc | 360 |
| agccgcacgt ggacgacctg atggggagg aagcatgagc gacgacggcc tcccggaggc | 420 |
| ggcgtggacc tatctgcgcg cgctcgacgc ggagttgtcc gacgtccgt ccggcacggc | 480 |
| ggaggagatc gtcgcggatg tccgcgcgca catcgccgac gccctcgaca cggacggag | 540 |
| cgccacgag atcctcgccg gcctcggcgc gcgcggac gtggcccggc aggcgcgcga | 600 |
| ggagctgggg ctgccggccc aggaccgccc ggcccgggc ggcggaccc tgtccctggc | 660 |
| cgcggtggcg gtcggcgtgc tgatcgccgt gtgcgtgagc ttcctgctgc cgtccgcagt | 720 |
| gccggtggag ccgatccagg ccggccccgg cgagcagggc gtcctccgcc ggctcggccc | 780 |

```
cggaatcgcg ctgctcacgc tgctgccggc gctcgtcgcg gccgcgccgc tcgtggcgcc    840
cgcccgggca cgtgccgggg tacggttcgc cggcgcggcg gtcctgacga tgttcgcctg    900
cgcggccggc gagacgggcc tgtactactt cccgctcgcg ctgatggcct gggcggcggc    960
gatcgtgccg tgggccctgc ggcgcggagc cggtggacgg tggtggcgct atctgaccgg   1020
tggattcgtg gcgatgcccg gcgtgctggt ggcggtcgcg tcggccggtg gctcggtcgg   1080
cgtcggctgg gtcggcgcgg cgctgtggat cgccgggccg ctcgcggccg gcgcgctgtg   1140
cgcctacggg atccgggccg gctacgccgt gaccgcgctg gccggcgcgc tggccatagc   1200
gctctcgatg gccgagcgcg gcttcctgtt cgccgccttc tggctgttcg gcgggctgta   1260
cctggcgctc ggcgccgctg cgtacaccgc ctcgcgggcc gtcgacggcg acgccgccgc   1320
gacgcccggc ccgccggccc ggccggaacc cgcgccggcc cccggaggct gacccggggg   1380
ccgtggcgcc ggccggctag gcggggacgg cctgcgggtc gccggcggcg tcgtgcgcgg   1440
ccatcgtctc ctgccggacg ggctcctcgc gcaggatcgc cgcgtgcagc cacgcgtccg   1500
ggatggcgaa gccgtccacg agcgtgcgca tgtccgggcg cagctccttg agcagcccgt   1560
tcaccacgct ggtgatggtc ttcgagcggg ccggggtgag ccggccgtgc tcgagcagcc   1620
agcccttgtt cgcctcgatc acggtgagcg cgtacaggtc gcagacccgg acagcagtt   1680 ccttgaccgc cgggtcggcg atggcgtcga tcccggcgac gaacgcctcc agcgtcaccc   1740
ggtcgatgtg cgccgcggcg acggcgagga cgtggtcctg gacgtcgttg aagatgtcga   1800
aggggcggtc cttcttggtg gacgcgccac cgcgcaggcg gcggaccgcg ctgtcgagca   1860
ggtgctcctc gcggtcctcg aagagcttga gctgccagcc ccggtcggtg acggcgacct   1920
cgtcgtcgcg cccgggcacg gcgctgacca gacgtgcgat cagcgcccgc gcggcggtgc   1980
gttccagcac catctcgcgt acctgctcgg ccacgaagga ggcgcgtccc cagccgtcga   2040
gcgagccgaa ctcgtcccgg tagccggtca gcagccccct tggcgaccagt tgcagcagca   2100 ccgtgttgtc gccctcgaag gtggtgaaga catcggtgtc ggccttgagg ctgggcaggc   2160
ggttctcgga caggtagccg gcgccgccac acgcctcccg gcagatctgg atggtgcggg   2220
tggcgtgcca ggtctgcgcc gccttcagac cggcggcccg ggactccagc tcccgctgcc   2280
ggtgctcgtc gaccggcccg tcgccgccct ggatgtcgtc gagcgccgcg accagctccg   2340
cctgggcgaa ggtcagcgcg tacgtggtgg ccagcgcggg cagcagcttg cgctggtgcg   2400
ccaggtagtc gttgagcagc acctcgcggt cgccgtcggc gtcggcgaac tgccggcgga   2460
tgtcgccgta gcgcaccgcg atggccagcg ccgacttggt ggccgccgac gcggcgccgc   2520
ccacgctcac ccgccccggg accagggtgc ccagcatggt gaagaagcgc cgggagtcgt   2580
tctcgatcgg gctggagtac gtgccgtcct cggcgacctg cgcgtactgg tccagcagca   2640
tctcccgcgg cacccgcacg tggtcgaagc tgagccgccc gttgtccacg ccgagcaggc   2700
cggccttggg cccggcgtcg ccgatggtca cgccgggcat cggcttgccg tgctcgtcgc   2760
ggatcggcac cagccaggcg tgcaccccgt ggcggcgccc gccggtgacg agctgggcga   2820
acaccacagc catccgcccg tcccggccg cgttgccgat gtagtccttg cgcgcggcct   2880
cgtgcggggt gtgcaggtcg aaggtctgcg tctgcgggtc gtagacgcag gtggtgcgca   2940
gttgctgcac gtccgagccg tggccggtct cggtcatcgc gaagcagccg aagagccggc   3000
ccgcgacgat gtcccgcagg taggcgtcgt ggtgccgctt cgtgccgagg gcggcgaccg   3060
cgccgccgaa caggccccac tgcacgccgg ccttcaccat cagtgacagg tccacctggg   3120
```

```
ccagcatctc ggtggcgacg atcgaggcgc ccacgtcgcc gcggccgccg tactcggcgg   3180
ggaaaccgga ggcgatgccc agctcgacgg ggagttcgga cagcagccgg gtgatgcgct   3240
cgcgggcctg gtcaccggtc tcgccgtaca ccgggaggaa gcgttcgtcg aggtgttcgc   3300
ggtgcgcccg gcggacctcg gcccaccggc cgtcgagcgc ttcccgcagg cgtgtgacgt   3360
cgatgcggcc ggatgcgtga tcgagcattg tcactcctcg gggcagcgga catttgcgta   3420
tactctcggc ctgatcaaca ttaccggcgg tgatcgcacc ccgctggcgg agcgcgtggt   3480
gagcccggcc acccccggcg gttcggccac ccgtgaagct gaggttaggc tgtcctcact   3540
tcacagcact ggaggcatcc cctcgtgtcc ccgcttcccc ccggcagcgc cgtcaccgcc   3600
cggcacgtgc tccgccaggc gctgcgccgc cagcgccgcc cggtgctgat cggcgtgacc   3660
ctgctcgggc tgcaccaggt caccgaggcg ctcgtgccgg tggcgatcgg cgtcatcatc   3720
gaccgggccg tggtgaccgg cgacccgtgg gcgctcgcgt actccgtcgc cggcctcgcc   3780
gccctgttca ccgtgctggc gttcgcctac cgcaacggcg cccgccaggc gttcgcggcg   3840
gtggaacggg aggcgcacct gctgcgggtc gagctggccg agcgcgcgct cgacccgcgc   3900
gggcaccgct ccgcctgcg cgacggcgag ctgctctcgg tcgccgcctc cgacgccgaa   3960
ctctccgcgt acgtggtccg ggtggccggc ttcggcgtcg ccgcggtgag cgcgctgacc   4020 gtcgcggcg tcgcgctgct ggtcatcgac gtcccgctcg gactcggcgt gctcatcggc   4080
gtaccggtgc tggtcctggc gctgcaacgg atggcgccgc tgctgtcccg gcgcagcgcc   4140
tcccagcagg aggccctcgc ggagaccacg gcgctcgccg tggacctcgt ctccggcctg   4200
cgcgtgctgc gcggcatcgg cgcccagcac cacgccgccg gccggtacgc cgaggccagc   4260
cgacgcgccc tcgccgtgac gctgcgcgcc gccaacacca agggcctgca cctcgggctc   4320
accaccgccg cgaacggcct cttcctcgcc gccgtcgccg gggtcgccgg ctggctcgcg   4380
ctgcgcggcc ggctcaccat cggcgagctg gtcaccgtgg tcgggctcgc gcagttcgtc   4440
gccgagccgg tgcagacgct gggctactgc gtgcagctgt tcgcgatggc ccgcgcctcc   4500
gccgcccggg tcgggcgcgt gctcggcgcc gagccgctga cccggccggg cagcgcgccc   4560
cggccggacc gcacggacgg gccgcggctc gtcctcgacc acgtcggcca cgccgcgctg   4620
gacggggtgt gcctgcgcgt cgacccggga gagatcgtcg gcgtcctggc gtacgacccg   4680
gccgacgcgg acgcgctggt ggcgctgctg tccgggcggg tgcccgcgga ccggcgccgg   4740
ggcacggtac gcgtcgacgg ggtacccgcc gacgacctgg acgtcgacgc gctgcgcggc   4800
gccgtcctgg tcgagccgca cgacgtgacg ctgttcgagg gaaccgtggc cgccaacctc   4860
gccgccggga gcaggaccga ggaggggcgc ctgcgcgccg cggtccgggc ggccgcggcg   4920
gacgacgtgg tggacgcgca ccccggcggc ctcgccacc ggctcgtcga gcggggcgcc   4980
aacctctccg gcgggcagcg ccagcggctc gggctggcgc gggcgctgca cgccgacccg   5040
ccggtgctgg tgctgcacga ccccaccacc gccgtggacg cggccaccga ggcccaactc   5100
gccgacggac tggccggcgc gcgccgcgaa gcgccccggg gcacgctgct ggtcaccagc   5160
agccccgccc tgctgcggat caccgaccgg gtggtggtga tcgccgacgg ccgggtgacc   5220 gccgaggga cgcacgagca cctgctggcc accgacgccc gctaccgcga ggagacactg   5280
cggtgaccgt tgaccgcgt accgccgaac ccacccgggt gttgctgccc accgcgaccg   5340
cccggcggac ctggacgacg ctcggcgcgg agttccgccg gcggcccggc ctcagcgccg   5400
ccgcgaccgc cgtgctcgtc gccgccgcca cggcgggct ggtcgcgccc tgggtgctcg   5460
gccgcctcgt cgacgacgtc atcgccgacg ccccggtctc ccggatcgcc ggccgggtgg   5520
```

```
cggtgatcgc cggcgcggca gtgctcaccg gactgctcac cgccgccggg gccgcgctcg    5580
cgtcccgcct gggggagacg gtgctggccc ggctgcgcga gcgggtcctc gaccgggcgc    5640
tgcacctgcc ctcggcgacg ctggaacggg ccggcaccgg cgacctgctg gcccgggtcg    5700
gcgacgacgt ggcggtggtg acgaacgtga tcgcggtcag cggcccggcg ttcgtcggcg    5760
cgctgctgtc cgtggtgctg accgtgttcg ggctggtcgc gctcgactgg cggctcggcc    5820
tcgccgggct ggtcgccgcg cccgcctacg cgctggcgct gcgctggtac ctgcgccggt    5880
cggcgccgta ctacgcccgc gagcgcgtcg ccaccggcga gcggacgcag gcgatggccg    5940
gcgcgctgcg tggcgcggcc accgtgcgcg cgtaccggac cgaggacgcg cacgtcgcgg    6000
cgatcgccga gcgctccggc gtggcgcgcg acctgtcgct ggagatcttc aacctgcaca    6060
cccggttcgg gctgcggatc aacaggtcgg agttcctcgg cctggccgcg gtgctcgtcg    6120
ccgggttctt cctggtccgc gccgacctgg tcacagtggg cgcggcgacc accgccgcgc    6180
tctacttcca ccggctgttc aacccgatcg gcctgctgct gatggagtcc gactcggtgc    6240
tgcaggccgg cgcgagcctc gcccggctgg tcggcgtggc cacgctgccc gacaccgccc    6300
cgtccgggcc cgcgccgtcg gcggccgggc ggcgcggccc ggcggcgctg gacgtcacgg    6360
tccgccggca ccgctacgac gacgacggcc ctctggtcct ggccgacgtc gacctgcgcc    6420
tggccccggg cgagcgggtc gcgctcgtgg gcgccagcgg cgcgggcaag agcacgctcg    6480
ccggcatcgc cgccgggatc atcgcgccca ccgacgggtc ggtacgcctg gcggcgtgc    6540 cgctgaccga gcggggcgag cacgccgtgc ggcgcgacgt cgcgctggtc agccaggagg    6600
tgcacgtctt cgctggaccg ctcgccgagg atctgcgcct ggctgccccg gacgccaccg    6660
acgccgaact gctcgacgcg ctggaccggg tcggcgccac cacctggctg cgcgcgctgc    6720
cggacgggct ggccacagcg gtcggcgagg gcggccaccg gctcaccgcc gcgcaggccc    6780
agcaggtcgc cctggcccgg ctggtgctgg ccgcgcccgc cgtcgccgtg ctggacgagg    6840
ccaccgccga ggccggcagc ccggagcgcg gtgacctgga ccgggcggcg ctggccgcca    6900
ccgagggacg gaccacgctg atcgtggcgc accggctcag ccaggcggtc gccgccgacc    6960
ggatcgtcct gctcgaccac gggcggatcg tggagcaggg cacgcactcg gaactgctcg    7020
ccgccgacgg ccggtacggg catctgtggc gctcctggag cgtcccggta tgatcgcgca    7080
ccgcccatcg gcccaggtga ggggaacatg accgacgcgc cggcccgctt cgtgctcttc    7140
ccggggcggc accacctgct gacccggttc caggccgact acctgcgcg gctggccggg    7200 gacgacgcca cagtggtctg ggcggtgacg tcggccaacc acgagaacac caggcgcaac    7260
ccggtgccct accaccggcg ggaggccgcg atcgaacgat tcagcgtgct gagcgggctg    7320
cgctcggtgg tggtgccgat cttcgacacc gcgtacaccg acgcgttcgc cgaggtgacg    7380
ctgaagtcca tcgcggtggc caccgggctc gaactcaccc ccgccgacac cgtgctggcc    7440
tgctccacgc cggaggtcgc gaagctgtac gagcagctcg gcttttcgat cgcgccggtc    7500
gaggcggacc cggacctgcc cgagccgccc gaacggccgt gggacgtgct gctgcgcctg    7560
gccgccgggg acgagacctg gcgcgcgctc acccacccgg ccaccatcga cgtgttcgag    7620
cgctaccgcc tggtcgagtc gatccggtcg gtggtgaacg acccgctcgt cggcgacgag    7680 gcggtctca cagtgacccg cgactaccgg acctacgtcg aggcgttcgc cacggccgcg    7740
cagcgcaagt gggactcggt acgcggtac gtgcagcccg gccgcatcgt ggacatcggc    7800
tgcggcgcgg gcgccgtcct ggaactcgcc gaccgggagg ccgcgctgcg tgagagcgac    7860
```

-continued

```
ctgatcggcg tggaggtcgc ccgccacctc taccaggagt gcctgcacaa gaaggcgcag    7920
ggcgtgttcc gcaacgccaa cgtctacttc ttccaccgca acgtcctcgg cggcgcggtg    7980
ttcaaggacc gctcggtcga caccacgctc acgttcgcgc tgacccacga gatctggtcg    8040
tacgggcggc ggcgggagtc gctgctgcag ttcgcccgcc gcatccacga ccacacggtg    8100
cccggcggcg tctggatcaa cagcgacgtg tgcggtccgg acgaccccg gcggcaggtg    8160 ctcctgcgac tgtccaccga cgacggcgac aacccgccg cgccccgccc cgacctcgcc    8220
gagctgacct cggcggaggt ccggcgttac gtcggcgggc tgtcgacgcg ggcgcggctg    8280
gaccagttcg ccgtcgactt cgcgttcgac ttcgactacg agccgctccc cgacggcgcg    8340
gtacgcctga cgctgggcgc cgcgatggac tacctgaccc gcaaggacta cacggacaac    8400
tggctgtcgg agacgcagga gcagttctgc ggcctgagct cgccgactg gacggacctg    8460 ctcaccgagg cggggttcga gatcggcccg gcgtcggcgc cggtgcgcaa cgagtgggtg    8520
atcgacaacc ggatcgcgcc agtcgcgtcc ctcaccgacc tcgacggccg gccgctggac    8580
tggccgacca cccacgtcct caccgtcgcc caccgccccc gcaaccagtg agaccgacgg    8640 cgccccgccgc gttcggcggg cgccgtcgtc gctcaccggc tcagcgcgat ccggatcgcc    8700
aggacgatca ggatgagccc ggtcagccgt tcgatcacca gcagcacgga cggccgggtc    8760
agccagggct gcaacctgtc gatgagcatg atgtagcagg cccaccagag caccgcgagg    8820
ccgatgaacg tggcggcgag caccgccgta cgggccgccg cccctcgcc gggcttgacg    8880 aactgcggca cgaacgagac gtagaagacg accaccttga cgttcagcag ctggctggtg    8940
acgcccatga cgaacgagcg gcgggccacg tgcggctcgt cggcggccgg ggtgtccggc    9000
accggcgcgg ggccggtgtc cgtgtccggc ccggcgccgc ccgcgccgac agtgaccggc    9060
tgcgccgccg gaccgtccg gcgcggccgg gtcgcccaga ggatcgtgcc gcccaggtag    9120
agcaggtaca gcgcgccggc gacgcgcagc accgtgtaga gcgtcggcga ggagaccagc    9180
agggcggaca ggccggcggt cgcgaacgac gcgtgcacca gcgcggcgac gaacagcccg    9240
gccagcacca cgaacccggc ccgccggccg tacctgacgg tctgccgggt gacgagcgcg    9300
aagtcgacgc ccggcacgat gatgatgagc aggctggcgg cgacgaaact gatgatctgg    9360
atgtcagaca cgacgccggc tctcctgtcc tccggcgagc gccggcactg cctcctcgat    9420
gacggagacg ccgctgtcct ggcgtggtcc gtgccggcgc cactgttccc gcagccggat    9480
ccggccgtcc ggcagccgtt cgggccggga ctcgcactcg ccgatgacta tggtgccgtc    9540
ggtgagcacc tccaggtagg cgaagcgcac gacgccctgc gcgtcgcagg tgccggccag    9600
ccggccgtgc cggaccgggc cgccggtgat ctccgcccag accaggtcgc cacgctggtg    9660
gtagtgcccc cgcagcggct cggcgccgtc accggcgtcg tggtccaccg agacgaagac    9720
gcggccgtcg tagtcgaatg tcgtcatcgc gctcacgccc ac                       9762
```

<210> SEQ ID NO 74
<211> LENGTH: 112
<212> TYPE: PRT
<213> ORGANISM: Micromonospora sp. strain 046-ECO11

<400> SEQUENCE: 74

Met Asp Gly Ala Arg Glu Arg Ile Thr Thr Asn Ile Arg Lys Gly Val
1               5                   10                  15

Leu Glu Tyr Cys Val Leu Ala Leu Leu Ser Arg Arg Asp Met Tyr Gly
            20                  25                  30

Leu Glu Leu Ala Asp Trp Leu Ala Val Arg Gly Leu Thr Ala Ser Glu

-continued

```
                35                  40                  45
Gly Ser Leu Tyr Pro Leu Leu Ala Arg Met Arg Gln Ala Gly Ser Val
         50                  55                  60

Gln Thr Arg Trp Val Ala Pro Glu Gln Gly His Ala Arg Arg Tyr Tyr
65                  70                  75                  80

Ala Ile Thr Asp Gln Gly Arg Ala His Leu Arg Val Phe Ala Ala Val
                 85                  90                  95

Trp Gln Glu Ile Gln Pro His Val Asp Asp Leu Met Gly Glu Glu Ala
                100                 105                 110

<210> SEQ ID NO 75
<211> LENGTH: 339
<212> TYPE: DNA
<213> ORGANISM: Micromonospora sp. strain 046-ECO11

<400> SEQUENCE: 75
atggacgggg cacgtgagcg gatcactacg aacatccgca agggcgtgct ggagtactgc     60
gtgctcgccc tgctctcgcg gcgcgacatg tacggcctgg aactggccga ctggctcgcc    120
gtccgcggtc tgaccgcgag cgagggcagc ctgtatccgc tgctcgcccg catgcggcag    180
gccggctccg tgcagacccg gtgggtggcc cccgagcagg ggcacgcccg cggtactac     240 gcgatcaccg accaggggcg ggcgcacctg cgggtgttcg cggcggtgtg caggagatc     300 cagccgcacg tggacgacct gatggggag gaagcatga                            339

<210> SEQ ID NO 76
<211> LENGTH: 325
<212> TYPE: PRT
<213> ORGANISM: Micromonospora sp. strain 046-ECO11

<400> SEQUENCE: 76

Met Ser Asp Asp Gly Leu Pro Glu Ala Ala Trp Thr Tyr Leu Arg Ala
1               5                   10                  15

Leu Asp Ala Glu Leu Ser Asp Val Pro Ser Gly Thr Ala Glu Glu Ile
                20                  25                  30

Val Ala Asp Val Arg Ala His Ile Ala Asp Ala Leu Asp Ser Gly Arg
            35                  40                  45

Ser Ala His Glu Ile Leu Ala Gly Leu Gly Ala Ala Arg Asp Val Ala
         50                  55                  60

Arg Gln Ala Arg Glu Glu Leu Gly Leu Pro Ala Gln Asp Arg Pro Ala
65                  70                  75                  80

Arg Ala Gly Arg Thr Leu Ser Leu Ala Ala Val Ala Val Gly Val Leu
                 85                  90                  95

Ile Ala Val Cys Val Ser Phe Leu Leu Pro Ser Ala Val Pro Val Glu
                100                 105                 110

Pro Ile Gln Ala Gly Pro Gly Glu Gln Gly Val Leu Arg Arg Leu Gly
            115                 120                 125

Pro Gly Ile Ala Leu Leu Thr Leu Leu Pro Ala Leu Val Ala Ala
        130                 135                 140

Pro Leu Val Ala Pro Ala Arg Ala Arg Ala Gly Val Arg Phe Ala Gly
145                 150                 155                 160

Ala Ala Val Leu Thr Met Phe Ala Cys Ala Ala Gly Glu Thr Gly Leu
                165                 170                 175

Tyr Tyr Phe Pro Leu Ala Leu Met Ala Trp Ala Ala Ile Val Pro
            180                 185                 190

Trp Ala Leu Arg Arg Gly Ala Gly Gly Arg Trp Trp Arg Tyr Leu Thr
```

```
                195                 200                 205
Gly Gly Phe Val Ala Met Pro Gly Val Leu Val Ala Val Ala Ser Ala
        210                 215                 220

Gly Gly Ser Val Gly Val Gly Trp Val Gly Ala Ala Leu Trp Ile Ala
225                 230                 235                 240

Gly Pro Leu Ala Ala Gly Ala Leu Cys Ala Tyr Gly Ile Arg Ala Gly
                245                 250                 255

Tyr Ala Val Thr Ala Leu Ala Gly Ala Leu Ala Ile Ala Leu Ser Met
            260                 265                 270

Ala Glu Arg Gly Phe Leu Phe Ala Ala Phe Trp Leu Phe Gly Gly Leu
        275                 280                 285

Tyr Leu Ala Leu Gly Ala Ala Ala Tyr Thr Ala Ser Arg Ala Val Asp
    290                 295                 300

Gly Asp Ala Ala Ala Thr Pro Gly Pro Pro Ala Arg Pro Glu Pro Ala
305                 310                 315                 320

Pro Ala Pro Gly Gly
            325

<210> SEQ ID NO 77
<211> LENGTH: 978
<212> TYPE: DNA
<213> ORGANISM: Micromonospora sp. strain 046-ECO11

<400> SEQUENCE: 77
atgagcgacg acggcctccc ggaggcggcg tggacctatc tgcgcgcgct cgacgcggag      60
ttgtccgacg tcccgtccgg cacggcggag gagatcgtcg cggatgtccg cgcgcacatc    120
gccgacgccc tcgacagcgg acggagcgcc cacgagatcc tcgccggcct cggcgccgcg    180
cgggacgtgg cccggcaggc gcgcgaggag ctggggctgc cggcccagga ccgcccggcc    240
cgggccggcc ggaccctgtc cctggccgcg gtggcggtcg gcgtgctgat cgccgtgtgc    300
gtgagcttcc tgctgccgtc cgcagtgccg gtggagccga tccaggccgg ccccggcgag    360
cagggcgtcc tccgccggct cggccccgga atcgcgctgc tcacgctgct gccggcgctc    420
gtcgcggccg cgccgctcgt ggcgcccgcc cgggcacgtg ccggggtacg gttcgccggc    480
gcggcggtcc tgacgatgtt cgcctgcgcg gccggcgaga cgggcctgta ctacttcccg    540
ctcgcgctga tggcctgggc ggcggcgatc gtgccgtggg ccctgcggcg cggagccggt    600
ggacggtggt ggcgctatct gaccggtgga ttcgtggcga tgcccggcgt gctggtggcg    660
gtcgcgtcgg ccggtggctc ggtcggcgtc ggctgggtcg gcgcggcgct gtggatcgcc    720
gggccgctcg cggccggcgc gctgtgcgcc tacgggatcc gggccggcta cgccgtgacc    780
gcgctggccg gcgcgctggc catagcgctc tcgatggccg agcgcggctt cctgttcgcc    840
gccttctggc tgttcggcgg gctgtacctg gcgctcggcg ccgctgcgta caccgcctcg    900
cgggccgtcg acgcgacgc cgccgcgacg cccggcccgc cggcccggcc ggaacccgcg    960
ccggcccccg gaggctga                                                   978

<210> SEQ ID NO 78
<211> LENGTH: 663
<212> TYPE: PRT
<213> ORGANISM: Micromonospora sp. strain 046-ECO11

<400> SEQUENCE: 78

Met Leu Asp His Ala Ser Gly Arg Ile Asp Val Thr Arg Leu Arg Glu
1               5                   10                  15
```

```
Ala Leu Asp Gly Arg Trp Ala Glu Val Arg Arg Ala His Arg Glu His
            20                  25                  30

Leu Asp Glu Arg Phe Leu Pro Val Tyr Gly Glu Thr Gly Asp Gln Ala
            35                  40                  45

Arg Glu Arg Ile Thr Arg Leu Leu Ser Glu Leu Pro Val Glu Leu Gly
        50                  55                  60

Ile Ala Ser Gly Phe Pro Ala Glu Tyr Gly Gly Arg Gly Asp Val Gly
65                  70                  75                  80

Ala Ser Ile Val Ala Thr Glu Met Leu Ala Gln Val Asp Leu Ser Leu
                85                  90                  95

Met Val Lys Ala Gly Val Gln Trp Gly Leu Phe Gly Gly Ala Val Ala
            100                 105                 110

Ala Leu Gly Thr Lys Arg His His Asp Ala Tyr Leu Arg Asp Ile Val
        115                 120                 125

Ala Gly Arg Leu Phe Gly Cys Phe Ala Met Thr Glu Thr Gly His Gly
130                 135                 140

Ser Asp Val Gln Gln Leu Arg Thr Thr Cys Val Tyr Asp Pro Gln Thr
145                 150                 155                 160

Gln Thr Phe Asp Leu His Thr Pro His Glu Ala Arg Lys Asp Tyr
            165                 170                 175

Ile Gly Asn Ala Ala Arg Asp Gly Arg Met Ala Val Val Phe Ala Gln
            180                 185                 190

Leu Val Thr Gly Gly Arg Arg His Gly Val His Ala Trp Leu Val Pro
        195                 200                 205

Ile Arg Asp Glu His Gly Lys Pro Met Pro Gly Val Thr Ile Gly Asp
    210                 215                 220

Ala Gly Pro Lys Ala Gly Leu Leu Gly Val Asp Asn Gly Arg Leu Ser
225                 230                 235                 240

Phe Asp His Val Arg Val Pro Arg Glu Met Leu Leu Asp Gln Tyr Ala
                245                 250                 255

Gln Val Ala Glu Asp Gly Thr Tyr Ser Ser Pro Ile Glu Asn Asp Ser
            260                 265                 270

Arg Arg Phe Phe Thr Met Leu Gly Thr Leu Val Arg Gly Arg Val Ser
        275                 280                 285

Val Gly Gly Ala Ala Ser Ala Ala Thr Lys Ser Ala Leu Ala Ile Ala
    290                 295                 300

Val Arg Tyr Gly Asp Ile Arg Arg Gln Phe Ala Asp Ala Asp Gly Asp
305                 310                 315                 320

Arg Glu Val Leu Leu Asn Asp Tyr Leu Ala His Gln Arg Lys Leu Leu
                325                 330                 335

Pro Ala Leu Ala Thr Thr Tyr Ala Leu Thr Phe Ala Gln Ala Glu Leu
            340                 345                 350

Val Ala Ala Leu Asp Asp Ile Gln Gly Gly Asp Gly Pro Val Asp Glu
        355                 360                 365

His Arg Gln Arg Glu Leu Glu Ser Arg Ala Ala Gly Leu Lys Ala Ala
370                 375                 380

Gln Thr Trp His Ala Thr Arg Thr Ile Gln Ile Cys Arg Glu Ala Cys
385                 390                 395                 400

Gly Gly Ala Gly Tyr Leu Ser Glu Asn Arg Leu Pro Ser Leu Lys Ala
                405                 410                 415

Asp Thr Asp Val Phe Thr Thr Phe Glu Gly Asp Asn Thr Val Leu Leu
            420                 425                 430

Gln Leu Val Ala Lys Gly Leu Leu Thr Gly Tyr Arg Asp Glu Phe Gly
```

```
                  435                 440                 445
Ser Leu Asp Gly Trp Gly Arg Ala Ser Phe Val Ala Glu Gln Val Arg
    450                 455                 460

Glu Met Val Leu Glu Arg Thr Ala Ala Arg Ala Leu Ile Ala Arg Leu
465                 470                 475                 480

Val Ser Ala Val Pro Gly Arg Asp Asp Glu Val Ala Val Thr Asp Arg
                485                 490                 495

Gly Trp Gln Leu Lys Leu Phe Glu Asp Arg Glu His Leu Leu Asp
                    500                 505                 510

Ser Ala Val Arg Arg Leu Arg Gly Gly Ala Ser Thr Lys Lys Asp Arg
            515                 520                 525

Pro Phe Asp Ile Phe Asn Asp Val Gln Asp His Val Leu Ala Val Ala
    530                 535                 540

Ala Ala His Ile Asp Arg Val Thr Leu Glu Ala Phe Val Ala Gly Ile
545                 550                 555                 560

Asp Ala Ile Ala Asp Pro Ala Val Lys Glu Leu Leu Ser Arg Val Cys
                565                 570                 575

Asp Leu Tyr Ala Leu Thr Val Ile Glu Ala Asn Lys Gly Trp Leu Leu
                    580                 585                 590

Glu His Gly Arg Leu Thr Pro Ala Arg Ser Lys Thr Ile Thr Ser Val
            595                 600                 605

Val Asn Gly Leu Leu Lys Glu Leu Arg Pro Asp Met Arg Thr Leu Val
    610                 615                 620

Asp Gly Phe Ala Ile Pro Asp Ala Trp Leu His Ala Ala Ile Leu Arg
625                 630                 635                 640

Glu Glu Pro Val Arg Gln Glu Thr Met Ala Ala His Asp Ala Ala Gly
                645                 650                 655

Asp Pro Gln Ala Val Pro Ala
                660

<210> SEQ ID NO 79
<211> LENGTH: 1992
<212> TYPE: DNA
<213> ORGANISM: Micromonospora sp. strain 046-ECO11

<400> SEQUENCE: 79
atgctcgatc acgcatccgg ccgcatcgac gtcacacgcc tgcgggaagc gctcgacggc      60
cggtgggccg aggtccgccg ggcgcaccgc gaacacctcg acgaacgctt cctcccggtg     120 tacgcgaga ccggtgacca ggcccgcgag cgcatcaccc ggctgctgtc cgaactcccc      180
gtcgagctgg gcatcgcctc cggtttcccc gccgagtacg gcggccgcgg cgacgtgggc     240
gcctcgatcg tcgccaccga gatgctggcc caggtggacc tgtcactgat ggtgaaggcc     300
ggcgtgcagt ggggcctgtt cggcggcgcg gtcgccgccc tcggcacgaa gcggcaccac     360
gacgcctacc tgcgggacat cgtcgcgggc cggctcttcg gctgcttcgc gatgaccgag     420
accggccacg gctcggacgt gcagcaactg cgcaccacct gcgtctacga cccgcagacg     480
cagaccttcg acctgcacac cccgcacgag gccgcgcgca aggactacat cggcaacgcg     540
gcccgggacg gcggatggc tgtggtgttc gcccagctcg tcaccggcgg cgccgccac      600 ggggtgcacg cctggctggt gccgatccgc gacgagcacg gcaagccgat gcccggcgtg     660
accatcggcg acgccgggcc caaggccggc ctgctcggcg tggacaacgg cggctcagc     720 ttcgaccacg tgcgggtgcc gcgggagatg ctgctggacc agtacgcgca ggtcgccgag     780
gacggcacgt actccagccc gatcgagaac gactcccggc gcttcttcac catgctgggc     840
```

-continued

```
accctggtcc ggggccgggt gagcgtgggc ggcgccgcgt cggcggccac caagtcggcg      900
ctggccatcg cggtgcgcta cggcgacatc cgccggcagt tcgccgacgc cgacggcgac      960
cgcgaggtgc tgctcaacga ctacctggcg caccagcgca agctgctgcc cgcgctggcc     1020
accacgtacg cgctgacctt cgcccaggcg gagctggtcg cggcgctcga cgacatccag     1080
ggcggcgacg gccggtcga cgagcaccgg cagcgggagc tggagtcccg gccgccggt      1140
ctgaaggcgg cgcagacctg gcacgccacc cgcaccatcc agatctgccg ggaggcgtgt     1200
ggcggcgccg gctacctgtc cgagaaccgc ctgcccagcc tcaaggccga caccgatgtc     1260
ttcaccacct cgagggcga caacacggtg ctgctgcaac tggtcgccaa ggggctgctg      1320
accggctacc gggacgagtt cggctcgctc gacggctggg gacgcgcctc cttcgtggcc     1380
gagcaggtac gcgagatggt gctggaacgc accgccgcgc gggcgctgat cgcacgtctg     1440
gtcagcgccg tgcccgggcg cgacgacgag gtcgccgtca ccgaccgggg ctggcagctc     1500
aagctcttcg aggaccgcga ggagcacctg ctcgacagcg cggtccgccg cctgcgcggt     1560
ggcgcgtcca ccaagaagga ccgccccttc gacatcttca cgacgtcca ggaccacgtc      1620
ctcgccgtcg ccgcggcgca catcgaccgg gtgacgctgg aggcgttcgt cgccgggatc     1680
gacgccatcg ccgaccccggc ggtcaaggaa ctgctgtccc gggtctgcga cctgtacgcg     1740
ctcaccgtga tcgaggcgaa caagggctgg ctgctcgagc acgccggct caccccggcc      1800
cgctcgaaga ccatcaccag cgtggtgaac gggctgctca aggagctgcg cccggacatg      1860
cgcacgctcg tggacggctt cgccatcccg gacgcgtggc tgcacgcggc gatcctgcgc     1920
gaggagcccg tccggcagga gacgatggcc gcgcacgacg ccgccggcga cccgcaggcc     1980
gtccccgcct ag                                                        1992
```

<210> SEQ ID NO 80
<211> LENGTH: 573
<212> TYPE: PRT
<213> ORGANISM: Micromonospora sp. strain 046-ECO11

<400> SEQUENCE: 80

```
Val Ser Pro Leu Pro Pro Gly Ser Ala Val Thr Ala Arg His Val Leu
1               5                  10                  15

Arg Gln Ala Leu Arg Arg Gln Arg Pro Val Leu Ile Gly Val Thr
            20                  25                  30

Leu Leu Gly Leu His Gln Val Thr Glu Ala Leu Val Pro Val Ala Ile
        35                  40                  45

Gly Val Ile Ile Asp Arg Ala Val Thr Gly Asp Pro Trp Ala Leu
    50                  55                  60

Ala Tyr Ser Val Ala Gly Leu Ala Ala Leu Phe Thr Val Leu Ala Phe
65                  70                  75                  80

Ala Tyr Arg Asn Gly Ala Arg Gln Ala Phe Ala Val Glu Arg Glu
                85                  90                  95

Ala His Leu Leu Arg Val Glu Leu Ala Glu Arg Ala Leu Asp Pro Arg
            100                 105                 110

Gly His Arg Ser Gly Leu Arg Asp Gly Glu Leu Leu Ser Val Ala Ala
        115                 120                 125

Ser Asp Ala Glu Leu Ser Ala Tyr Val Val Arg Val Ala Gly Phe Gly
    130                 135                 140

Val Ala Ala Val Ser Ala Leu Thr Val Ala Ala Val Ala Leu Leu Val
145                 150                 155                 160
```

-continued

```
Ile Asp Val Pro Leu Gly Leu Gly Val Leu Ile Gly Val Pro Val Leu
            165                 170                 175

Val Leu Ala Leu Gln Arg Met Ala Pro Leu Leu Ser Arg Arg Ser Ala
            180                 185                 190

Ser Gln Gln Glu Ala Leu Ala Glu Thr Thr Ala Leu Ala Val Asp Leu
            195                 200                 205

Val Ser Gly Leu Arg Val Leu Arg Gly Ile Gly Ala Gln His His Ala
        210                 215                 220

Ala Gly Arg Tyr Ala Glu Ala Ser Arg Arg Ala Leu Ala Val Thr Leu
225                 230                 235                 240

Arg Ala Ala Asn Thr Lys Gly Leu His Leu Gly Leu Thr Thr Ala Ala
            245                 250                 255

Asn Gly Leu Phe Leu Ala Ala Val Ala Gly Val Ala Gly Trp Leu Ala
            260                 265                 270

Leu Arg Gly Arg Leu Thr Ile Gly Glu Leu Val Thr Val Gly Leu
            275                 280                 285

Ala Gln Phe Val Ala Glu Pro Val Gln Thr Leu Gly Tyr Cys Val Gln
            290                 295                 300

Leu Phe Ala Met Ala Arg Ala Ser Ala Ala Arg Val Gly Arg Val Leu
305                 310                 315                 320

Gly Ala Glu Pro Leu Thr Arg Pro Gly Ser Ala Pro Arg Pro Asp Arg
            325                 330                 335

Thr Asp Gly Pro Arg Leu Val Leu Asp His Val Gly His Ala Ala Leu
            340                 345                 350

Asp Gly Val Cys Leu Arg Val Asp Pro Gly Glu Ile Val Gly Val Leu
            355                 360                 365

Ala Tyr Asp Pro Ala Asp Ala Asp Ala Leu Val Ala Leu Leu Ser Gly
            370                 375                 380

Arg Val Pro Ala Asp Arg Arg Gly Thr Val Arg Val Asp Gly Val
385                 390                 395                 400

Pro Ala Asp Asp Leu Asp Val Asp Ala Leu Arg Gly Ala Val Leu Val
            405                 410                 415

Glu Pro His Asp Val Thr Leu Phe Glu Gly Thr Val Ala Ala Asn Leu
            420                 425                 430

Ala Ala Gly Ser Arg Thr Glu Glu Gly Arg Leu Arg Ala Ala Val Arg
            435                 440                 445

Ala Ala Ala Ala Asp Asp Val Val Asp Ala His Pro Gly Gly Leu Gly
            450                 455                 460

His Arg Leu Val Glu Arg Gly Ala Asn Leu Ser Gly Gly Gln Arg Gln
465                 470                 475                 480

Arg Leu Gly Leu Ala Arg Ala Leu His Ala Asp Pro Pro Val Leu Val
            485                 490                 495

Leu His Asp Pro Thr Thr Ala Val Asp Ala Ala Thr Glu Ala Gln Leu
            500                 505                 510

Ala Asp Gly Leu Ala Gly Ala Arg Arg Glu Ala Pro Arg Gly Thr Leu
            515                 520                 525

Leu Val Thr Ser Ser Pro Ala Leu Leu Arg Ile Thr Asp Arg Val Val
            530                 535                 540

Val Ile Ala Asp Gly Arg Val Thr Ala Glu Gly Thr His Glu His Leu
545                 550                 555                 560

Leu Ala Thr Asp Ala Arg Tyr Arg Glu Glu Thr Leu Arg
            565                 570
```

<210> SEQ ID NO 81
<211> LENGTH: 1722
<212> TYPE: DNA
<213> ORGANISM: Micromonospora sp. strain 046-ECO11

<400> SEQUENCE: 81

```
gtgtcccgc ttccccggg cagcgccgtc accgcccggc acgtgctccg ccaggcgctg      60
cgccgccagc gccgcccggt gctgatcggc gtgaccctgc tcgggctgca ccaggtcacc     120
gaggcgctcg tgccggtggc gatcggcgtc atcatcgacc gggccgtggt gaccggcgac    180
ccgtgggcgc tcgcgtactc cgtcgccggc ctcgccgccc tgttcaccgt gctggcgttc    240
gcctaccgca acggcgcccg ccaggcgttc gcggcggtgg aacgggaggc gcacctgctg    300
cgggtcgagc tggccgagcg cgcgctcgac ccgcgcgggc accgctccgg cctgcgcgac    360
ggcgagctgc tctcggtcgc cgcctccgac gccgaactct ccgcgtacgt ggtccgggtg    420
gccggcttcg gcgtcgccgc ggtgagcgcg ctgaccgtcg cggcggtcgc gctgctggtc    480
atcgacgtcc cgctcggact cggcgtgctc atcggcgtac cggtgctggt cctggcgctg    540
caacggatgg cgccgctgct gtcccggcgc agcgcctccc agcaggaggc cctcgcggag    600
accacggcgc tcgccgtgga cctcgtctcc ggcctgcgcg tgctgcgcgg catcggcgcc    660
cagcaccacg ccgccggccg gtacgccgag gccagccgac gcgccctcgc cgtgacgctg    720
cgcgccgcca acaccaaggg cctgcacctc gggctcacca ccgccgcgaa cggcctcttc    780
ctcgccgccg tcgccggggt cgccggctgg ctcgcgctgc gcggccggct caccatcggc    840
gagctggtca ccgtggtcgg gctcgcgcag ttcgtcgccg agccggtgca gacgctgggc    900
tactgcgtgc agctgttcgc gatggcccgc gcctccgccg cccgggtcgg gcgcgtgctc    960
ggcgccgagc cgctgacccg gccgggcagc gcgcccggc cggaccgcac ggacgggccg   1020
cggctcgtcc tcgaccacgt cggccacgcc gcgctggacg gggtgtgcct gcgcgtcgac   1080
ccgggagaga tcgtcggcgt cctggcgtac gacccggccg acgcggacgc gctggtggcg   1140
ctgctgtccg gcgggtgcc cgcggaccgg cgccggggca cggtacgcgt cgacggggta   1200
cccgccgacac acctggacgt cgacgcgctg cgcggcgccc tcctggtcga ccgcacgac   1260
gtgacgctgt tcgagggaac cgtggccgcc aacctcgccg ccgggagcag gaccgaggag   1320
gggcgcctgc gcgccgcggt ccgggcggcc cggcggacg acgtggtgga cgcgcacccc   1380
ggcggcctcg ccaccggct cgtcgagcgg ggcgccaacc tctccggcgg gcagcgccag   1440
cggctcgggc tggcgcgggc gctgcacgcc gaccgccgg tgctggtgct gcacgacccc   1500
accaccgccg tggacgcggc caccgaggcc caactcgccg acggactggc cggcgcgcgc   1560
cgcgaagcgc cccggggcac gctgctggtc accagcagcc ccgccctgct gcggatcacc   1620
gaccgggtgg tggtgatcgc cgacggccgg gtgaccgccg aggggacgca cgagcacctg   1680
ctggccaccg acgccgcta ccgcgaggag acactgcggt ga                     1722
```

<210> SEQ ID NO 82
<211> LENGTH: 596
<212> TYPE: PRT
<213> ORGANISM: Micromonospora sp. strain 046-ECO11

<400> SEQUENCE: 82

```
Val Thr Ala Asp Pro Arg Thr Ala Glu Pro Thr Arg Val Leu Leu Pro
1               5                   10                  15

Thr Ala Thr Ala Arg Arg Thr Trp Thr Thr Leu Gly Ala Glu Phe Arg
            20                  25                  30
```

-continued

```
Arg Arg Pro Gly Leu Ser Ala Ala Thr Ala Val Leu Val Ala Ala
        35                  40                  45

Ala Thr Gly Gly Leu Val Ala Pro Trp Val Leu Gly Arg Leu Val Asp
    50                  55                  60

Asp Val Ile Ala Asp Ala Pro Val Ser Arg Ile Ala Gly Arg Val Ala
65                  70                  75                  80

Val Ile Ala Gly Ala Val Leu Thr Gly Leu Leu Thr Ala Ala Gly
                85                  90                  95

Ala Ala Leu Ala Ser Arg Leu Gly Glu Thr Val Leu Ala Arg Leu Arg
            100                 105                 110

Glu Arg Val Leu Asp Arg Ala Leu His Leu Pro Ser Ala Thr Leu Glu
        115                 120                 125

Arg Ala Gly Thr Gly Asp Leu Leu Ala Arg Val Gly Asp Asp Val Ala
    130                 135                 140

Val Val Thr Asn Val Ile Ala Val Ser Gly Pro Ala Phe Val Gly Ala
145                 150                 155                 160

Leu Leu Ser Val Val Leu Thr Val Phe Gly Leu Val Ala Leu Asp Trp
                165                 170                 175

Arg Leu Gly Leu Ala Gly Leu Val Ala Ala Pro Ala Tyr Ala Leu Ala
            180                 185                 190

Leu Arg Trp Tyr Leu Arg Arg Ser Ala Pro Tyr Tyr Ala Arg Glu Arg
        195                 200                 205

Val Ala Thr Gly Glu Arg Thr Gln Ala Met Ala Gly Ala Leu Arg Gly
    210                 215                 220

Ala Ala Thr Val Arg Ala Tyr Arg Thr Glu Asp Ala His Val Ala Ala
225                 230                 235                 240

Ile Ala Glu Arg Ser Gly Val Ala Arg Asp Leu Ser Leu Glu Ile Phe
                245                 250                 255

Asn Leu His Thr Arg Phe Gly Leu Arg Ile Asn Arg Ser Glu Phe Leu
            260                 265                 270

Gly Leu Ala Ala Val Leu Val Ala Gly Phe Phe Leu Val Arg Ala Asp
        275                 280                 285

Leu Val Thr Val Gly Ala Ala Thr Thr Ala Ala Leu Tyr Phe His Arg
    290                 295                 300

Leu Phe Asn Pro Ile Gly Leu Leu Leu Met Glu Ser Asp Ser Val Leu
305                 310                 315                 320

Gln Ala Gly Ala Ser Leu Ala Arg Leu Gly Val Ala Thr Leu Pro
                325                 330                 335

Asp Thr Ala Pro Ser Gly Pro Ala Pro Ser Ala Ala Gly Arg Arg Gly
            340                 345                 350

Pro Ala Ala Leu Asp Val Thr Val Arg Arg His Arg Tyr Asp Asp Asp
        355                 360                 365

Gly Pro Leu Val Leu Ala Asp Val Asp Leu Arg Leu Ala Pro Gly Glu
    370                 375                 380

Arg Val Ala Leu Val Gly Ala Ser Gly Ala Gly Lys Ser Thr Leu Ala
385                 390                 395                 400

Gly Ile Ala Ala Gly Ile Ile Ala Pro Thr Asp Gly Ser Val Arg Leu
                405                 410                 415

Gly Gly Val Pro Leu Thr Glu Arg Gly Glu His Ala Val Arg Arg Asp
            420                 425                 430

Val Ala Leu Val Ser Gln Glu Val His Val Phe Ala Gly Pro Leu Ala
        435                 440                 445

Glu Asp Leu Arg Leu Ala Ala Pro Asp Ala Thr Asp Ala Glu Leu Leu
```

```
                450              455              460
Asp Ala Leu Asp Arg Val Gly Ala Thr Thr Trp Leu Arg Ala Leu Pro
465                 470                 475                 480

Asp Gly Leu Ala Thr Ala Val Gly Glu Gly Gly His Arg Leu Thr Ala
                485                 490                 495

Ala Gln Ala Gln Gln Val Ala Leu Ala Arg Leu Val Leu Ala Ala Pro
            500                 505                 510

Ala Val Ala Val Leu Asp Glu Ala Thr Ala Glu Ala Gly Ser Ala Gly
        515                 520                 525

Ala Arg Asp Leu Asp Arg Ala Leu Ala Ala Thr Glu Gly Arg Thr
530                 535                 540

Thr Leu Ile Val Ala His Arg Leu Ser Gln Ala Val Ala Ala Asp Arg
545                 550                 555                 560

Ile Val Leu Leu Asp His Gly Arg Ile Val Glu Gln Gly Thr His Ser
                565                 570                 575

Glu Leu Leu Ala Ala Asp Gly Arg Tyr Gly His Leu Trp Arg Ser Trp
            580                 585                 590

Ser Val Pro Val
        595

<210> SEQ ID NO 83
<211> LENGTH: 1791
<212> TYPE: DNA
<213> ORGANISM: Micromonospora sp. strain 046-ECO11

<400> SEQUENCE: 83
gtgaccgctg acccgcgtac cgccgaaccc acccgggtgt tgctgcccac cgcgaccgcc      60
cggcggacct ggacgacgct cggcgcggag ttccgccggc ggcccggcct cagcgccgcc     120
gcgaccgccg tgctcgtcgc cgccgccacc ggcgggctgg tcgcgccctg ggtgctcggc     180
cgcctcgtcg acgacgtcat cgccgacgcc ccggtctccc ggatcgccgg ccgggtggcg     240
gtgatcgccg gcgcggcagt gctcaccgga ctgctcaccg ccgccggggc cgcgctcgcg     300
tcccgcctgg gggagacggt gctggcccgg ctgcgcgagc gggtcctcga ccgggcgctg     360
cacctgcccct cggcgacgct ggaacgggcc ggcaccggcg acctgctggc ccgggtcggc     420
gacgacgtgg cggtggtgac gaacgtgatc gcggtcagcg gccgggcgtt cgtcggcgcg     480
ctgctgtccg tggtgctgac cgtgttcggg ctggtcgcgc tcgactggcg gctcggcctc     540
gccgggctgg tcgccgcgcc cgcctacgcg ctggcgctgc gctggtacct cgccggtcg     600
gcgccgtact acgccgcga gcgcgtcgcc accggcgagc ggacgcaggc gatggccggc     660
gcgctgcgtg gcgcggccac cgtgcgcgcg taccggaccg aggacgcgca cgtcgcggcg     720
atcgccgagc gctccggcgt ggcgcgcgac ctgtcgctgg agatcttcaa cctgcacacc     780
cggttcgggc tgcggatcaa caggtcggag ttcctcggcc tggccgcggt gctcgtcgcc     840
gggttcttcc tggtccgcgc cgacctggtc acagtgggcg cggcgaccac cgccgcgctc     900
tacttccacc ggctgttcaa cccgatcggc ctgctgctga tggagtccga ctcggtgctg     960
caggccggcg cgagcctcgc ccggctggtc ggcgtggcca cgctgcccga caccgccccg    1020
tccgggcccg cgccgtcggc ggccgggcgg cgcggcccgg cggcgctgga cgtcacggtc    1080
cgccggcacc gctacgacga cgacggccct ctggtcctgg ccgacgtcga cctgcgcctg    1140
gccccggcg agcgggtcgc gctcgtgggc ccagcggcg cgggcaagag cacgctcgcc    1200
ggcatcgccg ccgggatcat cgcgcccacc gacgggtcgg tacgcctggg cggcgtgccg    1260
```

-continued

```
ctgaccgagc ggggcgagca cgccgtgcgg cgcgacgtcg cgctggtcag ccaggaggtg    1320
cacgtcttcg ctggaccgct cgccgaggat ctgcgcctgg ctgccccgga cgccaccgac    1380
gccgaactgc tcgacgcgct ggaccgggtc ggcgccacca cctggctgcg cgcgctgccg    1440
gacgggctgg ccacagcggt cggcgagggc ggccaccggc tcaccgccgc gcaggcccag    1500
caggtcgccc tggcccggct ggtgctggcg cgcccgccg tcgccgtgct ggacgaggcc     1560
accgccgagg ccggcagcgc cggagcgcgt gacctggacc gggcggcgct ggccgccacc    1620
gagggacgga ccacgctgat cgtggcgcac cggctcagcc aggcggtcgc gccgaccgg     1680 atcgtcctgc tcgaccacgg gcggatcgtg gagcagggca cgcactcgga actgctcgcc    1740
gccgacggcc ggtacgggca tctgtggcgc tcctggagcg tcccggtatg a             1791
```

<210> SEQ ID NO 84
<211> LENGTH: 507
<212> TYPE: PRT
<213> ORGANISM: Micromonospora sp. strain 046-ECO11

<400> SEQUENCE: 84

```
Met Thr Asp Ala Pro Ala Arg Phe Val Leu Phe Pro Gly Arg His His
1               5                   10                  15

Leu Leu Thr Arg Phe Gln Ala Asp Tyr Leu Arg Arg Leu Ala Gly Asp
            20                  25                  30

Asp Ala Thr Val Val Trp Ala Val Thr Ser Ala Asn His Glu Asn Thr
        35                  40                  45

Arg Arg Asn Pro Val Pro Tyr His Arg Arg Glu Ala Ala Ile Glu Arg
    50                  55                  60

Phe Ser Val Leu Ser Gly Leu Arg Ser Val Val Pro Ile Phe Asp
65                  70                  75                  80

Thr Ala Tyr Thr Asp Ala Phe Ala Glu Val Thr Leu Lys Ser Ile Ala
                85                  90                  95

Val Ala Thr Gly Leu Glu Leu Thr Pro Ala Asp Thr Val Leu Ala Cys
            100                 105                 110

Ser Thr Pro Glu Val Ala Lys Leu Tyr Glu Gln Leu Gly Phe Ser Ile
        115                 120                 125

Ala Pro Val Glu Ala Asp Pro Asp Leu Pro Glu Pro Pro Glu Arg Pro
    130                 135                 140

Trp Asp Val Leu Leu Arg Leu Ala Ala Gly Asp Glu Thr Trp Arg Ala
145                 150                 155                 160

Leu Thr His Pro Ala Thr Ile Asp Val Phe Glu Arg Tyr Arg Leu Val
                165                 170                 175

Glu Ser Ile Arg Ser Val Val Asn Asp Pro Leu Val Gly Asp Glu Gly
            180                 185                 190

Gly Leu Thr Val Thr Arg Asp Tyr Arg Thr Tyr Val Glu Ala Phe Ala
        195                 200                 205

Thr Ala Ala Gln Arg Lys Trp Asp Ser Val Arg Arg Tyr Val Gln Pro
    210                 215                 220

Gly Arg Ile Val Asp Ile Gly Cys Gly Ala Gly Ala Val Leu Glu Leu
225                 230                 235                 240

Ala Asp Arg Glu Ala Ala Leu Arg Glu Ser Asp Leu Ile Gly Val Glu
                245                 250                 255

Val Ala Arg His Leu Tyr Gln Glu Cys Leu His Lys Lys Ala Gln Gly
            260                 265                 270

Val Phe Arg Asn Ala Asn Val Tyr Phe Phe His Arg Asn Val Leu Gly
        275                 280                 285
```

```
Gly Ala Val Phe Lys Asp Arg Ser Val Asp Thr Thr Leu Thr Phe Ala
        290                 295                 300
Leu Thr His Glu Ile Trp Ser Tyr Gly Arg Arg Glu Ser Leu Leu
305                 310                 315                 320
Gln Phe Ala Arg Arg Ile His Asp His Thr Val Pro Gly Gly Val Trp
                325                 330                 335
Ile Asn Ser Asp Val Cys Gly Pro Asp Pro Arg Arg Gln Val Leu
            340                 345                 350
Leu Arg Leu Ser Thr Asp Asp Gly Asp Asn Pro Ala Ala Pro Arg Pro
                355                 360                 365
Asp Leu Ala Glu Leu Thr Ser Ala Glu Val Arg Arg Tyr Val Gly Gly
        370                 375                 380
Leu Ser Thr Arg Ala Arg Leu Asp Gln Phe Ala Val Asp Phe Ala Phe
385                 390                 395                 400
Asp Phe Asp Tyr Glu Pro Leu Pro Asp Gly Ala Val Arg Leu Thr Leu
                405                 410                 415
Gly Ala Ala Met Asp Tyr Leu Thr Arg Lys Asp Tyr Thr Asp Asn Trp
                420                 425                 430
Leu Ser Glu Thr Gln Glu Gln Phe Cys Gly Leu Ser Phe Ala Asp Trp
        435                 440                 445
Thr Asp Leu Leu Thr Glu Ala Gly Phe Glu Ile Gly Pro Ala Ser Ala
        450                 455                 460
Pro Val Arg Asn Glu Trp Val Ile Asp Asn Arg Ile Ala Pro Val Ala
465                 470                 475                 480
Ser Leu Thr Asp Leu Asp Gly Arg Pro Leu Asp Trp Pro Thr Thr His
                485                 490                 495
Val Leu Thr Val Ala His Arg Pro Arg Asn Gln
                500                 505

<210> SEQ ID NO 85
<211> LENGTH: 1524
<212> TYPE: DNA
<213> ORGANISM: Micromonospora sp. strain 046-ECO11

<400> SEQUENCE: 85
atgaccgacg cgccggcccg cttcgtgctc ttcccggggc ggcaccacct gctgacccgg      60
ttccaggccg actacctgcg gcggctggcc ggggacgacg ccacagtggt ctgggcggtg     120
acgtcggcca accacgagaa caccaggcgc aacccggtgc cctaccaccg gcgggaggcc     180
gcgatcgaac gattcagcgt gctgagcggg ctgcgctcgg tggtggtgcc gatcttcgac     240
accgcgtaca ccgacgcgtt cgccgaggtg acgctgaagt ccatcgcggt ggccaccggg     300
ctcgaactca ccccgccga caccgtgctg gcctgctcca cgccggaggt cgcgaagctg     360
tacgagcagc tcggcttttc gatcgcgccg gtcgaggcgg accggacct gcccgagccg     420
cccgaacggc cgtgggacgt gctgctgcgc ctggccgccg gggacgagac ctggcgcgcg     480
ctcacccacc cggccaccat cgacgtgttc gagcgctacc gcctggtcga gtcgatccgg     540
tcggtggtga acgacccgct cgtcggcgac gagggcggtc tcacagtgac ccgcgactac     600
cggacctacg tcgaggcgtt cgccacggcc gcgcagcgca gtgggactc ggtacgccgg     660
tacgtgcagc ccggccgcat cgtggacatc ggctgcggcg cgggcgccgt cctggaactc     720
gccgaccggg aggccgcgct gcgtgagagc gacctgatcg gcgtggaggt cgcccgccac     780
ctctaccagg agtgcctgca agaaggcg cagggcgtgt ccgcaacgc caacgtctac     840
```

-continued

```
ttcttccacc gcaacgtcct cggcggcgcg gtgttcaagg accgctcggt cgacaccacg    900
ctcacgttcg cgctgaccca cgagatctgg tcgtacgggg gcggcggga gtcgctgctg    960
cagttcgccc gccgcatcca cgaccacacg gtgcccggcg cgtctggat caacagcgac   1020
gtgtgcggtc cggacgaccc ccggcggcag gtgctcctgc gactgtccac cgacgacggc   1080
gacaacccgg ccgcgccccg ccccgacctc gccgagctga cctcggcgga ggtccggcgt   1140
tacgtcggcg ggctgtcgac gcgggcgcgg ctggaccagt cgccgtcga cttcgcgttc   1200
gacttcgact acgagccgct ccccgacggc gcggtacgcc tgacgctggg cgccgcgatg   1260
gactacctga cccgcaagga ctacacggac aactggctgt cggagacgca ggagcagttc   1320
tgcggcctga gcttcgccga ctggacggac ctgctcaccg aggcggggtt cgagatcggc   1380
ccggcgtcgg cgccggtgcg caacgagtgg gtgatcgaca accggatcgc gccagtcgcg   1440
tccctcaccg acctcgacgg ccggccgctg gactggccga ccacccacgt cctcaccgtc   1500
gcccaccgcc cccgcaacca gtga                                          1524
```

<210> SEQ ID NO 86
<211> LENGTH: 232
<212> TYPE: PRT
<213> ORGANISM: Micromonospora sp. strain 046-ECO11

<400> SEQUENCE: 86

```
Val Ser Asp Ile Gln Ile Ile Ser Phe Val Ala Ala Ser Leu Leu Ile
 1               5                  10                  15

Ile Ile Val Pro Gly Val Asp Phe Ala Leu Val Thr Arg Gln Thr Val
            20                  25                  30

Arg Tyr Gly Arg Arg Ala Gly Phe Val Val Leu Ala Gly Leu Phe Val
        35                  40                  45

Ala Ala Leu Val His Ala Ser Phe Ala Thr Ala Gly Leu Ser Ala Leu
    50                  55                  60

Leu Val Ser Ser Pro Thr Leu Tyr Thr Val Leu Arg Val Ala Gly Ala
65                  70                  75                  80

Leu Tyr Leu Leu Tyr Leu Gly Gly Thr Ile Leu Trp Ala Thr Arg Pro
                85                  90                  95

Arg Arg Thr Val Pro Ala Ala Gln Pro Val Thr Val Gly Ala Gly Gly
            100                 105                 110

Ala Gly Pro Asp Thr Asp Thr Gly Pro Ala Pro Val Pro Asp Thr Pro
        115                 120                 125

Ala Ala Asp Glu Pro His Val Ala Arg Arg Ser Phe Val Met Gly Val
    130                 135                 140

Thr Ser Gln Leu Leu Asn Val Lys Val Val Phe Tyr Val Ser Phe
145                 150                 155                 160

Val Pro Gln Phe Val Lys Pro Gly Glu Gly Ala Ala Arg Thr Ala
                165                 170                 175

Val Leu Ala Ala Thr Phe Ile Gly Leu Ala Val Leu Trp Trp Ala Cys
            180                 185                 190

Tyr Ile Met Leu Ile Asp Arg Leu Gln Pro Trp Leu Thr Arg Pro Ser
        195                 200                 205

Val Leu Leu Val Ile Glu Arg Leu Thr Gly Leu Ile Leu Ile Val Leu
    210                 215                 220

Ala Ile Arg Ile Ala Leu Ser Arg
225                 230
```

<210> SEQ ID NO 87

<211> LENGTH: 699
<212> TYPE: DNA
<213> ORGANISM: Micromonospora sp. strain 046-ECO11

<400> SEQUENCE: 87

```
gtgtctgaca tccagatcat cagtttcgtc gccgccagcc tgctcatcat catcgtgccg      60
ggcgtcgact tcgcgctcgt cacccggcag accgtcaggt acggccggcg ggccgggttc     120
gtggtgctgg ccgggctgtt cgtcgccgcg ctggtgcacg cgtcgttcgc gaccgccggc     180
ctgtccgccc tgctggtctc ctcgccgacg ctctacacgg tgctgcgcgt cgccggcgcg     240
ctgtacctgc tctacctggg cggcacgatc tctgggcga cccggccgcg ccggacggtc      300
ccggcggcgc agccggtcac tgtcggcgcg ggcggcgccg ggccggacac ggacaccggc     360
cccgcgccg tgccggacac cccggccgcc gacgagccgc acgtggcccg ccgctcgttc      420
gtcatgggcg tcaccagcca gctgctgaac gtcaaggtgg tcgtcttcta cgtctcgttc     480
gtgccgcagt tcgtcaagcc cggcgagggg gcggcggccc gtacggcggt gctcgccgcc     540
acgttcatcg gcctcgcggt gctctggtgg gcctgctaca tcatgctcat cgacaggttg     600
cagccctggc tgacccggcc gtccgtgctg ctggtgatcg aacggctgac cgggctcatc     660
ctgatcgtcc tggcgatccg gatcgcgctg agccggtga                            699
```

<210> SEQ ID NO 88
<211> LENGTH: 132
<212> TYPE: PRT
<213> ORGANISM: Micromonospora sp. strain 046-ECO11

<400> SEQUENCE: 88

```
Val Gly Val Ser Ala Met Thr Thr Phe Asp Tyr Asp Gly Arg Val Phe
1               5                   10                  15

Val Ser Val Asp His Asp Ala Gly Asp Gly Ala Glu Pro Leu Arg Gly
            20                  25                  30

His Tyr His Gln Arg Gly Asp Leu Val Trp Ala Glu Ile Thr Gly Gly
        35                  40                  45

Pro Val Arg His Gly Arg Leu Ala Gly Thr Cys Asp Ala Gln Gly Val
    50                  55                  60

Val Arg Phe Ala Tyr Leu Glu Val Leu Thr Asp Gly Thr Ile Val Ile
65                  70                  75                  80

Gly Glu Cys Glu Ser Arg Pro Glu Arg Leu Pro Asp Gly Arg Ile Arg
                85                  90                  95

Leu Arg Glu Gln Trp Arg Arg His Gly Pro Arg Gln Asp Ser Gly Val
            100                 105                 110

Ser Val Ile Glu Glu Ala Val Pro Ala Leu Ala Gly Gly Gln Glu Ser
        115                 120                 125

Arg Arg Arg Val
    130
```

<210> SEQ ID NO 89
<211> LENGTH: 399
<212> TYPE: DNA
<213> ORGANISM: Micromonospora sp. strain 046-ECO11

<400> SEQUENCE: 89

```
gtgggcgtga gcgcgatgac gacattcgac tacgacggcc gcgtcttcgt ctcggtggac      60
cacgacgccg gtgacggcgc cgagccgctg cggggggcact accaccagcg tggcgacctg     120
gtctgggcgg agatcaccgg cggcccggtc cggcacggcc ggctggccgg cacctgcgac     180
```

```
                                                              -continued
gcgcagggcg tcgtgcgctt cgcctacctg gaggtgctca ccgacggcac catagtcatc    240
ggcgagtgcg agtcccggcc cgaacggctg ccggacggcc ggatccggct gcgggaacag    300
tggcgccggc acggaccacg ccaggacagc ggcgtctccg tcatcgagga ggcagtgccg    360
gcgctcgccg gaggacagga gagccggcgt cgtgtctga                           399
```

FARNESYL DIBENZODIAZEPINONE AND PROCESSES FOR ITS PRODUCTION

RELATED APPLICATIONS

This application is a divisional of U.S. Utility Application Ser. No. 10/762,107, filed Jan. 21, 2004, now U.S. Pat. No. 7,101,872, and claims priority to U.S. Provisional Application 60/441,126, filed Jan. 21, 2003; U.S. Provisional Application 60/492,997, filed Aug. 7, 2003; and U.S. Provisional Application 60/518,286, filed Nov. 10, 2003. The entire teachings of the above-noted priority applications are incorporated herein by reference.

FIELD OF THE INVENTION

This invention relates to a novel farnesylated dibenzodiazepinone, named ECO-04601, its pharmaceutically acceptable salts and derivatives, and to methods for obtaining the compound. One method of obtaining the compound is by cultivation of a novel strain of *Micromonospora* sp., i.e., 046-ECO11 or [S01]046; another method involves expression of biosynthetic pathway genes in transformed host cells. The present invention further relates to *Micromonospora* sp. strains 046-ECO11 and [S01]046, to the use of ECO-04601 and its pharmaceutically acceptable salts and derivatives as pharmaceuticals, in particular to their use as inhibitors of cancer cell growth, bacterial cell growth, mammalian lipoxygenase, and for treating acute and chronic inflammation, and to pharmaceutical compositions comprising ECO-04601 or a pharmaceutically acceptable salt or derivative thereof. Finally, the invention relates to novel polynucleotide sequences and their encoded proteins, which are involved in the biosynthesis of ECO-04601.

BACKGROUND OF THE INVENTION

The *euactinomycetes* are a subset of a large and complex group of Gram-positive bacteria known as actinomycetes. Over the past few decades these organisms, which are abundant in soil, have generated significant commercial and scientific interest as a result of the large number of therapeutically useful compounds, particularly antibiotics, produced as secondary metabolites. The intensive search for strains able to produce new antibiotics has led to the identification of hundreds of new species.

Many of the euactinomycetes, particularly *Streptomyces* and the closely related *Saccharopolyspora* genera, have been extensively studied. Both of these genera produce a notable diversity of biologically active metabolites. Because of the commercial significance of these compounds, much is known about the genetics and physiology of these organisms.

Another representative genus of *euactinomycetes*, *Micromonospora*, has also generated commercial interest. For example, U.S. Pat. No. 5,541,181 (Ohkuma et al.) discloses a dibenzodiazepinone compound, specifically 5-farnesyl-4,7,9-trihydroxy-dibenzodiazepin-11-one (named "BU-4664L"), produced by a known euactinomycetes strain, *Micromonospora* sp. M990-6 (ATCC 55378). The Ohkurma et al. patent reports that BU-4664L and its chemically synthesized di- and tri-alkoxy and acyloxy derivatives possess anti-inflammatory and anti-tumor cell activities.

Although many biologically active compounds have been identified from bacteria, there remains the need to obtain novel naturally occurring compounds with enhanced properties. Current methods of obtaining such compounds include screening of natural isolates and chemical modification of existing compounds, both of which are costly and time consuming. Current screening methods are based on general biological properties of the compound, which require prior knowledge of the structure of the molecules. Methods for chemically modifying known active compounds exist, but still suffer from practical limitations as to the type of compounds obtainable.

Thus, there exists a considerable need to obtain pharmaceutically active compounds in a cost-effective manner and with high yield. The present invention solves these problems by providing a novel strain of *Micromonospora* capable of producing a potent new therapeutic compound, as well as reagents (e.g., polynucleotides, vectors comprising the polynucleotides and host cells comprising the vectors) and methods to generate novel compounds by de novo biosynthesis rather than by chemical synthesis.

SUMMARY OF THE INVENTION

In one aspect, the invention relates to a compound of the formula

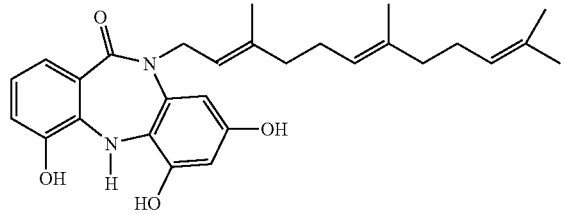

(Formula II) or a pharmaceutically acceptable salt thereof.

In another aspect, the invention relates to a pharmaceutical composition comprising a compound of the formula

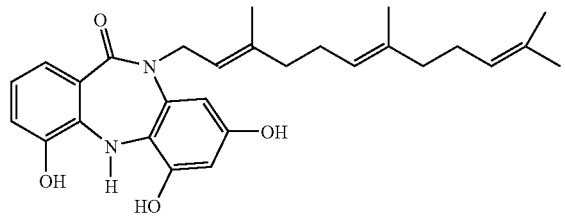

or a pharmaceutically acceptable salt thereof, together with a pharmaceutically acceptable carrier.

In a further aspect, the invention relates to a class of compounds represented by Formula I:

FORMULA I

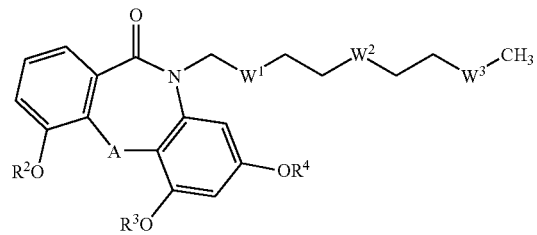

wherein,
W¹, W² and W³ is each independently selected from

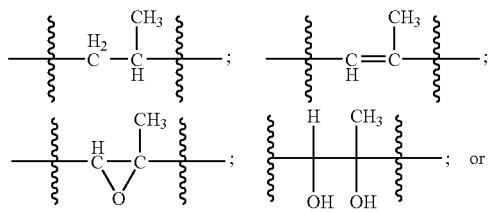

the chain from the tricycle may terminate at W³, W² or W¹ with W³, W² or W¹ respectively being either —CH=O or —CH₂OH;

A is selected from —NH—, —NCH₂R¹, —NC(O)R¹;

R¹ is selected from C1-6 alkyl, C2-6 alkene, aryl or heteroaryl;

R², R³, and R⁴ is each independently selected from H, R⁵, —C(O)R⁶

R⁵ is each independently selected from $C_{1-6}$ alkyl, $C_{2-7}$ alkalene, aryl or heteroaryl;

R⁶ is each independently selected from H, $C_{1-6}$ alkyl, $C_{2-7}$ alkalene, aryl or heteroaryl; or a pharmaceutically acceptable salt thereof.

In one embodiment, A is NH.
In another embodiment, A is —NCH₂R¹.
In another embodiment, A is —NC(o)R¹.
In another embodiment, R² is H.
In another embodiment, R³ is H.
In another embodiment, R⁴ is H.
In another embodiment, R², R³ and R⁴ are each H.
In another embodiment, R², R³ and R⁴ are each H, and W¹ is —CH=CH—.
In another embodiment, R², R³ and R⁴ are each H, and W² is —CH=CH—.
In another embodiment, R², R³ and R⁴ are each H, and W³ is —CH=CH—.
In another embodiment, A is NH and R², R³ and R⁴ are each H.
In another embodiment, A is NH, each of W¹, W², and W³ is —CH=CH—.

The invention further encompasses a compound selected from the group consisting of:

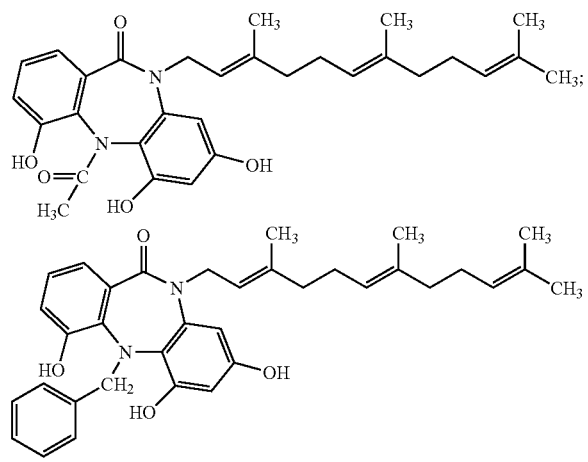

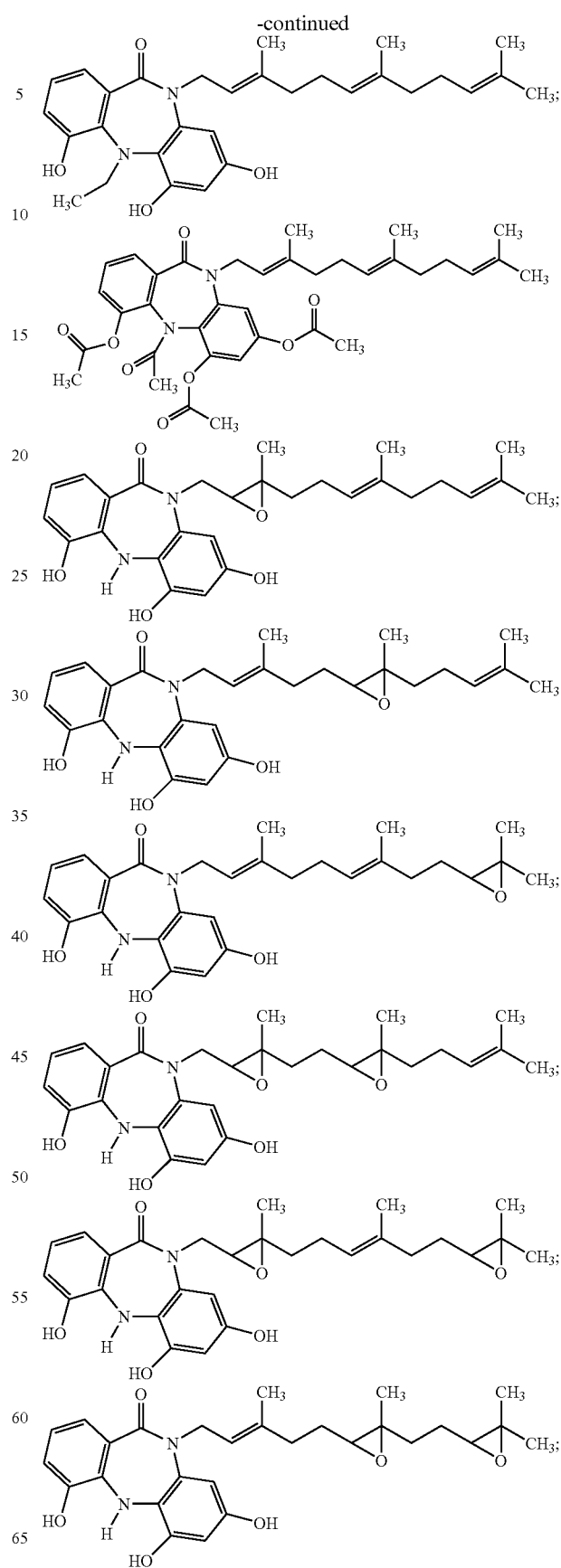

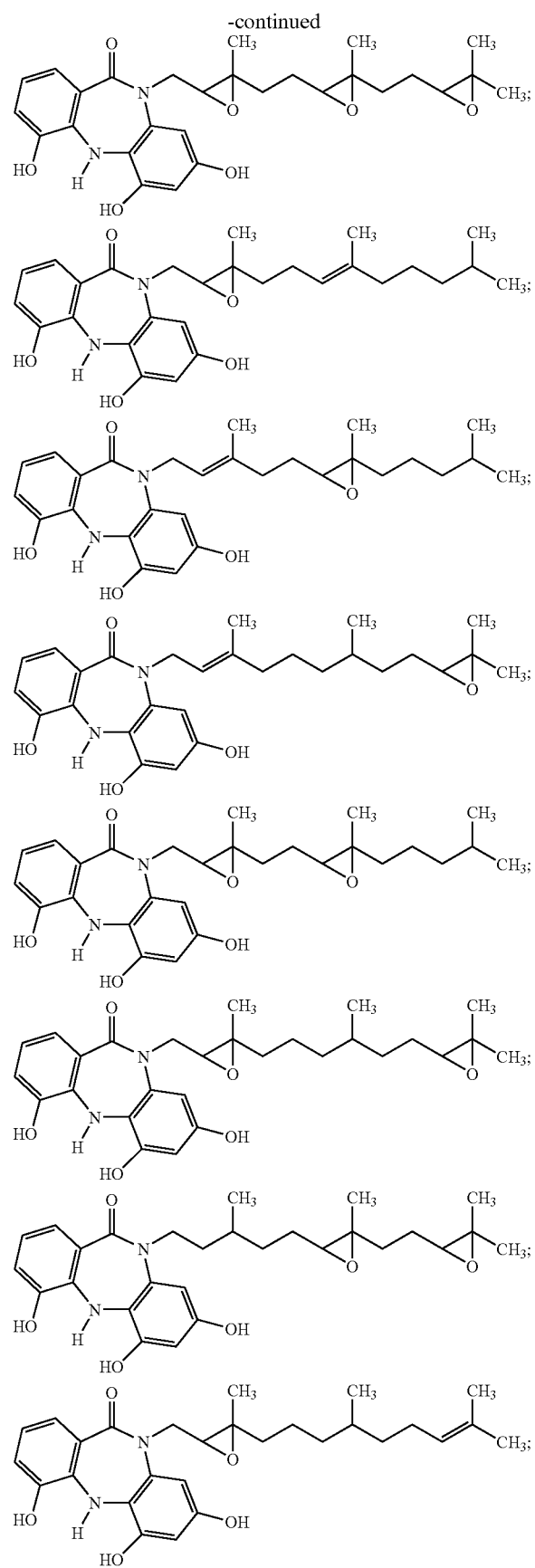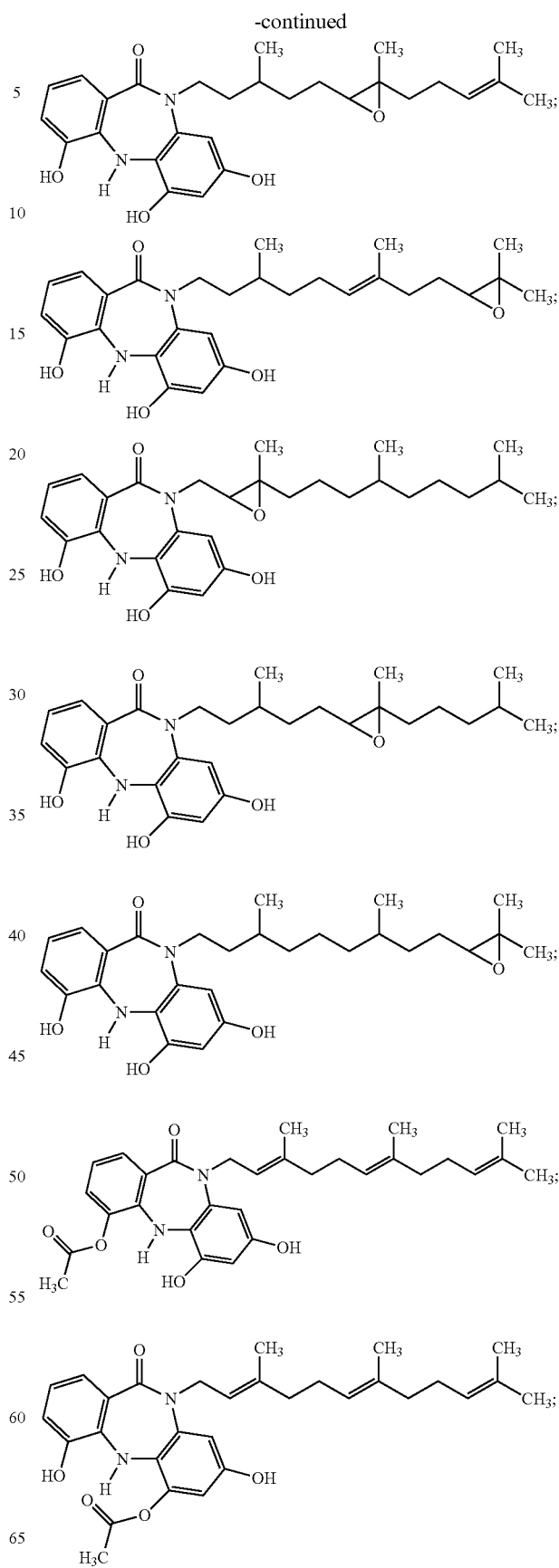

-continued
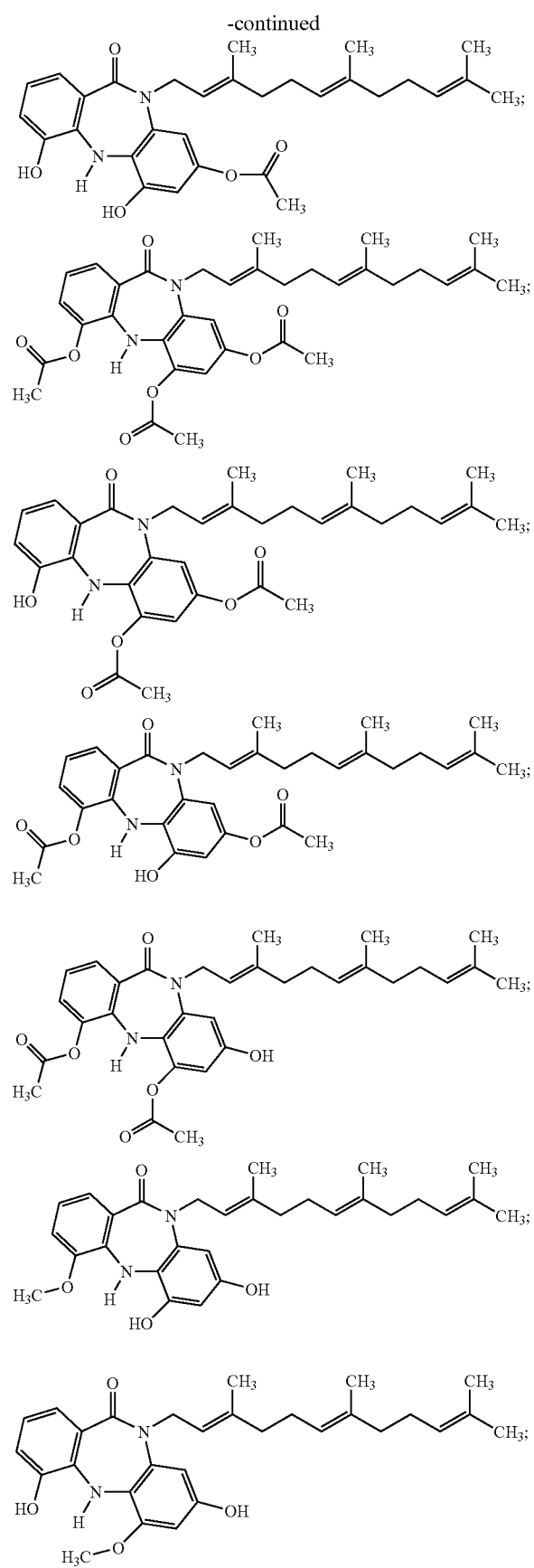
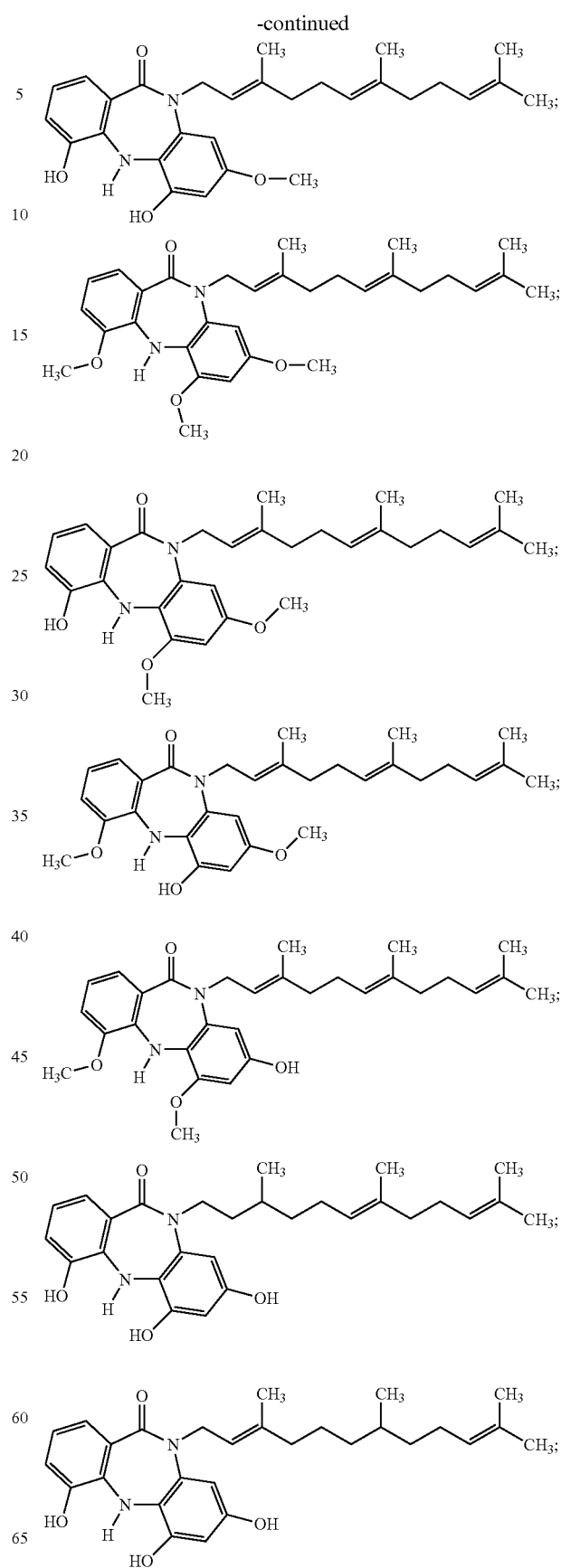

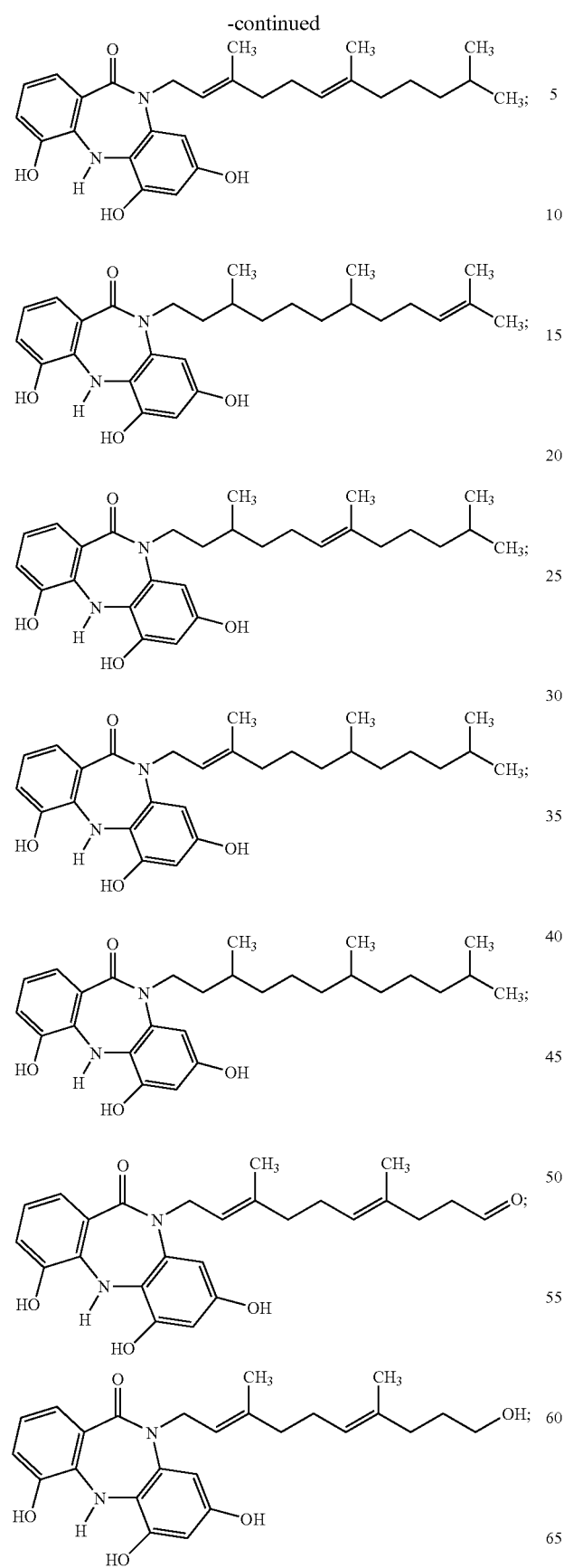
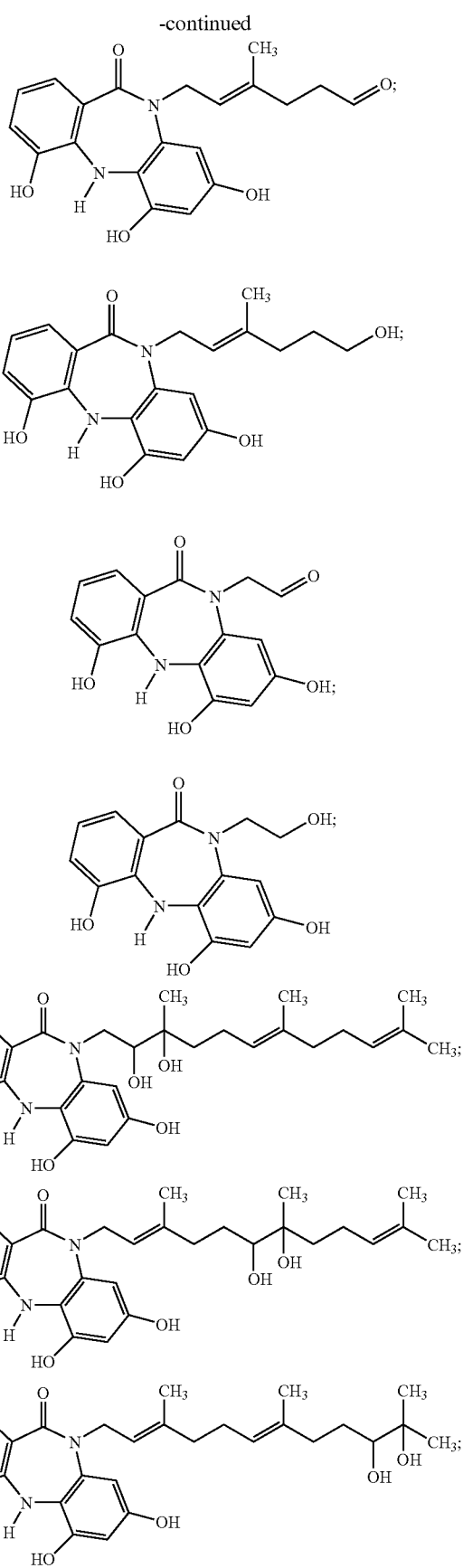

-continued

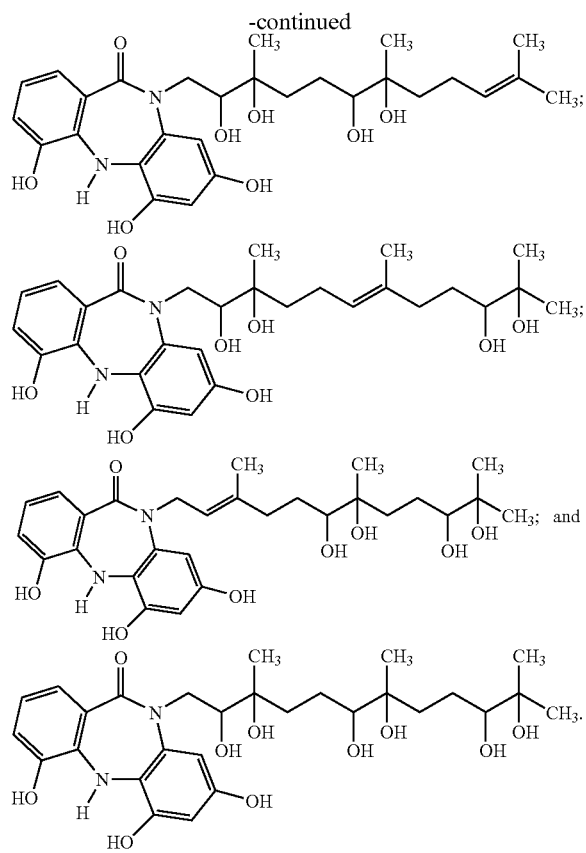

In one embodiment, the invention relates to compositions of the compounds of Formula I together with a pharmaceutically acceptable carrier.

The invention further encompasses a farnesyl dibenzodiazepinone obtained by a method comprising: a) cultivating *Micromonospora* sp. strain [S01]046, wherein the cultivation is performed under aerobic conditions in a nutrient medium comprising at least one source of carbon atoms and at least one source of nitrogen atoms; and b) isolating a farnesyl dibenzodiazapinone from the bacteria cultivated in step (a). In one embodiment the farnesyl dibenzodiazapinone is the compound of Formula II.

In one embodiment, the farnesyl dibenzodiazepinone generates NMR spectra essentially as shown in FIGS. 3, 4, 5, 6 and 7. In another embodiment, the farnesyl dibenzodiazepinone generates an $^1$H NMR spectrum of FIG. 3.

The invention further encompasses a process for making a farnesyl dibenzodiazapinone compound, comprising cultivation of *Micromonospora* sp. strain 046-ECO11, in a nutrient medium comprising at least one source of carbon atoms and at least one source of nitrogen atoms, and isolation and purification of the compound.

The invention further encompasses a process for making a farnesyl dibenzodiazepinone compound comprising cultivation of *Micromonospora* sp. strain [S01]046 in a nutrient medium comprising at least one source of carbon atoms and at least one source of nitrogen atoms, and isolation and purification of the compound.

In one embodiment, the cultivation occurs under aerobic conditions.

In another embodiment, the carbon atom and nitrogen atom sources are chosen from the components shown in Table 16.

In another embodiment, the cultivation is carried out at a temperature ranging from 18° C. to 40° C. In a further embodiment, the temperature range is 18° C. to 29° C.

In another embodiment, the cultivation is carried out at a pH ranging from 6 to 9.

The invention further encompasses the *Micromonospora* sp. having IDAC Accession No. 231203-01.

The invention further encompasses a method of inhibiting the growth of a cancer cell, the method comprising contacting the cancer cell with a compound of Formula I, such that growth of the cancer cell is inhibited.

In one embodiment, the compound is ECO-04601.

The invention further encompasses a method of inhibiting the growth of a cancer cell in a mammal, the method comprising administering a compound of Formula I to a mammal comprising a cancer cell, such that growth of the cancer cell is inhibited in the mammal.

In one embodiment, the compound is ECO-04601.

The invention further encompasses a method of treating a pre-cancerous or cancerous condition in a mammal, comprising the step of administering to the mammal a therapeutically effective amount of a compound of Formula I, such that a pre-cancerous or cancerous condition is treated.

In one embodiment, the compound is ECO-04601.

The invention further encompasses a method of treating a bacterial infection in a mammal, comprising administering a therapeutically effective amount of a compound of Formula I to a mammal having a bacterial infection, such that the bacterial infection is treated.

In one embodiment, the compound is ECO-04601.

The invention further encompasses a method of reducing inflammation in a mammal, comprising administering to a mammal having inflammation a therapeutically effective amount of a compound of Formula I, such that the inflammation is reduced.

In one embodiment, the compound is ECO-04601.

The invention further encompasses an isolated polynucleotide comprising one or more of SEQ ID NOs. 1, 64 and 73, wherein the polynucleotide encodes a polypeptide that participates in a biosynthetic pathway for a farnesyl dibenzodiazepinone.

The invention further encompasses an isolated polynucleotide comprising SEQ ID NOs. 1, 64 and 73, wherein the polynucleotide encodes a polypeptide that participates in a biosynthetic pathway for a farnesyl dibenzodiazepinone.

The invention further encompasses an isolated polynucleotide that encodes a polypeptide selected from the group consisting of SEQ ID NOs. 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89.

In one embodiment, the isolated polynucleotide comprising SEQ ID No. 1 encodes a polypeptide selected from the group consisting of SEQ ID Nos. 3, 5, 7, 9, 11, 13, 15, 17, 19, 21, 23, 25, 27, 29, 31, 33, 35, 37, 39, 41, 43, 45, 47, 49, 51, 53, 55, 57, 59, 61 and 63.

In another embodiment, the isolated polynucleotide comprising SEQ ID No. 64 encodes a polypeptide selected from the group consisting of SEQ ID NOS: 66, 68, 70 and 72.

In another embodiment, the isolated polynucleotide comprising SEQ ID No. 73, encodes a polypeptide selected from the group consisting of SEQ ID NOS: 75, 77, 79, 81, 83, 85, 87 and 89.

The invention further encompasses an isolated polypeptide of SEQ ID NO. 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 or 89.

In one embodiment, the polypeptide participates in a biosynthetic pathway for a farnesyl dibenzodiazepinone.

The invention further encompasses an expression vector comprising one or more of the polynucleotides described herein.

The invention further encompasses a recombinant prokaryotic organism comprising one or more such expression vectors.

In one embodiment, the organism is an actinomycete.

In another embodiment, the organism requires the expression vector to synthesize a farnesyl dibenzodiazepinone. That is, the organism is deficient in the ability to synthesize a farnesyl dibenzodiazepinone before transformation with a polynucleotide as described herein.

The invention further encompasses a method of making a farnesyl dibenzodiazepinone de novo in a prokaryote, comprising the steps of: (a) providing a prokaryote that is incapable of synthesizing a farnesyl dibenzodiazepinone; (b) transforming the prokaryote with an expression vector as described herein; and (c) culturing the prokaryote; wherein the culturing results in the synthesis of a farnesyl dibenzodiazepinone in the prokaryote.

In one embodiment, the prokaryote is an actinomycete.

In another embodiment, the vector expresses a polypeptide of SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 or 89.

BRIEF DESCRIPTION OF THE FIGURES

FIG. 1 shows the mass of ECO-04601 determined by electrospray mass spectrometry to be 462.6.

FIG. 16 shows a sequence listing table indicating the SEQ ID NO. and function for each of the open reading frames (ORFs) of the 046D biosynthetic locus and the corresponding gene product.

FIG. 17 shows results of the fatty acid analysis of *Micromonospora* sp. strain 046ECO11 (Accession No. IDAC 070303-01). Analysis was conducted using gas chromatography on fatty acid methyl esters (FAME).

FIG. 19 shows the complete $^1$H and $^{13}$C NMR assignments for ECO-04601 when measured in MeOH-d4.

DETAILED DESCRIPTION OF THE INVENTION

Figure 18:
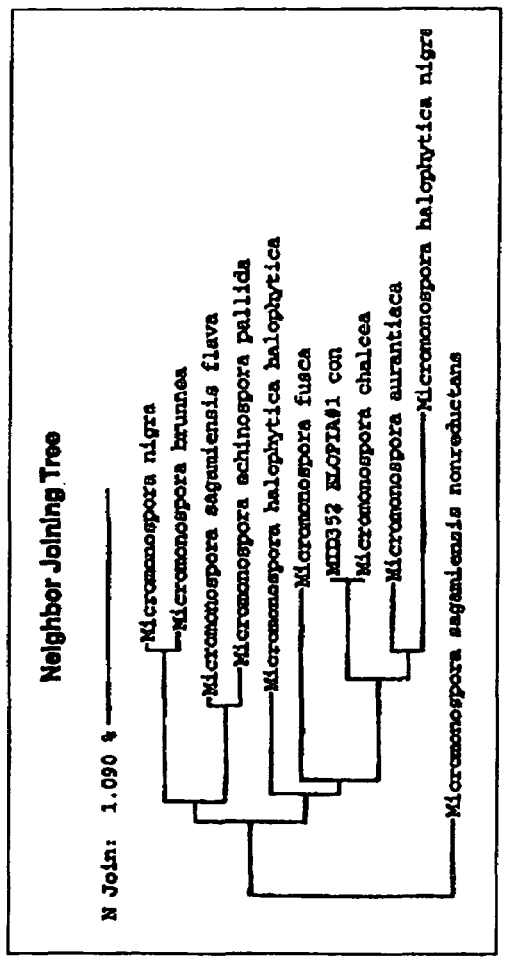
FIG. 18 illustrates the 16S ribosomal RNA analysis of *Micromonospora* sp. strain 046ECO11 (Accession No. IDAC 070303-01). Alignment of 16S ribosomal RNA sequences demonstrates the phylogenetic relatedness of *Micromonospora* sp. strain 046ECO11 (indicated as MID352 ECO-PIA#1 con) to *Micromonospora chalcea*.

The present invention relates to a novel farnesyl dibenzodiazepinone, referred to herein as "ECO-04601," which was isolated from novel strains of actinomycetes, *Micromonospora* sp. strain 046-ECO11 and strain [S01]046. These microorganisms were analysed using gas chromatography as Fatty acid methyl esters (FAME) (FIG. 17) 6S ribosomal RNA determination (FIG. 18) and were found to belong to the genus of *Micromonospora*. These organisms were deposited on Mar. 7, 2003, and Dec. 23, 2003, respectively, with the International Depository Authority of Canada (IDAC), Bureau of Microbiology, Health Canada, 1015 Arlington Street, Winnipeg, Manitoba, Canada R3E 3R2, under Accession Nos. IDAC 070303-01 and IDAC 231203-01, respectively.

The invention further relates to pharmaceutically acceptable salts and derivatives of ECO-04601, and to methods for obtaining such compounds. One method of obtaining the compound is by cultivating *Micromonospora* sp. strain 046-ECO11, or a mutant or a variant thereof, under suitable *Micromonospora* culture conditions, preferably using the fermentation protocol described hereinbelow.

The invention also relates to a method for producing novel polyketide compounds, namely farnesyl dibenzodiazepinones, by selectively altering the genetic information of an organism. The present invention further provides isolated and purified polynucleotides that encode farnesyl dibenzodiazepinone domains, i.e., polypeptides from farnesyl dibenzodiazepinone-producing microorganisms, fragments thereof, vectors containing those polynucleotides, and host cells transformed with those vectors. These polynucleotides, fragments thereof, and vectors comprising the polynucleotides can be used as reagents in the above described method. Portions of the polynucleotide sequences disclosed herein are also useful as primers for the amplification of DNA or as probes to identify related domains from other farnesyl dibenzodiazepinone producing microorganisms.

The present invention also relates to pharmaceutical compositions comprising ECO-04601 and its pharmaceutically acceptable salts and derivatives. ECO-04601 is useful as a pharmaceutical, in particular for use as an inhibitor of cancer cell growth, bacterial cell growth, and mammalian lipoxygenase. The invention also relates to novel polynucleotide sequences and their encoded proteins, which are involved in the biosynthesis of ECO-04601.

The following detailed description discloses how to make and use ECO-04601 and compositions containing this compound to inhibit microbial growth and/or specific disease pathways.

Accordingly, certain aspects of the present invention relate to pharmaceutical compositions comprising the farnesylated dibenzodiazepinone compounds of the present invention together with a pharmaceutically acceptable carrier, methods of using the compositions to inhibit bacterial growth, and methods of using the pharmaceutical compositions to treat diseases, including cancer, and chronic and acute inflammation.

I. Definitions

For convenience, the meaning of certain terms and phrases used in the specification, examples, and appended claims, are provided below.

As used herein, the term "farnesyl dibenzodiazepinone" refers to a class of dibenzodiazepinone compounds containing a farnesyl moiety. The term includes, but is not limited to, the exemplified compound of the present invention, 10-farnesyl-4,6,8-trihydroxy-dibenzodiazepin-11-one, which is referred to herein as "ECO-04601." As used herein, the term "farnesyl dibenzodiazepinone" includes compounds of this class that can be used as intermediates in chemical syntheses. As used herein, the term "alkyl" refers to linear or branched hydrocarbon groups. Examples of alkyl groups include, without limitation, methyl, ethyl, n-propyl, isopropyl, n-butyl, pentyl, hexyl, heptyl, cyclopentyl, cyclohexyl, cyclohexymethyl, and the like. Alkyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, oxo, guanidino and formyl.

The term "alkenyl" refers to linear, branched or cyclic hydrocarbon groups containing at least one carbon-carbon double bond. Examples of alkenyl groups include, without limitation, vinyl, 1-propen-2-yl, 1-buten-4-yl, 2-buten-4-yl, 1-penten-5-yl and the like. Alkenyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. The double bond portion(s) of the unsaturated hydrocarbon chain may be either in the cis or trans configuration.

The terms "cycloalkyl" and "cycloalkyl ring" refer to a saturated or partially unsaturated carbocyclic ring in a single or fused carbocyclic ring system having from three to fifteen ring members. Examples of cycloalkyl groups include, without limitation, cyclopropyl, cyclobutyl, cyclohexyl, and cycloheptyl. Cycloalkyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The terms "heterocyclyl" and "heterocyclic" refer to a saturated or partially unsaturated ring containing one to four hetero atoms or hetero groups selected from O, N, NH, NRx, PO2, S, SO or $SO_2$ in a single or fused heterocyclic ring system having from three to fifteen ring members. Examples of a heterocyclyl or heterocyclic ring include, without limitation, morpholinyl, piperidinyl, and pyrrolidinyl. Heterocyclyl, heterocyclic or heterocyclyl ring may optionally be substituted with substituents selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The term "amino acid" refers to any natural amino acid, all natural amino acids are well known to a person skilled in the art.

The term "halo" refers to a halogen atom, e.g., bromine, chlorine, fluorine and iodine.

The terms "aryl" and "aryl ring" refer to aromatic groups in a single or fused ring system, having from five to fifteen ring members. Examples of aryl include, without limitation, phenyl, naphthyl, biphenyl, terphenyl. Aryl may optionally be substituted with one or more substituent group selected from acyl, amino, acylamino, acyloxy, azido, alkythio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The terms "heteroaryl" and "heteroaryl ring" refer to aromatic groups in a single or fused ring system, having from five to fifteen ring members and containing at least one hetero atom such as O, N, S, SO and $SO_2$. Examples of heteroaryl groups include, without limitation, pyridinyl, thiazolyl, thiadiazoyl, isoquinolinyl, pyrazolyl, oxazolyl, oxadiazoyl, triazolyl, and pyrrolyl groups. Heteroaryl groups may optionally be substituted with one or more substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, and formyl.

The terms "aralkyl" and "heteroaralkyl" refer to an aryl group or a heteroaryl group, respectively bonded directly through an alkyl group, such as benzyl. Aralkyl and heteroaralkyl may be optionally substituted as the aryl and heteroaryl groups.

Similarly, the terms "aralkenyl" and "heteroaralkenyl" refer to an aryl group or a heteroaryl group, respectively bonded directly through an alkene group, such as benzyl. Aralkenyl and heteroaralkenyl may be optionally substituted as the aryl and heteroaryl groups.

The compounds of the present invention can possess one or more asymmetric carbon atoms and can exist as optical isomers forming mixtures of racemic or non-racemic compounds. The compounds of the present invention are useful as single isomers or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes.

The invention encompasses isolated or purified compounds. An "isolated" or "purified" compound refers to a compound which represents at least 10%, 20%, 50%, 80% or 90% of the compound of the present invention present in a mixture, provided that the mixture comprising the compound of the invention has demonstrable (i.e. statistically significant) biological activity including antibacterial, cytostatic, cytotoxic, antiinflammatory or enzyme inhibitory action when tested in conventional biological assays known to a person skilled in the art.

The terms "farnesyl dibenzodiazepinone-producing microorganism" and "producer of farnesyl dibenzodiazepinone," as used herein, refer to a microorganism that carries genetic information necessary to produce a farnesyl dibenzodiazepinone compound, whether or not the organism naturally produces the compound. The terms apply equally to organisms in which the genetic information to produce the farnesyl dibenzodiazepinone compound is found in the organism as it exists in its natural environment, and to organisms in which the genetic information is introduced by recombinant techniques.

Specific organisms contemplated herein include, without limitation, organisms of the family Micromonosporaceae, of which preferred genera include *Micromonospora*, *Actinoplanes* and *Dactylosporangium*; the family Streptomycetaceae, of which preferred genera include *Streptomyces* and *Kitasatospora*; the family Pseudonocardiaceae, of which preferred genera are *Amycolatopsis* and *Saccharopolyspora*; and the family Actinosynnemataceae, of which preferred genera include *Saccharothrix* and *Actinosynnema*; however the terms are intended to encompass all organisms containing genetic information necessary to produce a farnesyl dibenzodiazepinone compound. A preferred producer of a farnesyl dibenzodiazepinone compound includes microbial strain 046-ECO11, a deposit of which was made on Mar. 7, 2003, with the International Depository Authority of Canada (IDAC), Bureau of Microbiology, Health Canada, 1015 Arlington Street, Winnipeg, Manitoba, Canada R3E 3R2, under Accession No. IDAC 070303-01.

The term "gene" means the segment of DNA involved in producing a polypeptide chain; it includes regions preceding and following the coding region (leader and trailer) as well as, where applicable, intervening regions (introns) between individual coding segments (exons).

The terms "gene locus, "gene cluster," and "biosynthetic locus" refer to a group of genes or variants thereof involved in the biosynthesis of a farnesyl benzodiazepinone compound. The biosynthetic locus in strain 046-ECO11 that directs the production of ECO-04601 is often referred to herein, in both the written description and Figures, as "046D." Genetic modification of gene locus, gene cluster or biosynthetic locus refers to any genetic recombinant techniques known in the art including mutagenesis, inactivation, or replacement of nucleic acids that can be applied to generate variants of ECO-04601.

A DNA or nucleotide "coding sequence" or "sequence encoding" a particular polypeptide or protein, is a DNA sequence which is transcribed and translated into a polypeptide or protein when placed under the control of an appropriate regulatory sequence.

"Oligonucleotide" refers to a nucleic acid, generally of at least 10, preferably 15 and more preferably at least 20 nucleotides in length, preferably no more than 100 nucleotides in length, that are hybridizable to a genomic DNA molecule, a cDNA molecule, or an mRNA molecule encoding a gene, mRNA, cDNA or other nucleic acid of interest.

A promoter sequence is "operably linked to" a coding sequence recognized by RNA polymerase which initiates transcription at the promoter and transcribes the coding sequence into mRNA.

The term "replicon" as used herein means any genetic element, such as a plasmid, cosmid, chromosome or virus, that behaves as an autonomous unit of polynucleotide replication within a cell. A "expression vector" or "vector" is a replicon in which another polynucleotide fragment is attached, such as to bring about the replication and/or expression of the attached fragment. "Plasmids" are designated herein by a lower case "p" preceded or followed by capital letters and/or numbers. The starting plasmids disclosed herein are commercially available, publicly available on an unrestricted basis, or can be constructed from available plasmids in accordance with published procedures. In addition, equivalent plasmids to those described herein are known in the art and will be apparent to the skilled artisan.

The terms "express" and "expression" means allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted.

"Digestion" of DNA refers to enzymatic cleavage of the DNA with a restriction enzyme that acts only at certain sequences in the DNA. The various restriction enzymes used herein are commercially available and their reaction conditions, cofactors and other requirements were used as would be known to the ordinary skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular enzymes are specified by the manufacturer. Incubation times of about 1 hour at 37° C. are ordinarily used, but may vary in accordance with the supplier's instructions. After digestion the gel electrophoresis may be performed to isolate the desired fragment.

The term "isolated" as used herein means that the material is removed from its original environment (e.g. the natural environment where the material is naturally occurring). For example, a naturally occurring polynucleotide or polypeptide present in a living animal is not isolated, but the same polynucleotide or polypeptide, which is separated from some or all of the coexisting materials in the natural system, is isolated. Such polynucleotides could be part of a vector and/or such polynucleotides or polypeptides could be part of a composition, and still be isolated in that the vector or composition is not part of the natural environment.

The term "restriction fragment" as used herein refers to any linear DNA generated by the action of one or more restriction enzymes.

The term "transformation" means the introduction of a foreign gene, foreign nucleic acid, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone" or "recombinant". The DNA or RNA introduced to a host cell can come from any source, including cells of the same genus or species as the host cell, or cells of a different genus or species.

The terms "recombinant polynucleotide" and "recombinant polypeptide" as used herein mean a polynucleotide or polypeptide which by virtue of its origin or manipulation is not associated with all or a portion of the polynucleotide or polypeptide with which it is associated in nature and/or is linked to a polynucleotide or polypeptide other than that to which it is linked in nature.

The term "host cell" as used herein, refer to both prokaryotic and eukaryotic cells which are used as recipients of the recombinant polynucleotides and vectors provided herein. In one embodiment, the host cell is a prokaryote.

The terms "open reading frame" and "ORF" as used herein refers to a region of a polynucleotide sequence which encodes a polypeptide; this region may represent a portion of a coding sequence or a total coding sequence.

As used herein and as known in the art, the term "identity" is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M. Stockton Press, New York (1991)). Methods commonly employed to determine identity between sequences include, for example, those disclosed in Carillo, H., and Lipman, D., *SIAM J. Applied Math*. (1988) 48:1073. "Substantially identical," as used herein, means there is a very high degree of homology (preferably 100% sequence identity) between subject polynucleotide sequences. However, polynucleotides having greater than 90%, or 95% sequence identity may be used in the present invention, and thus sequence variations that might be expected due to genetic mutation, strain polymorphism, or evolutionary divergence can be tolerated.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a farnesyl dibenzodiazepinone and a pharmaceutically acceptable carrier. As used herein, "pharmacologically effective amount," "therapeutically effective amount" or simply "effective amount" refers to that amount of a farnesyl dibenzodiazepinone effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

The term "pharmaceutically acceptable salt" refers to both acid addition salts and base addition salts. The nature of the salt is not critical, provided that it is pharmaceutically acceptable. Exemplary acid addition salts include, without limitation, hydrochloric, hydrobromic, hydroiodic, nitric, carbonic, sulphuric, phosphoric, formic, acetic, citric, tartaric, succinic, oxalic, malic, glutamic, propionic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric, galacturonic acid and the like. Suitable pharmaceutically acceptable base addition salts include, without limitation, metallic salts made from aluminium, calcium, lithium, magnesium, potassium, sodium and zinc or organic salts made from N,N'-dibenzylethylenediamine, chloroprocaine, choline, diethanolamine, ethylenediamine, N-methylglucamine, lysine, procaine and the like. Additional examples of pharmaceutically acceptable salts are listed in Journal of Pharmaceutical Sciences (1977) 66:2. All of these salts may be prepared by conventional means from a farnesyl dibenzodiazepinone by treating the compound with the appropriate acid or base.

II. Farnesylated Dibenzodiazepinone Compounds

In one aspect, the invention relates to a novel farnesyl dibenzodiazepinone, referred to herein as "ECO-04601" and having the chemical structure represented by the following formula:

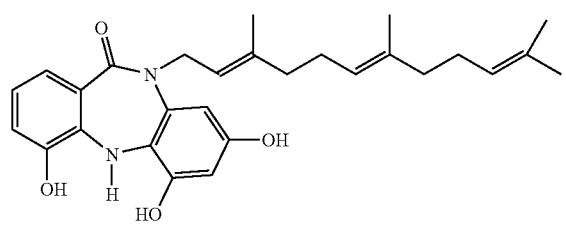

Figure 2:
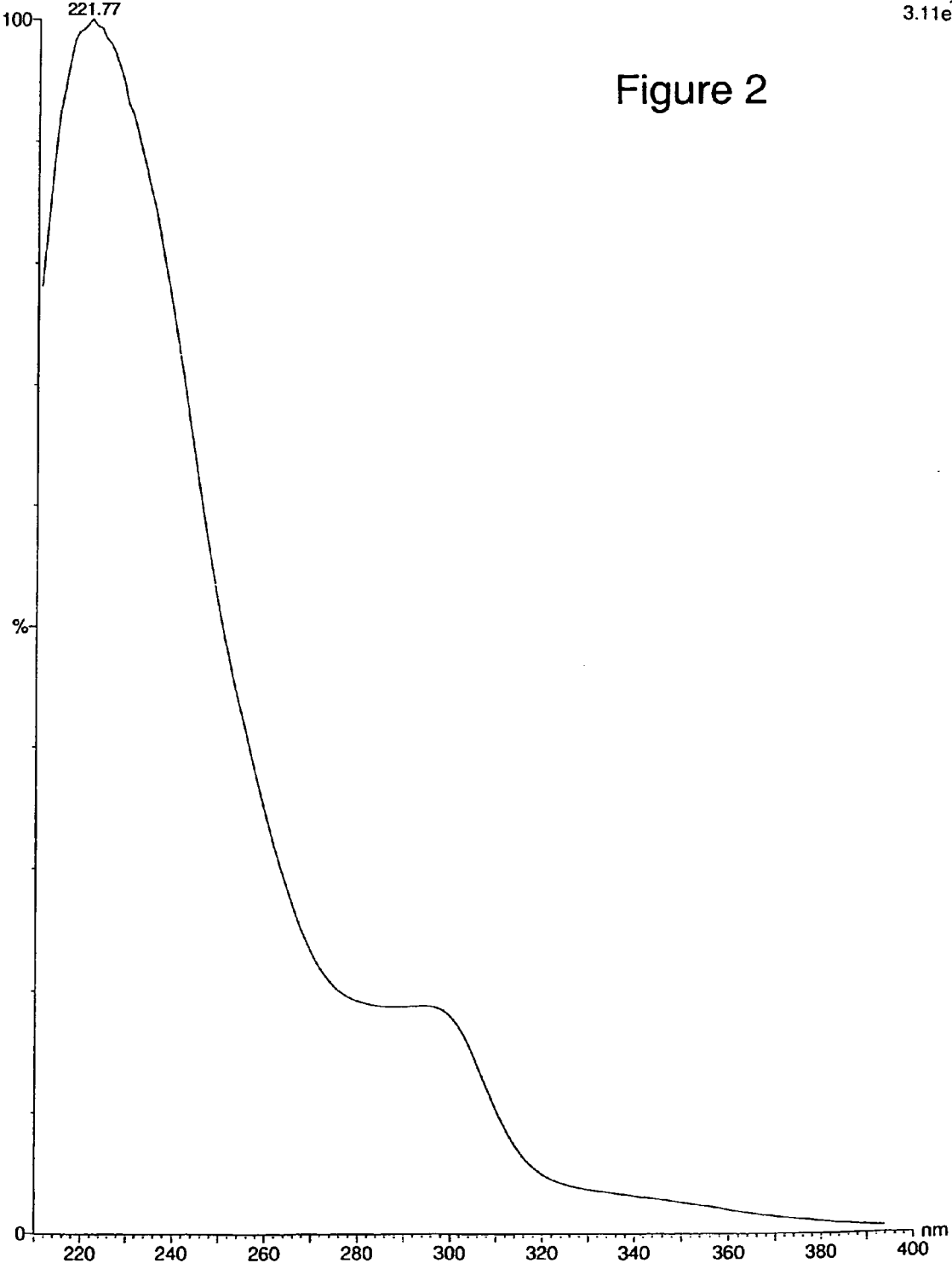
FIG. 2 shows the absorption spectrum of purified ECO-04601 with a UVmax at 230 nm and a shoulder at 290 nm.
Figure 3:
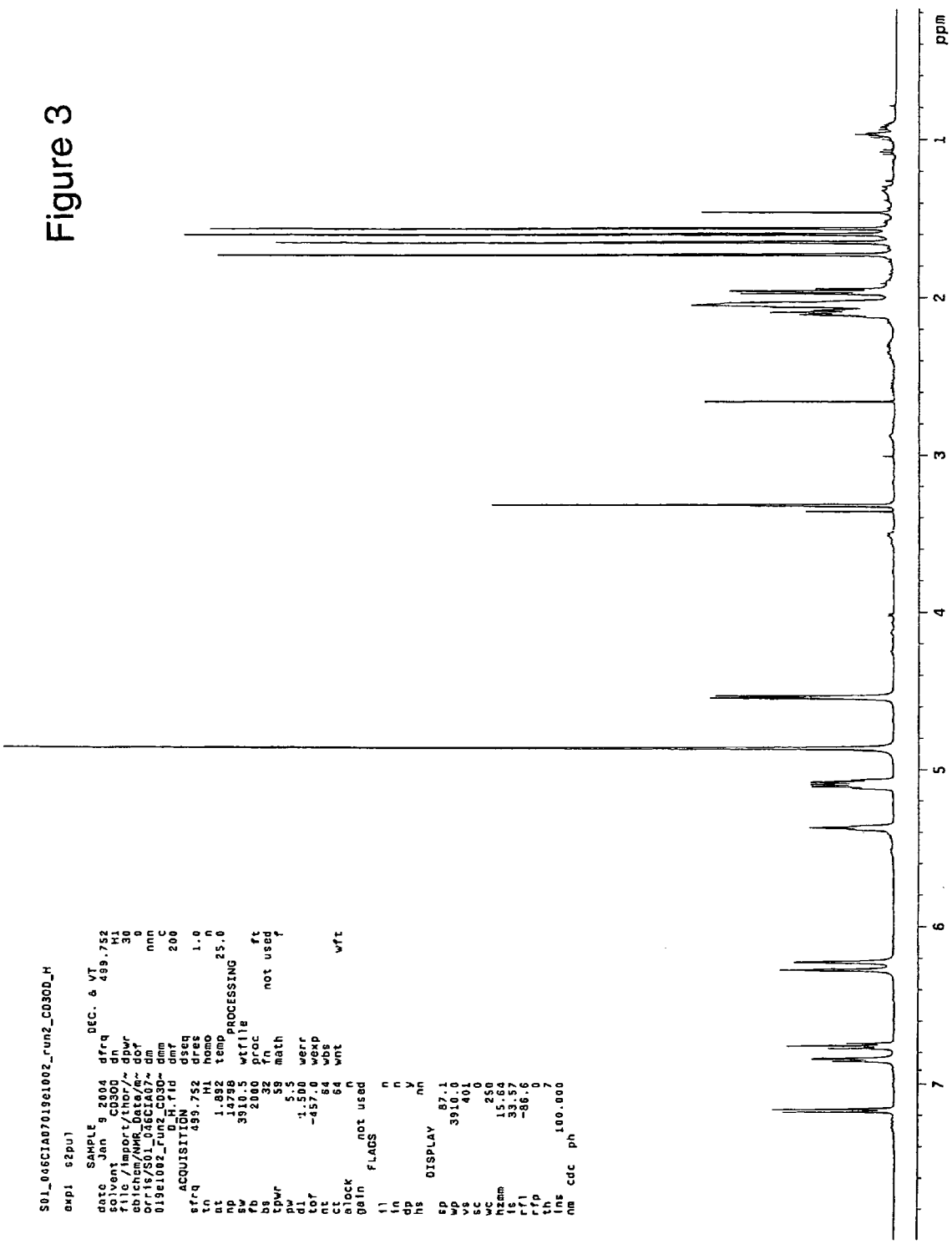
FIG. 3 shows proton NMR data for the compound dissolved in MeOH-$d_4$.
Figure 4:
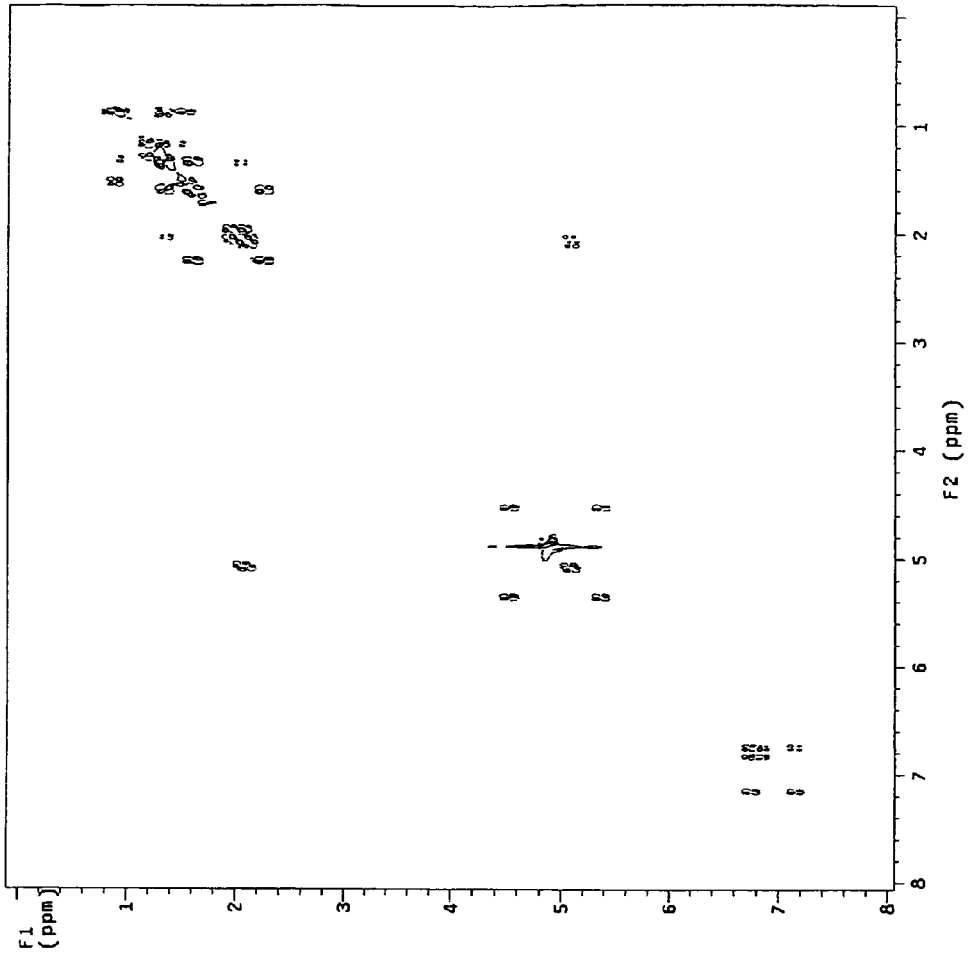
FIG. 4 shows multidimensional pulse sequences gDQ-COSY.
Figure 5:
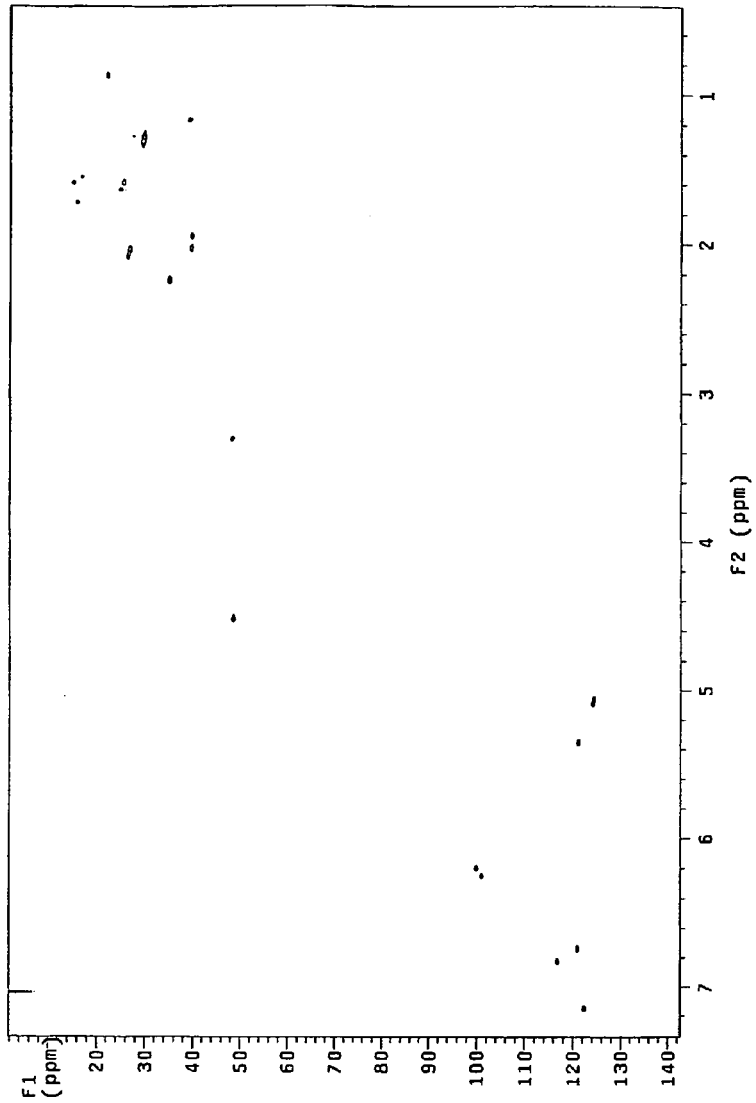
FIG. 5 shows multidimensional pulse sequences gHSQC.
Figure 6:
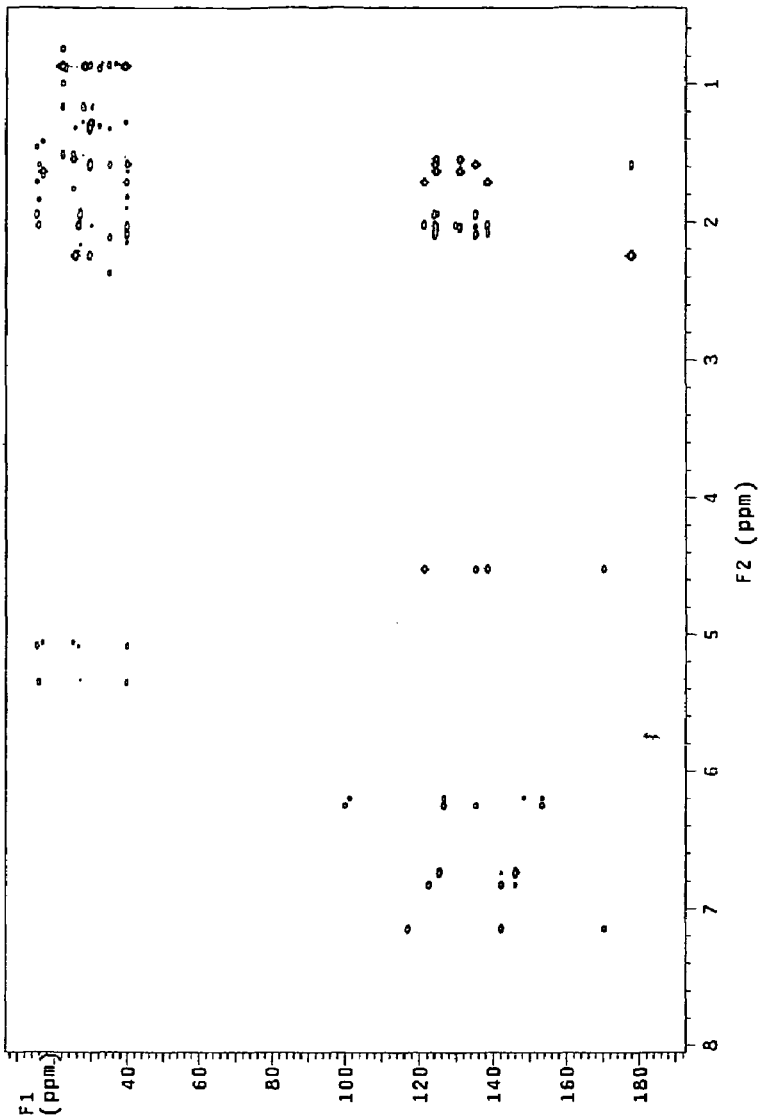
FIG. 6 shows multidimensional pulse sequences gHMBC.
Figure 7:
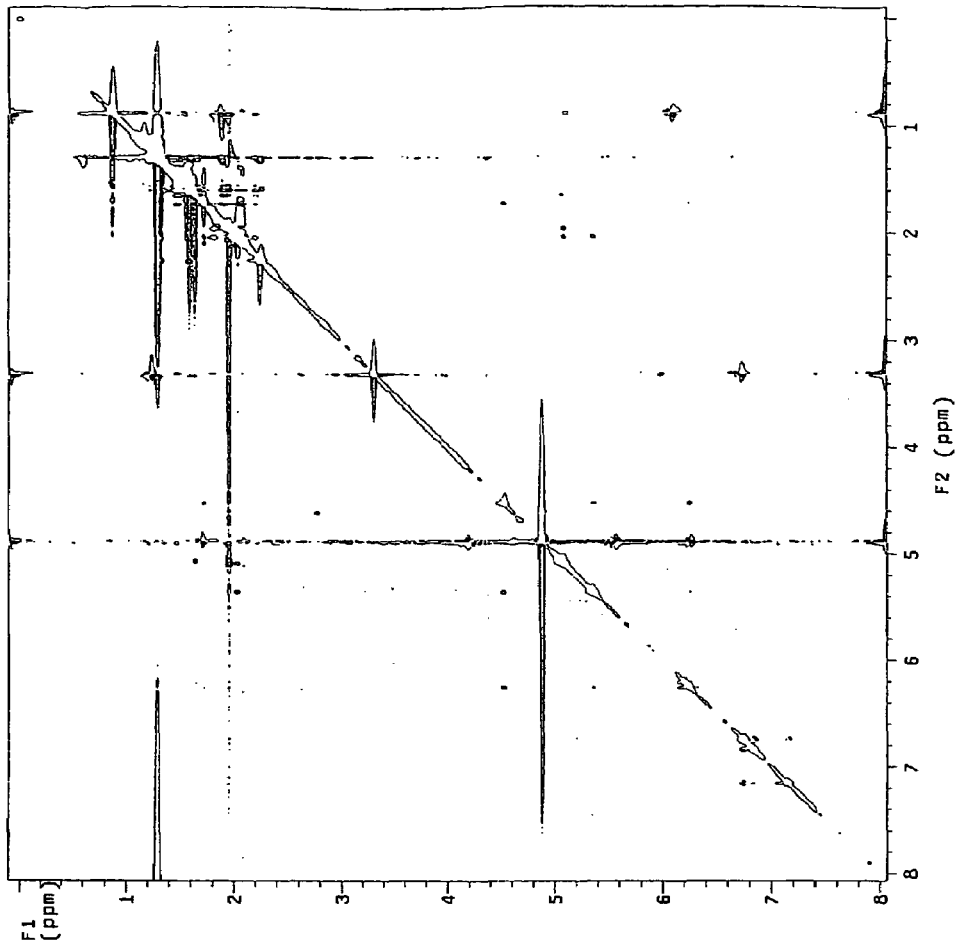
FIG. 7 shows multidimensional pulse sequences NOESY.

ECO-04601 may be described as a new dibenzodiazepinone having a 10-farnesyl substituent located on the nitrogen atom in the 10 position of the dibenzodiazepine ring (i.e., the amide nitrogen in the diazepinone ring), and three phenolic hydroxy substituents in the 4, 6 and 8 positions of the dibenzodiazepinone ring. ECO-04601 may be characterized by any one or more of its physicochemical and spectral properties given below, such as its mass, UV, and NMR spectroscopic data. Mass was determined by electrospray mass spectrometry to be 462.6 (FIG. 1); UV=230 nm with a shoulder at 290 nm (FIG. 2). NMR data were collected using MeOH-d4, including proton (FIG. 3), and multidimensional pulse sequences gDQCOSY (FIG. 4), gHSQC (FIG. 5), gHMBC (FIG. 6), and NOESY (FIG. 7).

In another aspect, the invention relates to a novel class of farnesyl dibenzodiazepinone compounds represented by Formula I:

FORMULA I

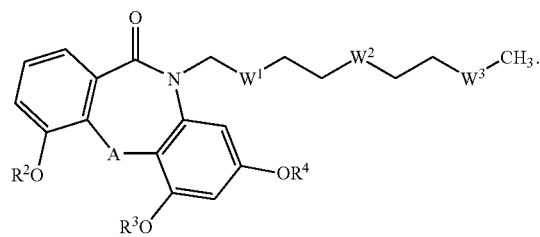

wherein, $W^1$, $W^2$ and $W^3$ is each independently selected from

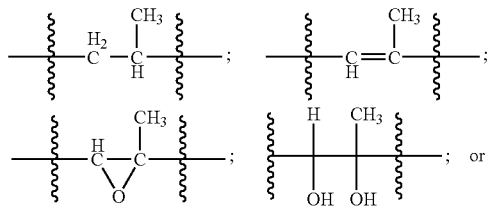

; or the chain from the tricycle may terminate at $W^3$, $W^2$ or $W^1$ with $W^3$, $W^2$ or $W^1$ respectively being either —CH=O or —CH$_2$OH;

A is selected from —NH—, —NCH$_2$R$^1$, —NC(O)R$^1$;

$R^1$ is selected from C1-6 alkyl, C2-6 alkene, aryl or heteroaryl;

$R^2$, $R^3$, and $R^4$ is each independently selected from H, $R^5$, —C(O)R$^6$ $R^5$ is each independently selected from $C_{1-6}$ alkyl, $C_{2-7}$ alkalene, aryl or heteroaryl;

$R^6$ is each independently selected from H, $C_{1-6}$ alkyl, $C_{2-7}$ alkalene, aryl or heteroaryl; or a pharmaceutically acceptable salt thereof.

In other embodiments, the invention provides compounds of Formula I, wherein A is selected from the group consisting of NH, NCH2R1, and NC(O)R1; wherein R2 is H; R3 is H; and R4 is H. In another embodiment, R2, R3 and R4 are each H; and all other groups are as previously defined. In a further embodiment, R2, R3 and R4 are each H; and W1 is —CH=CH— and all other groups are as previously defined. In a further embodiment, R2, R3 and R4 are each H, and W2 is —CH=CH— and all other groups are as previously defined. In a further embodiment, R2, R3 and R4 are each H; and W3 is —CH=CH—; and all other groups are as previously defined. In a further embodiment, A is NH; R2, R3 and R4 are each H; and all other groups are as previously defined. In a further embodiment, A is NH; each of W1, W2, and W3 is —CH=CH—; and all other groups are as previously defined. The invention encompasses all pharmaceutically acceptable salts of the foregoing compounds.

The following are exemplary compounds of the invention:

FORMULA II

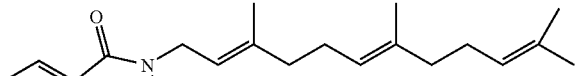

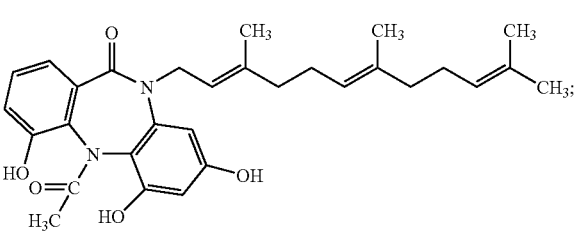

FORMULA III

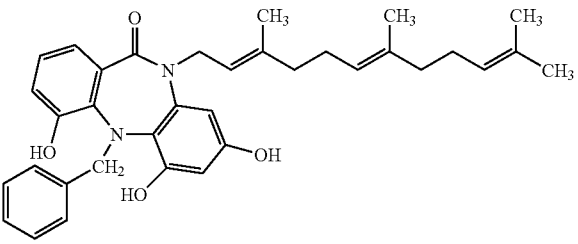

FORMULA IV

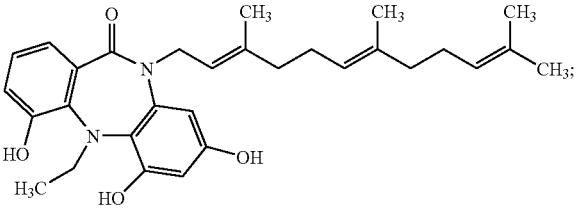

FORMULA V

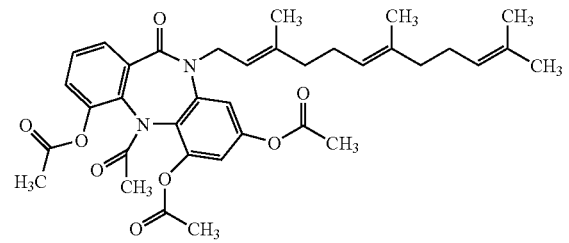

FORMULA VI

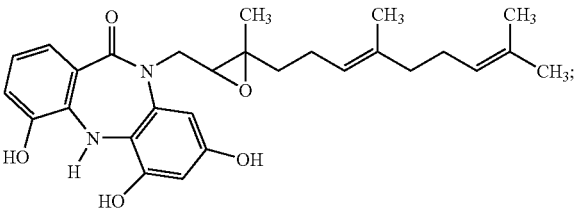

FORMULA VII

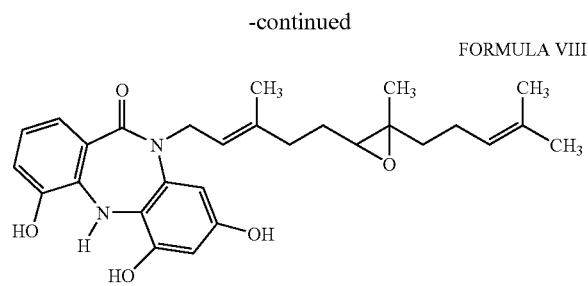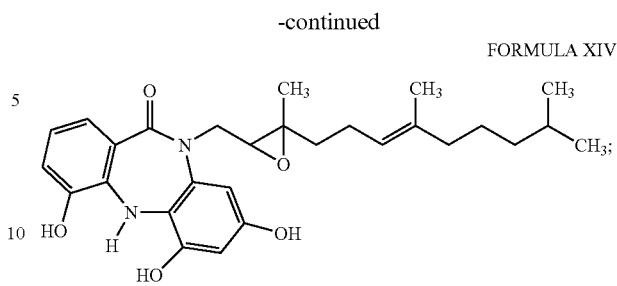

FORMULA XX
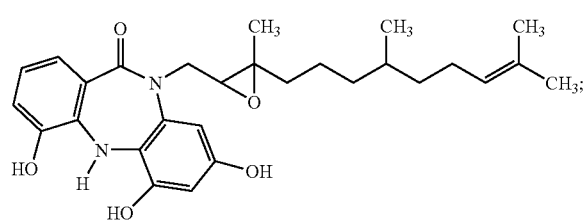
FORMULA XXI
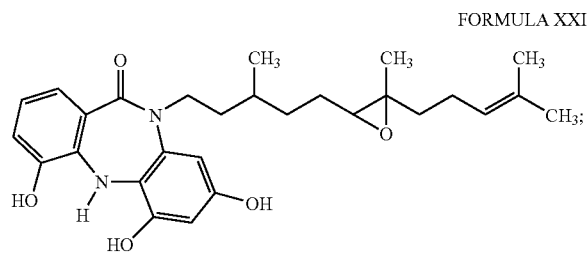
FORMULA XXII
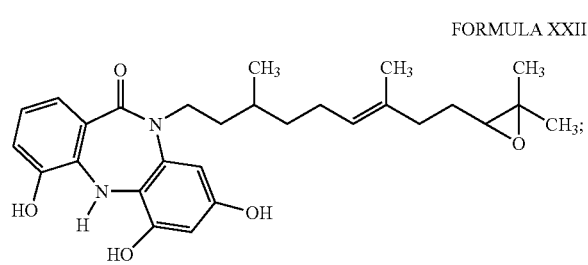
FORMULA XXIII
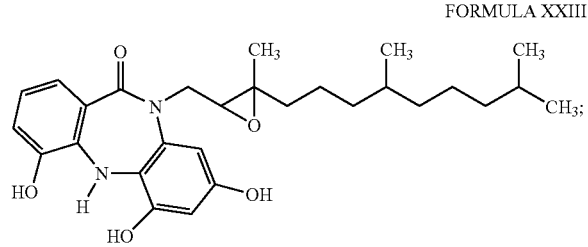
FORMULA XXIV
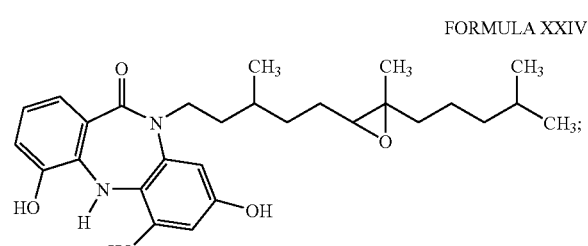
FORMULA XXV
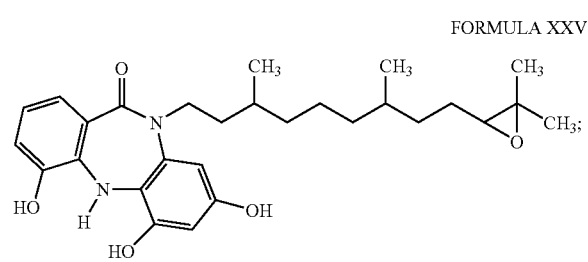
FORMULA XXVI
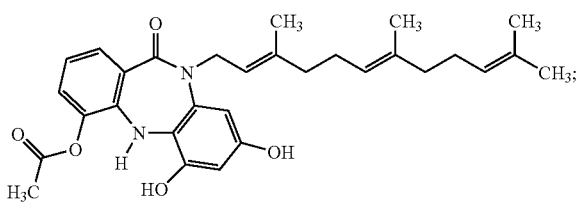
FORMULA XXVII
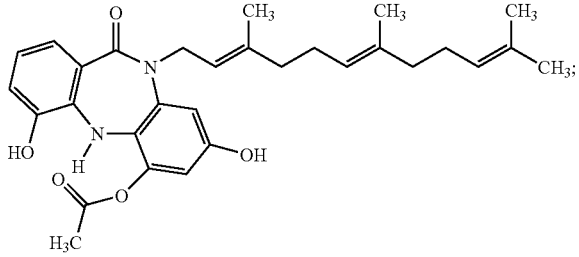
FORMULA XXVIII
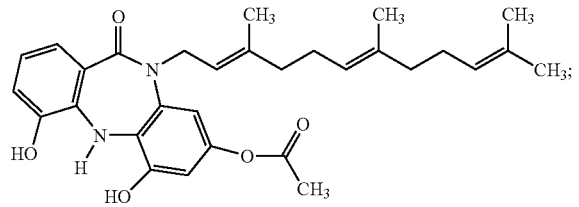
FORMULA XXIX
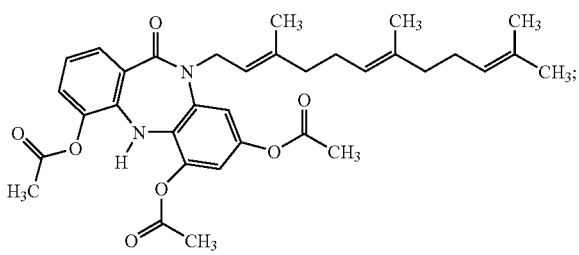
FORMULA XXX
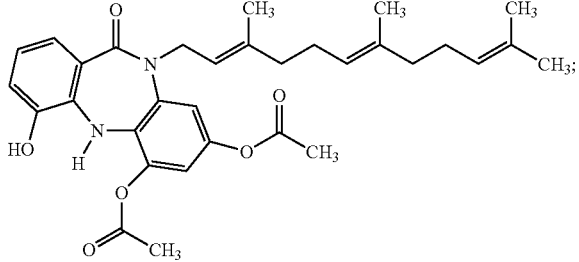
FORMULA XXXI
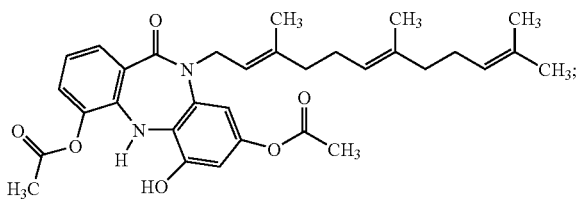

-continued
FORMULA XXXII
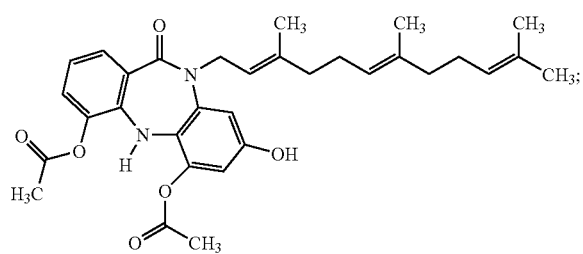
FORMULA XXXIII
FORMULA XXXIV
FORMULA XXXV
FORMULA XXXVI
FORMULA XXXVII
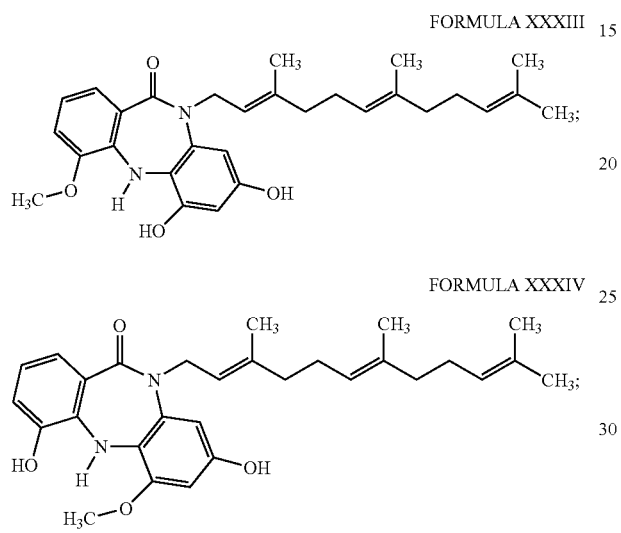
FORMULA XXXVIII
FORMULA XXXIX
FORMULA XL
FORMULA XLI
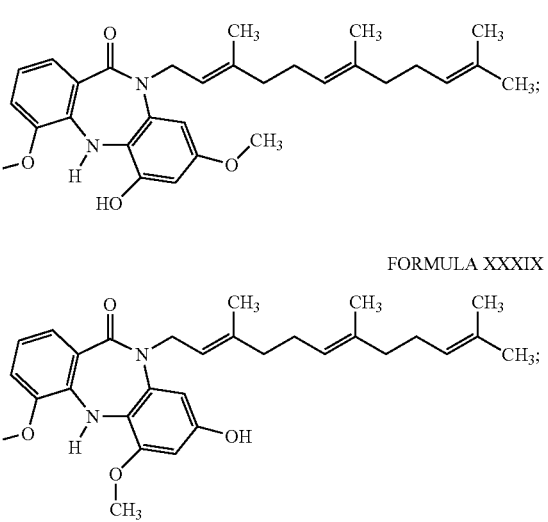
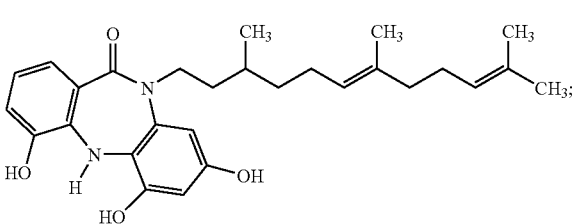
FORMULA XLII
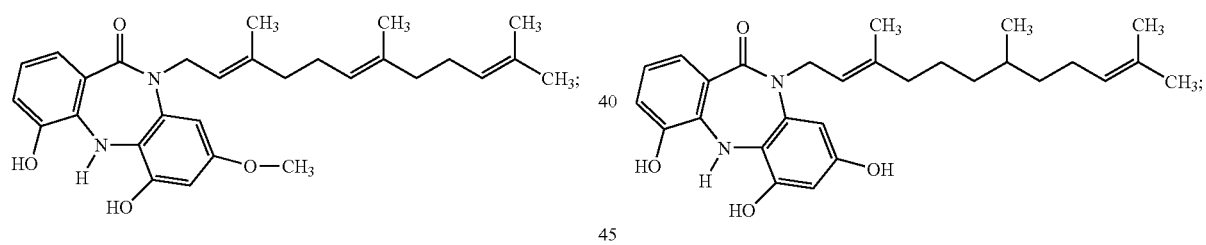
FORMULA XLIII
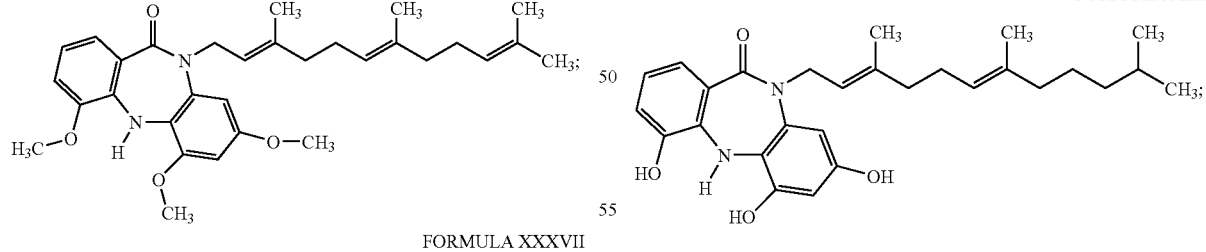
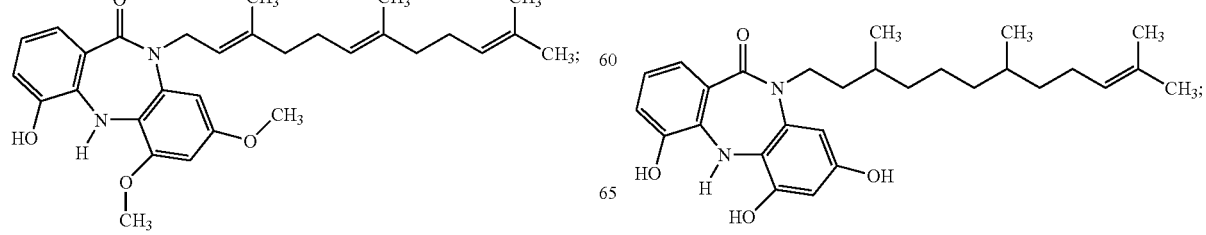

FORMULA XLIV
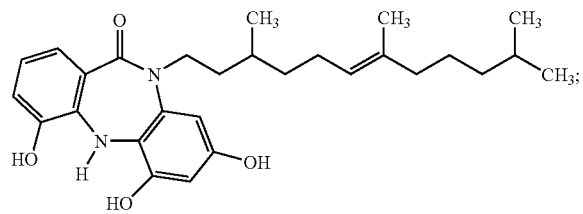
FORMULA XLV
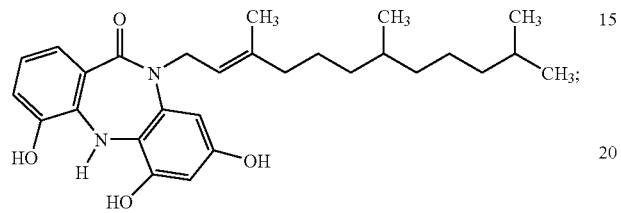
FORMULA XLVI
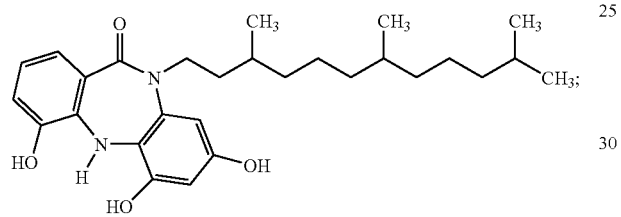
FORMULA XLVII
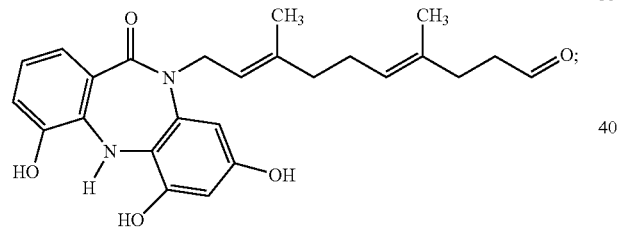
FORMULA XLVIII
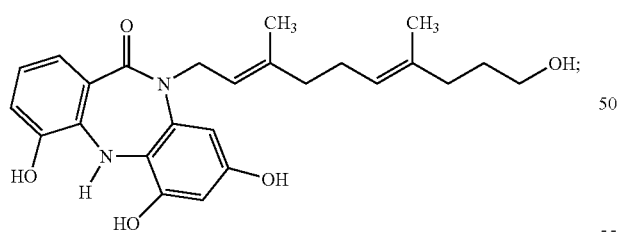
FORMULA XLIX
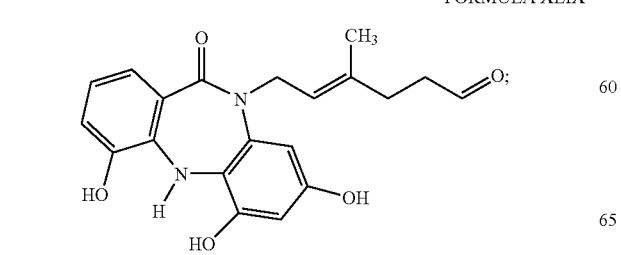
FORMULA L
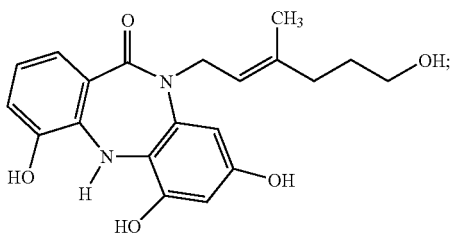
FORMULA LI
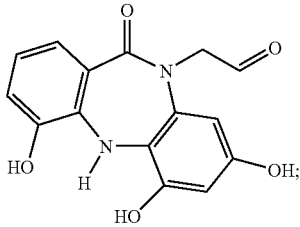
FORMULA LII
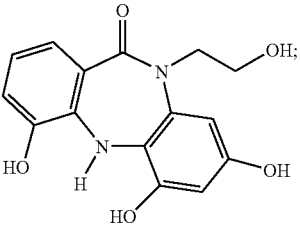
FORMULA LIII
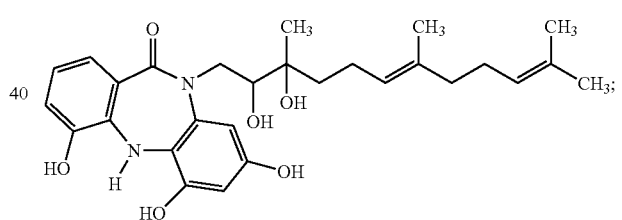
FORMULA LIV
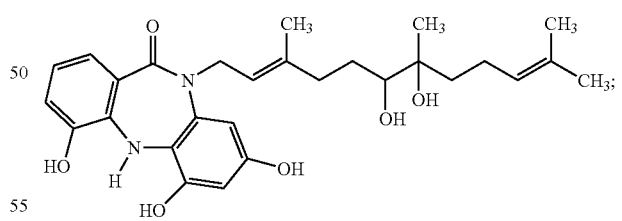
FORMULA LV
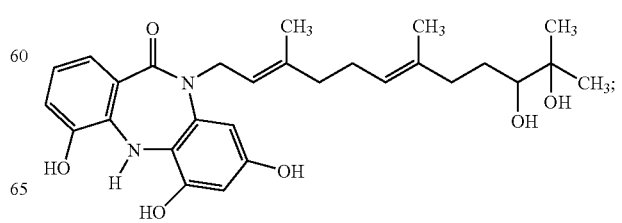

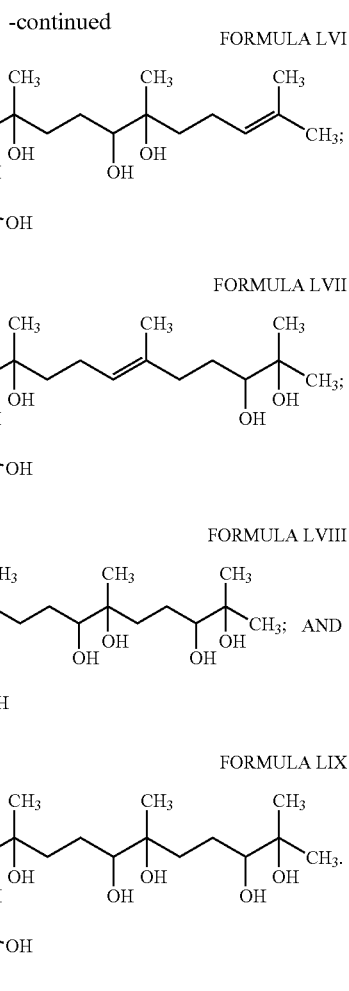

Certain embodiments expressly exclude one or more of the compounds of Formula I. In one embodiment, the compound of Formula II is excluded.

The compounds of this invention may be formulated into pharmaceutical compositions comprised of compounds of Formula I in combination with a pharmaceutical acceptable carrier, as discussed in Section V below.

III. Method of Making a Farnesyl Dibenzodiazepinone by Fermentation

In one embodiment, ECO-04601 is obtained by cultivating a novel strain of *Micromonospora*, namely *Micromonospora* sp. strain 046-ECO11. Strain 046-ECO11 was deposited on Mar. 7, 2003, with the International Depositary Authority of Canada (IDAC), Bureau of Microbiology, Health Canada, 1015 Arlington Street, Winnipeg, Manitoba, Canada R3E 3R2, under Accession No. 070303-01. The deposit of the strain was made under the terms of the Budapest Treaty on the International Recognition of the Deposit of Microorganisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement, such as that required under 35 U.S.C. §112.

It is to be understood that the present invention is not limited to use of the particular strain 046-ECO11. Rather, the present invention contemplates the use of other ECO-04601 producing organisms, such as mutants or variants of 046-ECO11 that can be derived from this organism by known means such as X-ray irradiation, ultraviolet irradiation, treatment with nitrogen mustard, phage exposure, antibiotic selection and the like; or through the use of recombinant genetic engineering techniques, as described in Section IV below.

The farnesyl dibenzodiazepinone compounds of the present invention may be biosynthesized by various microorganisms. Microorganisms that may synthesize the compounds of the present invention include but are not limited to bacteria of the order Actinomycetales, also referred to as actinomycetes. Non-limiting examples of members belonging to the genera of Actinomycetes include *Nocardia, Geodermatophilus, Actinoplanes, Micromonospora, Nocardioides, Saccharothrix, Amycolatopsis, Kutzneria, Saccharomonospora, Saccharopolyspora, Kitasatospora, Streptomyces, Microbispora, Streptosporangium*, and *Actinomadura*. The taxonomy of actinomycetes is complex and reference is made to Goodfellow, *Supragenenic Classification of Actinomycetes* (1989); *Bergey's Manual of Systematic Bacteriology*, Vol. 4 (Williams and Wilkins, Baltimore, pp. 2322-2339); and to Embley and Stackebrandt, "The molecular phylogeny and systematics of the actinomycetes," *Annu. Rev. Microbiol.* (1994) 48:257-289, each of which is hereby incorporated by reference in its entirety, for genera that may synthesize the compounds of the invention.

Farnesyl dibenzodiazepinone-producing microorganisms are cultivated in culture medium containing known nutritional sources for actinomycetes. Such media having assimilable sources of carbon, nitrogen, plus optional inorganic salts and other known growth factors at a pH of about 6 to about 9. Suitable media include, without limitation, the growth media provided in Table 16. Microorganisms are cultivated at incubation temperatures of about 18° C. to about 40° C. for about 3 to about 40 days.

The culture media inoculated with the farnesyl dibenzodiazepinone-producing microorganisms may be aerated by incubating the inoculated culture media with agitation, for example, shaking on a rotary shaker, or a shaking water bath. Aeration may also be achieved by the injection of air, oxygen or an appropriate gaseous mixture to the inoculated culture media during incubation. Following cultivation, the farnesyl dibenzodiazepinone compounds can be extracted and isolated from the cultivated culture media by techniques known to a skilled person in the art and/or disclosed herein, including for example centrifugation, chromatography, adsorption, filtration. For example, the cultivated culture media can be mixed with a suitable organic solvent such as n-butanol, n-butyl acetate or 4-methyl-2-pentanone, the organic layer can be separated for example, by centrifugation followed by the removal of the solvent, by evaporation to dryness or by evaporation to dryness under vacuum. The resulting residue can optionally be reconstituted with for example water, ethanol, ethyl acetate, methanol or a mixture thereof, and re-extracted with a suitable organic solvent such as hexane, carbon tetrachloride, methylene chloride or a mixture thereof. Following removal of the solvent, the compounds may be further purified by the use of standard techniques, such as chromatography.

The farnesyl dibenzodiapezinones biosynthesized by microorganisms may optionally be subjected to random and/ or directed chemical modifications to form compounds that are derivatives or structural analogs. Such derivatives or structural analogs having similar functional activities are within the scope of the present invention. Farnesyl dibenzodiapezinone compounds may optionally be modified using methods known in the art and described herein.

IV. Method of Making a Farnesyl Dibenzodiazepinone by Recombinant Technology In another embodiment, the present invention relates to nucleic acid molecules that encode proteins useful in the production of farnesyl benzodiazepinones. Specifically, the present invention provides recombinant DNA vectors and nucleic acid molecules that encode all or part of the biosynthetic locus in strain 046-ECO11, which directs the production of ECO-04601, and is referred to herein as "046D." The invention further includes genetic modification of 046D using conventional genetic recombinant techniques, such as mutagenesis, inactivation, or replacement of nucleic acids, to produce chemical variants of ECO-04601.

The invention thus provides a method for making a farnesyl benzodiazepinone compound using a transformed host cell comprising a recombinant DNA vector that encodes one or more of the polypeptides of the present invention, and culturing the host cell under conditions such that farnesyl benzodiazepinone is produced. The host cell is a prokaryote. In one embodiment, the host cell is an actinomycete. In another embodiment, the host cell is a *Streptomyces* host cell.

The invention provides recombinant nucleic acids that produce a variety of farnesyl dibenzodiazepinone compounds that cannot be readily synthesized by chemical methodology alone. The invention allows direct manipulation of 046D biosynthetic locus via genetic engineering of the enzymes involved in the biosynthesis of a farnesyl benzodiazepinone according to the invention. The 046A biosynthetic locus is described in Example 11.

Recombinant DNA Vectors

Vectors of the invention typically comprise the DNA of a transmissible agent, into which foreign DNA is inserted. A common way to insert one segment of DNA into another segment of DNA involves the use of specific enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, a nucleic acid molecule that encodes a protein useful in the production of a farnesyl benzodiazepinone is inserted at one or more restriction sites of the vector DNA, and then is carried by the vector into a prokaryote e.g. actinomycte, by transformation (see below). A segment or sequence of DNA having inserted or added DNA, such as an expression vector, can also be called a "DNA construct". A common type of vector is a "plasmid" which generally is a self-contained molecule of double-stranded DNA, usually of bacterial origin, that can readily accept additional (foreign) DNA and which can be readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. In one embodiment of the invention, the coding DNA encodes for polypeptides of SEQ ID NOs. 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 or 89 that are required for the biosynthesis of a farnesyl benzodiazepinone.

Promoter DNA of a recombinant vector is a DNA sequence that initiates, regulates, or otherwise mediates or controls the expression of the coding DNA. Promoter DNA and coding may be from the same or different organisms. Recombinant cloning vectors will often include one or more replication systems for cloning or expression, one or more markers for selection in the host, e.g. antibiotic resistance, and one or more expression cassettes. Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

Examples of promoters that function in actinomycetes, e.g. *Streptomyces*, are taught in U.S. Pat. Nos. 5,830,695 and 5,466,590. Another example of a transcription promoter useful in Actinomycetes expression vectors is tipA, a promoter inducible by the antibiotic thiostrepton [c.f. Murakami, T., et al., (1989), J. Bacteriol., 171, 1459].

Transformation of Actinomycetes

A suitable transformation method for use with an actinomycete comprises forming the actinomycete culture into spheroplasts using lysozyme. A buffer solution containing recombinant DNA vectors and polyethylene glycol is then added, in order to introduce the vector into the host cells, by using either of the methods of Thompson or Keiser [c. f. Thompson, C. J., et al., (1982), J. Bacteriol., 151, 668-677 or Keiser, T. et al. (2000), "Practical *Streptomyces* Genetics", The John Innes Foundation, Norwich], for example. A thiostrepton-resistance gene is frequently used as a selective marker in the transformation plasmid [c.f. Hopwood, D. A., et al., (1987), "Methods in Enzymology" 153, 116, Academic Press, New York], but the present invention is not limited thereto. Additional methods for the transformation of actinomycetes are taught in U.S. Pat. No. 5,393,665.

Assay for Farnesyl Dibenzodiazepinone or Biosynthetic Intermediates

Actinomycetes defective in farnesyl dibenzodiazepinone biosynthesis are transformed with one or more expression vectors encoding one or more proteins in the farnesyl benzodiazepinone biosynthetic pathway, thus restoring farnesyl benzodiazepinone biosynthesis by genetic complementation of the specific defect.

The presence or absence of farnesyl dibenzodiazepinone or intermediates in the biosynthetic pathway (see FIGS. 13, 14 and 15) in a recombinant actinomycete can be determined using methodologies that are well known to persons of skill in the art. For example, ethyl acetate extracts of fermentation media used for the culture of a recombinant actinomycete are processed as described in Example 2 and fractions containing farnesyl dibenzodiazepinone or intermediates detected by TLC on commercial Kieselgel 60F$_{254}$ plates. Farnesyl dibenzodiazepinone and intermediate compounds are visualized by inspection of dried plates under UV light or by spraying the plates with a spray containing vanillin (0.75%) and concentrated sulfuric acid (1.5%, v/v) in ethanol and subsequently heating the plate. The exact identity of the compounds separated by TLC is then determined using gas chromatography-mass spectroscopy. Methods of mass spectroscopy are taught in the published U.S. patent application No. US2003/0052268.

Mutagenesis

The invention allows direct manipulation of 046D biosynthetic locus via genetic engineering of the enzymes involved in the biosynthesis of a farnesyl benzodiazepinone according to the invention.

A number of methods are known in the art that permit the random as well as targeted mutation of the DNA sequences of the invention (see for example, Ausubel et. al. Short Protocols in Molecular Biology (1995) 3rd Ed. John Wiley & Sons, Inc.). In addition, there are a number of commercially available kits for site-directed mutagenesis, including both conventional and PCR-based methods. Examples include the EXSITE™ PCR-Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

In addition the nucleotides of the invention may be generated by insertional mutation or truncation (N-terminal, internal or C-terminal) according to methodology known to a person skilled in the art.

Older methods of site-directed mutagenesis known in the art rely on sub-cloning of the sequence to be mutated into a vector, such as an M13 bacteriophage vector, that allows the isolation of single-stranded DNA template. In these methods, one anneals a mutagenic primer (i.e., a primer capable of annealing to the site to be mutated but bearing one or more mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease Dpn I (recognition target sequence: 5-Gm6ATC-3, where the A residue is methylated) is used to select against parental DNA, since most common strains of $E.$ $coli$ Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

A non-limiting example for the isolation of mutant polynucleotides is described in detail as follows:

Plasmid template DNA (approximately 0.5 pmole) is added to a PCR cocktail containing: 1×mutagenesis buffer (20 mM Tris HCl, pH 7.5; 8 mM MgCl2; 40□g/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 □M each dNTP, 2.5 U Taq DNA polymerase, and 2.5 U of Taq Extender (Available from Stratagene; See Nielson et al. (1994) Strategies 7: 27, and U.S. Pat. No. 5,556,772). Primers can be prepared using the triester method of Matteucci et al., 1981, J. Am. Chem. Soc. 103:3185-3191, incorporated herein by reference. Alternatively automated synthesis may be preferred, for example, on a Biosearch 8700 DNA Synthesizer using cyanoethyl phosphoramidite chemistry.

The PCR cycling is performed as follows: 1 cycle of 4 min at 94oC, 2 min at 50° C. and 2 min at 72oC; followed by 5-10 cycles of 1 min at 94oC, 2 min at 54oC and 1 min at 72oC. The parental template DNA and the linear, PCR-generated DNA incorporating the mutagenic primer are treated with Dpnl (10 U) and Pfu DNA polymerase (2.5 U). This results in the Dpnl digestion of the in vivo methylated parental template and hybrid DNA and the removal, by Pfu DNA polymerase, of the non-template-directed Taq DNA polymerase-extended base(s) on the linear PCR product. The reaction is incubated at 37oC for 30 min and then transferred to 72oC for an additional 30 min. Mutagenesis buffer (115 ul of 1×) containing 0.5 mM ATP is added to the Dpnl-digested, Pfu DNA polymerase-polished PCR products. The solution is mixed and 10 ul are removed to a new microfuge tube and T4 DNA ligase (2-4 U) is added. The ligation is incubated for greater than 60 min at 37oC. Finally, the treated solution is transformed into competent $E. coli$ according to standard methods.

Methods of random mutagenesis, which will result in a panel of mutants bearing one or more randomly situated mutations, exist in the art. Such a panel of mutants may then be screened for those exhibiting reduced uracil detection activity relative to the wild-type polymerase (e.g., by measuring the incorporation of 10 nmoles of dNTPs into polymeric form in 30 minutes in the presence of 200□M dUTP and at the optimal temperature for a given DNA polymerase). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Genes for desired mutant polypeptides generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

V. Genes and Proteins for the Production of ECO-04601

As discussed in more detail below, the isolated, purified or enriched nucleic acids of one of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 may be used to prepare one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88, respectively, or fragments comprising at least 50, 75, 100, 200, 300, 500 or more consecutive amino acids of one of the polypeptides of SEQ ID NO: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88.

Accordingly, another aspect of the present invention is an isolated, purified or enriched nucleic acid which encodes one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200, 300 or more consecutive amino acids of one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88. The coding sequences of these nucleic acids may be identical to one of the coding sequences of one of the nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 or a fragment thereof, or may be different coding sequences which encode one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200, 300 consecutive amino acids of one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 as a result of the redundancy or degeneracy of the genetic code. The genetic code is well known to those of skill in the art and can be obtained, for example, from Stryer, *Biochemistry*, 3$^{rd}$ edition, W. H. Freeman & Co., New York.

The isolated, purified or enriched nucleic acid which encodes one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 may include, but is not limited to: (1) only the coding sequences of one of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89; (2) the coding sequences of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 and additional coding sequences, such as leader sequences or proprotein; and (3) the coding sequences of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 and non-coding sequences, such as non-coding sequences 5' and/or 3' of the coding sequence. Thus, as used herein, the term "polynucleotide encoding a polypeptide" encompasses a polynucleotide that includes only coding sequence for the polypeptide as well as a polynucleotide that includes additional coding and/or non-coding sequence.

The invention relates to polynucleotides based on SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 but having polynucleotide changes that are "silent", for example changes which do not alter the amino acid sequence encoded by the polynucleotides of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89. The invention also relates to polynucleotides which have nucleotide changes which result in amino acid substitutions, additions, deletions, fusions and truncations of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88. Such nucleotide changes may be introduced using techniques such as site directed mutagenesis, random chemical mutagenesis, exonuclease III deletion, and other recombinant DNA techniques.

The isolated, purified or enriched nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89, the sequences complementary thereto, or a fragment comprising at least 100, 150, 200, 300, 400 or more consecutive bases of one of the sequence of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89, or the sequences complementary thereto may be used as probes to identify and isolate DNAs encoding the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 respectively. In such procedures, a genomic DNA library is constructed from a sample microorganism or a sample containing a microorganism capable of producing a farnesyl dibenzodiazepinone. The genomic DNA library is then contacted with a probe comprising a coding sequence or a fragment of the coding sequence, encoding one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88, or a fragment thereof under conditions which permit the probe to specifically hybridize to sequences complementary thereto. In a preferred embodiment, the probe is an oligonucleotide of about 10 to about 30 nucleotides in length designed based on a nucleic acid of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89. Genomic DNA clones which hybridize to the probe are then detected and isolated. Procedures for preparing and identifying DNA clones of interest are disclosed in Ausubel et al., Current Protocols in Molecular Biology, John Wiley 503 Sons, Inc. 1997; and Sambrook et al., Molecular Cloning: A Laboratory Manual 2d Ed., Cold Spring Harbor Laboratory Press, 1989. In another embodiment, the probe is a restriction fragment or a PCR amplified nucleic acid derived from SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89.

The isolated, purified or enriched nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89, the sequences complementary thereto, or a fragment comprising at least 10, 15, 20, 25, 30, 35, 40, 50, 75, 100, 150, 200, 300, 400 or 500 consecutive bases of one of the sequences of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 or the sequences complementary thereto may be used as probes to identify and isolate related nucleic acids. In some embodiments, the related nucleic acids may be genomic DNAs (or cDNAs) from potential farnesyl dibenzodiazepinone producers. In such procedures, a nucleic acid sample containing nucleic acids from a potential farnesyl dibenzodiazepinone producer is contacted with the probe under conditions that permit the probe to specifically hybridize to related sequences. The nucleic acid sample may be a genomic DNA (or cDNA) library from the potential farnesyl dibenzodiazepinone-producer. Hybridization of the probe to nucleic acids is then detected using any of the methods described above.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH$_2$PO$_4$, pH 7.0, 5.0 mM Na$_2$EDTA, 0.5% SDS, 10×Denhardt's, and 0.5 mg/ml polyriboadenylic acid. Approximately $2 \times 10^7$ cpm (specific activity $4$-$9 \times 10^8$ cpm/ug) of $^{32}$P end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM Na$_2$EDTA) containing 0.5% SDS, followed by a 30 minute wash in fresh 1×SET at Tm-10° C. for the oligonucleotide probe where Tm is the melting temperature. The membrane is then exposed to autoradiographic film for detection of hybridization signals.

By varying the stringency of the hybridization conditions used to identify nucleic acids, such as genomic DNAs or cDNAs, which hybridize to the detectable probe, nucleic acids having different levels of homology to the probe can be identified and isolated. Stringency may be varied by conducting the hybridization at varying temperatures below the melting temperatures of the probes. The melting temperature of the probe may be calculated using the following formulas:

For oligonucleotide probes between 14 and 70 nucleotides in length the melting temperature (Tm) in degrees Celcius may be calculated using the formula: Tm=81.5+16.6(log [Na+])+0.41(fraction G+C)−(600/N) where N is the length of the oligonucleotide.

If the hybridization is carried out in a solution containing formamide, the melting temperature may be calculated using the equation Tm=81.5+16.6(log [Na+])+0.41 (fraction G+C)−(0.63% formamide)−(600/N) where N is the length of the probe.

Prehybridization may be carried out in 6×SSC, 5×Denhardt's reagent, 0.5% SDS, 0.1 mg/ml denatured fragmented salmon sperm DNA or 6×SSC, 5×Denhardt's reagent, 0.5% SDS, 0.1 mg/ml denatured fragmented salmon sperm DNA, 50% formamide. The composition of the SSC and Denhardt's solutions are listed in Sambrook et al., supra.

Hybridization is conducted by adding the detectable probe to the hybridization solutions listed above. Where the probe comprises double stranded DNA, it is denatured by incubating at elevated temperatures and quickly cooling before addition to the hybridization solution. It may also be desirable to similarly denature single stranded probes to eliminate or diminish formation of secondary structures or oligomerization. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. Preferably, the hybridization is conducted in 6×SSC, for shorter probes. Preferably, the hybridization is conducted in 50% formamide containing solutions, for longer probes. All the foregoing hybridizations would be considered to be examples of hybridization performed under conditions of high stringency.

Following hybridization, the filter is washed for at least 15 minutes in 2×SSC, 0.1% SDS at room temperature or higher, depending on the desired stringency. The filter is then washed with 0.1×SSC, 0.5% SDS at room temperature (again) for 30 minutes to 1 hour. Nucleic acids which have hybridized to the probe are identified by conventional autoradiography and non-radioactive detection methods.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1 M. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate stringency" conditions above 25% formamide and "low stringency" conditions below 25% formamide. A specific example of "moderate stringency" hybridization conditions is when the above hybridization is conducted at 30% formamide. A specific example of "low stringency" hybridization conditions is when the above hybridization is conducted at 10% formamide. Nucleic acids which have hybridized to the probe are identified by conventional autoradiography and non-radioactive detection methods.

The preceding methods may be used to isolate nucleic acids having at least 97%, at least 95%, at least 90%, at least 85%, at least 80%, or at least 70% sequence identity to a nucleic acid sequence selected from the group consisting of the sequences of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89. The isolated nucleic acid may have a coding sequence that is a naturally occurring allelic variant of one of the coding sequences described herein. Such allelic variant may have a substitution, deletion or addition of one or more nucleotides when compared to the nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89, or the sequences complementary thereto.

Additionally, the above procedures may be used to isolate nucleic acids which encode polypeptides having at least 99%, at least 95%, at least 90%, at least 85%, at least 80%, or at least 70% identity to a polypeptide having the sequence of one of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200, 300 consecutive amino acids thereof.

Another aspect of the present invention is an isolated or purified polypeptide comprising the sequence of one of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200 or 300 consecutive amino acids thereof. As discussed herein, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for modulating expression levels, an origin of replication and a selectable marker.

Promoters suitable for expressing the polypeptide or fragment thereof in bacteria include the *E. coli* lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the α factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donors and acceptor sites, transcriptional termination sequences, and 5' flanking nontranscribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors preferably contain one or more selectable marker genes to permit selection of host cells containing the vector. Examples of selectable markers that may be used include genes encoding dihydrofolate reductase or genes conferring neomycin resistance for eukaryotic cell culture, genes conferring tetracycline or ampicillin resistance in *E. coli*, and the *S. cerevisiae* TRP1 gene.

The appropriate DNA sequence may be inserted into the vector by a variety of procedures. In general, the DNA sequence is ligated to the desired position in the vector following digestion of the insert and the vector with appropriate restriction endonucleases. Alternatively, appropriate restriction enzyme sites can be engineered into a DNA sequence by PCR. A variety of cloning techniques are disclosed in Ausbel et al. Current Protocols in Molecular Biology, John Wiley 503 Sons, Inc. 1997 and Sambrook et al., Molecular Cloning: A Laboratory Manual 2d Ed., Cold Spring Harbour Laboratory Press, 1989. Such procedures and others are deemed to be within the scope of those skilled in the art.

The vector may be, for example, in the form of a plasmid, a viral particle, or a phage. Other vectors include derivatives of chromosomal, nonchromosomal and synthetic DNA sequences, viruses, bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook et al., Molecular Cloning: A Laboratory Manual, Second Edition, Cold Spring Harbor, N.Y., (1989).

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), pGEM1 (Promega Biotec, Madison, Wis., USA) pQE70, pQE60, pQE-9 (Qiagen), pD10, phiX174, pBluescript™ II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and stable in the host cell.

The host cell may be any of the host cells familiar to those skilled in the art, including prokaryotic cells or eukaryotic cells. As representative examples of appropriate hosts, there may be mentioned: bacteria cells, such as *E. coli, Streptomyces lividans, Streptomyces griseofuscus, Streptomyces ambofaciens, Bacillus subtilis, Salmonella typhimurium* and various species within the genera *Pseudomonas, Streptomyces, Bacillus,* and *Staphylococcus,* fungal cells, such as yeast, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including electroporation transformation, transfection, transduction, viral infection, gene guns, or Ti-mediated gene transfer. Where appropriate, the engineered host cells can be cultured in conventional nutrient media modified as appropriate for activating promoters, selecting transformants or amplifying the genes of the present invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175 (1981)), and other cell lines capable of expressing proteins from a compatible vector, such as the C127, 3T3, CHO, HeLa and BHK cell lines. The constructs in host cells can be used in a conventional manner to produce the gene product encoded by the recombinant sequence. Polypeptides of the invention may or may not also include an initial methionine amino acid residue.

Alternatively, the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200 or 300 consecutive amino acids thereof can be synthetically produced by conventional peptide synthesizers. In other embodiments, fragments or portions of the polynucleotides may be employed for producing the corresponding full-length polypeptide by peptide synthesis; therefore, the fragments may be employed as intermediates for producing the full-length polypeptides.

Cell-free translation systems can also be employed to produce one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200 or 300 consecutive amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The present invention also relates to variants of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200 or 300 consecutive amino acids thereof. The term "variant" includes derivatives or analogs of these polypeptides. In particular, the variants may differ in amino acid sequence from the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids that encode polypeptides having characteristics which enhance their value in industrial or laboratory applications. In such procedures, a large number of variant sequences having one or more nucleotide differences with respect to the sequence obtained from the natural isolate are generated and characterized. Preferably, these nucleotide differences result in amino acid changes with respect to the polypeptides encoded by the nucleic acids from the natural isolates.

The variants of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 may be variants in which one or more of the amino acid residues of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue.

Other variants are those in which one or more of the amino acid residues of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 include a substituent group. Still other variants are those in which the polypeptide is associated with another compound, such as a compound to increase the half-life of the polypeptide (for example, polyethylene glycol). Additional variants are those in which additional amino acids are fused to the polypeptide, such as leader sequence, a secretory sequence, a proprotein sequence or a sequence that facilitates purification, enrichment, or stabilization of the polypeptide.

In some embodiments, the fragments, derivatives and analogs retain the same biological function or activity as the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88. In other embodiments, the fragment, derivative or analogue includes a fused heterologous sequence that facilitates purification, enrichment, detection, stabilization or secretion of the polypeptide that can be enzymatically cleaved, in whole or in part, away from the fragment, derivative or analogue.

Another aspect of the present invention are polypeptides or fragments thereof which have at least 70%, at least 80%, at least 85%, at least 90%, or more than 95% identity to one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or a fragment comprising at least 50, 75, 100, 150, 200 or 300 consecutive amino acids thereof. It will be appreciated that amino acid "substantially identity" includes conservative substitutions such as those described above.

The polypeptides or fragments having homology to one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or a fragment comprising at least 50, 75, 100, 150, 200 or 300 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or a fragment comprising at least 5, 10, 15, 20, 25, 30, 35, 40, 50, 75, 100, or 150 consecutive amino acids thereof.

The polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments, derivatives or analogs thereof comprising at least 40, 50, 75, 100, 150, 200 or 300 consecutive amino acids thereof invention may be used in a variety of applications. For example, the polypeptides or fragments, derivatives or analogs thereof may be used to catalyze biochemical reactions as described elsewhere in the specification.

(a)

VI. Pharmaceutical Compositions Comprising Farnesyl Dibenzodiazepinones

In another embodiment, the invention relates to a pharmaceutical composition comprising a farnesyl dibenzodiazepinone, as described in the preceding section, and a pharmaceutically acceptable carrier, as described below. The pharmaceutical composition comprising the farnesyl dibenzodiazepinone is useful for treating a variety of diseases and disorders, including cancer, inflammation and bacterial infections.

The compounds of the present invention, or pharmaceutically acceptable salts thereof, can be formulated for oral, intravenous, intramuscular, subcutaneous, topical or parenteral administration for the therapeutic or prophylactic treatment of diseases, particularly bacterial infections, acute and chronic inflammation and cancer. For oral or parental administration, compounds of the present invention can be mixed with conventional pharmaceutical carriers and excipients and used in the form of tablets, capsules, elixirs, suspensions, syrups, wafers and the like. The compositions comprising a compound of this present invention will contain from about 0.1% to about 99.9%, about 1% to about 98%, about 5% to about 95%, about 10% to about 80% or about 15% to about 60% by weight of the active compound.

The pharmaceutical preparations disclosed herein are prepared in accordance with standard procedures and are administered at dosages that are selected to reduce, prevent, or eliminate bacterial infection, cancer or inflammation. (See, e.g., *Remington's Pharmaceutical Sciences*, Mack Publishing Company, Easton, Pa.; and Goodman and Gilman, *Pharmaceutical Basis of Therapeutics*, Pergamon Press, New York, N.Y., the contents of which are incorporated herein by reference, for a general description of the methods for administering various antimicrobial agents for human therapy). The compositions of the present invention can be delivered using controlled (e.g., capsules) or sustained release delivery systems (e.g., bioerodable matrices). Exemplary delayed release delivery systems for drug delivery that are suitable for administration of the compositions of the invention (preferably of Formula I) are described in U.S. Pat. Nos. 4,452,775 (issued to Kent), 5,239,660 (issued to Leonard), 3,854,480 (issued to Zaffaroni).

The pharmaceutically acceptable compositions of the present invention comprise one or more compounds of the present invention in association with one or more non-toxic, pharmaceutically acceptable carriers and/or diluents and/or adjuvants and/or excipients, collectively referred to herein as "carrier" materials, and if desired other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain crosarmellose sodium, microcrystalline cellulose, sodium starch glycolate and alginic acid.

Tablet binders that can be included are acacia, methylcellulose, sodium carboxymethylcellulose, polyvinylpyrrolidone (Providone), hydroxypropyl methylcellulose, sucrose, starch and ethylcellulose.

Lubricants that can be used include magnesium stearate or other metallic stearates, stearic acid, silicon fluid, talc, waxes, oils and colloidal silica.

Flavouring agents such as peppermint, oil of wintergreen, cherry flavouring or the like can also be used. It may also be desirable to add a coloring agent to make the dosage form more aesthetic in appearance or to help identify the product comprising a compound of the present invention.

For oral use, solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically -effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica or talc: disintegrants, for example, potato starch, flavoring or coloring agents, or acceptable wetting agents. Oral liquid preparations generally are in the form of aqueous or oily solutions, suspensions, emulsions, syrups or elixirs and may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (iv) use, compounds of the present invention can be dissolved or suspended in any of the commonly used intravenous fluids and administered by infusion. Intravenous fluids include, without limitation, physiological saline or Ringer's solution.

Formulations for parental administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For intramuscular preparations, a sterile formulation of compounds of the present invention or suitable soluble salts forming the compound, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For topical use the compounds of present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compound of the present invention can be in powder form for reconstitution in the appropriate pharmaceutically acceptable carrier at the time of delivery. In another embodiment, the unit dosage form of the compound can be a solution of the compound or a salt thereof in a suitable diluent in sterile, hermetically sealed ampoules.

The amount of the compound of the present invention in a unit dosage comprises a therapeutically-effective amount of at least one active compound of the present invention which may vary depending on the recipient subject, route and frequency of administration. A recipient subject refers to a plant, a cell culture or an animal such as an ovine or a mammal including a human.

According to this aspect of the present invention, the novel compositions disclosed herein are placed in a pharmaceutically acceptable carrier and are delivered to a recipient subject (including a human subject) in accordance with known methods of drug delivery. In general, the methods of the invention for delivering the compositions of the invention in vivo utilize art-recognized protocols for delivering the agent with the only substantial procedural modification being the substitution of the compounds of the present invention for the drugs in the art-recognized protocols.

Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the present invention for the agents used in the art-recognized protocols.

The compounds of the present invention provide a method for treating bacterial infections, pre-cancerous or cancerous conditions, and acute or chronic inflammatory disease. As used herein, the term "unit dosage" refers to a quantity of a therapeutically effective amount of a compound of the present invention that elicits a desired therapeutic response. As used herein, the phrase "therapeutically effective amount" means an amount of a compound of the present invention that prevents the onset, alleviates the symptoms, or stops the progression of a bacterial infection, inflammatory condition, or pre-cancerous or cancerous condition. The term "treating" is defined as administering, to a subject, a therapeutically effective amount of at least one compound of the present invention, both to prevent the occurrence of a bacterial infection, inflammation or pre-cancer or cancer condition, or to control or eliminate a bacterial infection, inflammation or pre-cancer or cancer condition. The term "desired therapeutic response" refers to treating a recipient subject with a compound of the present invention such that a bacterial or inflammatory condition or pre-cancer or cancer condition is reversed, arrested or prevented in a recipient subject.

The compounds of the present invention can be administered as a single daily dose or in multiple doses per day. The treatment regime may require administration over extended periods of time, e.g., for several days or for from two to four weeks. The amount per administered dose or the total amount administered will depend on such factors as the nature and severity of the disease condition, the age and general health of the recipient subject, the tolerance of the recipient subject to the compound and the type of the bacterial infection, inflammatory disorder, or type of cancer.

A compound according to this invention may also be administered in the diet or feed of a patient or animal. The diet for animals can be normal foodstuffs to which the compound can be added or it can be added to a premix.

The compounds of the present invention may be taken in combination, together or separately with any known clinically approved antibiotic, inflammation or anti-cancer agent to treat a recipient subject in need of such treatment.

VII. Method of Inhibiting Tumor Growth

In another embodiment, the present invention relates to a method of inhibiting tumor growth. Compounds as described herein can possess antitumor activity. The compounds are effective against mammalian tumor cells such as leukemia cells, melanoma cells, breast carcinoma cells, lung carcinoma cells, pancreatic carcinoma cells, ovarian carcinoma cells, renal carcinoma cells, colon carcinoma cells prostate carcinoma cells and glioma cells. The antitumor method of the invention results in inhibition of tumor cells. The term "inhibition", when used in conjunction with the antitumor method refers to suppression, killing, stasis, or destruction of tumor cells. The antitumor method preferably results in prevention, reduction or elimination of invasive activity and related metastasis of tumor cells. The term "effective amount" when used in conjunction with the antitumor cell method refers to the amount of the compound sufficient to result in the inhibition of mammalian tumor cells.

The inhibition of mammalian tumor growth according to this method can be monitored in several ways. First, tumor cells grown in vitro can be treated with the compound and monitored for growth or death relative to the same cells cultured in the absence of the compound. A cessation of growth or a slowing of the growth rate (i.e., the doubling rate), e.g., by 10% or more, is indicative of tumor cell inhibition. Alternatively, tumor cell inhibition can be monitored by administering the compound to an animal model of the tumor of interest. Examples of experimental animal tumor models are known in the art and described in the examples herein. A cessation of tumor growth (i.e., no further increase in size) or a reduction in tumor size (i.e., tumor volume) or cell number (e.g., at least a 10% decrease in either) in animals treated with a compound as described herein relative to tumors in control animals not treated with the compound is indicative of tumor growth inhibition.

To monitor the efficacy of tumor treatment in a human, tumor size or tumor cell titer is measured before and after initiation of the treatment, and treatment is considered effective if either the tumor size or titer ceases further growth, or if the tumor is reduced in size or titer, e.g., by at least 10% or more (e.g., 20%, 30%, 40%, 50%, 60%, 70%, 80%, 90% or even 100%, that is, the absence of the tumor). Methods of determining the size or cell titer of a tumor in vivo vary with the type of tumor, and include, for example, various imaging techniques well known to those in the medical imaging or oncology fields (MRI, CAT, PET, etc.), as well as histological techniques and flow cytometry.

For the antitumor method of the invention, a typical effective dose of the compounds given orally or parenterally would be from about 5 to about 100 mg/kg of body weight of the subject with a daily dose ranging from about 15 to about 300 mg/kg of body weight of the subject.

VIII. Method of Inhibiting Lipoxygenase

In another embodiment, the present invention also provides for a method of treating diseased states, in particular inflammation, caused by the 5-lipoxygenase system and/or by the synthesis of the Leukotrienes $C_4$, $D_4$, $E_4$ and $F_4$ as well as Leukotriene $B_4$ in mammals, especially in human subjects. This method comprises administering to a subject an effective amount of ECO-04601. Compound ECO-04601 may be used alone or in combination with other anti-inflammatory compounds to treat or prevent disease states related to inflammation including pulmonary conditions, inflammation, cardiovascular conditions, central nervous system conditions or skin conditions. More specific diseases include gastritis; erosive esophagitis; inflammatory bowel disease; ethanol-induced hemorrhagic erosions; hepatic ischemia; ischemic neuronal injury; noxious agent induced damage or necrosis of hepatic, pancreatic, renal, neuronal or myocardial tissue; liver parenchymal damage caused by hepatoxic agents such as $CCl_4$ and D-galactosamine; ischemic renal failure; disease-induced hepatic damage; trauma- or stress-induced cell damage; asthma; multiple sclerosis; ischemic reperfusion; edema; rheumatoid arthritis; viral encephalitis; bacterial pneumonia; neurodegeneration; Alzheimer's disease and glycerol-induced renal failure.

For the method of the invention related to the 5-lipoxygenase system and/or the biosynthesis of Leukotrienes, a typical effective unit dose of ECO-04601 given orally or parenterally would be from about 5 to about 100 mg/kg of body weight of the subject with a daily dose ranging from about 15 to about 300 mg/kg of body weight of the subject.

The inhibition of lipoxygenase enzymes is monitored using methods well known in the art and as described in the examples herein. A decrease in enzyme activity by at least 10%, relative to the activity in the absence of a compound as described herein is indicative of effective inhibition of lipoxygenase activity.

Farnesyl dibenzodiazepinone compounds useful according to the invention can be used to reduce or prevent inflammation. Among the hallmarks of local acute inflammation are heat, redness, swelling, pain and loss of function. These changes are induced largely by changes in vascular flow and caliber, changes in vascular permeability and leukocyte exudation (Robbins et al., "Pathologic Basis of Disease", $6^{th}$ Ed., W.B. Saunders Co., Philadelphia, Pa.). Anti-inflammatory therapy performed using compounds useful according to the invention can be monitored for success by tracking any of these changes. For example, a decrease in swelling (e.g., at least 10% decrease following treatment) or reported pain (e.g., a sustained decrease of 1 point or more on a 1-10 scale reported by the patient, with 10 being the worst pain experienced in association with this disorder prior to treatment, and 0 being no pain) can be used to indicate successful treatment.

Other measurable hallmarks of inflammation include leukocyte infiltration and inflammatory cytokine levels. These hallmarks can be monitored by biopsy of the affected tissue. A decrease of 10% or more in leukocyte infiltration in fixed, stained tissue relative to infiltration in similar tissue prior to treatment can be used to indicate successful treatment, as can a decrease of 10% or more in the level of any given inflammatory cytokine, relative to the level before treatment. Those skilled in the art can readily assay for inflammatory cytokine levels in tissue, blood, or other fluid samples. Alternatively, the level of systemic indicators of inflammation such as C reactive protein levels and erythrocyte sedimentation rate can be monitored. Each of these has established normal ranges in medicine, and treatment is considered successful if one or more of such indicators goes from outside the normal range to inside the normal range after the initiation of treatment.

IX. Method of Inhibiting Bacterial Growth

In another embodiment, the present invention relates to a method for treating bacterial infection in a mammalian subject in need thereof, comprising the step of administering to the mammal a therapeutically effective amount of compound ECO-04601, a compound as described herein, or a pharmaceutically acceptable derivative or prodrug thereof.

According to another embodiment, the invention provides a method of decreasing bacterial quantity in a biological sample. This method comprises the step of contacting the biological sample with a compound ECO-04601, a compound as described herein, or a pharmaceutically acceptable derivative or prodrug thereof. This method is effective if the number of bacteria decreases by at least 10%, and preferably more, e.g., 25%, 50%, 75% or even 100% after contacting the biological sample with compound ECO-04601, a compound as described herein, or a pharmaceutically acceptable derivative or prodrug thereof.

These pharmaceutical compositions effective to treat or prevent a bacterial infection which comprise ECO-04601, a compound as described herein, or a pharmaceutically acceptable derivative or prodrug thereof in an amount sufficient to measurably decrease bacterial quantity, and a pharmaceutically acceptable carrier, are another embodiment of the present invention. The term "measurably decrease bacterial quantity", as used herein means a measurable change in the number of bacteria between a sample containing the inhibitor and a sample not containing the inhibitor.

Agents which increase the susceptibility of bacterial organisms to antibiotics are known. For example, U.S. Pat. No. 5,523,288, U.S. Pat. No. 5,783,561 and U.S. Pat. No. 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. in Microbiological Reviews (1992) pp. 395-411, and the sensitization of gram-negative bacteria has been described by Tsubery, H., et al, in J. Med. Chem. (2000) pp. 3085-3092.

For the method of the invention related to treatment of subjects with a bacterial infection, a typical effective unit dose of ECO-04601, a compound described herein or a pharmaceutically acceptable derivative or prodrug thereof given orally or parenterally would be from about 5 to about 100 mg/kg of body weight of the subject with a daily dose ranging from about 15 to about 300 mg/kg of body weight of the subject.

Another preferred embodiment of this invention relates to a method, as described above, of treating a bacterial infection in a mammal in need thereof, but further comprising the step of administering to the mammal an agent which increases the susceptibility of bacterial organisms to antibiotics.

According to another preferred embodiment, the invention provides a method, as described above, of decreasing bacterial quantity in a biological sample, but further comprising the step of contacting the biological sample with an agent which increases the susceptibility of bacterial organisms to antibiotics.

Methods of decreasing bacterial quantity are effective if the number of bacteria decreases at least 10%, and preferably more, e.g., 25%, 50%, 75% or even 100% after contacting the biological sample with compound ECO-04601, a compound as described herein, or a pharmaceutically acceptable derivative or prodrug thereof.

The pharmaceutical compositions and methods of this invention will be useful generally for controlling bacterial infections in vivo. Examples of bacterial organisms that may be controlled by the compositions and methods of this invention include, but are not limited to the following organisms: *Streptococcus pneumoniae, Streptococcus pyrogenes, Enterococcus fecalis, Enterococcus faecium, Klebsiella pneumoniae, Enterobacterspp., Proteus* spp., *Pseudomonas aeruginosa, E. coli, Serratia marcesens, Staphylococcus aureus, Coagulase* negative *Staphylococcus, Haemophilus infuenzae, Bacillus anthracis, Mycoplasma pneumoniae*, and *Staphylococcus epidermidis*. The compositions and methods will therefore be useful for controlling, treating or reducing the advancement, severity or effects of nosocomial or non-nosocomial infections. Examples of nosocomial uses include, but are not limited to, urinary tract infections, pneumonia, surgical wound infections, bacteremia and therapy for febrile neutropenic patients. Examples of non-nosocomial uses include but are not limited to urinary tract infections, pneumonia, prostatitis, skin and soft tissue infections and intra-abdominal infections.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Unless otherwise indicated, all numbers expressing quantities of ingredients, properties such as molecular weight, reaction conditions, $IC_{50}$ and so forth used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Preparation of Production Culture

Unless otherwise noted, all reagents were purchased from Sigma Chemical Co. (St. Louis, Mo.), (Aldrich). *Micromonospora* spp. (deposit accession number IDAC 070303-01) was maintained on agar plates of ISP2 agar (Difco Laboratories, Detroit, Mich.). An inoculum for the production phase was prepared by transferring the surface growth of the *Micromonospora* spp. from the agar plates to 125-mL flasks containing 25 mL of sterile medium comprised of 24 g potato dextrin, 3 g beef extract, 5 g Bacto-casitone, 5 g glucose, 5 g yeast extract, and 4 g $CaCO_3$ made up to one liter with distilled water (pH 7.0). The culture was incubated at about 28° C. for approximately 60 hours on a rotary shaker set at 250 rpm. Following incubation, 10 mL of culture was transferred to a 2 L baffled flask containing 500 mL of sterile production medium containing 20 g/L potato dextrin, 20 g/L glycerol, 10 g/L Fish meal, 5 g/L Bacto-peptone, 2 g/L $CaCO_3$, and 2 g/L $(NH_4)_2SO_4$, pH 7.0. Fermentation broth was prepared by incubating the production culture at 28° C. in a rotary shaker set at 250 rpm for one week.

Example 2

Isolation 500 mL ethyl acetate was added to 500 mL of fermentation broth prepared as described in Example 1 above. The mixture was agitated for 30 minutes on an orbital shaker at 200 rpm to create an emulsion. The phases were separated by centrifugation and decantation. Between 4 and 5 g of anhydrous $MgSO_4$ was added to the organic phase, which was then filtered and the solvents removed in vacuo.

An ethyl acetate extract from 2 L fermentation was mixed with HP-20 resin (100 mL; Mitsubishi Casei Corp., Tokyo, Japan) in water (300 mL). Ethyl acetate was removed in vacuo, the resin was filtered on a Buchner funnel and the filtrate was discarded. The adsorbed HP-20 resin was then washed successively with 2×125 mL of 50% acetonitrile in water, 2×125 mL of 75% acetonitrile in water and 2×125 mL of acetonitrile.

Fractions containing the compound of Formula II were evaporated to dryness and 100 mg was digested in the 5 mL of the upper phase of a mixture prepared from chloroform, cyclohexane, methanol, and water in the ratios, by volume, of 5:2:10:5. The sample was subjected to centrifugal partition chromatography using a High Speed Countercurrent (HSCC) system (Kromaton Technologies, Angers, France) fitted with a 200 mL cartridge and prepacked with the upper phase of this two-phase system. The HSCC was run with the lower phase mobile and the compound of Formula II was eluted at approximately one-half column volume. Fractions were collected and the compound of Formula II was detected by TLC of aliquots of the fractions on commercial Kieselgel $60F_{254}$ plates. Compound could be visualized by inspection of dried plates under UV light or by spraying the plates with a spray containing vanillin (0.75%) and concentrated sulfuric acid (1.5%, v/v) in ethanol and subsequently heating the plate. Fractions contained substantially pure compound of Formula II, although highly colored. A buff-colored sample could be obtained by chromatography on HPLC as follows.

6 mg of sample was dissolved in acetonitrile and injected onto a preparative HPLC column (XTerra ODS (10 µm), 19×150 mm, Waters Co., Milford, Mass.), with a 9 mL/min flow rate and UV peak detection at 300 nm. The column was eluted with acetonitrile/buffer (20 mM of $NH_4HCO_3$) according to the following gradient shown in Table 1

TABLE 1

| Time (min) | Water (%) | Acetonitrile (%) |
|---|---|---|
| 0 | 70 | 30 |
| 10 | 5 | 95 |
| 15 | 5 | 95 |
| 20 | 70 | 30 |

Fractions containing the compound of Formula II eluted at approximately 11:0 min and were combined, concentrated and lyophilized to give a yield of 3.8 mg compound.

Alternative Protocol 1

The compound of Formula II was also isolated using the following alternative protocol. At the end of the incubation period, the fermentation broth from the baffled flasks of Example 1 was centrifuged and the supernatant decanted from the pellet containing the bacterial mycelia. 100 mL of 100% MeOH was added to the mycelial pellet and the sample was stirred for 10 minutes and centrifuged for 15 minutes. The methanolic supernatant was decanted and saved. 100 mL of acetone was then added to the mycelial pellet and stirred for 10 minutes then centrifuged for 15 minutes. The acetonic supernatant was decanted and combined with the methanolic supernatant. Finally, 100 mL of 20% $MeOH/H_2O$ was added to the mycelial pellet, stirred for 10 minutes and centrifuged for 15 minutes. The supernatant was combined with the acetonic and methanolic supernatants.

The combined supernatant was added to 400 ml of HP-20 resin in 1000 mL of water and the organics were removed in vacuo. The resulting slurry was filtered on a Buchner funnel and the filtrate was discarded. Adsorbed HP-20 resin was washed successively with 2×500 mL of 50% $MeOH/H_2O$, 2×500 mL of 75% $MeOH/H_2O$ and 2×500 mL of MeOH.

The individual washes were collected separately and analyzed by TLC as described above. Those fractions containing the compound of Formula II were evaporated to near dryness and lyophilized. The lyophilizate was dissolved in methanol and injected onto a preparative HPLC column (Xterra ODS (10 µm), 19×150 mm, Waters Co., Milford, Mass.) with a flow rate of 9 mL/min and peak detection at 300 nm.

The column was eluted with acetonitrile/buffer (5 mM of $NH_4HCO_3$) according to gradient shown in Table 2.

TABLE 2

| Time (min) | Buffer (%) | Acetonitrile (%) |
|---|---|---|
| 0 | 95 | 5 |
| 15 | 45 | 55 |
| 20 | 5 | 95 |
| 30 | 5 | 95 |
| 35 | 95 | 5 |

Fractions containing the compound of Formula II were combined, concentrated and lyophilized to yield about 33.7 mg of compound.

Alternative Protocol 2

10 liters of the whole broth from Example 1 are extracted twice with equal volumes of ethyl acetate and the two extracts are combined and concentrated to dryness. The dried extract is weighed, and for every gram of dry extract, 100 mL of $MeOH$—$H_2O$ (2:1 v/v) and 100 mL of hexane is added. The mixture is swirled gently but well to achieve dissolution. The two layers are separated and the aqueous layer is washed with 100 mL of hexane. The two hexane layers are combined and the combined hexane solution is washed with 100 mL methanol:water (2:1, v/v). The two methanol:water layers are combined and treated with 200 mL of EtOAc and 400 mL of water. The layers are separated and the aqueous layer is extracted twice more with 200 mL portions of EtOAc. The EtOAc layers are combined and concentrated. The residue obtained will be suitable for final purification, either by HSCC or by HPLC as described above. This extraction process achieves a ten-fold purification when compared with the extraction protocol used above.

Example 3

Elucidation of the Structure of Compound of Formula II

The structure of the compound of Formula II was derived from spectroscopic data, including mass, UV, and NMR spectroscopy. Mass was determined by electrospray mass spectrometry to be 462.6 (FIG. 1), UVmax 230 nm with a shoulder at 290 nm (FIG. 2). NMR data were collected dissolved in MeOH-d4 including proton (FIG. 3), and multidimensional pulse sequences gDQCOSY (FIG. 4), gHSQC (FIG. 5), gHMBC (FIG. 6), and NOESY (FIG. 7).

A number of cross peaks in the 2D spectra of ECO-04601 are key in the structural determination. For example, the farnesyl chain is placed on the amide nitrogen by a strong cross peak between the proton signal of the terminal methylene of that chain at 4.52 ppm and the amide carbonyl carbon at 170 ppm in the gHMBC experiment. This conclusion is confirmed by a cross peak in the NOESY spectrum between the same methylene signals at 4.52 ppm and the aromatic proton signal at 6.25 ppm from one of the two protons of the tetra substituted benzenoid ring.

Based on the mass, UV and NMR spectroscopy data, the structure of the compound was determined to be the structure of Formula II.

Example 4

Antibacterial Activity

Minimal Inhibitory Concentration Determination

Minimal Inhibitory Concentration (MIC) is defined as the lowest concentration of drug that inhibits more than 99% of the bacterial population. The MIC determination of ECO-04601 against bacteria strains (*Bacillus subtilis*-ATCC 23857; *Micrococcus luteus*-ATCC 9341) was performed using broth microdilution assay (Methods for Dilution Antimicrobial Susceptibility Tests for Bacteria That Grow Aerobically; Approved Standard-Fifth Edition. NCCLS document M7-A5 (ISBN 1-56238-394-9). NCCLS, 940 West Valley Road, Suite 1400, Wayne, Pa. 19087-1898 USA.).

Test compound preparation: The test article ECO-04601 is prepared as 100× stock solutions in DMSO, with concentrations ranging from 3.2 mg/ml to 0.0625 mg/ml (a two-fold dilution series over 10 points). The first dilution (3.2 mg/ml) was prepared by resuspending 0.5 mg of each test article in 156.25 μl of DMSO. The stock is then serially diluted by two-fold decrement to obtain the desired concentration range.

Inoculum Preparation From an overnight culture in Mueller Hinton (MH) broth, cell density for each indicator strain (*Bacillus subtilis*; *Micrococcus luteus*) was adjusted to 0.5 Mc Farland units in 0.85% saline, then further diluted 1/100 in appropriate assay medium (~1×10$^6$ cells/ml).

MIC determination: The 100×ECO-04601 solutions was diluted 50 times in MH broth and dispensed in a 96 well plate, one test concentration per column of wells, 10 columns in total. The 11$^{th}$ column of wells contained MH broth with 1% DMSO, the 12$^{th}$ column of wells contained 100 μl of broth alone. 50 μl of the final cell dilution of each indicator strain was added to each corresponding well of the microplate containing 50 μl of diluted drug or media alone. Assay plates were incubated at 35° C. for 24 hrs.

The results of the MIC for the compound of ECO-04601, shown in Table 3, demonstrate a range of antibacterial effects:

TABLE 3

| Indicator strain | MIC (μg/mL) |
| --- | --- |
| *Bacillus subtilis* ATCC 23857 | 12.5 |
| *Micrococcus luteus* ATCC 9341 | 6.25 |

Example 5

Anticancer Activity In Vitro Against Human and Animal Tumor Cell Lines from Various Tissues Culture conditions: The cell lines listed in Table 4 were used to characterize the cytotoxicity of ECO-04601 against human and animal tumor cell lines. These cell lines were shown to be free of mycoplasma infection and were maintained on the appropriate media (Table 4) supplemented with 10% heat-inactivated fetal bovine serum and 1% penicillin-streptomycin, under 5% $CO_2$ at 37° C. Cells were passaged twice to three times per week. Viability was examined by staining with 0.25% trypan blue and only flasks where cell viability was >95% were used for this study.

Cell lines amplification and plating: Tumor cells were seeded ($1-3\times10^3$ cells per 100 μL) in 96-wells flat bottom microtiter plates and incubated at 37° C. and 5% $CO_2$ for 16 hrs before treatment in drug-free medium supplemented with 10% serum.

Evaluation of inhibitory activity on cell proliferation: Cells were incubated for 96 hrs with 6 $\log_{10}$-fold concentrations of the test substance starting at 10 μg/ml (20 μM). The test substance stock solution (5 mg/mL) was initially diluted at 1/70 fold in medium supplemented with serum. Other concentrations were then obtained from 1/10 fold successive dilutions in the same supplemented medium. Cell survival was evaluated 96 h later by replacing the culture media with 150 μL fresh medium containing 10 mM 4-(2-hydroxyethyl)-1-piperazineethanesulfonic acid buffer, pH 7.4. Next, 50 μL of 2.5 mg/mL of 3-(4,5-dimethylthiazo-2-yl)-2,5-diphenyltetrazolium bromide (MTT) in phosphate buffer solution, pH 7.4, was added. After 3-4 h of incubation at 37° C., the medium and soluble MTT was removed, and 200 μL of dimethylsulfoxide was added to dissolve the precipitate of reduced MTT followed by addition of 25 μL glycine buffer (0.1 M glycine plus 0.1 M NaCl, pH 10.5). The absorbance was determined at 570 nm with a microplate reader. Results were expressed as the concentration of drug which inhibits 50% of the cell growth ($IC_{50}$). The $IC_{50}$ values shown in Table 4 demonstrated a pharmacologically relevant cytotoxic activity of ECO-04601 against a variety of tumor types such as leukemias, melanomas, pancreatic and breast carcinomas.

TABLE 4

| Cell lines | Type | Origin | Source | Culture medium | $IC_{50}$ (×10$^{-6}$M) |
|---|---|---|---|---|---|
| K562 | Leukemia myelogeneous | Human | ATCC | RPMI 1640 | 8.6 |
| P388 | Leukemia | Mouse | ATCC | RPMI 1640 | 10.9 |
| I83 | Leukemia | Human | ATCC | RPMI 1640 | 2.7 |
| B16 (F10) | Melanoma | Mouse | ATCC | RPMI 1640 | 11.4 |
| SK-MEL 28 | Melanoma | Human | ATCC | RPMI 1640 | 14.0 |
| SK-MEL 28$^{VEGF}$ | Melanoma (expressing VEGF) | Human | ATCC | RPMI 1640 | 14.3 |
| SK-MEL-1 | Melanoma | Human | ATCC | EMEM 1% non-essential amino acid 1% Sodium puryvate | 14.1 |
| Panc 96 | Pancreatic carcinoma | Human | ATCC | RPMI 1% Sodium puryvate | 12.5 |
| Panc 10.05 | Pancreatic carcinoma | Human | ATCC | RPMI 1% Sodium puryvate Insulin | 14.2 |
| MCF-7 | Breast adenocarcinoma | Human | ATCC | RPMI 1640 | 9.7 |

Example 6

Anticancer Activity In Vitro Against Various Human Tumor Cell Lines from the U.S. National Cancer Institute Panel A study measuring the in vitro antitumor activity of ECO-04601 was performed by the National Cancer Institute (National Institutes of Health, Bethesda, Md., USA) against panel of human cancer cell lines in order to determine the ECO-04601 concentrations needed to obtain a 50% inhibition of cell proliferation ($GI_{50}$). The operation of this unique screen utilizes 50 different human tumor cell lines, representing leukemia, melanoma and cancers of the lung, colon, brain, ovary, breast, prostate, and kidney.

Culture conditions and plating: The human tumor cell lines of the cancer-screening panel were grown in RPMI 1640 medium containing 5% fetal bovine serum and 2 mM L-glutamine. For a typical screening experiment, cells were inoculated into 96 well microtiter plates in 100 µL at plating densities ranging from 5,000 to 40,000 cells/well depending on the doubling time of individual cell lines (Table 5). After cell inoculation, the microtiter plates were incubated at 37° C., 5% $CO_2$, 95% air and 100% relative humidity for 24 h prior to addition of experimental drugs. After 24 h, two plates of each cell line were fixed in situ with TCA, to represent a measurement of the cell population for each cell line at the time of drug addition (Tz).

Evaluation of inhibitory activity on cell proliferation: ECO-04601 was provided as a lyophilized powder with an estimated purity of 90+%. The compound was stored at −20° C. until day of use. ECO-04601 was solubilized in dimethyl sulfoxide at 400-fold the desired final maximum test concentration. At the time of drug addition, an aliquot of frozen concentrate was thawed and diluted to twice the desired final maximum test concentration with complete medium containing 50 µg/mL gentamicin. Additional four, 10-fold or ½ log serial dilutions were made to provide a total of five drug concentrations plus control. Aliquots of 100 µl of these different drug dilutions were added to the appropriate microtiter wells already containing 100 µl of medium, resulting in the required final drug concentrations ($8.0 \times 10^{-5}$ M to $8.0 \times 10^{-9}$ M).

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 µl of cold 50% (w/v) TCA (final concentration, 10% TCA) and incubated for 60 minutes at 4° C. Supernatants were discarded, and the plates were washed five times with tap water and air-dried. Sulforhodamine B (SRB) solution (100 µl) at 0.4% (w/v) in 1% acetic acid was added to each well, and plates were incubated for 10 minutes at room temperature. After staining, unbound dye was removed by washing five times with 1% acetic acid and the plates were air-dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 µl of 80% TCA (final concentration, 16% TCA).

The growth inhibitory activity of ECO-04601 was measured by NCI utilizing the $GI_{50}$ value, rather than the classical $IC_{50}$ value. The $GI_{50}$ value emphasizes the correction for the cell count at time zero and, using the seven absorbance measurements [time zero, (Tz), control growth, (C), and test growth in the presence of drug at the five concentration levels (Ti)], $GI_{50}$ is calculated as $[(Ti-Tz)/(C-Tz)] \times 100 = -50$, which is the drug concentration resulting in a 50% reduction in the net protein increase (as measured by SRB staining) in control cells during the drug incubation.

Result: ECO-04601 shows a significant antitumor activity against several types of tumor as revealed by the NCI screening. Results of the screen are shown in Table 5, and more detailed results of activity against gliomas are shown in Example 7 (Table 6).

TABLE 5

| Cell Line Name | Type | Origin | Inoculation Density (number of cells/well) | $GI_{50}$ (×10$^{-6}$M) |
|---|---|---|---|---|
| CCRF-CEM | Leukemia | Human | 40,000 | 1.08 |
| K-562 | Leukemia | Human | 5,000 | 1.43 |
| RPMI-8226 | Leukemia | Human | 20,000 | 3.15 |

TABLE 5-continued

| Cell Line Name | Type | Origin | Inoculation Density (number of cells/well) | GI$_{50}$ ($\times 10^{-6}$M) |
|---|---|---|---|---|
| A549/ATCC | Non-Small Cell Lung | Human | 7,500 | 9.10 |
| EKVX | Non-Small Cell Lung | Human | 20,000 | 0.23 |
| HOP-62 | Non-Small Cell Lung | Human | 10,000 | 8.29 |
| NCI-H226 | Non-Small Cell Lung | Human | 20,000 | 2.00 |
| NCI-H23 | Non-Small Cell Lung | Human | 20,000 | 2.02 |
| NCI-H460 | Non-Small Cell Lung | Human | 7,500 | 13.60 |
| NCI-H522 | Non-Small Cell Lung | Human | 20,000 | 3.44 |
| COLO 205 | Colon | Human | 15,000 | 12.70 |
| HCT-116 | Colon | Human | 5,000 | 2.92 |
| HCT-15 | Colon | Human | 10,000 | 9.73 |
| HT29 | Colon | Human | 5,000 | 20.70 |
| SW-620 | Colon | Human | 10,000 | 2.72 |
| SF-268 | CNS | Human | 15,000 | 4.94 |
| SF-295 | CNS | Human | 10,000 | 12.70 |
| SF-539 | CNS | Human | 15,000 | 0.0075 |
| SNB-19 | CNS | Human | 15,000 | 2.90 |
| SNB-75 | CNS | Human | 20,000 | 7.71 |
| U251 | CNS | Human | 7,500 | 2.19 |
| LOX IMVI | Melanoma | Human | 7,500 | 4.53 |
| M14 | Melanoma | Human | 15,000 | 4.57 |
| SK-MEL-2 | Melanoma | Human | 20,000 | 25.0 |
| SK-MEL-28 | Melanoma | Human | 10,000 | 11.6 |
| SK-MEL-5 | Melanoma | Human | 10,000 | 7.80 |
| UACC-257 | Melanoma | Human | 20,000 | 2.31 |
| UACC-62 | Melanoma | Human | 10,000 | 1.55 |
| IGR-OV1 | Ovarian | Human | 10,000 | 3.11 |
| OVCAR-3 | Ovarian | Human | 10,000 | 13.50 |
| OVCAR-4 | Ovarian | Human | 15,000 | 9.67 |
| OVCAR-5 | Ovarian | Human | 20,000 | 2.81 |
| OVCAR-8 | Ovarian | Human | 10,000 | 2.65 |
| SK-OV-3 | Ovarian | Human | 20,000 | 4.00 |
| 786-0 | Renal | Human | 10,000 | 6.99 |
| A498 | Renal | Human | 25,000 | 22.30 |
| ACHN | Renal | Human | 10,000 | 3.10 |
| CAKI-1 | Renal | Human | 10,000 | 15.20 |
| RXF 393 | Renal | Human | 15,000 | 7.71 |
| SN12C | Renal | Human | 15,000 | 3.85 |
| UO-31 | Renal | Human | 15,000 | 19.70 |
| DU-145 | Prostate | Human | 10,000 | 3.56 |
| MCF7 | Breast | Human | 10,000 | 10.10 |
| NCI/ADR-RES | Breast | Human | 15,000 | 18.30 |
| MDA-MB-231/ATCC | Breast | Human | 20,000 | 2.72 |
| HS 578T | Breast | Human | 20,000 | 2.76 |
| MDA-MB-435 | Breast | Human | 15,000 | 15.30 |
| BT-549 | Breast | Human | 20,000 | 0.11 |
| T-47D | Breast | Human | 20,000 | 0.77 |

The results indicate that ECO-04601 was effective against most of the human tumor cell lines that have been assayed in the NCI screening panel suggesting a broad anticancer activity against several types of human cancer.

Example 7

In Vitro Antiproliferative Study Against a Panel of Glioma Cell Lines

The anticancer activity of ECO-04601 was evaluated using a panel of glioma cancer cell lines shown in Table 6, and the 50% inhibition of cell proliferation (IC$_{50}$) was determined.

Culture conditions: The cell lines listed in Table 6 were shown to be free of mycoplasma infection and were maintained on DMEM medium supplemented with 10% heat-inactivated fetal bovine serum and 1% penicillin-streptomycin, under 5% CO$_2$ at 37° C. Cells were passaged once a week. Prior to use the cells were detached from the culture flask by treating with trypsin for five to ten minutes. The cells were counted with a Neubauer glass slide and viability assessed by 0.25% trypan blue exclusion. Only flasks with >95% cell viability, were used in the study.

Cell lines amplification and plating: Cells, 5×10$^3$ cells per well in 100 μL drug-free medium supplemented with 10% serum, were plated in 96-well flat bottom microtiter plates and incubated at 37° C. for 48 hrs before treatment.

Evaluation of inhibitory activity on cell proliferation: Cells (in triplicate wells) were incubated 96 hrs with medium containing different concentrations of ECO-04601, starting at 5.0 μg/ml (10 μM). The compound was used in a solution of 1% DMSO in D-MEM or RPMI media (or other equivalent media). The concentrations of ECO-04601 were as follows: 10 μM (5.0 μg/ml), 1 μM (0.50 μg/ml), 0.5 μM (0.25 μg/ml), 0.1 μM (0.050 μg/ml), 0.5 μM (0.025 μg/ml), 0.01 μM (0.0050 μg/ml), 0.001 μM (0.00050 μg/ml). Negative controls were cells treated with vehicle alone (1% DMSO in culture medium). Positive controls were cells treated with 4 to 6 increasing concentrations of cisplatin (CDDP) (data not shown). The optical density was measured before incubation (time 0) and following 96 hrs of incubation with test compound in order to measure the growth rate of each cell line.

At the end of the cell treatment, cell culture media was replaced with 150 μl of fresh medium containing 10 mM of 4-(2-hydroxyethyl)-1-piperazineethanesulfonic acid buffer, pH 7.4. Then 50 μl of 2.5 mg/ml of 3-(4,5-dimethylthiazo-2-yl)-2,5-diphenyltetrazolium bromide in PBS pH 7.4, were added to each well and the culture plates incubated for 4 hrs at 37° C. The resulting supernatant was removed and formazan crystals were dissolved with 200 μl of DMSO followed by 25 μl of glycine buffer (0.1 M glycine plus 0.1 M NaCl, pH 10.5). The optical density was read in each well using a single wavelength spectrophotometer plate reader at 570 nm. Results were expressed as the concentration of drug, which inhibits 50% of the cell growth (IC$_{50}$). Each of the cell lines was tested in at least 3 independent experiments.

Results shown in Table 6 confirmed the activity of ECO-04601 against different brain cancer cell lines including gliosarcoma, which is the most malignant form of type IV glioblastoma multiform. Gliosarcomas are a mixture of glial and endothelial cells and are resistant to any chemotherapy.

TABLE 6

| Cell lines | Type | Origin | Source | IC$_{50}$ ($\times 10^{-6}$ M) |
|---|---|---|---|---|
| 9L | Gliosarcoma | Rat | ATCC | 6.82 ± 2.90 |
| GHD | Astrocytoma | Human | ATCC | 6.29 ± 2.98 |
| U 373 | Astrocytoma | Human | ATCC | 3.83 ± 1.37 |
| GL26 | Glioblastoma | Human | ATCC | 8.93 ± 1.10 |
| C6 | Glioblastoma | Rat | ATCC | 4.28 ± 2.82 |
| DN | Oligodendroglioma | Human | ATCC | 3.26 ± 0.93 |
| GHA | Oligodendroglioma | Human | ATCC | 1.78 ± 0.84 |

Example 8

Effect on the Enzymatic Activity of Human Lipoxygenase

5-LO

5-Lipoxygenase catalyzes the oxidative metabolism of arachidonic acid to 5-hydroxyeicosatetraenoic acid (5-HETE), the initial reaction leading to formation of leukotrienes. Eicosanoids derived from arachidonic acid by the action of lipoxygenases or cycloxygenases have been found to be involved in acute and chronic inflammatory diseases (i.e. asthma, multiple sclerosis, rheumatoid arthritis, ischemia, edema) as well in neurodegeneration (Alzheimer disease), aging and various steps of carcinogenesis, including tumor promotion, progression and metastasis.

The aim of this study was to determine whether ECO-04601, is able to block the formation of leukotrienes by inhibiting the enzymatic activity of human 5-LO. Methods employed are based on Carter et al (1991) J. Pharmacol. Exp. Ther. 256(3):929-937, and Safayhi (2000), Planta Medica 66:110-113 which are incorporated herein in their entirety by reference.

Experimental Design Human peripheral blood mononuclear cells (PMNs) were isolated through a Ficoll-Paque density gradient. PMNs were stimulated by addition A23187 (30 µM final concentration). Stimulated PMNs were adjusted to a density of $5 \times 10^6$ cells/mL in HBBS medium and incubated with the vehicle control (DMSO), ECO-04601 (at final concentrations of 0.1, 0.5, 1, 2.5, 5 and 10 µM) and NDGA as positive control (at final concentrations of 3, 1, 0.3, 0.1 and 0.03 µM) for 15 minutes at 37° C. Following incubation, samples were neutralized with NaOH and centrifuged. Leukotriene B4 content was measured in the supernatant using an Enzyme Immunosorbant Assay (EIA) assay.

Figure 8:
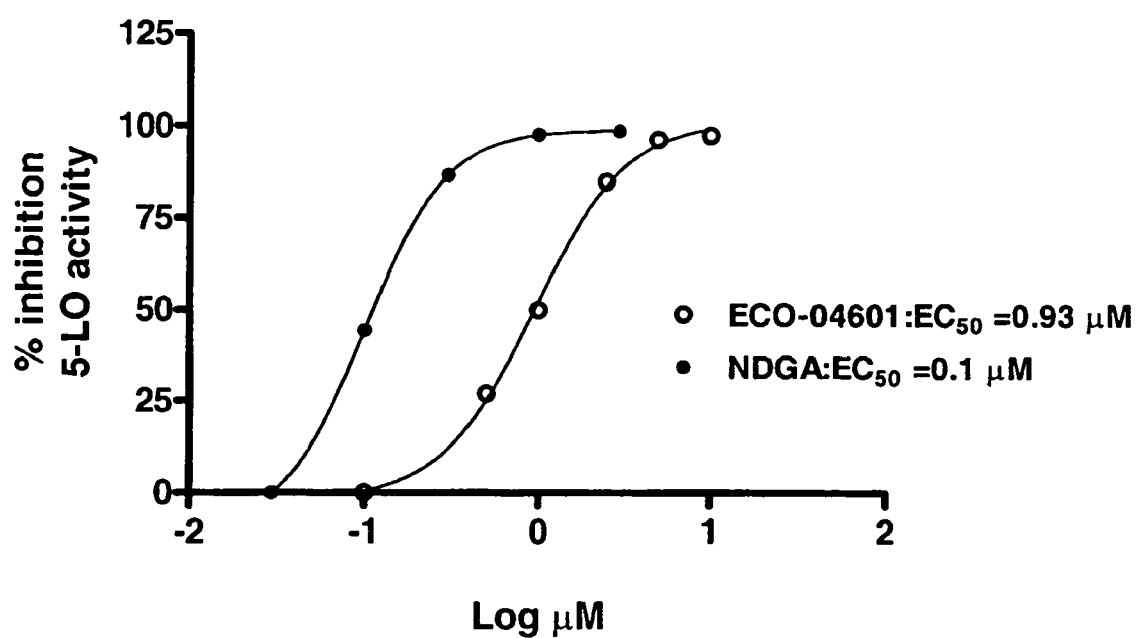
FIG. 8 shows the in vitro anti-inflammatory activity of ECO-04601. Graph shows percent inhibition of 5-lipoxygenase activity plotted against the Log μM concentration of ECO-04601 and NDGA. Graph shows the $EC_{50}$ of ECO-04601 to be 0.93 μM.

Results: Results shown in FIG. 8 demonstrated that ECO-04601 inhibited the activity of human 5-LO with an apparent $IC_{50}=0.93$ µM (versus 0.1 µM for the positive control NDGA) and therefore displays anti-inflammatory properties.

Example 9

In Vivo Efficacy in a Glioma Model

The aim of this study was to test whether ECO-04601 administered by i.p. route prevents or delays tumor growth in C6 glioblastoma cell-bearing mice, and to determine an effective dosage regimen.

Animals: A total of 60 six-week-old female mice (*Mus musculus* nude mice), ranging between 18 to 25 g in weight, were observed for 7 days before treatment. Animal experiments were performed according to ethical guidelines of animal experimentation (*Charte du comité d'éthique du CNRS, juillet* 2003) and the English guidelines for the welfare of animals in experimental neoplasia (WORKMAN, P., TWENTYMAN, P., BALKWILL, F., et al. (1998). *United Kingdom Coordinating Committee on Cancer Research (UKCCCR) Guidelines for the welfare of animals in experimental neoplasia* (Second Edition, July 1997; British Journal of Cancer 77:1-10). Any dead or apparently sick mice were promptly removed and replaced with healthy mice. Sick mice were euthanized upon removal from the cage. Animals were maintained in rooms under controlled conditions of temperature (23±2° C.), humidity (45±5%), photoperiodicity (12 hrs light/12 hrs dark) and air exchange. Animals were housed in polycarbonate cages (5/single cage) that were equipped to provide food and water. Animal bedding consisted of sterile wood shavings that were replaced every other day. Food was provided ad libitum, being placed in the metal lid on the top of the cage. Autoclaved tap water was provided ad libitum. Water bottles were equipped with rubber stoppers and sipper tubes. Water bottles were cleaned, sterilized and replaced once a week. Two different numbers engraved on two earrings identified the animals. Each cage was labelled with a specific code.

Tumor Cell Line: The C6 cell line was cloned from a rat glial tumor induced by N-nitrosomethyurea (NMU) by Premont et al. (Premont J, Benda P, Jard S., [3H] norepinephrine binding by rat glial cells in culture. Lack of correlation between binding and adenylate cyclase activation. *Biochim Biophys Acta*. 1975 Feb. 13; 381(2):368-76.) after series of alternate culture and animal passages.

Cells were grown as adherent monolayers at 37° C. in a humidified atmosphere (5% $CO_2$, 95% air). The culture medium was DMEM supplemented with 2 mM L-glutamine and 10% fetal bovine serum. For experimental use, tumor cells were detached from the culture flask by a 10 min treatment with trypsin-versen. The cells were counted in a hemocytometer and their viability assessed by 0.25% trypan blue exclusion.

Preparation of the Test Article: for the Test Article, the Following Procedure was Followed for reconstitution (performed immediately preceding injection). The vehicle consisted of a mixture of benzyl alcohol (1.5%), ethanol (8.5%), propylene glycol (27%), PEG 400 (27%), dimethylacetamide (6%) and water (30%). The vehicle solution was first vortexed in order to obtain a homogeneous liquid. 0.6 mL of the vortexed vehicle solution was added to each vial containing the test article (ECO-04601). Vials were mixed thoroughly by vortexing for 1 minute and inverted and shaken vigorously. Vials were mixed again prior to injection into each animal.

Animal Inoculation with tumor cells: Experiment started at day 0 ($D_0$). On $D_0$, mice received a superficial intramuscular injection of C6 tumor cells ($5 \times 10^5$ cells) in 0.1 mL of DMEM complete medium into the upper right posterior leg.

Treatment Regimen and Results

Figure 9:
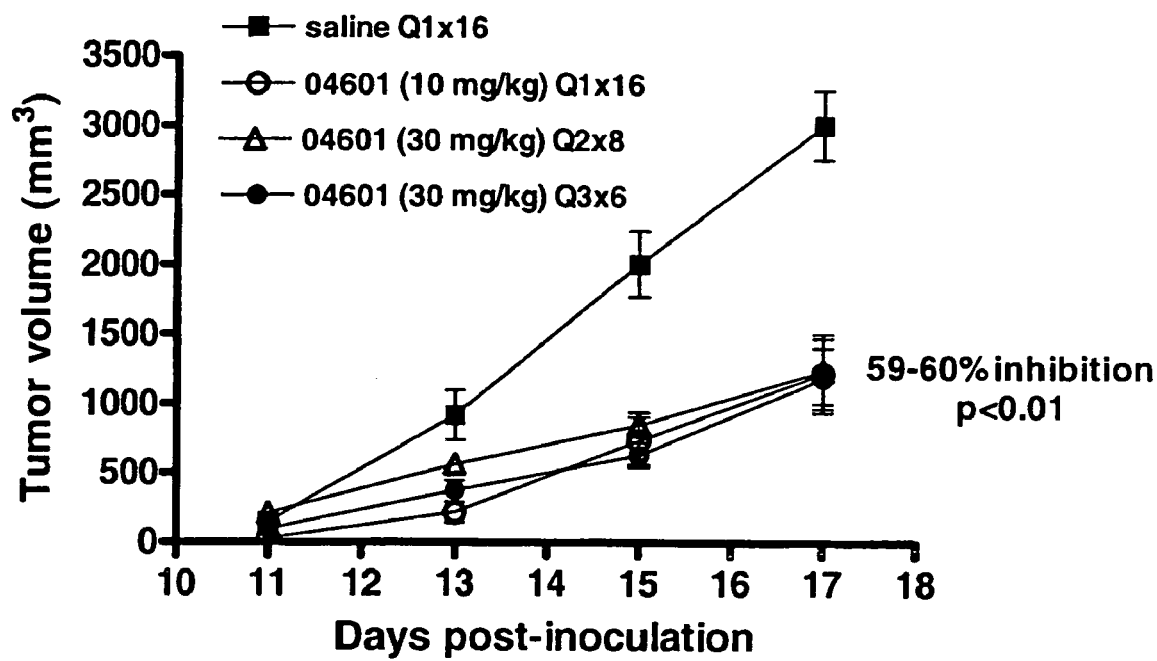
FIG. 9 shows inhibition of tumor growth resulting from administration of 10 to 30 mg/kg of ECO-04601 to glioblastoma-bearing mice beginning one day after tumor cell inoculation.

In a first series of experiments, treatment started 24 hrs following inoculation of C6 cells. On the day of the treatment, each mouse was slowly injected with 100 µL of test or control articles by i.p. route. For all groups, treatment was performed until the tumor volume of the saline-treated mice (group 1) reached approximately 3 $cm^3$ (around day 16). Mice of group 1 were treated daily with a saline isosmotic solution for 16 days. Mice of group 2 were treated daily with the vehicle solution for 16 days. Mice of group 3 were treated daily with 10 mg/kg of ECO-04601 for 16 days. Mice of group 3 were treated every two days with 30 mg/kg of ECO-04601 and received 8 treatments. Mice of group 5 were treated every three days with 30 mg/kg of ECO-04601 and received 6 treatments. Measurement of tumor volume started as soon as tumors became palpable (>100 $mm^3$; around day 11 postinoculation) and was evaluated every second day until the end of the treatment using callipers. As shown in Table 7 and FIG. 9, the mean value of the tumor volume of all ECO-04601 treated groups (6 mice/group) was significantly reduced as demonstrated by the one-way analysis of variance (Anova) test followed by the non-parametric Dunnett's multiple comparison test comparing treated groups to the saline group. An asterisk in the P value column of Table 7 indicates a statistically significant value, while "ns" signifies not significant.

TABLE 7

| Treatment | Treatment regimen | Tumor volume (mm³) (mean ± SEM) | % Inhibition | P value |
|---|---|---|---|---|
| Saline | Q1 x 16 | 3,004.1 ± 249.64 | — | — |
| Vehicle solution | Q1 x 16 | 2,162.0 ± 350.0 | 28.0% | >0.05 ns |
| ECO-04601 (10 mg/kg) | Q1 x 16 | 1,220.4 ± 283.46 | 59.4% | <0.01 * |
| ECO-04601 (30 mg/kg) | Q2 x 8 | 1,236.9 ± 233.99 | 58.8% | <0.01 * |
| ECO-04601 (30 mg/kg) | Q3 x 6 | 1,184.1 ± 221.45 | 60.6% | <0.01 * |

Figure 10:
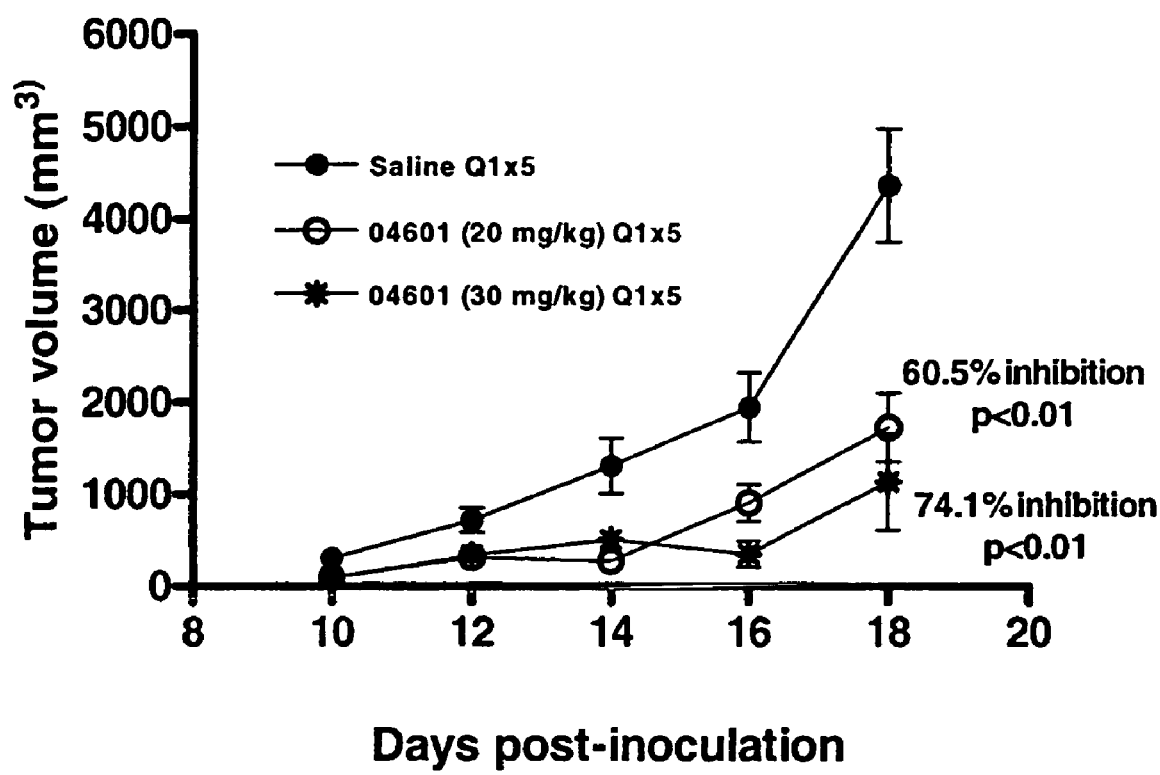
FIG. 10 shows inhibition of tumor growth resulting from administration of 20-30 mg/kg of ECO-04601 to glioblastoma-bearing mice beginning ten days after tumor cell inoculation.

In a second series of experiments, treatment started at day 10 following inoculation of C6 cells when tumors became palpable (around 100 to 200 mm³). Treatment was repeated daily for 5 consecutive days. On the day of the treatment, each mouse was slowly injected with 100 µL of ECO-04601 by i.p. route. Mice of group 1 were treated daily with saline isosmotic solution. Mice of group 2 were treated daily with the vehicle solution. Mice of group 3 were treated daily with 20 mg/kg of ECO-04601. Mice of group 4 were treated daily with 30 mg/kg of ECO-04601. Mice were treated until the tumor volume of the saline-treated control mice (group 1) reached around 4 cm³. Tumor volume was measured every second day until the end of the treatment using callipers. As shown in Table 8 and FIG. 10, the mean value of the tumor volume of all ECO-04601 treated groups (6 mice/group) was significantly reduced as demonstrated by the one-way analysis of variance (Anova) test followed by the non-parametric Dunnett's multiple comparison test comparing treated groups to the saline group. An asterisk in the P value column of Table 8 indicates a statistically significant value, while "ns" signifies not statistically significant.

Figure 11:
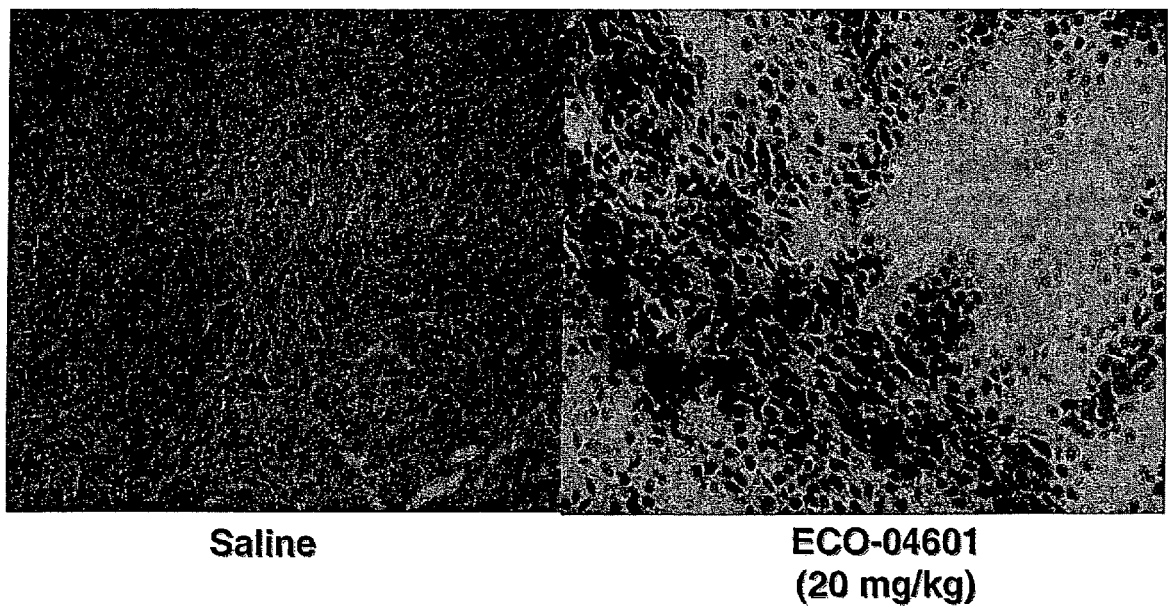
FIG. 11 shows micrographs of tumor sections from mice bearing glioblastoma tumors and treated with saline or ECO-04601. The cell density of tumor treated with ECO-04601 appears decreased and nuclei from ECO-04601-treated tumor cells are larger and pynotic suggesting a cytotoxic effect.

Histological analysis of tumor sections showed pronounced morphological changes between ECO-04601-treated tumors and control groups. In tumors treated with ECO-04601 (20-30 mg/kg), cell density was decreased and the nuclei of remaining tumor cells appeared larger and pycnotic while no such changes were observed for vehicle-treated mice (FIG. 11).

TABLE 8

| Treatment | Treatment regimen | Tumor volume (mm³) (mean ± SEM) | % Inhibition | P value |
|---|---|---|---|---|
| Saline | Q1 x 5 | 4,363.1 ± 614.31 | — | — |
| Vehicle solution | Q1 x 5 | 3,205.0 ± 632.37 | 26.5% | >0.05 ns |
| ECO-04601 (20 mg/kg) | Q1 x 5 | 1,721.5 ± 374.79 | 60.5% | <0.01 * |
| ECO-04601 (30 mg/kg) | Q1 x 5 | 1,131.6 ± 525.21 | 74.1% | <0.01 * |

Example 10

Generation of Variants of ECO-04601 According to the Invention

Variants of the ECO-04601 molecule, for example those identified herein as Formulae III-LIX, can be generated by standard organic chemistry approaches. General principles of organic chemistry required for making and manipulating the compounds described herein, including functional moieties, reactivity and common protocols are described, for example, in "Advanced Organic Chemistry," $3^{rd}$ Edition by Jerry March (1985) which is incorporated herein by reference in its entirety. In addition, it will be appreciated by one of ordinary skill in the art that the synthetic methods described herein may use a variety of protecting groups, whether or not they are explicitly described. A "protecting group" as used herein means a moiety used to block one or more functional moieties such as reactive groups including oxygen, sulfur or nitrogen, so that a reaction can be carried out selectively at another reactive site in a polyfunctional compound. General principles for the use of protective groups, their applicability to specific functional groups and their uses are described for example in T. H. Greene and P. G. M. Wuts, Protective Groups in Organic Synthesis, $3^{rd}$ Edition, John Wiley & Sons, New York (1999).

Scheme 1: Epoxide Variants

The epoxide compounds of the present invention (e.g., compounds according to exemplary Formulae VII-XIV) are made from the compound of Formula II (ECO-04601) by treatment with any of a number of epoxidizing reagents such as perbenzoic acid, monoperphthalic acid or more preferably by m-chloroperbenzoic acid in an inert solvent such as tetrahydrofuran (THF) dichloromethane or 1,2-dichloroethane. It will be appreciated by one of ordinary skill in the art that slightly greater than one molecule equivalent of epoxidizing agent will result in the maximal yield of mono-epoxides, and that the reagent, solvent, concentration and temperature of the reaction will dictate the ratio of specific mono-epoxides formed. It will also be appreciated that the mono-epoxides will be enantiomeric mixtures, and that the di-epoxides and the tri-epoxide can be prepared as diastereomers and that the conditions of the reaction will determine the ratios of the products. One skilled in the art will appreciate that under most conditions of reactions the product will be a mixture of all possible epoxides and that these may be separated by standard methods of chromatography. Exemplary approaches to the generation of mono-, di-, and tri-epoxides are provided below.

A) Mono-Epoxides of the Formulae VII, VIII, and IX by Epoxidation of the Compound of Formula II:

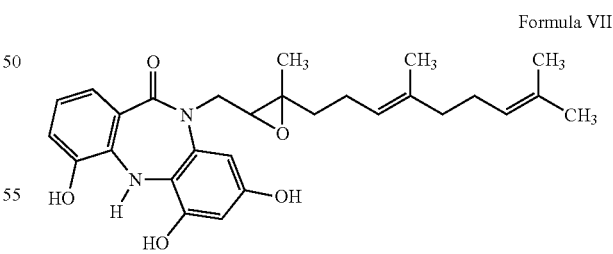

Formula VII

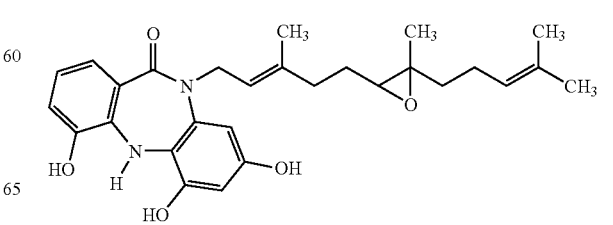

Formula VIII

-continued

Formula IX

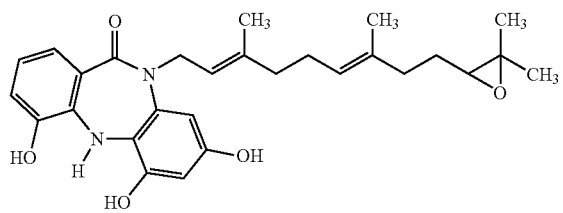

To a solution of the compound of Formula II dissolved in tetrahydrofuran (THF) is added 1.1 equivalents of meta-chloroperbenzoic acid. The reaction is cooled in an ice bath and stirred at 0° C. for 1-2 hours. The reaction mixture is then evaporated to dryness, re-dissolved in methanol and subjected to liquid chromatography on a column of Sephadex LH-20 to isolate a mixture of predominantly the compounds of Formulae VII, VIII and IX, contaminated with some unchanged starting material and some di- and tri-epoxides. The compounds of Formulae VII, VIII and XIX are separated and purified by HPLC using the system described in Example 2 for the purification of the compound of Formulae II. In a typical experiment yields of 15% to 25% are obtained for each of the compounds of Formulae VII, VIII and IX.

B) Synthesis of Compounds of Formulae X, XI, and XII by Di-Epoxidation of Compound of Formula II:

Formula X

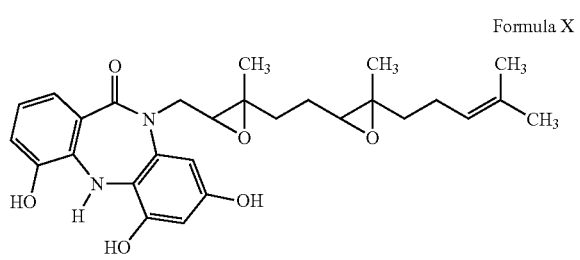

Formula XI

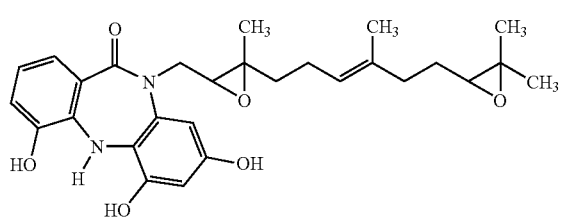

Formula XII

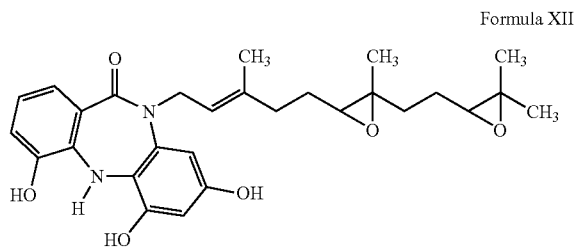

To a solution of the compound of Formula II dissolved in tetrahydrofuran (THF) is added 2.3 equivalents of meta-chloroperbenzoic acid. The reaction is cooled in an ice bath and stirred at 0° C. for 1-2 hours. The reaction mixture is then evaporated to dryness, re-dissolved in methanol and subjected to liquid chromatography on a column of Sephadex LH-20 to isolate a mixture of predominantly the compounds of Formulae X, XI and XII, contaminated with traces of unchanged starting material and some mono- and tri-epoxides. The Compounds of Formulae X, XI and XII are separated and purified by HPLC using the system described in Example 2 for the purification of the compound of Formulae II. In a typical experiment, yields of 15% to 20% are obtained for each of the compounds of Formulae X, XI and XII.

C) Synthesis of Compound of Formula XIII by tri-epoxidation of Compound of Formula II:

Formula XIII

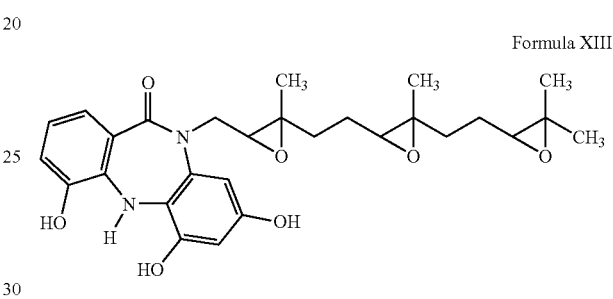

To a solution of the compound of Formula II, dissolved in tetrahydrofuran (THF), is added 3.5 equivalents of meta-chloroperbenzoic acid. The reaction is cooled in an ice bath and stirred at 0° C. for 1-2 hours. The reaction mixture is then evaporated to dryness, re-dissolved in methanol and subjected to liquid chromatography on a column of Sephadex LH-20 to isolate the compound of Formula XIII as a mixture of diasteriomers in a yield of 80+%.

Scheme 2: Synthesis of Compound of Formula III by N-acetylation of Compound of Formula II.

Formula III

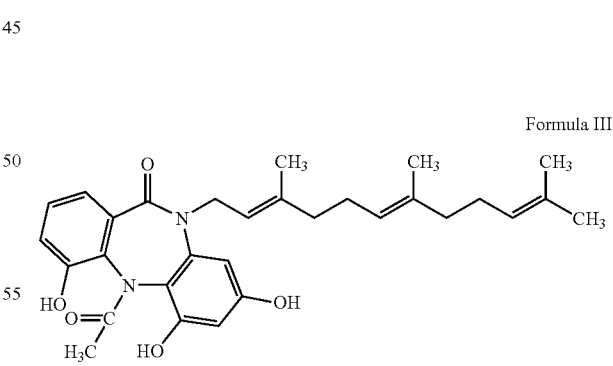

To a solution of Compound of Formula II dissolved in tetrahydrofuran (THF) is added 1.2 equivalents of acetic anhydride and a few drops of triethylamine. The reaction mixture allowed to stand at room temperature for 1-2 hours and then evaporated to dryness under reduced pressure to obtain the Compound of Formula III in an essentially pure form in an almost quantitative yield Scheme 3: Syntheses of Compounds of Formulae IV and V by N-alkylation of Compound of Formula II.

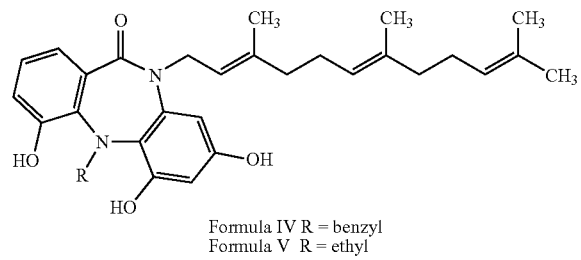

Formula IV R = benzyl
Formula V R = ethyl

To a solution of Compound of Formula II dissolved in terachloroethylene is added 1.2 equivalents of the appropriate alkyl bromide (benzyl bromide for the compound of formula IV or ethyl bromide for the Compound of Formula V). The reaction mixture the reaction mixture is heated under reflux for 1-2 hours and then evaporated to dryness under reduced pressure to obtain the Compound of Formula IV or the Compound of Formula V respectively, in an essentially pure form in an almost quantitative yield.

Scheme 4: Syntheses of Compounds of Formulae XL, XLI and XLII by catalytic reduction of Compound of Formula II.

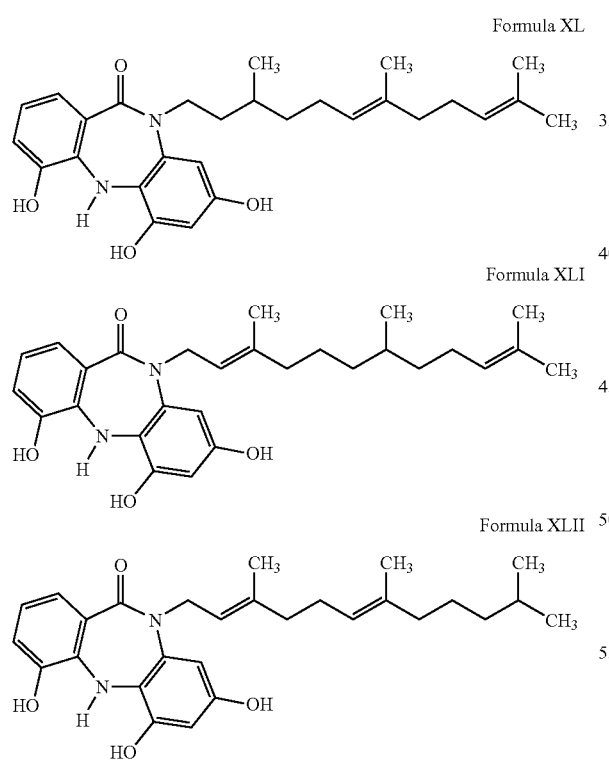

Formula XL

Formula XLI

Formula XLII

A solution of the Compound of Formula II (462 mg) in ethanol (200 ml) with palladium on charcoal (25 mg of 5%) is shaken in an hydrogenation apparatus in an atmosphere of hydrogen. The uptake of hydrogen by the reaction is measured carefully and at the point where one millimole of hydrogen has been consumed, shaking is stopped, the vessel is rapidly evacuated and the atmosphere is replaced with nitrogen. The catalyst is removed by filtration and the filtrate is concentrated to obtain a crude mixture of the Compounds of Formulae XL, XLI and XLII contaminated by unreacted starting material and minor amounts of over reduced products. The desired products may be separated and purified by HPLC or HSCC chromatography using the systems as described in Example 2 above, to obtain approximately 100 mg of each of the Compounds of Formulae XL, XLI and XLII.

Scheme 5: Syntheses of Compounds of Formulae XLIII, XLIV and XLV by catalytic reduction of Compound of Formula II.

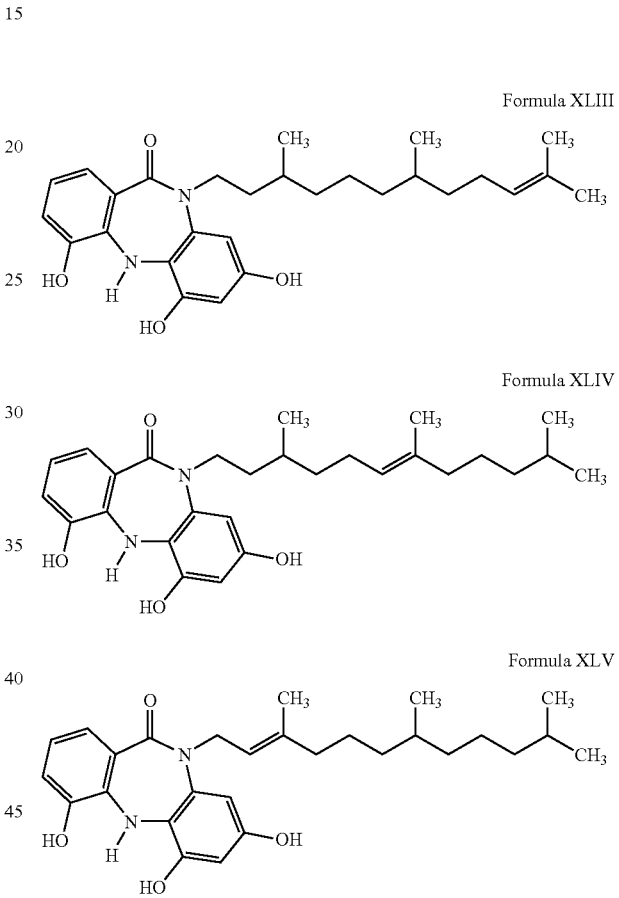

Formula XLIII

Formula XLIV

Formula XLV

A solution of the Compound of Formula II (462 mg) in ethanol (200 ml) with palladium on charcoal (25 mg of 5%) is shaken in an hydrogenation apparatus in an atmosphere of hydrogen. The uptake of hydrogen by the reaction is measured carefully and at the point where two millimoles of hydrogen has been consumed, shaking is stopped, the vessel is rapidly evacuated and the atmosphere is replaced with nitrogen. The catalyst is removed by filtration and the filtrate is concentrated to obtain a crude mixture of the Compounds of Formulae XLIII, XLIV and XLV contaminated by trace amounts unreacted starting material and minor amounts of under and over reduced products. The desired products may be separated and purified by HPLC or HSCC chromatography using the systems as described in Example 2 above, to obtain approximately 100 mg of each of the Compounds of Formulae XLIII, XLIV and XLV.

Scheme 6: Syntheses of Compound of Formula XLVI by catalytic reduction of Compound of Formula II.

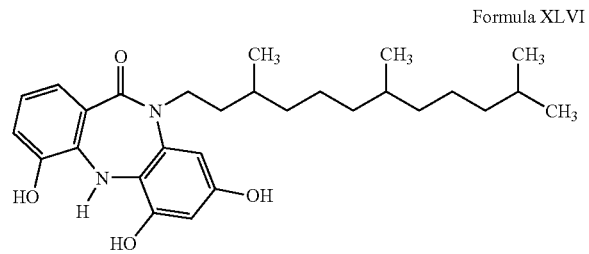

Formula XLVI

A solution of the Compound of Formula II (462 mg) in ethanol (200 ml) with palladium on charcoal (25 mg of 5%) is shaken in an hydrogenation apparatus in an atmosphere of hydrogen. The uptake of hydrogen by the reaction is measured carefully and at the point where three millimoles of hydrogen has been consumed, shaking is stopped, the vessel is rapidly evacuated and the atmosphere is replaced with nitrogen. The catalyst is removed by filtration and the filtrate is concentrated to obtain an essentially pure sample of the Compound of Formula XLVI Scheme 7: Syntheses of Compound of Formula VI by peracetylation of Compound of Formula II.

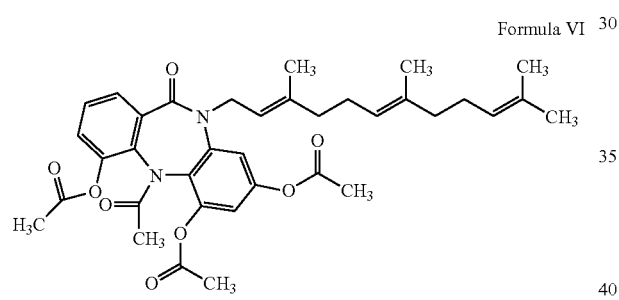

Formula VI

A solution of the Compound of Formula II (100 mg) in acetic anhydride (5 ml) is treated with pyridine (250 ul). The reaction mixture is allowed to stand overnight at room temperature and is then diluted with toluene (100 ml). The toluene solution is washed well with aqueous 5% sodium bicarbonate solutions, then with water and is finally concentrated under reduced pressure to give an essentially pure sample of the Compound of Formula VI in almost quantitative yield.

Scheme 8: Syntheses of Compound of Formula LI by opening the epoxide of Compound of Formula VII.

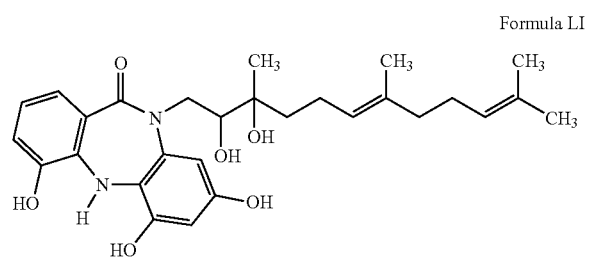

Formula LI

A solution of the Compound of Formula VII (100 mg) in tetrahydrofuran (50 ml) is treated with 1N aqueous hydrochloric acid (5 ml). The reaction mixture is stirred overnight at room temperature and is then diluted with toluene (100 ml) and water (200 ml). The toluene layer is separated and the aqueous layer is extracted with a further 100 ml of toluene. The combined toluene layers are washed once more with water (50 ml) and the separated and dried under vacuum to give the vicinal glycol Compound of Formula LI.

Scheme 9: Syntheses of Compounds of Formulae XLVII, XLIX and LI by ozonolysis of Compound of Formula II.

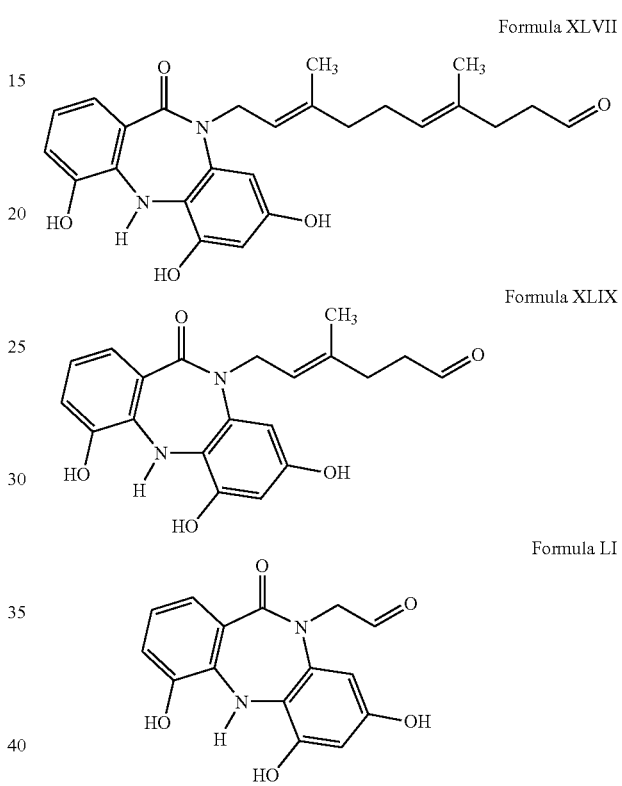

A solution of the Compound of Formula II (462 mg) in dry ethyl acetate (200 ml) in an ozonolysis apparatus is cooled to below −20° C. A stream of ozone-containing oxygen is passed into the solution from an ozone generator, which has been precalibrated such that the rate of ozone generation is known. To obtain predominantly the compound of Formula XLVII the passage of ozone is halted after 0.9 millimole have been generated. To obtain predominantly the compound of Formula XLIX the ozone passage is halted after 2 millimoles have been generated and to obtain the compound of Formula LI as the predominant product 3.3 millimoles of ozone are generated.

At the completion of the ozonolysis, the reaction mixture is transferred to an hydrogenation apparatus, 5% palladium on calcium carbonate catalyst (0.2 g) is added to the reaction mixture which is maintained at less than −20° C. and is hydrogenated. When hydrogen uptake is complete the hydrogen atmosphere is replaced with nitrogen and the reaction mixture is allowed to come to room temperature, filtered to remove catalyst and the filtrate is concentrated. The crude product may be purified by chromatography using either HPLC or HSCC with the systems as described in Example 2 to give, dependent on the amount of ozone used, Compounds of Formulae XLVII, XLIX and LI.

Scheme 10: Synthesis of Compound of Formulae XLVIII by reduction of the aldehyde of Compound of Formula XLVII.

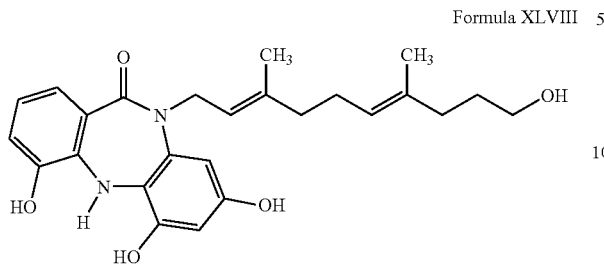

Formula XLVIII

A solution of the Compound of Formula XLVIII (50 mg) in isopropanol (5 ml) is cooled in an ice-salt bath and sodium borohydride (10 mg) is added and the mixture is stirred for 20 minutes. It is then diluted with water (20 ml) and extracted twice with toluene (10 ml portions) at ambient temperature. The combined toluene extracts are filtered and the filtrate is concentrated to give the Compound of Formula XLVII.

Scheme 11: Syntheses of Compounds of Formulae XIV and XV by epoxidation of the Compound of Formula XLII.

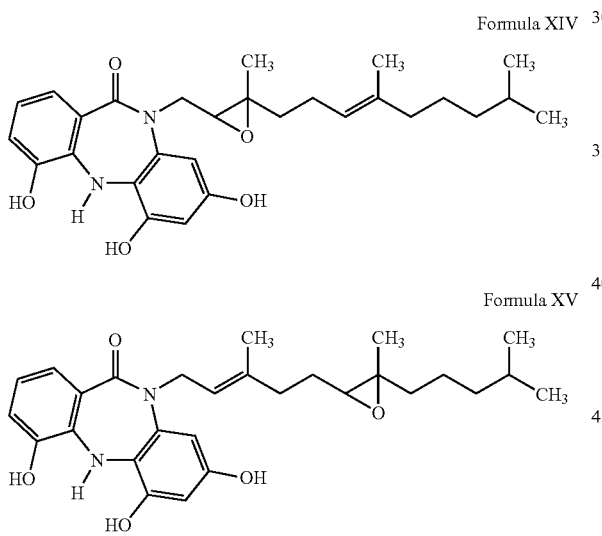

Formula XIV

Formula XV

To a solution of Compound of Formula XLII dissolved in tetrahydrofuran (THF) is added 1.1 equivalents of meta-chloroperbenzoic acid. The reaction is cooled in an ice bath and stirred at 0° C. for 1-2 hours. The reaction mixture is then evaporated to dryness, re-dissolved in methanol and subjected to liquid chromatography on a column of Sephadex LH-20 to isolate a mixture of predominantly the Compounds of Formulae XIV, and XV, contaminated with some unchanged starting material and some diepoxide. The Compounds of Formulae XIV and XV are separated and purified by HPLC or HSCC using one of the systems described in Example 2 for the purification of the Compound of Formulae II. In a typical experiment yields of 35% to 40% are obtained for each of the Compounds of Formulae XIV and XV.

Scheme 12: Synthesis of Compound of Formulae XIX by epoxidation of the Compound of Formula XL.

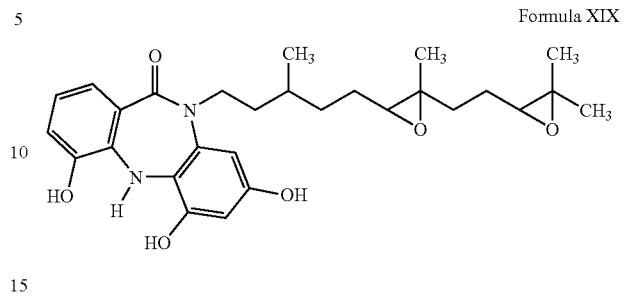

Formula XIX

To a solution of Compound of Formula XL dissolved in tetrahydrofuran (THF) is added 2.2 equivalents of meta-chloroperbenzoic acid. The reaction is cooled in an ice bath and stirred at 0° C. for 1-2 hours. The reaction mixture is then evaporated to dryness, re-dissolved in methanol and subjected to liquid chromatography on a column of Sephadex LH-20 to isolate essentially pure Compound of Formulae XIX in good yield.

Scheme 13: Syntheses of Compounds of Formulae XXVI, XXVII and XXVIII by esterification of the Compound of Formula II.

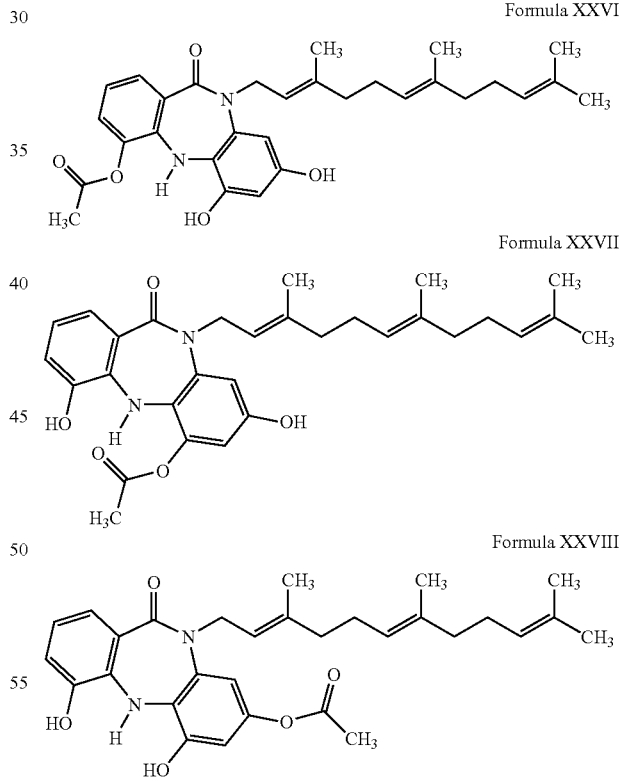

Formula XXVI

Formula XXVII

Formula XXVIII

To a solution of Compound of Formula II dissolved in toluene (9 parts) tetrahydrofuran (1 part), cooled in an ice-bath is added 1.1 equivalents of acetic anhydride and two drops of boron trifluoride etherate. The reaction is maintained cool in an ice bath and stirred at 0° C. for 1-2 hours. The reaction mixture is then poured into aqueous 5% sodium bicarbonate solution shaken and the toluene layer is removed.

The aqueous layer is re-extracted with toluene and the combined toluene layers are concentrated to a mixture of predominantly the Compounds of Formulae XXVI, XXVII and XXVIII, contaminated with some unchanged starting material and some diacetates. The Compounds of Formulae XXVI, XXVII and XXVIII are separated and purified by HPLC or HSCC using one of the systems described in Example 2 for the purification of the Compound of Formulae II. In a typical experiment yields of 25% to 30% are obtained for each of the Compounds of Formulae XXVI, XXVII and XXVIII.

Scheme 14: Syntheses of Compounds of Formulae XXXIII, XXXIV and XXXV by methylation of the Compound of Formula II.

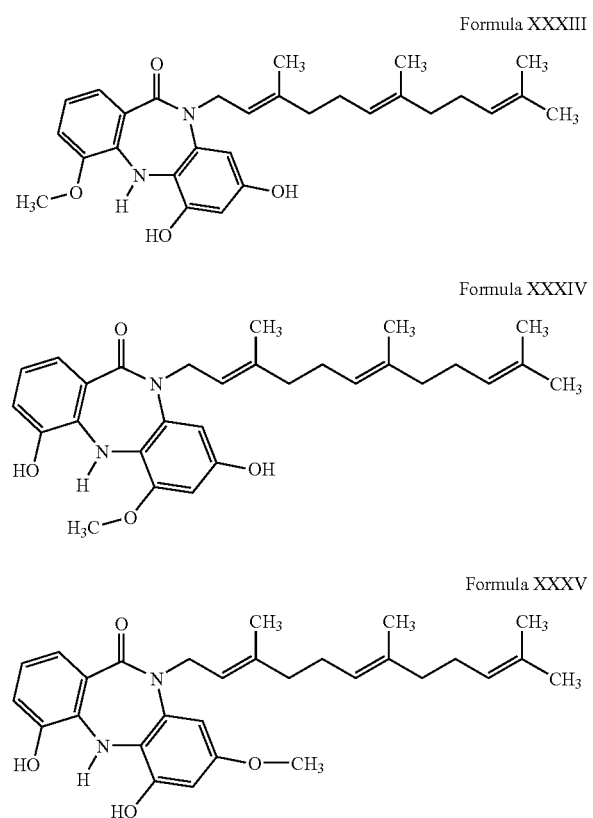

Formula XXXIII

Formula XXXIV

Formula XXXV

A solution of the Compound of Formula II (1 g) in tetrahydrofuran 50 (ml) is titrated with exactly one equivalent of sodium methoxide, allowed to stand for 30 minutes at room temperature and then treated with 1.2 equivalents of dimethylsulphate. Heat the mixture under reflux for one hour, cool to room temperature and pour into a mixture of toluene (200 ml) and water (200 ml). The layers are separated and the aqueous layer is extracted once more with an equal portion of toluene. The combined toluene layers are washed once with 1N aqueous acetic acid and then concentrated to s crude product, which is predominantly a mixture of the Compounds of Formulae XXXIII, XXXIV and XXXV with some unchanged starting material and traces of over-methylated derivatives. The desired products may be separated and purified by HPLC or HSCC chromatography using the systems as described in Example 2 above, to obtain approximately 200 mg of each of the Compounds of Formulae XXXIII, XXXIV and XXXV.

Example 11

Genes and Proteins for the Production of Compounds of Formula

*Micromonospora* sp. strain 046-ECO11 is a representative microorganism useful in the production of the compound of the invention. Strain 046-ECO11 has been deposited with the International Depositary Authority of Canada (IDAC), Bureau of Microbiology, Health Canada, 1015 Arlington Street, Winnipeg, Manitoba, Canada R3E 3R2 on Mar. 7, 2003 and was assigned IDAC accession no. 070303-01. The biosynthetic locus for the production of the compound of Formula II was identified in the genome of *Micromonospora* sp. strain 046-ECO11 using the genome scanning method described in U.S. Ser. No. 10/232,370, CA 2,352,451 and Zazopoulos et. al., *Nature Biotechnol.*, 21, 187-190 (2003).

Figure 12:
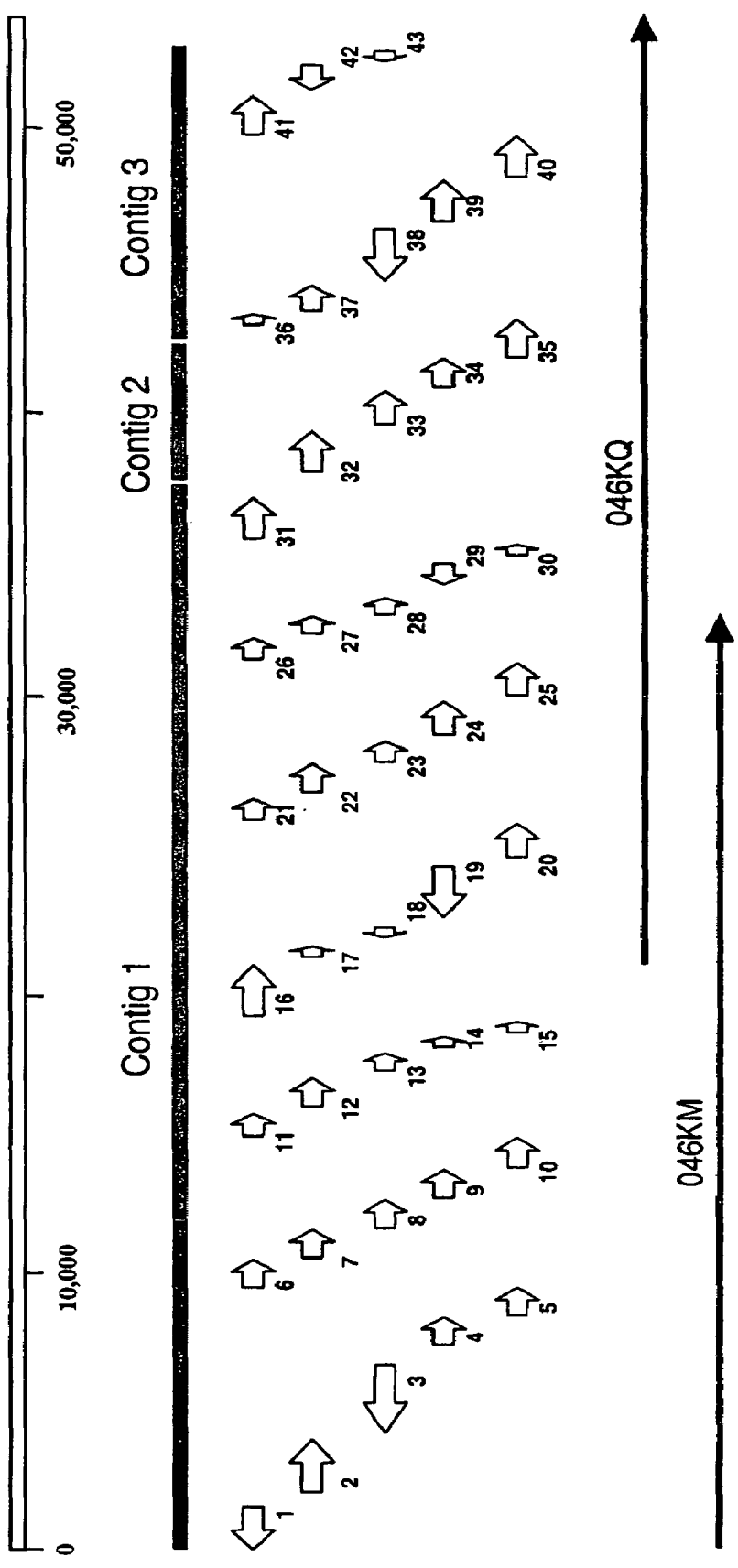
FIG. 12 shows the biosynthetic locus of ECO-04601, isolated from *Micromonospora* sp. strain 046-ECO11, including the positions of cosmids 046KM and 046KQ.

The biosynthetic locus spans approximately 52,400 base pairs of DNA and encodes 43 proteins. More than 10 kilobases of DNA sequence were analyzed on each side of the locus and these regions were deemed to contain primary genes or genes unrelated to the synthesis of the compound of Formula II. As illustrated in FIG. 12, the locus is contained within three sequences of contiguous base pairs, namely Contig 1 having the 36,602 contiguous base pairs of SEQ ID NO: 1 and comprising ORFs 1 to 31 (SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61 and 63), Contig 2 having the 5,960 contiguous base pairs of SEQ ID NO: 64 and comprising ORFs 32 to 35 (SEQ ID NOS: 66, 68, 70 and 72), and Contig 3 having the 9,762 base pairs of SEQ ID NO: 73 and comprising ORFs 36 to 43 (SEQ ID NOS: 75, 77, 79, 81, 83, 85, 87 and 89). The order, relative position and orientation of the 43 open reading frames representing the proteins of the biosynthetic locus are illustrated schematically in FIG. 12. The top line in FIG. 12 provides a scale in base pairs. The gray bars depict the three DNA contigs (SEQ ID NOS: 1, 64 and 73) that cover the locus. The empty arrows represent the 43 open reading frames of this biosynthetic locus. The black arrows represent the two deposited cosmid clones covering the locus.

The biosynthetic locus will be further understood with reference to the sequence listing which provides contiguous nucleotide sequences and deduced amino acid sequences of the locus from *Micromonospora* sp. strain 046-ECO11. The contiguous nucleotide sequences are arranged such that, as found within the biosynthetic locus, Contig 1 (SEQ ID NO: 1) is adjacent to the 5' end of Contig 2 (SEQ ID NO: 64), which in turn is adjacent to Contig 3 (SEQ ID NO: 73). The ORFs illustrated in FIG. 12 and provided in the sequence listing represent open reading frames deduced from the nucleotide sequences of Contigs 1, 2 and 3 (SEQ ID NOS: 1, 64 and 73). Referring to the Sequence Listing, ORF 1 (SEQ ID NO: 3) is the polynucleotide drawn from residues 2139 to 424 of SEQ ID NO: 1, and SEQ ID NO: 2 represents that polypeptide deduced from SEQ ID NO: 3. ORF 2 (SEQ ID NO: 5) is the polynucleotide drawn from residues 2890 to 4959 of SEQ ID NO: 1, and SEQ ID NO: 4 represents the polypeptide deduced from SEQ ID NO: 5. ORF 3 (SEQ ID NO: 7) is the polynucleotide drawn from residues 7701 to 5014 of SEQ ID NO: 1, and SEQ ID NO: 6 represents the polypeptide deduced from SEQ ID NO: 7. ORF 4 (SEQ ID NO: 9) is the polynucleotide drawn from residues 8104 to 9192 of SEQ ID NO: 1, and SEQ ID NO: 8 represents the polypeptide deduced from SEQ ID NO:

9. ORF 5 (SEQ ID NO: 11) is the polynucleotide drawn from residues 9192 to 10256 of SEQ ID NO: 1, and SEQ ID NO: 10 represents the polypeptide deduced from SEQ ID NO: 11. ORF 6 (SEQ ID NO: 13) is the polynucleotide drawn from residues 10246 to 11286 of SEQ ID NO: 1, and SEQ ID NO: 12 represents the polypeptide deduced from SEQ ID NO: 13. ORF 7 (SEQ ID NO: 15) is the polynucleotide drawn from residues 11283 to 12392 of SEQ ID NO: 1, and SEQ ID NO: 14 represents the polypeptide deduced from SEQ ID NO: 15. ORF 8 (SEQ ID NO: 17) is the polynucleotide drawn from residues 12389 to 13471 of SEQ ID NO: 1, and SEQ ID NO: 16 represents the polypeptide deduced from SEQ ID NO: 17. ORF 9 (SEQ ID NO: 19) is the polynucleotide drawn from residues 13468 to 14523 of SEQ ID NO: 1, and SEQ ID NO: 18 represents the polypeptide deduced from SEQ ID NO: 19. ORF 10 (SEQ ID NO: 21) is the polynucleotide drawn from residues 14526 to 15701 of SEQ ID NO: 1, and SEQ ID NO: 20 represents the polypeptide deduced from SEQ ID NO: 21. ORF 11 (SEQ ID NO: 23) is the polynucleotide drawn from residues 15770 to 16642 of SEQ ID NO: 1, and SEQ ID NO: 22 represents the polypeptide deduced from SEQ ID NO: 23. ORF 12 (SEQ ID NO: 25) is the polynucleotide drawn from residues 16756 to 17868 of SEQ ID NO: 1, and SEQ ID NO: 24 represents the polypeptide deduced from SEQ ID NO: 25. ORF 13 (SEQ ID NO: 27) is the polynucleotide drawn from residues 17865 to 18527 of SEQ ID NO: 1, and SEQ ID NO: 26 represents the polypeptide deduced from SEQ ID NO: 27. ORF 14 (SEQ ID NO: 29) is the polynucleotide drawn from residues 18724 to 19119 of SEQ ID NO: 1, and SEQ ID NO: 28 represents the polypeptide deduced from SEQ ID NO: 29. ORF 15 (SEQ ID NO: 31) is the polynucleotide drawn from residues 19175 to 19639 of SEQ ID NO: 1, and SEQ ID NO: 30 represents the polypeptide deduced from SEQ ID NO: 31. ORF 16 (SEQ ID NO: 33) is the polynucleotide drawn from residues 19636 to 21621 of SEQ ID NO: 1, and SEQ ID NO: 32 represents the polypeptide deduced from SEQ ID NO: 33. ORF 17 (SEQ ID NO: 35) is the polynucleotide drawn from residues 21632 to 22021 of SEQ ID NO: 1, and SEQ ID NO: 34 represents the polypeptide deduced from SEQ ID NO: 35. ORF 18 (SEQ ID NO:37) is the polynucleotide drawn from residues 22658 to 22122 of SEQ ID NO: 1, and SEQ ID NO: 36 represents the polypeptide deduced from SEQ ID NO: 37. ORF 19 (SEQ ID NO: 39) is the polynucleotide drawn from residues 24665 to 22680 of SEQ ID NO: 1, and SEQ ID NO: 38 represents the polypeptide deduced from SEQ ID NO: 39. ORF 20 (SEQ ID NO: 41) is the polynucleotide drawn from residues 24880 to 26163 of SEQ ID NO: 1, and SEQ ID NO: 40 represents the polypeptide deduced from SEQ ID NO: 41. ORF 21 (SEQ ID NO: 43) is the polynucleotide drawn from residues 26179 to 27003 of SEQ ID NO: 1, and SEQ ID NO: 42 represents the polypeptide deduced from SEQ ID NO: 43. ORF 22 (SEQ ID NO: 45) is the polynucleotide drawn from residues 27035 to 28138 of SEQ ID NO: 1, and SEQ ID NO: 44 represents the polypeptide deduced from SEQ ID NO: 45. ORF 23 (SEQ ID NO: 47) is the polynucleotide drawn from residues 28164 to 28925 of SEQ ID NO: 1, and SEQ ID NO: 46 represents the polypeptide deduced from SEQ ID NO: 47. ORF 24 (SEQ ID NO: 49) is the polynucleotide drawn from residues 28922 to 30238 of SEQ ID NO: 1, and SEQ ID NO: 48 represents the polypeptide deduced from SEQ ID NO: 49. ORF 25 (SEQ ID NO: 51) is the polynucleotide drawn from residues 30249 to 31439 of SEQ ID NO: 1, and SEQ ID NO: 50 represents the polypeptide deduced from SEQ ID NO: 51. ORF 26 (SEQ ID NO: 53) is the polynucleotide drawn from residues 31439 to 32224 of SEQ ID NO: 1, and SEQ ID NO: 52 represents the polypeptide deduced from SEQ ID NO: 53. ORF 27 (SEQ ID NO: 55) is the polynucleotide drawn from residues 32257 to 32931 of SEQ ID NO: 1, and SEQ ID NO: 54 represents the polypeptide deduced from SEQ ID NO: 55. ORF 28 (SEQ ID NO: 57) is the polynucleotide drawn from residues 32943 to 33644 of SEQ ID NO: 1, and SEQ ID NO: 56 represents the polypeptide deduced from SEQ ID NO: 57. ORF 29 (SEQ ID NO: 59) is the polynucleotide drawn from residues 34377 to 33637 of SEQ ID NO: 1, and SEQ ID NO: 58 represents the polypeptide deduced from SEQ ID NO: 59. ORF 30 (SEQ ID NO: 61) is the polynucleotide drawn from residues 34572 to 34907 of SEQ ID NO: 1, and SEQ ID NO: 60 represents the polypeptide deduced from SEQ ID NO: 61. ORF 31 (SEQ ID NO: 63) is the polynucleotide drawn from residues 34904 to 36583 of SEQ ID NO: 1, and SEQ ID NO: 62 represents the polypeptide deduced from SEQ ID NO: 63. ORF 32 (SEQ ID NO: 66) is the polynucleotide drawn from residues 23 to 1621 of SEQ ID NO: 64, and SEQ ID NO: 65 represents the polypeptide deduced from SEQ ID NO: 66. ORF 33 (SEQ ID NO: 68) is the polynucleotide drawn from residues 1702 to 2973 of SEQ ID NO: 64, and SEQ ID NO: 67 represents the polypeptide deduced from SEQ ID NO: 68. ORF 34 (SEQ ID NO: 70) is the polynucleotide drawn from residues 3248 to 4270 of SEQ ID NO: 64, and SEQ ID NO: 69 represents the polypeptide deduced from SEQ ID NO: 70. ORF 35 (SEQ ID NO: 72) is the polynucleotide drawn from residues 4452 to 5933 of SEQ ID NO: 64, and SEQ ID NO: 71 represents the polypeptide deduced from SEQ ID NO: 72. ORF 36 (SEQ ID NO: 75) is the polynucleotide drawn from residues 30 to 398 of SEQ ID NO: 73, and SEQ ID NO: 74 represents the polypeptide deduced from SEQ ID NO: 75. ORF 37 (SEQ ID NO: 77) is the polynucleotide drawn from residues 395 to 1372 of SEQ ID NO: 73, and SEQ ID NO: 76 represents the polypeptide deduced from SEQ ID NO: 77. ORF 38 (SEQ ID NO: 79) is the polynucleotide drawn from residues 3388 to 1397 of SEQ ID NO: 73, and SEQ ID NO: 78 represents the polypeptide deduced from SEQ ID NO: 79. ORF 39 (SEQ ID NO: 81) is the polynucleotide drawn from residues 3565 to 5286 of SEQ ID NO: 73, and SEQ ID NO: 80 represents the polypeptide deduced from SEQ ID NO: 81. ORF 40 (SEQ ID NO: 83) is the polynucleotide drawn from residues 5283 to 7073 of SEQ ID NO: 73, and SEQ ID NO: 82 represents the polypeptide deduced from SEQ ID NO: 83. ORF 41 (SEQ ID NO: 85) is the polynucleotide drawn from residues 7108 to 8631 of SEQ ID NO: 73, and SEQ ID NO: 84 represents the polypeptide deduced from SEQ ID NO: 85. ORF 42 (SEQ ID NO: 87) is the polynucleotide drawn from residues 9371 to 8673 of SEQ ID NO: 73, and SEQ ID NO: 86 represents the polypeptide deduced from SEQ ID NO: 87. ORF 43 (SEQ ID NO: 89) is the polynucleotide drawn from residues 9762 to 9364 of SEQ ID NO: 73, and SEQ ID NO: 88 represents the polypeptide deduced from SEQ ID NO: 89.

Some open reading frames provided in the Sequence Listing, namely ORF 2 (SEQ ID NO: 5), ORF 5 (SEQ ID NO: 11), ORF 12 (SEQ ID NO: 25), ORF 13 (SEQ ID NO: 27), ORF 15 (SEQ ID NO: 31), ORF 17 (SEQ ID NO: 35), ORF 19 (SEQ ID NO: 39), ORF 20 (SEQ ID NO: 41), ORF 22 (SEQ ID NO: 45), ORF 24 (SEQ ID NO: 49), ORF 26 (SEQ ID NO: 53) and ORF 27 (SEQ ID NO: 55) initiate with non-standard initiation codons (eg. GTG—Valine, or CTG—Leucine) rather than standard initiation codon ATG methionine. All ORFs are listed with the appropriate M, V or L amino acids at the amino-terminal position to indicate the specificity of the first codon of the ORF. It is expected, however, that in all cases the biosynthesized protein will contain a methionine residue, and more specifically a formylmethionine residue, at the amino terminal position, in keeping with the widely accepted principle that protein synthesis in bacteria initiate with methionine (formylmethionine) even when the encoding gene specifies a non-standard initiation codon (e.g. Stryer BioChemistry 3$^{rd}$ edition, 1998, W.H. Freeman and Co., New York, pp. 752-754).

ORF 32 (SEQ ID NO: 65) is incomplete and contains a truncation of 10 to 20 amino acids from its carboxy terminus. This is due to incomplete sequence information between Contigs 2 and 3 (SEQ ID NOS: 64 and 73, respectively).

Deposits of *E. coli* DH10B vectors, each harbouring a cosmid clone (designated in FIG. 12 as 046KM and 046KQ respectively) of a partial biosynthetic locus for the compound of Formula II from *Micromonospora* sp. strain 046-ECO11 and together spanning the full biosynthetic locus for production of the compound of Formula II have been deposited with the International Depositary Authority of Canada, Bureau of Microbiology, Health Canada, 1015 Arlington Street, Winnipeg, Manitoba, Canada R3E 3R2 on Feb. 25, 2003. The cosmid clone designated 046KM was assigned deposit accession numbers IDAC 250203-06, and the cosmid clone designated 046KQ was assigned deposit accession numbers IDAC 250203-07. Cosmid 046KM covers residue 1 to residue 32,250 of Contig 1 (SEQ ID NO: 1). Cosmid 046KQ covers residue 21,700 of Contig 1 (SEQ ID NO: 1) to residue 9,762 of Contig 3 (SEQ ID NO: 73). The sequence of the polynucleotides comprised in the deposited strains, as well as the amino acid sequence of any polypeptide encoded thereby are controlling in the event of any conflict with any description of sequences herein.

The deposit of the deposited strains has been made under the terms of the Budapest Treaty on the International Recognition of the Deposit of Micro-organisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement, such as that required under 35 U.S.C. §112. A license may be required to make, use or sell the deposited strains, and compounds derived therefrom, and no such license is hereby granted.

In order to identify the function of the proteins coded by the genes forming the biosynthetic locus for the production of the compound of Formula II the gene products of ORFs 1 to 43, namely SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 65, 67, 69, 71, 74, 76, 78, 80, 82, 84, 86 and 88 were compared, using the BLASTP version 2.2.10 algorithm with the default parameters, to sequences in the National Center for Biotechnology Information (NCBI) nonredundant protein database and the DECIPHER® database of microbial genes, pathways and natural products (Ecopia BioSciences Inc. St.-Laurent, QC, Canada).

The accession numbers of the top GenBank™ hits of this BLAST analysis are presented in Table 14 along with the corresponding E values. The E value relates the expected number of chance alignments with an alignment score at least equal to the observed alignment score. An E value of 0.00 indicates a perfect homolog. The E values are calculated as described in Altschul et al. *J. Mol. Biol.*, 215, 403-410 (1990). The E value assists in the determination of whether two sequences display sufficient similarity to justify an inference of homology.

TABLE 14

| ORF | Family | # aa | GenBank homology | Probability | % Identity | % Similarity | Proposed function of GenBank match |
|---|---|---|---|---|---|---|---|
| 1 | ABCC | 571 | NP_736627.1, 590aa | 1.00E−107 | 222/496 (44.76%) | 278/496 (56.05%) | ABC transporter [*Corynebacterium efficiens*] |
| | | | NP_600638.1, 510aa | 5.00E−80 | 184/500 (36.8%) | 260/500 (52%) | ABC transporter [*Corynebacterium efficiens*] |
| | | | NP_600638.1, 510aa | 3.00E−12 | 58/195 (29.74%) | 84/195 (43.08%) | ABC transporter [*Corynebacterium efficiens*] |
| 2 | RECH | 689 | CAC93719.1, 923aa | 3.00E−17 | 57/158 (36.08%) | 87/158 (55.06%) | regulator [*Lechevalieria aerocolonigenes*] |
| | | | BAC55205.1, 943aa | 3.00E−12 | 51/170 (30%) | 81/170 (47.65%) | transcriptional activator [*Streptomyces* sp.] |
| | | | NP_631154.1, 932aa | 3.00E−07 | 29/63 (46.03%) | 40/63 (63.49%) | regulator. [*Streptomyces coelicolor* A3(2) |
| 3 | REGD | 895 | CAC93719.1, 923aa | 3.00E−20 | 92/330 (27.88%) | 142/330 (43.03%) | regulator [*Lechevalieria aerocolonigenes*] |
| | | | BAC55205.1, 943aa | 1.00E−15 | 80/277 (28.88%) | 101/277 (36.46%) | activator [*Streptomyces* sp. TP-A0274] |
| | | | NP_733725.1, 908aa | 3.00E−12 | 95/339 (28.02%) | 140/339 (41.3%) | regulator [*Streptomyces coelicolor* A3(2)] |
| 4 | IDSA | 362 | NP_601376.2, 371aa | 2.00E−80 | 158/321 (49.22%) | 208/321 (64.8%) | GGPP synthase [*Corynebacterium glutamicum*] |
| | | | NP_738677.1, 366aa | 3.00E−79 | 158/330 (47.88%) | 204/330 (61.82%) | polyprenyl synthase, *Corynebacterium efficiens* |
| | | | NP_216689.1, 352aa | 2.00E−78 | 153/331 (46.22%) | 203/331 (61.33%) | idsA2 [*Mycobacterium tuberculosis* H37Rv] |
| 5 | MVKA | 354 | BAB07790.1, 345aa | 2.00E−71 | 150/326 (46.01%) | 193/326 (59.2%) | mevalonate kinase [*Streptomyces* sp. CL190] |
| | | | BAB07817.1, 334aa | 5.00E−66 | 145/324 (44.75%) | 185/324 (57.1%) | mevalonate kinase [*Kitasatospora griseola*] |
| | | | NP_720650.1, 332aa | 3.00E−36 | 95/327 (29.05%) | 157/327 (48.01%) | mevalonate kinase [*Streptococcus mutans*] |
| 6 | DMDA | 346 | BAB07791.1, 350aa | 2.00E−88 | 177/305 (58.03%) | 199/305 (65.25%) | diphosphomevalonate decarboxylase [*Streptomyces* sp.] |
| | | | BAB07818.1, 300aa | 2.00E−69 | 145/275 (52.73%) | 168/275 (61.09%) | mevalonate diPH decaroboxylase [*Kitasatospora griseola*] |
| | | | NP_785307.1, 325aa | 3.00E−44 | 105/307 (34.2%) | 141/307 (45.93%) | diphosphomevalonate decarboxylase [*Lactobacillus plantarum*] |

TABLE 14-continued

| ORF | Family | # aa | GenBank homology | Probability | % Identity | % Similarity | Proposed function of GenBank match |
|---|---|---|---|---|---|---|---|
| 7 | MVKP | 369 | BAB07792.1, 374aa | 4.00E−93 | 183/365 (50.14%) | 220/365 (60.27%) | phosphomevalonate kinase [*Streptomyces* sp. CL190] |
|  |  |  | BAB07819.1, 360aa | 6.00E−77 | 171/358 (47.77%) | 202/358 (56.42%) | phosphomevalonate kinase [*Kitasatospora griseola*] |
|  |  |  | AAG02442.1, 368aa | 2.00E−31 | 102/354 (28.81%) | 149/354 (42.09%) | 3 phosphomevalonate kinase [*Enterococcus faecalis*] |
| 8 | IPPI | 360 | Q9KWF6, 364aa | 1.00E−128 | 238/361 (65.93%) | 269/361 (74.52%) | Isopentenyl-diphosphate delta-isomerase |
|  |  |  | Q9KWG2, 363aa | 1.00E−128 | 230/349 (65.9%) | 270/349 (77.36%) | Isopentenyl-diphosphate delta-isomerase |
|  |  |  | NP_814639.1, 347aa | 5.00E−73 | 154/348 (44.25%) | 212/348 (60.92%) | isopentenyl diphosphate isomerase [*Enterococcus faecalis* |
| 9 | HMGA | 351 | BAA70975.1, 353aa | 1.00E−165 | 284/348 (81.61%) | 317/348 (91.09%) | 3-hydroxy-3-methylglutaryl coenzyme A reductase [*Streptomyces* sp.] |
|  |  |  | BAA74565.1, 353aa | 1.00E−160 | 282/347 (81.27%) | 310/347 (89.34%) | 3-hydroxy-3-methylglutaryl coenzyme A reductase [*Kitasatospora griseola*] |
|  |  |  | BAA74566.1, 353aa | 1.00E−155 | 277/347 (79.83%) | 299/347 (86.17%) | 3-hydroxy-3-methylglutaryl coenzyme A reductase [*Streptomyces* sp.] |
| 10 | KASH | 391 | BAB07795.1, 389aa | 1.00E−148 | 260/386 (67.36%) | 300/386 (77.72%) | 3-hydroxy-3-methylglutaryl CoA synthase [*Streptomyces* sp. CL190] |
|  |  |  | BAB07822.1, 346aa | 1.00E−136 | 239/343 (69.68%) | 268/343 (78.13%) | HMG-CoA synthase [*Kitasatospora griseola*] |
|  |  |  | CAD24420.1, 388aa | 6.00E−79 | 166/385 (43.12%) | 210/385 (54.55%) | HMG-CoA synthase [*Paracoccus zeaxanthinifaciens*] |
| 11 | IPTN | 290 | NP_631248.1, 295aa | 5.00E−22 | 79/282 (28.01%) | 124/282 (43.97%) | hypothetical protein [*Streptomyces coelicolor* A3(2)] |
|  |  |  | AAN65239.1, 324aa | 5.00E−06 | 70/278 (25.18%) | 112/278 (40.29%) | cloQ [*Streptomyces roseochromogenes* subsp. *oscitans*] |
| 12 | SPKG | 370 | AAM78435.1, 344aa | 5.00E−48 | 112/208 (53.85%) | 131/208 (62.98%) | two-component sensor [*Streptomyces coelicolor* A3(2)] |
|  |  |  | NP_630507.1, 382aa | 5.00E−48 | 112/208 (53.85%) | 131/208 (62.98%) | sensor kinase [*Streptomyces coelicolor* A3(2)] |
|  |  |  | ZP_00058991.1, 407aa | 9.00E−34 | 88/198 (44.44%) | 114/198 (57.58%) | Signal transduction histidine kinase [*Thermobifida fusca*] |
| 13 | RREB | 220 | NP_630508.1, 224aa | 3.00E−79 | 148/220 (67.27%) | 179/220 (81.36%) | regulatory protein [*Streptomyces coelicolor* A3(2)] |
|  |  |  | ZP_00058992.1, 221aa | 4.00E−67 | 129/218 (59.17%) | 163/218 (74.77%) | Response regulator [*Thermobifida fusca*] |
|  |  |  | NP_625364.1, 221 aa | 6.00E−66 | 134/222 (60.36%) | 164/222 (73.87%) | response regulator [*Streptomyces coelicolor* A3(2)] |
| 14 | UNES | 131 | No hit | — | — | — | — |
| 15 | UNEZ | 154 | NP_649459.2, 628aa | 7.60E−02 | 21/55 (38.18%) | 33/55 (60%) | CG1090-PB [*Drosophila melanogaster*] |
|  |  |  | NP_730819.1, 473aa | 7.60E−02 | 21/55 (38.18%) | 33/55 (60%) | CG1090-PA [*Drosophila melanogaster*] |
|  |  |  | AAM11079.1, 428aa | 7.60E−02 | 21/55 (38.18%) | 33/55 (60%) | GH23040p [*Drosophila melanogaster*] |
| 16 | OXDS | 661 | NP_242948.1, 500aa | 1.00E−52 | 129/433 (29.79%) | 197/433 (45.5%) | unknown conserved protein [*Bacillus halodurans*] |
|  |  |  | ZP_00091617.1, 480aa | 3.00E−32 | 123/426 (28.87%) | 175/426 (41.08%) | Putative multicopper oxidases [*Azotobacter vinelandii*] |
|  |  |  | NP_252457.1, 463aa | 1.00E−31 | 115/408 (28.19%) | 170/408 (41.67%) | metallo-oxidoreductase [*Pseudomonas aeruginosa* PA01] |
| 17 | UNFD | 129 | NP_437360.1, 127aa | 7.00E−33 | 73/121 (60.33%) | 87/121 (71.9%) | bleomycin resistance protein family [*Sinorhizobium meliloti*] |
|  |  |  | AAO91879.1, 123aa | 1.00E−31 | 68/117 (58.12%) | 86/117 (73.5%) | unknown [uncultured bacterium] |
|  |  |  | NP_103287.1, 131aa | 1.00E−23 | 59/122 (48.36%) | 76/122 (62.3%) | unknown protein [*Mesorhizobium loti*] |
| 18 | UNFA | 178 |  |  |  |  |  |
| 19 | CSMB | 661 | ZP_00137697.1, 769aa | 1.00E−166 | 319/622 (51.29%) | 408/622 (65.59%) | Anthranilate/para-aminobenzoate synthase [*Pseudomonas aeruginosa* |
|  |  |  | NP_250594.1, 627aa | 1.00E−166 | 319/622 (51.29%) | 408/622 (65.59%) | phenazine biosynthesis protein PhzE [*Pseudomonas aeruginosa* PA01] |
|  |  |  | ZP_00137701.1, 687aa | 1.00E−166 | 319/622 (51.29%) | 408/622 (65.59%) | Anthranilate/para-aminobenzoate synthas [*Pseudomonas aeruginosa* |
| 20 | AAKD | 427 | P41403, 421aa | 1.00E−64 | 161/420 (38.33%) | 214/420 (50.95%) | Aspartokinase (Aspartate kinase) |
|  |  |  | ZP_00057166.1, 445aa | 2.00E−64 | 154/415 (37.11%) | 218/415 (52.53%) | Aspartokinases [*Thermobifida fusca*] |
|  |  |  | AAD49567.1, 421aa | 6.00E−64 | 152/412 (36.89%) | 216/412 (52.43%) | aspartokinase subunit A [*Amycolatopsis mediterranei*] |
| 21 | ALDB | 274 | NP_275722.1, 266aa | 2.00E−53 | 104/231 (45.02%) | 147/231 (63.64%) | conserved protein [*Methanothermobacter thermautotrophicus*] |
|  |  |  | NP_614692.1, 270aa | 2.00E−52 | 104/240 (43.33%) | 146/240 (60.83%) | Fructose-1,6-bisphosphate aldolase [*Methanopyrus kandleri* AV19] |

TABLE 14-continued

| ORF | Family | # aa | GenBank homology | Probability | % Identity | % Similarity | Proposed function of GenBank match |
|---|---|---|---|---|---|---|---|
| | | | NP_615406.1, 267aa | 2.00E-50 | 99/231 (42.86%) | 141/231 (61.04%) | fructose-bisphosphate aldolase [*Methanosarcina acetivorans* str. C2A] |
| 22 | UNFC | 367 | NP_275723.1, 378aa | 4.00E-46 | 116/308 (37.66%) | 171/308 (55.52%) | conserved protein [*Methanothermobacter thermautotrophicus*] |
| | | | NP_614691.1, 402aa | 2.00E-45 | 115/295 (38.98%) | 163/295 (55.25%) | alternative 3-dehydroquinate synthase [*Methanopyrus kandleri*] |
| | | | NP_248244.1, 361aa | 2.00E-43 | 103/255 (40.39%) | 150/255 (58.82%) | conserved hypothetical protein [*Methanococcus jannaschii*] |
| 23 | HYDK | 253 | NP_577771.1, 247aa | 4.00E-14 | 55/178 (30.9%) | 87/178 (48.88%) | metal-dependent hydrolase [*Pyrococcus furiosus* DSM 3638] |
| | | | NP_142108.1, 247aa | 1.00E-12 | 50/151 (33.11%) | 78/151 (51.66%) | hypothetical protein PH0093 [*Pyrococcus horikoshii*] |
| | | | NP_125791.1, 248aa | 1.00E-11 | 42/151 (27.81%) | 76/151 (50.33%) | hypothetical protein [*Pyrococcus abyssi*] |
| 24 | ADSA | 438 | NP_070499.1, 433aa | 2.00E-41 | 122/347 (35.16%) | 171/347 (49.28%) | coenzyme F390 synthetase [*Archaeoglobus fulgidus*] |
| | | | NP_618724.1, 434aa | 5.00E-41 | 119/345 (34.49%) | 171/345 (49.57%) | coenzyme F390 synthetase [*Methanosarcina acetivorans*] |
| | | | NP_632700.1, 437aa | 7.00E-41 | 121/345 (35.07%) | 171/345 (49.57%) | Coenzyme F390 synthetase [*Methanosarcina mazei* Goe1] |
| 25 | HOXV | 396 | ZP_00027430.1, 442aa | 8.00E-76 | 152/358 (42.46%) | 211/358 (58.94%) | 2-polyprenyl-6-methoxyphenol hydroxylase [*Burkholderia fungorum*] |
| | | | NP_627457.1, 420aa | 1.00E-71 | 161/420 (38.33%) | 216/420 (51.43%) | salicylate hydroxylase [*Streptomyces coelicolor* A3(2)] |
| | | | ZP_00033877.1, 403aa | 2.00E-68 | 146/395 (36.96%) | 200/395 (50.63%) | 2-polyprenyl-6-methoxyphenol hydroxylase [*Burkholderia fungorum*] |
| 26 | SDRA | 261 | NP_391080.1, 261aa | 6.00E-58 | 119/261 (45.59%) | 149/261 (57.09%) | 2,3-dihydro-2,3-dihydroxybenzoate dehydrogenase [*Bacillus subtilis*] |
| | | | ZP_00059512.1, 260aa | 1.00E-55 | 116/259 (44.79%) | 144/259 (55.6%) | Dehydrogenase [*Thermobifida fusca*] |
| | | | AAG31126.1, 257aa | 9.00E-55 | 117/257 (45.53%) | 144/257 (56.03%) | MxcC [*Stigmatella aurantiaca*] |
| 27 | DHBS | 224 | Q51790, 207aa | 7.00E-60 | 110/198 (55.56%) | 142/198 (71.72%) | isochorismatase |
| | | | Q51518, 207aa | 1.00E-58 | 110/198 (55.56%) | 140/198 (70.71%) | isochorismatase |
| | | | NP_391077.1, 312aa | 2.00E-58 | 106/203 (52.22%) | 139/203 (68.47%) | isochorismatase [*Bacillus subtilis*] |
| 28 | SDRA | 233 | NP_103491.1, 242aa | 9.00E-21 | 74/230 (32.17%) | 112/230 (48.7%) | acyl-carrier protein reductase [*Mesorhizobium loti*] |
| | | | AAL14912.1, 245aa | 1.00E-15 | 65/229 (28.38%) | 100/229 (43.67%) | short-chain dehydrogenase [*Rhizobium leguminosarum* bv. *trifolii*] |
| | | | NP_902480.1, 235aa | 7.00E-15 | 67/229 (29.26%) | 100/229 (43.67%) | oxidoreductase [*Chromobacterium violaceum*] |
| 29 | UNIQ | 246 | S18541, 281aa | 4.50E-02 | 43/146 (29.45%) | 63/146 (43.15%) | hypothetical protein 3 - *Streptomyces coelicolor* |
| | | | NP_629228.1, 281aa | 5.90E-02 | 43/146 (29.45%) | 63/146 (43.15%) | hypothetical protein [*Streptomyces coelicolor* A3(2)] |
| 30 | UNFE | 111 | ZP_00058149.1, 130aa | 1.00E-10 | 35/97 (36.08%) | 47/97 (48.45%) | membrane protein [*Thermobifida fusca*] |
| | | | NP_737701.1, 120aa | 1.00E-09 | 37/111 (33.33%) | 51/111 (45.95%) | hypothetical protein [*Corynebacterium efficiens*] |
| | | | NP_827629.1, 118aa | 7.00E-09 | 35/105 (33.33%) | 51/105 (48.57%) | hypothetical protein [*Streptomyces avermitilis* MA-4680] |
| 31 | EFFT | 559 | ZP_00058148.1, 537aa | 2.00E-67 | 165/517 (31.91%) | 253/517 (48.94%) | Predicted symporter [*Thermobifida fusca*] |
| | | | NP_626090.1, 544aa | 4.00E-66 | 162/521 (31.09%) | 257/521 (49.33%) | transport protein [*Streptomyces coelicolor* A3(2)] |
| | | | NP_827630.1, 549aa | 7.00E-63 | 160/523 (30.59%) | 256/523 (48.95%) | sodium-dependent symporter [*Streptomyces avermitilis*] |
| 32 | HOYH | 532 | AAM96655.1, 544aa | 2.00E-92 | 206/526 (39.16%) | 279/526 (53.04%) | 2,4-dihydroxybenzoate monooxygenase [*Sphingobium chlorophenolicum*] |
| | | | ZP_00029353.1, 543aa | 1.00E-73 | 188/539 (34.88%) | 263/539 (48.79%) | 2-polyprenyl-6-methoxyphenol hydroxylase [*Burkholderia fungorum*] |
| | | | NP_769326.1, 569aa | 5e-62 | 173/519 (33.33%) | 251/519 (48.36%) | blr2686 [*Bradyrhizobium japonicum*] dbj |
| 33 | DAHP | 423 | T03226, 391aa | 1.00E-111 | 207/383 (54.05%) | 259/383 (67.62%) | hypothetical protein - *Streptomyces hygroscopicus* |
| | | | ZP_00137693.1, 405aa | 3.00E-87 | 172/385 (44.68%) | 233/385 (60.52%) | DAHP synthase [*Pseudomonas aeruginosa* UCBPP-PA14] |
| | | | NP_250592.1, 405aa | 1.00E-86 | 169/380 (44.47%) | 232/380 (61.05%) | phenazine biosynthesis protein PhzC [*Pseudomonas aeruginosa* |

TABLE 14-continued

| ORF | Family | # aa | GenBank homology | Probability | % Identity | % Similarity | Proposed function of GenBank match |
|---|---|---|---|---|---|---|---|
| 34 | REGG | 340 | BAC53615.1, 346aa | 1.00E−67 | 142/307 (46.25%) | 192/307 (62.54%) | regulator protein [*Streptomyces kasugaensis*] |
| | | | S44506, 424aa | 3.00E−66 | 141/305 (46.23%) | 182/305 (59.67%) | regulator protein - *Streptomyces glaucescens* |
| | | | AAK81822.1, 348aa | 1.00E−65 | 141/323 (43.65%) | 192/323 (59.44%) | transcriptional regulator [*Streptomyces lavendulae*] |
| 35 | UNFJ | 493 | ZP_00073237.1, 678aa | 7.00E−35 | 124/454 (27.31%) | 197/454 (43.39%) | RTX toxins [*Trichodesmium erythraeum* IMS101] |
| | | | NP_484716.1, 433aa | 3.00E−05 | 109/470 (23.19%) | 172/470 (36.6%) | similar to vanadium chloroperoxidase [*Nostoc* sp.] |
| | | | ZP_00067005.1, 667aa | 7.40E−02 | 37/139 (26.62%) | 52/139 (37.41%) | hypothetical protein [*Microbulbifer degradans* 2-40] |
| 36 | RECI | 112 | NP_627088.1, 125aa | 3.00E−17 | 48/100 (48%) | 59/100 (59%) | hypothetical protein [*Streptomyces coelicolor* A3(2)] |
| | | | NP_846017.1, 109aa | 7.00E−15 | 40/101 (39.6%) | 60/101 (59.41%) | hypothetical protein [*Bacillus anthracis* str. Ames] |
| | | | NP_241272.1, 174aa | 9.00E−15 | 39/106 (36.79%) | 62/106 (58.49%) | unknown conserved protein [*Bacillus halodurans*] |
| 37 | UNIQ | 325 | NP_422203.1, 187aa | 1.00E−03 | 24/61 (39.34%) | 36/61 (59.02%) | hypothetical protein [*Caulobacter crescentus* CB15] |
| 38 | OXAH | 663 | ZP_00058724.1, 659aa | 0.00E+00 | 370/647 (57.19%) | 435/647 (67.23%) | Acyl-CoA dehydrogenases [*Thermobifida fusca*] |
| | | | AAB97825.1, 433aa | 5.00E−93 | 203/446 (45.52%) | 251/446 (56.28%) | acyl-CoA oxidase [*Myxococcus xanthus*] |
| | | | AAF14635.1, 694aa | 5.00E−85 | 211/565 (37.35%) | 292/565 (51.68%) | 1 acyl-CoA oxidase [*Petroselinum crispum*] |
| 39 | ABCA | 537 | T14162, 574aa | 9.00E−62 | 189/509 (37%) | 240/509 (47%) | hABC transport protein - *Mycobacterium smegmatis* |
| | | | NP_624808.1 | 4.00E−60 | 184/540 (35%) | 251/540 (46%) | ABC transporter [*Streptomyces coelicolor* A3(2)] |
| | | | NP_822745.1 | 8.00E−32 | 124/392 (31%) | 168/392 (42%) | ABC transportert [*Streptomyces avermitilis* MA-4680] |
| 40 | ABCA | 596 | T14180, 1122aa | 1.00E−107 | 236/594 (39.73%) | 300/594 (50.51%) | exiT protein - *Mycobacterium smegmatis* |
| | | | AAC82548.1, 589aa | 1.00E−107 | 234/583 (40.14%) | 295/583 (50.6%) | unknown [*Mycobacterium smegmatis*] |
| | | | NP_624810.1, 601aa | 3.00E−97 | 222/593 (37.44%) | 283/593 (47.72%) | ABC-transporter [*Streptomyces coelicolor* A3(2)] |
| 41 | UNIQ | 507 | NP_831570.1, 676aa | 8.00E−07 | 62/262 (23.66%) | 116/262 (44.27%) | methyltransferases [*Bacillus cereus*] |
| | | | NP_655735.1, 676aa | 2.00E−06 | 61/262 (23.28%) | 116/262 (44.27%) | ubiE/COQ5 methyltransferase family [*Bacillus anthracis*] |
| | | | NP_844290.1, 681aa | 2.00E−06 | 61/262 (23.28%) | 116/262 (44.27%) | hypothetical protein [*Bacillus anthracis* str. Ames] |
| 42 | | 232 | NP_830809.1, 208aa | 8.00E−08 | 46/210 (21.9%) | 74/210 (35.24%) | Transporter, LysE family [*Bacillus cereus*] |
| | | | NP_844737.1, 210aa | 2.00E−07 | 46/210 (21.9%) | 74/210 (35.24%) | homoserine/threonine efflux protein [*Bacillus anthracis*] |
| | | | NP_655752.1, 208aa | 1.00E−06 | 47/210 (22.38%) | 75/210 (35.71%) | LysE, LysE type translocator [*Bacillus anthracis*] |
| 43 | | 132 | NP_827272.1, 127aa | 4.00E−09 | 38/107 (35.51%) | 52/107 (48.6%) | hypothetical protein [*Streptomyces avermitilis* MA-4680] |
| | | | NP_246491.1, 112aa | 5.90E−02 | 21/94 (22.34%) | 44/94 (46.81%) | unknown [*Pasteurella multocida*] |

The ORFs encoding proteins involved in the biosynthesis of compounds of Formula II are assigned a putative function and grouped together in families based on sequence similarity to known proteins. To correlate structure and function, the protein families are given a four-letter designation used throughout the description and figures as indicated in Table 15. The meaning of the four letter designations is as follows: AAKD designates an amino acid kinase; ABCA and ABCC designate ABC transporters; ADSA designates an amide synthetase; ALDB designates an aldolase function; CSMB designates a chorismate transaminase; DAHP designates a 3,4-dideoxy-4-amino-D-arabino-heptulosonic acid 7-phosphate synthase activity; DHBS designates a 2,3-dihydro-2,3-dihydroxybenzoate synthase activity; DMDA designates a diphosphomevalonate decarboxylase; EFFT designates an efflux protein; HMGA designates a 3-hydroxy-3-methylglutaryl-CoA reductase; HOXV designates a monooxygenase activity; HOYH designates a hydroxylase/decarboxylase activity; HYDK designates a hydrolase activity; IDSA designates an isopentenyl diphosphate synthase; IPPI designates an isopentenyl diphosphate isomerase; IPTN designates an isoprenyltransferase; KASH designates 3-hydroxy-3-methylglutaryl-CoA synthase; MVKA designates a mevalonate kinase; MVPK designates a phosphomevalonate kinase; OXAH designates an acylCoA oxidase; OXDS designates an oxidoreductase; RECH, RECI, REGD, REGG and RREB designate regulators; SDRA designates a dehydrogenase/ketoreductase, SPKG designates a sensory protein kinase; UNES, UNEZ, UNFA, UNFC, UNFD, UNFE, UNFJ and UNIQ designate proteins of unknown function.

TABLE 15

| FAMILY | FUNCTION |
|---|---|
| AAKD | amino acid kinase; strong homology to primary aspartate kinases, converting L-aspartate to 4-phospho-L-aspartate |
| ABCA | ABC transporter |
| ABCC | ABC transporter |
| ADSA | adenylating amide synthetase |

TABLE 15-continued

| FAMILY | FUNCTION |
|---|---|
| ALDB | aldolase; similarity to fructose-1,6-biphosphate aldolase that generates D-glyceraldehyde-3Ph, precursor of D-erythrose-4Ph involved in the shikimate pathway |
| CSMB | chorismate transaminase, similarity to anthranilate synthase |
| DAHP | DAHP synthase, class II; involved in formation of aminoDAHP from PEP and erythrose-4-phosphate |
| DHBS | 2,3-dihydro-2,3-dihydroxybenzoate synthase (isochorismatase) |
| DMDA | diphosphomevalonate decarboxylase (mevalonate pyro-phosphate decarboxylase) |
| EFFT | efflux protein |
| HMGA | HMG-CoA reductase; converts 3-hydroxy-3-methylglutaryl-CoA to mevalonate plus CoA in isoprenoid biosynthesis |
| HOXV | FAD monooxygenase; shows homology to a variety of monooxygenases including salicylate hydroxylases, zeaxanthin epoxidases |
| HOYH | hydroxylase/decarboxylase; FAD-dependent monooxygenase |
| HYDK | hydrolase |
| IDSA | isoprenyl diphosphate synthase, catalyzes the addition of 2 molecules of isopentenyl pyrophosphate to dimethylallyl pyrophosphate to generate GGPP |
| IPPI | isopentenyl diphosphate isomerase, catalyzes the isomerization of IPP to produce dimethylallyl diphosphate |
| IPTN | isoprenyltransferase; catalyzes covalent N-terminal attachment of isoprenyl units to amide groups of nitrogen-containing heterocycle rings |
| KASH | HMG-CoA synthase; condenses acetyl-CoA with acetoacetyl-CoA to form 3-hydroxy-3-methylglutaryl-CoA |
| MVKA | mevalonate kinase; converts mevalonate to 5-phosphomevalonate in the mevalonate pathway of isoprenoid biosynthesis |
| MVKP | phosphomevalonate kinase; converts 5-phosphomevalonate to 5-diphosphomevalonate in the mevalonate pathway of isoprenoid biosynhesis |
| OXAH | acyl CoA oxidase |
| OXDS | oxidoreductase |
| RECH | regulator |
| RECI | regulator; similarity to PadR transcriptional regulators involved in repression of phenolic acid metabolism |
| REGD | transcriptional regulator; relatively large regulators with an N-terminal ATP-binding domain containing Walker A and B motifs and a C-terminal LuxR type DNA-binding domain |
| REGG | regulator |
| RREB | response regulator; similar to response regulators that are known to bind DNA and act as transcriptional activators |
| SDRA | dehydrogenase/ketoreductase, NAD-dependent |
| SPKG | sensory protein kinase, two component system |
| UNES | unknown function |
| UNEZ | unknown function |
| UNFA | unknown function |
| UNFC | unknown function |
| UNFD | unknown function |
| UNFE | putative membrane protein |
| UNFJ | unknown function |
| UNIQ | unknown function |

Figure 14:
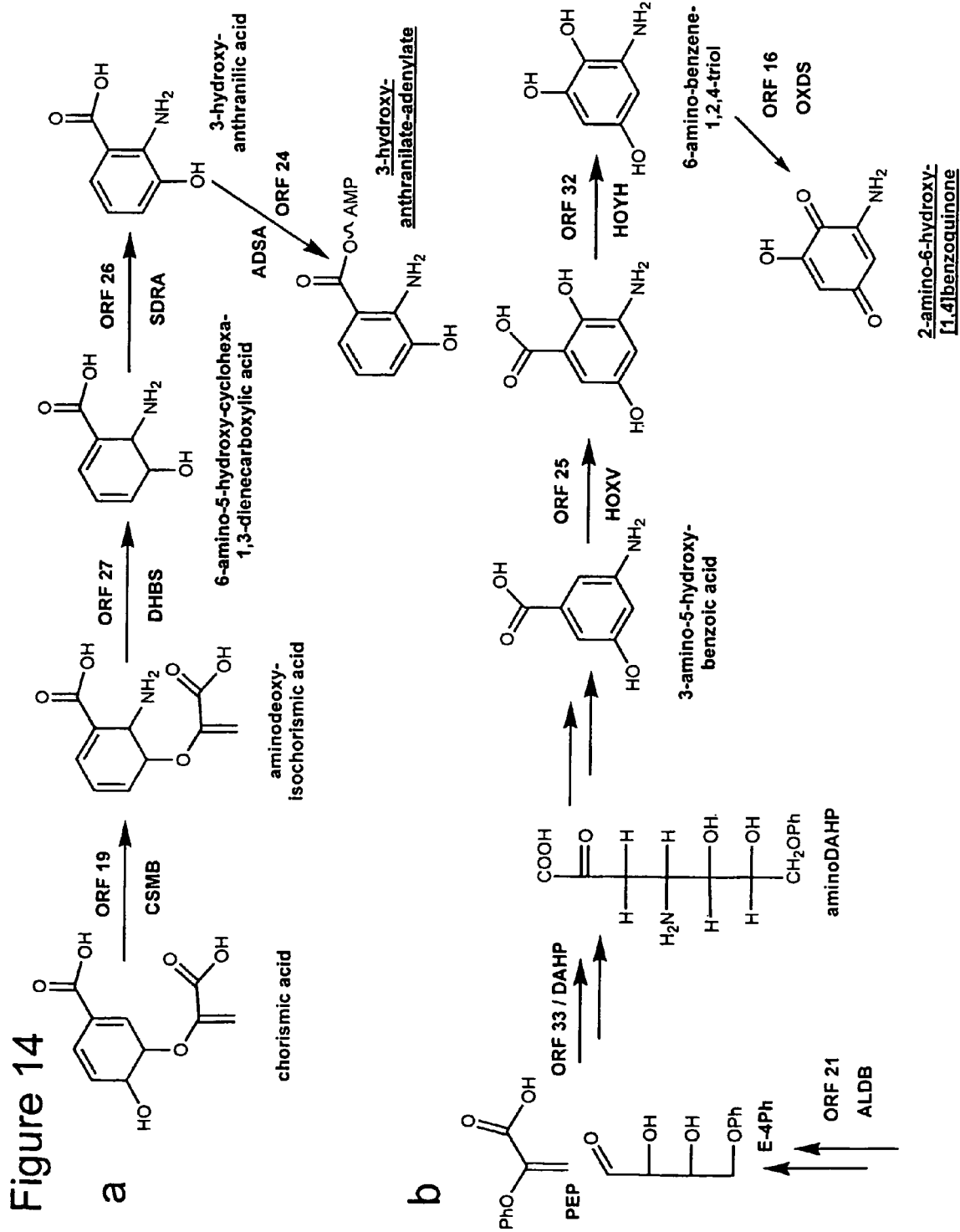
FIG. 14 shows a schematic diagram of the biosynthetic pathway for the production of (a) 3-hydroxy-anthranilate-adenylate, and (b) 2-amino-6-hydroxy-[1,4]benzoquinone components as specified by ORFs present in the locus encoding ECO-04601. Biosynthetic enzymes are indicated by their ORF number and family designation.
Figure 15:
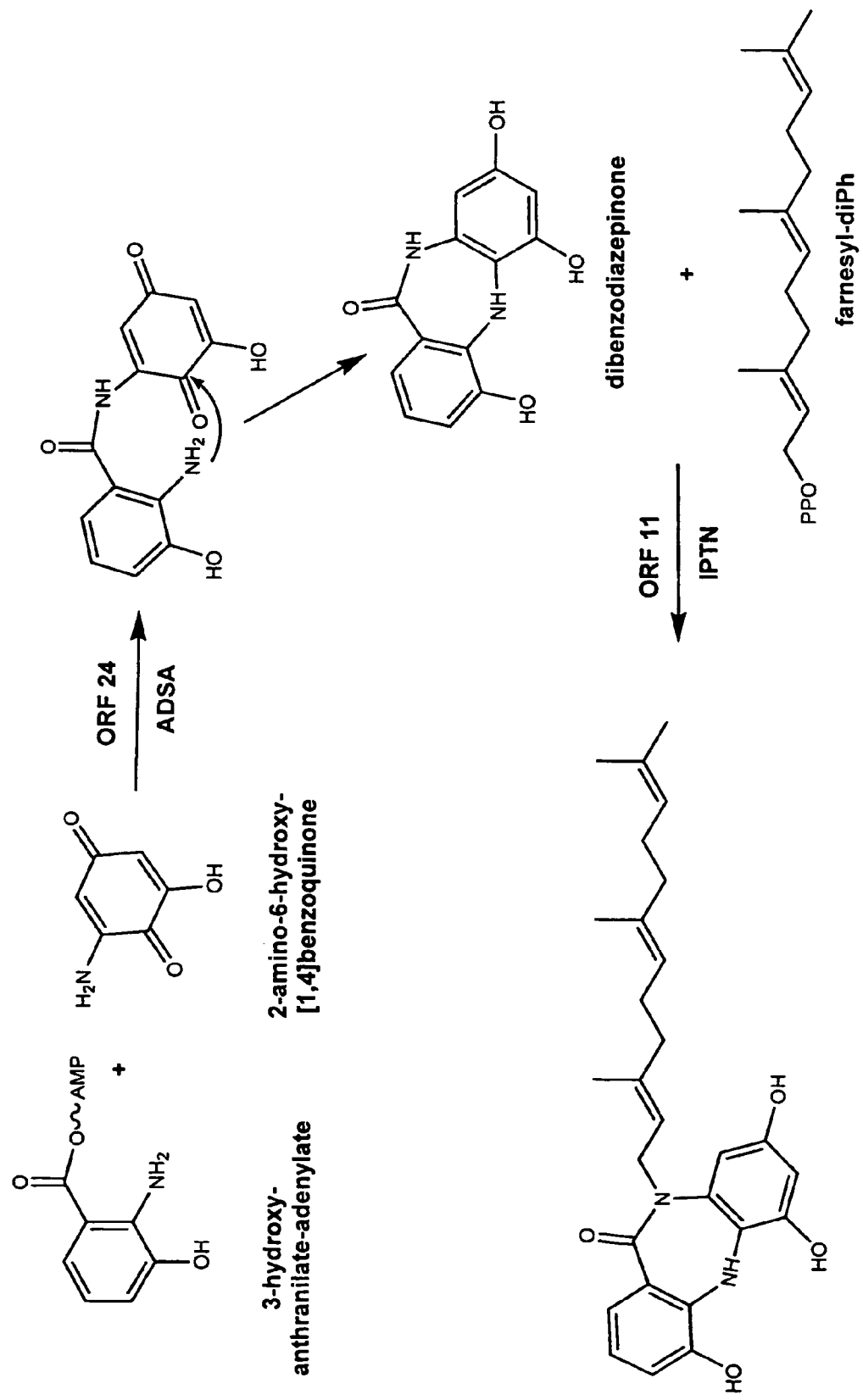
FIG. 15 shows a schematic diagram of the biosynthetic pathway for the assembly of the ECO-04601 precursors, farnesyl-diphosphate, 3-hydroxy-anthranilate-adenylate and 2-amino-6-hydroxy-[1,4]benzoquinone. Biosynthetic enzymes are indicated by their ORF number and family designation.

Biosynthesis of the compound of Formula II involves the action of various enzymes that synthesize the three building blocks of the compound, namely the farnesyl-diphosphate component (FIG. 13), the 3-hydroxy-anthranilate-adenylate component (FIG. 14a) and the 2-amino-6-hydroxy-benzoquinone component (FIG. 14b) that are subsequently condensed to form the final compound (FIG. 15).

Figure 13:
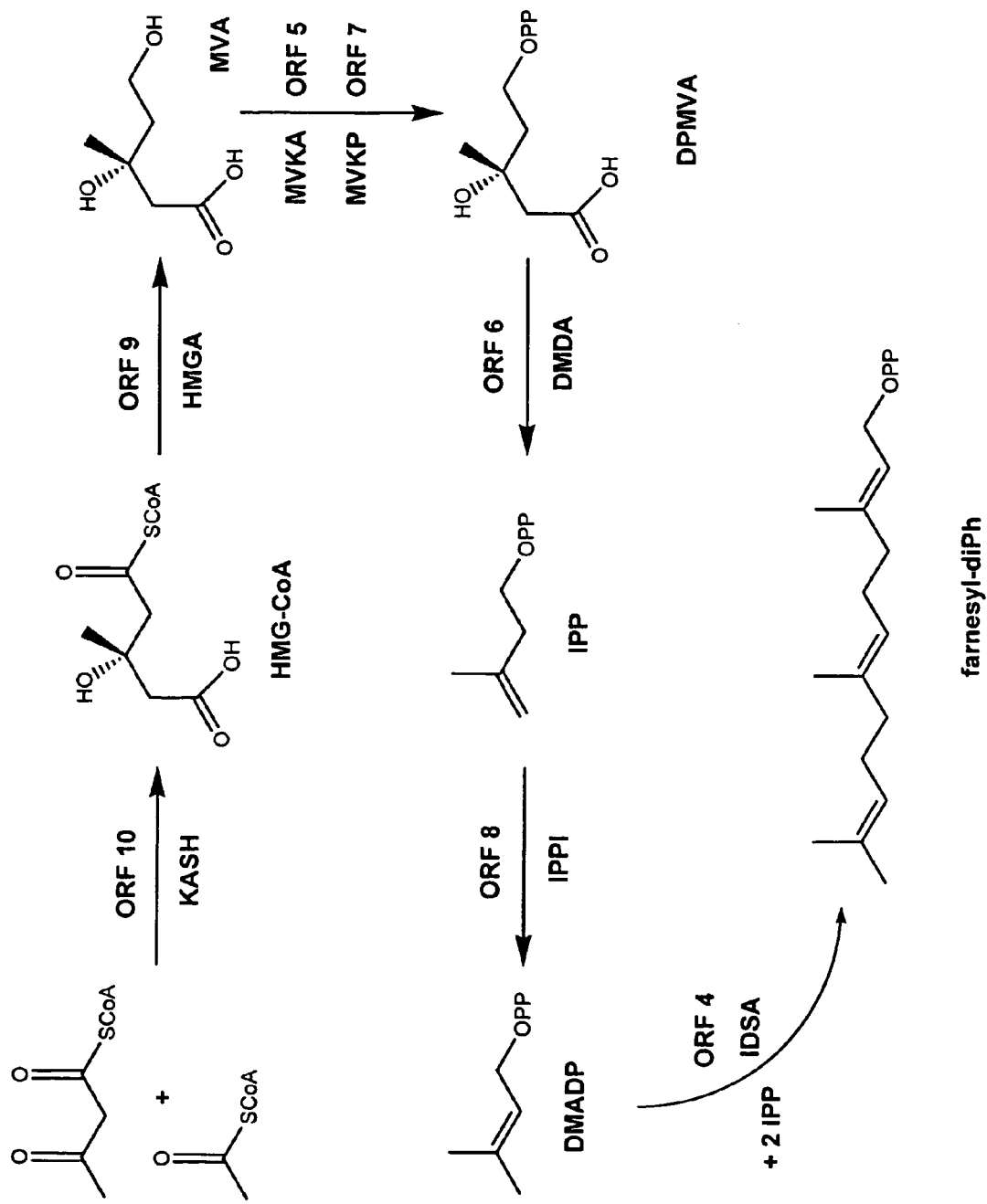
FIG. 13 shows a schematic diagram of the biosynthetic pathway for the production of the farnesyl-diphosphate group of ECO-04601 with biosynthetic enzymes indicated by their ORF number and family designation.

The farnesyl-diphosphate biosynthesis involves the concerted action of seven enzymes (FIG. 13). ORF 10 (KASH) (SEQ ID NO: 20) encodes a hydroxymethylglutaryl-CoA synthase that catalyzes an aldol addition of acetyl-CoA onto acetoacyl-CoA to yield 3-hydroxy-3-methylglutaryl-CoA (HMG-CoA). This product is subsequently reduced through the action of ORF 9 (HMGA) (SEQ ID NO: 18) to form mevalonic acid (MVA). ORF 5 (MVKA) (SEQ ID NO: 10) phosphorylates mevalonate to 5'-phosphomevalonate using ATP as the phosphate donor. The next step in the farnesyl-diphosphate biosynthesis is the phosphorylation reaction of the 5'-phosphomevalonate to 5'-pyrophosphomevalonate (DPMVA) that is catalyzed by ORF 7 (MVKP) (SEQ ID NO: 14). Subsequent decarboxylation of 5'-pyrophosphomevalonate catalyzed by ORF 6 (DMDA) (SEQ ID NO: 12) yields isopentenyl diphosphate (IPP) which is then converted to dimethylallyidiphosphate (DMADP) through the action of ORF 8 (IPPI) (SEQ ID NO: 16) that has isomerase enzymatic activity. The final step in the biosynthesis of farnesyl-diphosphate is the condensation of one molecule of dimethylallyidiphosphate with two molecules of isopentenyl diphosphate catalyzed by the isoprenyl diphosphate synthase ORF 4 (IDSA) (SEQ ID NO: 8). The described pathway involved in synthesis of farnesyl-diphosphate is entirely consistent with related mevalonate pathways described in other actinomycete species (Takagi et al., J. Bacteriol. 182, 4153-4157, (2000)).

Biosynthesis of the 3-hydroxy-anthranilate component involves the use of precursors derived from the shikimate pathway (FIG. 14a). Chorismic acid is transaminated through the action of ORF 19 (CSMB) (SEQ ID NO: 38) to form aminodeoxyisochorismic acid. This enzyme resembles anthranilate synthases and is likely to catalyze specifically the transfer of the amino group using glutamine as the amino donor. The next step involves isochorismatase activity and is mediated by ORF 27 (DHBS) (SEQ ID NO: 54). This reaction consists in the removal of the pyruvate side chain from aminodeoxyisochorismic acid to form 6-amino-5-hydroxy-cyclohexa-1,3-dienecarboxylic acid. This compound is subsequently oxidized through the action of ORF 26 (SDRA) (SEQ ID NO: 52) yielding 3-hydroxy-anthranilic acid. ORF 24 (ADSA) (SEQ ID NO: 48) catalyzes the activation of 3-hydroxy-anthranilic acid through adenylation generating the 3-hydroxy-anthranilate-adenylate component (FIG. 14a).

Biosynthesis of the 2-amino-6-hydroxy-benzoquinone component of the compound of Formula II, requires components derived from the aminoshikimate pathway. FIG. 14b depicts the series of enzymatic reactions involved in the biosynthesis of this constituent. ORF 21 (ALDB) (SEQ ID NO: 42) resembles aldolases involved in the generation of precursors of D-erythrose-4-phosphate which is part of the aminoshikimate pathway used for the generation of 2-amino-6-hydroxy-[1,4]-benzoquinone. ORF 33 (DAHP) (SEQ ID NO: 67) catalyzes the initial step in the aminoshikimate pathway that corresponds to the formation of 3,4-dideoxy-4-amino-D-arabino-heptulosonic acid 7-phosphate (amino DAHP) from phosphoenolpyruvate (PEP) and erythrose 4-phosphate (E-4Ph). Subsequent reactions leading to 3-amino-5-hydroxy-benzoic acid are catalyzed by enzymes provided by primary metabolism biosynthetic pathways present in *Micromonospora* sp. strain 046-ECO11. ORF 25 (HOXV) (SEQ ID NO: 50) hydroxylates 3-amino-5-hydroxy-benzoic acid at position 2, generating 3-amino-2,5-dihydroxy-benzoic acid. This intermediate is further modified by ORF 32 (HOYH) (SEQ ID NO: 65) that catalyzes a decarboxylative oxidation reaction yielding 6-amino-benzene-1,2,4-triol. A final oxidation reaction is performed by ORF 16 (OXDS) (SEQ ID NO: 32) yielding 2-amino-6-hydroxy-[1,4]-benzoquinone (FIG. 14b).

Assembly of the three components resulting in the compound of Formula II is catalyzed by ORFs 24 and 11 (FIG. 15). ORF 24 (ADSA) (SEQ ID NO: 48) catalyzes the condensation of the adenylated 3-hydroxy-anthranilate with the 2-amino-6-hydroxy-[1,4]-benzoquinone component. A spontaneous condensation between the free amino group of the 3-hydroxy-anthranilate and one of the carbonyl groups present on the 2-amino-6-hydroxy-[1,4]-benzoquinone component occurs yielding a dibenzodiazepinone intermediate. This compound is further modified through transfer of the farnesyl group of the farnesyl-diphosphate intermediate onto the nitrogen of the amide of the dibenzodiazepinone catalyzed by ORF 11 (IPTN) (SEQ ID NO: 22) and resulting in the formation of the compound of Formula II (FIG. 15).

Additional ORFs, namely ORF 2 (RECH) (SEQ ID NO: 4), ORF 3 (REGD) (SEQ ID NO: 6), ORF 12 (SPKG) (SEQ ID NO: 24), ORF 13 (RREB) (SEQ ID NO: 26), ORF 34 (REGG) (SEQ ID NO: 69) and ORF 36 (RECI) (SEQ ID NO: 74) are involved in the regulation of the biosynthetic locus encoding the compound of Formula II. Other ORFs, namely ORF 1 (ABCC) (SEQ ID NO: 2), ORF 31 (EFFT) (SEQ ID NO: 62), ORFs 39 and 40 (ABCA) (SEQ ID NOS: 80 and 82, respectively) and ORF 42 (SEQ ID NO: 86) are involved in transport. Other ORFs involved in the biosynthesis of the compound of Formula II include ORF 20 (AAKD) (SEQ ID NO: 40), ORF 23 (HYDK) (SEQ ID NO: 46), ORF 38 (OXAH) (SEQ ID NO: 78) as well as ORFs 14, 15, 17, 18, 22, 29, 30, 35, 37, 41 and 43 (SEQ ID NOS: 28, 30, 34, 34, 44, 58, 60, 71, 76, 84 and 88, respectively) of unknown function.

TABLE 16

PREFERRED MEDIA COMPOSITION FOR PRODUCTION OF ECO-04601

| COMPONENT | QB | MA | KH | RM | JA | FA |
|---|---|---|---|---|---|---|
| pH*5 | 7.2 | 7.5 | 7 | 6.85 | 7.3 | 7.0 |
| Glucose | 12 | | 10 | 10 | | 10 |
| Sucrose | | | | 100 | | |
| Lactose | | | | | | |
| Cane molasses | | | | | | 15 |
| Corn starch | | | | | 30 | |
| Soluble starch | 10 | 25 | | | | |
| Potato dextrin | | | | 20 | | 40 |
| Corn steep solid | | | | | | |
| Corn steep | 5 | | | | 15 | |
| Dried yeast | | 2 | | | | |
| Yeast extract | | | | 5 | | |
| Malt extract | | | | | 35 | |
| Pharmamedia ™ | 10 | | | | 15 | |
| Glycerol | | | | | | |

TABLE 16-continued

PREFERRED MEDIA COMPOSITION FOR PRODUCTION OF ECO-04601

| COMPONENT | QB | MA | KH | RM | JA | FA |
|---|---|---|---|---|---|---|
| NZ-Amine | | | 5 | | | 10 |
| Soybean | | 15 | | | | |
| Soybean flour | | | | | | |
| Meat extract | | | | | | |
| Bacto-peptone | | | | | | |
| $MgSO_4 \cdot 7H_2O$ | | | | | | 1 |
| $MgCl_2 \cdot 6H_2O$ | | | | | | |
| $CaCO_3$ | | 4 | 1 | | 2 | 2 |
| NaCl | | 5 | | | | |
| $(NH_4)_2 SO_4$ | | 2 | | | | |
| $K_2 SO_4$ | | | | 0.25 | | |
| $MnCl_2 \cdot 4H_2O$ | | | | | | |
| $MgCl_2 \cdot 6H_2O$ | | | | 10 | | |
| $FeCl_2 \cdot 4H_2O$ | | | | | | |
| $ZnCl_2$ | | | | | | |
| $Na_2HPO_4$ | | | | | | 3 |
| Thiamine | | | | | | |
| Casamino acid | | | | 0.1 | | |
| Proflo oil | 4 | | | | | |
| MOPS | | | | 21 | | |
| Trace element solution*3 ml/L | | | | 2 | | |

Unless otherwise indicated all the ingredients are in gm/L.
*3Trace elements solution contains: $ZnCl_2$ 40 mg; Fe $Cl_3 6H_2O$ (200 mg); $CuCl_2$ $2H_2O$ (10 mg); $MnCl_2 \cdot 4H_2O$; $Na_2B_4O_7 \cdot 10H_2O$ (10 mg); $(NH_4)_6$ $MO_7O_{24} \cdot 4H_2O$ (10 mg) per liter.
*5The pH is to adjusted as marked prior to the addition of $CaCO_3$.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

We claim:

1. Cosmid 046KM deposited under IDAC accession no. 250203-06.

2. A prokaryotic host cell comprising the cosmid of claim 1.

3. The prokaryotic host cell of claim 2, wherein said host cell is selected from the group consisting of *E. coli, Streptomyces lividans, Streptomyces griseofuscus, Streptomyces ambofuchsus, Streptomyces ambofaciens, Actinomycetes, Bacillus, corynebacteria* and *Thermoactinomyces*.

4. An isolated DNA molecule having 95% sequence identity over the entire lenth of an open reading frame the cosmid of claim 1.

* * * * *